(12) United States Patent
Keil et al.

(10) Patent No.: US 7,709,481 B2
(45) Date of Patent: May 4, 2010

(54) PHENYL-1,2,4-OXADIAZOLONE DERIVATIVES, PROCESSES FOR THEIR PREPARATION AND METHODS FOR THEIR USE AS PHARMACEUTICALS

(75) Inventors: Stefanie Keil, Frankfurt am Main (DE); Matthias Urmann, Frankfurt am Main (DE); Patrick Bernardelli, Paris (FR); Maike Glien, Frankfurt am Main (DE); Wolfgang Wendler, Frankfurt am Main (DE); Karen Chandross, Somerset, NJ (US); Lan Lee, Pluckemin Park, NJ (US)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/055,780

(22) Filed: Mar. 26, 2008

(65) Prior Publication Data

US 2008/0261979 A1    Oct. 23, 2008

Related U.S. Application Data

(63) Continuation of application No. PCT/EP2006/009303, filed on Sep. 26, 2006.

(30) Foreign Application Priority Data

Sep. 29, 2005 (EP) .................... 05021277

(51) Int. Cl.
| | |
|---|---|
| *A61K 31/5377* | (2006.01) |
| *A61K 31/4245* | (2006.01) |
| *A61P 3/00* | (2006.01) |
| *C07D 413/12* | (2006.01) |
| *C07D 413/14* | (2006.01) |

(52) U.S. Cl. ................ 514/236.2; 514/364; 544/138; 548/132

(58) Field of Classification Search ................ None
See application file for complete search history.

(56) References Cited

U.S. PATENT DOCUMENTS

| | | | |
|---|---|---|---|
| 5,641,796 | A | 6/1997 | Dominianni et al. |
| 6,200,995 | B1 | 3/2001 | Brouse-Elwood et al. |
| 6,710,063 | B1 | 3/2004 | Choa et al. |
| 2004/0082563 | A1 | 4/2004 | Dorsch et al. |

FOREIGN PATENT DOCUMENTS

| | | |
|---|---|---|
| EP | 1424330 | 6/2004 |
| EP | 1586573 | 10/2005 |
| WO | WO 96/13264 | 5/1996 |
| WO | WO 96/34851 | 11/1996 |
| WO | WO 97/40017 | 10/1997 |
| WO | WO 00/78313 | 12/2000 |
| WO | WO 01/00603 | 1/2001 |
| WO | WO 02/057236 | 7/2002 |
| WO | WO 02/092590 | 11/2002 |
| WO | WO 03/015774 | 2/2003 |
| WO | WO 03/043997 | 5/2003 |
| WO | WO 03/074495 | 9/2003 |
| WO | WO 2004/080943 | 9/2004 |
| WO | WO 2004/093879 | 11/2004 |
| WO | WO 2005/054213 | 6/2005 |
| WO | WO 2005/097762 | 10/2005 |
| WO | WO 2005/097786 | 10/2005 |

OTHER PUBLICATIONS

Kulkarni, S.S., et. al., Three-Dimensional Quantitative Structure Activity Relationships (3-D-QSAR) of Antihyperglycemic Agents, Bioorganic & Medicinal Chemistry vol. 7, (1999) pp. 1475-1485.

*Primary Examiner*—Kamal A Saeed
(74) *Attorney, Agent, or Firm*—Jiang Lin

(57) ABSTRACT

The inventive compounds of the present invention are comprised of phenyl and pyridinyl-1,2,4-oxadiazolone derivatives and their physiologically acceptable salts and functional derivatives that are shown to provide peroxisome proliferator activator receptor (PPARdelta) agonist activity. The compounds of the present invention are comprised of the formula:

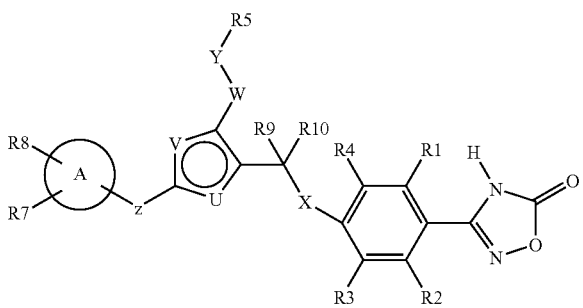

wherein the substituents R1-R5 and R7-R10 are defined herein. The compounds are therapeutically effective in the regulation and modulation of lipid and carbohydrate metabolism in mammals and are thus suitable for the treatment of diseases such as type-2 diabetes, atherosclerosis, cardiovascular disorders and the like.

30 Claims, No Drawings

PHENYL-1,2,4-OXADIAZOLONE DERIVATIVES, PROCESSES FOR THEIR PREPARATION AND METHODS FOR THEIR USE AS PHARMACEUTICALS

CROSS-REFERENCE TO RELATED APPLICATIONS

This application is a continuation of International Patent Application No. PCT/EP2006/009303 filed on Sep. 26, 2006 which is incorporated herein by reference in its entirety which also claims the benefit of priority of European Patent Application No. 05021277.8 filed on Sep. 29, 2005.

FIELD OF THE INVENTION

The present invention relates generally to pharmaceutical compositions for the treatment of metabolic disorders and the diseases and the physiological manifestations resulting therefrom. More specifically, the present invention relates to phenyl- and pyridinyl-1,2,4-oxadiazolone derivatives and their salts which are able to therapeutically modulate lipid and/or carbohydrate metabolism in mammals and are thus suitable for the prevention and/or treatment of diseases such as type-2 diabetes, atherosclerosis, cardiovascular disorders and the like. More specifically, the inventive compounds of the present invention are also useful in the treatment of the de-myelinating and other neurodegenerative disorders of the central and peripheral nervous systems.

BACKGROUND OF THE INVENTION

The present invention is directed to pharmaceutical compounds and compositions which are able to therapeutically modulate lipid and/or carbohydrate metabolism for the treatment of metabolic disorders and the diseases as well as de-myelinating and other neurodegenerative disorders of the central and peripheral nervous system. The inventive compounds of the present invention are comprised of phenyl and pyridinyl-1, 2,4-oxadiazolone derivatives and their physiologically acceptable salts and functional derivatives that are shown to provide peroxisome proliferator activator PPAR-delta agonists have been described in the prior art. (e.g. WO 01/00603 and WO 02/092590 to Keil et. al., WO2003/074495, WO2004/093879, WO2004/080943, WO2005/054213 and WO2005/097786). Compounds comprising an oxadiazolone component have been disclosed as inhibitors of factor Xa and described in DE 101 12 768 A1 and also as orally administrable hypoglycemic agents in WO 96/13264. WO 97/40017 teaches oxadiazolone compounds having a phenyl group linked to Heterocyclic rings and these are disclosed as modulators of those molecules that comprise phosphotyrosine recognition units. Benzene derivatives of oxadiazolone compounds are known to be useful as inhibitors of squalene synthase and protein farnesyltransferase and these are described in WO96/34851. The present invention however, is directed to pharmaceutical compounds and compositions comprised of phenyl and pyridinyl-1,2,4-oxadiazolone derivatives and their physiologically acceptable salts and functional derivatives showing that exhibit peroxisome proliferator activator receptor (PPAR) delta agonist activity. PPARdelta agonists have are well in the biochemical and pharmaceutical arts. Phenyl derivatives of oxadiazalones are described as agents for the therapeutic treatment of thrombobolic disorders as described in WO 02/057236. Benzene derivatives of oxadiazalone have also been shown to inhibitor squalene synthase and protein farnesyltransferase as described in WO96/34851. See also U.S. Pat. No. 6,200,995 to De La Brouse-Elwood et. al. as well as WO 03/043997 and WO 02/092590 to Johnston et. al.

The peroxisome proliferator-activated receptors (PPAR) are transducer proteins belonging to the steroid/thyroid/retinoid receptor superfamily. The PPAR receptors were originally identified as orphan receptors without known ligands, but were known for their ability to mediate the pleiotropic effects of fatty acid peroxisome proliferators. These receptors function as ligand-regulated transcription factors that control the expression of target genes by binding to their responsive DNA sequences as heterodimers with RXR. The target genes encode enzymes involved in a number of metabolic and cell growth/cell proliferation/cell differentiation inductions. These then act as targets for the development of therapeutic agents for the treatment of metabolic and central nervous system disorders, among others.

SUMMARY OF THE INVENTION

The present invention comprises derivatives of 2-aminothiazoles and 2-amino-oxazole compounds and the salts thereof as well as pharmaceutical compositions comprising them for the treatment of metabolic disorders and more particularly, those insulin-related metabolic disorders of the blood such as hyperlipidemia, diabetes, insulin-resistance and the like The compounds also effectively modulate lipid and/or carbohydrate metabolism and are thus suitable for the prevention and/or treatment of diseases such as type-2 diabetes, atherosclerosis and neurological disorders comprising de-myelinating and other neurodegenerative disorders of the central and peripheral nervous systems.

Known as peroxisome proliferator-activated receptor (PPAR) agonists/antagonists, the invention relates to compounds of formula I

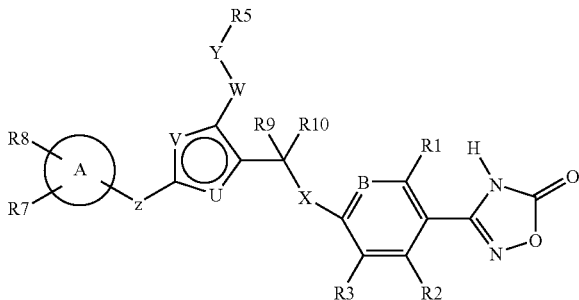

Formula I wherein
B is C(R4) or N;
R1 is selected from the group consisting of H, halogen, (C1-C8) alkyl, (C0-C4) alkylene-O—(C0-C4) alkylene-H, (C3-C7) cycloalkyl, SCH3 and CN, wherein alkyl and alkylene are unsubstituted or 1- to 5-fold substituted by F;
R2, R3 and R4 are independently selected from the group consisting of H, halogen, (C1-C8) alkyl, (C0-C4) alkylene-O—(C0-C4) alkylene-H, $SCH_3$ and CN, wherein alkyl and alkylene are unsubstituted or 1- to 5-fold substituted by F;
R2 and R3 together with the carbon atoms to which they are bonded form a (C6-C10) aryl- or a (C5-C10) heteroaryl ring;
X is selected from the group consisting of O, S, S(O), $S(O)_2$, O—$CH_2$, S—$CH_2$, $CH_2$—O, $CH_2$—S;

U or V is N and the other is S or O;

W is a bond, selected from the group consisting of (C1-C8) alkylene, (C2-C8) alkenylene, which are unsubstituted or mono-, di- or tri-substituted by OH and F;

Y is a bond, O, S, S(O), S(O)$_2$, N(R6);

R5 is selected from the group consisting of H, (C1-C8) alkyl, (C0-C4) alkylene-(C3-C13) cycloalkyl, (C0-C4) alkylene-(C6-C14) aryl, (C2-C8) alkenyl, (C0-C4) alkylene-(C3-C15) heterocycloalkyl, (C0-C4) alkylene-(C3-C15) heterocycloalkenyl, (C0-C4) alkylene-(C5-C15) heteroaryl, wherein alkyl and alkylene can be mono-, di- or tri-substituted by (C1-C4) alkyl and O—(C0-C4) alkylene-H, wherein alkyl and alkylene can be 1- to 5-fold substituted by F, and wherein cycloalkyl, aryl, heterocycloalkyl, heterocycloalkenyl and heteroaryl are mono-, di- or tri-substituted by F, Cl, Br, CF$_3$, (C1-C4) alkyl and O—(C0-C4) alkylene-H;

R6 is selected from the group consisting of H, (C1-C8) alkyl or (C2-C8) alkenyl, which are unsubstituted or mono-, di- or tri-substituted by F and O—(C0-C4)-alkylene-H;

R5 and R6 together with the nitrogen atom to which they are bonded (Y=N(R6)) form a (C3-C9)-heterocycloalkyl, a (C3-C9)-heterocycloalkenyl or selected from the group consisting of a (C5-C9)-heteroaryl which can contain additionally 1 to 3 heteroatoms N, O, S and which is unsubstituted or mono- or disubstituted by F, CF3, (C1-C4) alkyl, O—(C1-C4) alkyl, OH, CH2-OH, SO2-(C1-C4) alkyl, CO—(C1-C4) alkyl, CO—NH2, NH—CO—(C1-C4) alkyl, (C6-C14) aryl and (C5-C15) heteroaryl;

Z is a bond, or are selected from the group consisting of (C1-C8) alkylene, (C2-C8) alkenylene, (C2-C8) alkylidene, (C1-C6) alkylene-O—(C1-C6) alkyl;

A is selected from the group consisting of (C3-C13) cycloalkyl or (C4-C15) heterocycloalkyl, (C4-C15) heterocycloalkenyl or (C5-C15) heteroaryl ring;

R7, R8 are independently selected from the group consisting of H, halogen, (C1-C8) alkyl, (C0-C4) alkylene-O—(C0-C4) alkylene-H, SCF3, SF5, S(O)2CF3, O—(C6-C12) aryl, (C6-C12) aryl, NO2, wherein alkyl and alkylene are unsubstituted or mono-, di- or tri-substituted by F and aryl is unsubstituted or mono-, di- or tri-substituted by halogen, (C1-C4) alkyl or O—(C1-C4) alkyl;

R9 and R10 are independently selected from the group consisting of H, (C1-C6) alkyl, (C2-C6) alkenyl, (C0-C6) alkylene-(C6-C14) aryl, (C0-C6) alkylene-(C5-C15) heteroaryl, (C0-C6) alkylene-(C3-C8) cycloalkyl, (C0-C6) alkylene-(C3-C8) cycloalkenyl, wherein alkyl and alkylene are unsubstituted or mono-, di- or tri-substituted by F and aryl and heteroaryl are unsubstituted or mono-, di- or tri-substituted by halogen, (C1-C4) alkyl or O—(C1-C4) alkyl;

in all its stereoisomeric forms and mixtures in any ratio, and its physiologically acceptable salts and tautomeric forms.

A second embodiment according to the invention are compounds of the formula I wherein B is CH;

R1 is selected from the group consisting of H, halogen, (C1-C8) alkyl, (C0-C4) alkylene-O—(C0-C4) alkylene-H, SCH$_3$, and CN, wherein alkyl and alkylene are unsubstituted or mono-, di- or trisubstituted by F;

R2, R3 and R4 are independently selected from the group consisting of H, halogen, (C1-C8) alkyl, (C0-C4) alkylene-O—(C0-C4) alkylene-H, SCH$_3$ and CN, wherein alkyl and alkylene are unsubstituted or mono, di- or trisubstituted by F;

X is O, S, S(O), S(O)$_2$, O—CH$_2$, S—CH$_2$, CH$_2$—O, CH$_2$—S;

U or V is N and the other is S or O;

W is a bond or selected from the group consisting of (C1-C8) alkylene, (C2-C8) alkenylene, which are unsubstituted or mono-, di- or tri-substituted by OH and F;

Y is a bond or selected from the group consisting of O, S, S(O), S(O)2 and N(R6);

R5 is selected from the group consisting of H, (C1-C8) alkyl, (C0-C4) alkylene-(C3-C13) cycloalkyl, (C0-C4) alkylene-(C6-C14) aryl, (C2-C8) alkenyl, (C0-C4) alkylene-(C3-C15) heterocycloalkyl, (C0-C4) alkylene-(C3-C15) heterocycloalkenyl, (C0-C4) alkylene-(C5-C15) heteroaryl, wherein alkyl and alkylene can be mono-, di- or tri-substituted by F, (C1-C4) alkyl and O—(C0-C4) alkylene-H and wherein cycloalkyl, aryl, heterocycloalkyl, heterocycloalkenyl and heteroaryl are mono-, di- or tri-substituted by F, Cl, Br, CF3, (C1-C4) alkyl and O—(C0-C4) alkylene-H;

R6 is selected from the group consisting of H, (C1-C8) alkyl or (C2-C8) alkenyl, which are unsubstituted or mono-, di- or tri-substituted by F and O—(C0-C4)-alkylene-H;

R5 and R6 together with the nitrogen atom to which they are bonded (Y=N(R6)) form a (C3-C9)-heterocycloalkyl, a (C3-C9)-heterocycloalkenyl or a (C5-C9)-heteroaryl which can contain additionally 1 to 3 heteroatoms N, O, S and which is unsubstituted or mono- or disubstituted by F, CF$_3$, (C1-C4) alkyl, O—(C1-C4) alkyl, CH$_2$—OH, SO$_2$—(C1-C4) alkyl, CO—(C1-C4) alkyl, CO—NH$_2$, NH—CO—(C1-C4) alkyl, (C6-C14) aryl and (C5-C15) heteroaryl;

Z is a bond or selected from the group consisting of (C1-C8) alkylene, (C2-C8) alkenylene, (C2-C8) alkylidene, (C1-C6) alkylene-O—(C1-C6) alkyl;

A is selected from the group consisting of (C3-C13) cycloalkyl or (C4-C15) heterocycloalkyl, (C4-C15) heterocycloalkenyl or (C5-C15) heteroaryl ring;

R7 and R8 are independently selected from the group consisting of H, halogen, (C1-C8) alkyl, (C0-C4) alkylene-O—(C0-C4) alkylene-H, SCF$_3$, SF$_5$, S(O)$_2$CF$_3$, O—(C6-C12) aryl, (C6-C12) aryl and NO$_2$, wherein alkyl and alkylene are unsubstituted or mono-, di- or tri-substituted by F and aryl is unsubstituted or mono-, di- or tri-substituted by halogen, (C1-C4) alkyl or O—(C1-C4) alkyl;

R9 and R10 are independently selected from the group consisting of H, (C1-C6) alkyl, (C2-C6) alkenyl, (C0-C6) alkylene-(C6-C14) aryl, (C0-C6) alkylene-(C5-C15) heteroaryl, (C0-C6) alkylene-(C3-C8) cycloalkyl, and (C0-C6) alkylene-(C3-C8) cycloalkenyl, wherein alkyl and alkylene are unsubstituted or mono-, di- or tri-substituted by F;

in all its stereoisomeric forms and mixtures in any ratio, and its physiologically acceptable salts and tautomeric forms.

A third embodiment of the present invention are compounds of the formula I wherein B is C(R4) or N;

R1 is selected from the group consisting of H, halogen, (C1-C8) alkyl, (C0-C4) alkylene-O—(C0-C4) alkylene-H, (C3-C7) cycloalkyl, wherein alkyl and alkylene are unsubstituted or mono, di- or trisubstituted by F;

R2 is H;

R3 is H or halogen;

R4 is H;

R2 and R3 together with the Carbon atoms to which they are bonded form a (C6) aryl- or a (C5-C6) heteroaryl ring;

X is O, O—CH2;

U or V is N and other is S or O;

W is a bond or (C1-C5) alkylene;

Y is a bond or O, N(R6);
R5 is H or (C1-C8) alkyl, (C0-C4) alkylene-(C6-C14) aryl;
R6 is H or (C1-C8) alkyl;
R5 and R6 together with the nitrogen atom to which they are bonded (Y=N(R6)) form a (C3-C9)-heterocycloalkyl, which is un-substituted or mono-substituted by $CF_3$;
Z is a bond, (C1-C4) alkylene, (C2-C4) alkenylene;
A is (C3-C8) cycloalkyl, (C5-C6) heterocycloalkyl or a (C5-C12) heteroaryl ring;
R7 is selected from the group consisting of H, (C1-C8) alkyl, (C0-C4) alkylene-O—(C0-C4) alkylene-H, $S(O)_2CF_3$, (C6-C12) aryl, wherein alkyl and alkylene are un-substituted or mono-, di- or tri-substituted by F and aryl is un-substituted or mono-, di- or tri-substituted by halogen;
R8 is H;
R9 is selected from the group consisting of H, (C1-C6) alkyl, (C0-C6) alkylene-(C6-C14) aryl(C0-C6) alkylene-(C5-C15) heteroaryl, wherein alkyl and alkylene are unsubstituted or mono-, di- or tri-substituted by F and aryl is unsubstituted or mono-, di- or tri-substituted by halogen;
R10 is H.

Another embodiment according to the invention are compounds of the formula I where one or more substituents have the following meaning:
B is CH or N
R1 is selected from the group consisting of H, halogen, (C1-C8) alkyl, (C0-C4) alkylene-O—(C0-C4) alkylene-H and (C3-C7) cycloalkyl, wherein alkyl and alkylene are unsubstituted or mono, di- or tri-substituted by F;
R2 and R4 are H;
R3 is H or F;
R2 and R3 together with the carbon atoms to which they are bonded form a (C6)-aryl or a (C5-C6) heteroaryl;
X is O or $OCH_2$;
V is N and
U is O or S;
W is a bond or (C1-C4) alkylene;
Y is a bond or O, N(R6);
R5 is selected from the group consisting of H, (C1-C8) alkyl, (C0-C4) alkylene-(C6-C10) aryl, wherein alkyl and alkylene can be mono-, di- or tri-substituted by F, (C1-C4) alkyl and O—(C0-C4) alkylene-H;
R6 is H, (C1-C4) alkyl;
R5 and R6 together with the nitrogen atom to which they are bonded (Y=N(R6)) form a (C3-C6)-heterocycloalkyl, which can contain additionally 1 heteroatom N or O and which is unsubstituted or mono- or disubstituted by F, $CF_3$, $CH_3$, $OCH_3$ and phenyl;
Z is a bond or (C1-C4) alkylene, (C2-C4) alkenylene;
A is (C5-C8) cycloalkyl or (C5-C10) heterocycloalkyl, (C5-C10) heterocycloalkenyl or (C5-C10) heteroaryl ring;
R7 and R8 are independently selected from the group consisting of H, halogen, (C1-C8) alkyl, (C0-C4) alkylen-O—(C0-C4) alkylene-H, (C6-C12) aryl, S(O)2CF3, wherein alkyl and alkylene are unsubstituted or mono-, di- or tri-substituted by F and aryl is substituted by halogen;
R9 is selected from the group consisting of H, (C1-C4) alkyl, (C0-C4) alkylene-(C6-C10) aryl, (C0-C4) alkylene-(C5-C6) heteroaryl, wherein alkyl, alkylene, aryl and heteroaryl are unsubstituted or mono-, di- or tri-substituted by F;
R10 is H.

Another embodiment according to the invention are compounds of the formula I where one or more substituents have the following meaning:
B is C(R4);
R1 is H, halogen, (C1-C8) alkyl, (C0-C4) alkylene-O—(C0-C4) alkylene-H, (C3-C7) cycloalkyl, wherein alkyl and alkylene are unsubstituted or mono, di- or tri-substituted by F, preferably H, F, Cl, (C1-C4) alkyl, O—(C1-C4) alkyl;
R2 and R4 are H;
R3 is H or F;
X is O or S;
V is N and
U is O or S;
W is a bond or (C1-C4) alkylene;
Y is a bond, O or N(R6);
R5 is selected from the group consisting of H, (C1-C8) alkyl, (C0-C4) alkylene-(C3-C6) cycloalkyl, (C0-C4) alkylene-(C6-C10) aryl, (C0-C4) alkylene-(C4-C6) heterocycloalkyl, (C0-C4) alkylene-(C4-C6) heterocycloalkenyl, (C0-C4) alkylene-(C5-C6) heteroaryl, wherein alkyl and alkylene can be mono-, di- or tri-substituted by F, (C1-C4) alkyl and O—(C0-C4) alkylene-H and wherein cycloalkyl, aryl, heterocycloalkyl, heterocycloalkenyl and heteroaryl are mono-, di- or tri-substituted by F, $CF_3$, (C1-C4) alkyl and O—(C0-C4) alkylene-H;
R6 is H or (C1-C4) alkyl;
R5 and R6 together with the nitrogen atom to which they are bonded (Y=N(R6)) form a (C3-C6)-heterocycloalkyl, a (C3-C6)-heterocycloalkenyl or a (C5-C6)-heteroaryl which can contain additionally 1 heteroatom N or O and which is unsubstituted or mono- or disubstituted by F, $CF_3$, CH3, $OCH_3$, phenyl and (C5-C6) heteroaryl;
Z is a bond or selected from the group consisting of, (C1-C4) alkylene, (C2-C4) alkylidene, (C1-C4) alkylene-O—(C1-C4) alkyl;
A is (C5-C8) cycloalkyl or (C5-C10) heterocycloalkyl, (C5-C10) heterocycloalkenyl or (C5-C10) heteroaryl ring;
R7 and R8 are independently selected from the group consisting of H, halogen, (C1-C8) alkyl, (C0-C4) alkylen-O—(C0-C4) alkylene-H, (C6-C12) aryl, wherein alkyl and alkylene are unsubstituted or mono-, di- or tri-substituted by F and aryl is substituted by halogen;
R9 and R10 are independently selected from the group consisting of H, (C1-C4) alkyl, (C0-C4) alkylene-phenyl, and (C0-C4) alkylene-(C5-C6) heteroaryl.

Another embodiment according to the invention are compounds of the formula I where one or more substituents have the following meaning:
B is CH;
R1 selected from the group consisting of halogen, (C1-C8) alkyl, (C0-C4) alkylene-O—(C0-C4) alkylene-H, SCH3, CN, wherein alkyl and alkylene are unsubstituted or mono, di- or tri-substituted by F;
R1 is selected from the group consisting of F, Cl, (C1-C4) alkyl, O—(C1-C4) alkyl;
R2, R3 and R4 are H;
X is O, S;
V is N and
U is O, S;
W is a bond, (C1-C4) alkylene;
Y is a bond, O, N(R6);
R5 is H, (C1-C8) alkyl, (C0-C4) alkylene-(C3-C6) cycloalkyl, (C0-C4) alkylene-(C6-C10) aryl, (C0-C4) alkylene-(C4-C6) heterocycloalkyl, (C0-C4) alkylene-(C4-C6) heterocycloalkenyl, (C0-C4) alkylene-(C5-C6) heteroaryl, wherein alkyl and alkylene can be mono-, di- or tri-substituted by F, (C1-C4) alkyl and O—(C0-C4) alkylene-H and wherein cycloalkyl, aryl, heterocycloalkyl, heterocycloalkenyl and heteroaryl are mono-, di- or tri-substituted by F, $CF_3$, (C1-C4) alkyl and O—(C0-C4) alkylene-H;
R6 is H, (C1-C4) alkyl;

R5 and R6 together with the nitrogen atom to which they are bonded (Y=N(R6)) form a (C3-C6)-heterocycloalkyl, a (C3-C6)-heterocycloalkenyl or a (C5-C6)-heteroaryl which can contain additionally 1 heteroatom N or O and which is unsubstituted or mono- or disubstituted by F, CF$_3$, CH$_3$, OCH$_3$, phenyl and (C5-C6) heteroaryl;

Z is a bond or is selected from the group consisting of (C1-C4) alkylene, (C2-C4) alkylidene, (C1-C4) alkylene-O—(C1-C4) alkyl;

A is selected from the group consisting of (C5-C8) cycloalkyl or (C5-C10) heterocycloalkyl, (C5-C10) heterocycloalkenyl or (C5-C10) heteroaryl ring;

R7 and R8 are independently selected from the group consisting of H, halogen, (C1-C8) alkyl, (C0-C4) alkylen-O—(C0-C4) alkylene-H, (C6-C12) aryl, wherein alkyl and alkylene are unsubstituted or mono-, di- or tri-substituted by F and aryl is substituted by halogen;

R9 and R10 are selected from the group consisting of H, (C1-C4) alkyl, (C0-C4) alkylene-phenyl, (C0-C4) alkylene-(C5-C6) heteroaryl.

Preferably, another embodiment according to the invention are compounds of the formula I wherein R1 is selected from the group consisting of H, F, Cl, CH$_3$, OCH$_3$, OCHF$_2$, OCH$_2$CF$_3$ or cyclopropyl.

More preferably, another embodiment according to the invention are of the formula I wherein R1 is H, F or OCH$_3$.

More preferably, an embodiment according to the invention are compounds of the formula I wherein R1 is F or OCH$_3$.

More preferably, yet another embodiment according to the invention are compounds of the formula I wherein R1 is selected from the group consisting of OCH$_3$, OCHF$_2$ or OCH$_2$CF$_3$.

More preferably, another embodiment according to the invention are compounds of the formula I wherein R1 is selected from the group consisting of H, F, Cl, CH$_3$ or cyclopropyl.

Yet another embodiment according to the invention are compounds of the formula I wherein R1 is C$_1$ or CH$_3$.

Most preferably, another embodiment according to the invention are compounds of the formula I wherein R1 is Cl.

More preferably, another embodiment according to the invention are compounds of the formula I wherein R1 is F.

More preferably, another embodiment according to the invention are compounds of the formula I wherein R1 is cyclopropyl.

More preferably, another embodiment according to the invention are compounds of the formula I wherein R1 is O—CHF$_2$.

Another embodiment according to the invention are compounds of the formula I wherein R1 is O—CH$_2$—CF$_3$.

Another embodiment according to the invention are compounds of the formula I wherein R1 is H.

Another embodiment according to the invention are compounds of the formula I wherein R1 is selected from the group consisting of O—CH$_3$, O—CH$_2$CF$_3$ or —O—CHF$_2$ and R3 is F.

Another embodiment according to the invention are compounds of the formula I wherein R2 and R3 are H.

More preferably, another embodiment according to the invention are compounds of the formula I wherein R2 and R3 together with the carbon atoms to which they are bonded form a (C6) aryl- or a (C5) heteroaryl ring;

More preferably, another embodiment according to the invention are compounds of the formula I wherein R2 and R3 together with the carbon atoms to which they are bonded and the ring carrying them form a naphthalene or a quinoline-ring.

Another embodiment according to the invention are compounds of the formula I wherein
B is C(R4) and
R4 is H;

More preferably, another embodiment according to the invention are compounds of the formula I wherein X is O or —O—CH2-.

More preferably, another embodiment according to the invention are compounds of the formula I wherein X is O.

Even more preferably, another embodiment according to the invention are compounds of the formula I wherein X is —O—CH2-.

Another embodiment according to the invention are compounds of the formula I wherein V is N and U is O; or V is N and U is S.

Another embodiment according to the invention are compounds of the formula I wherein
V is N and
U is S.

Another embodiment according to the invention are compounds of the formula I wherein
W is —CH2-.

More preferably, another embodiment according to the invention are compounds of the formula I wherein Y is a bond.

Another embodiment according to the invention are compounds of the formula I wherein Y is N(R6).

Another embodiment according to the invention are compounds of the formula I wherein R5 is H, CH$_3$.

Another embodiment according to the invention are compounds of the formula I wherein R6 is H, CH$_2$CH$_3$.

Another embodiment according to the invention are compounds of the formula I wherein R5 and R6 together with the nitrogen atom to which they are bonded form a (C3-C7)-heterocycloalkyl, which can contain additionally 1 to 2 heteroatoms N, O or S such as pyrrolidine, morpholine, thiomorpholine, thiomorpholine-1-oxide, thiomorpholine-1-dioxide, piperidine, piperazine, azetidine, 2,3-dihydro-1H-isoindole, piperazin-2-one, preferably piperidine, which are unsubstituted or mono- or disubstituted by F, CF$_3$, CH$_3$, or OCH$_3$.

Another embodiment according to the invention are compounds of the formula I wherein Z is a bond.

Another embodiment according to the invention are compounds of the formula I wherein A is selected from the group consisting of 5- to 6-membered cycloalkyl, heterocycloalkyl, heterocycloalkenyl, heteroaryl ring, such as cyclohexyl, piperidine, pyridine, benzothiophene, pyrazole, quinoline.

Another embodiment according to the invention are compounds of the formula I wherein R7 is in para- or 1-4-position to Z, if A is a 6-membered ring.

Another embodiment according to the invention are compounds of the formula I wherein R7 is selected from the group consisting of H, F, CH$_3$, CH$_2$CH$_3$, CF$_3$, OCH$_3$, phenyl; and R8 is H.

Another embodiment according to the invention are compounds of the formula I wherein
R9 is ethyl, CF$_2$CH$_2$CH$_3$, CF$_3$, CH$_2$-phenyl, CH$_2$-(4-F-phenyl), CH$_2$-pyridyl and
R10 is H.

Another embodiment according to the invention are compounds of the formula I wherein R9 is CH$_2$— (4-F-phenyl).

Another embodiment according to the invention are compounds of the formula I wherein R9 is CH$_2$-(2-pyridyl).

Another embodiment according to the invention are compounds of the formula I wherein R9 is CF$_2$—CH$_2$—CH$_3$.

Another preferred embodiment according to the invention are compounds of the formula I wherein
R9 is CF$_3$.

Another preferred embodiment according to the invention are compounds of the formula I wherein
A is cyclohexyl,
R7 is 4-CF$_3$,
R8 is H.

Another preferred embodiment according to the invention are compounds of the formula I wherein
A is cyclohexyl,
R7 is 4-CF$_3$,
R8 is H and
R1 is O—CH$_3$, O—CH$_2$CF$_3$ or —O—CHF$_2$.

Another preferred embodiment according to the invention are compounds of the formula I wherein
A is 3-pyridyl,
R7 is 6-CF$_3$,
R8 is H.

Another preferred embodiment according to the invention are compounds of the formula I wherein
W is —CH$_2$—,
Y is a bond and
R5 is H.

Another preferred embodiment according to the invention are compounds of the formula I wherein
W is —CH$_2$—,
Y is N(R6) and
R5 and R6 together with the nitrogen to which they are bonded form piperidinyl which is substituted by CF$_3$.

Another preferred embodiment according to the invention are compounds of the formula I wherein
B is C(R4);
R1 is Cl;
R2, R3 and R4 are H;
X is O;
V is N;
U is S;
W is —CH$_2$—;
Y is a bond or O;
R5 is H, CH$_3$;
Z is a bond;
A is piperidine-4-yl, pyridine-2-yl or pyridine-3-yl;
R7 is CF$_3$ or phenyl;
R8 is H; and
R9, R10 are H.

Another embodiment according to the invention are compounds of the formula I wherein
B is C(R4);
R1 is H, F, Cl;
R2, R3 and R4 are H;
X is O or O—CH$_2$;
V is N;
U is S;
W is —CH$_2$—;
Y is a bond;
R5 is H;
Z is a bond;
A is pyridinyl or cyclohexyl;
R7 is CF$_3$;
R8 is H;
R9 is CH$_2$—CH$_3$, CF$_3$, CF$_2$—CH$_2$—CH$_3$, CH$_2$-4F-phenyl, CH$_2$-pyridyl and
R10 is H.

Another preferred embodiment according to the invention are compounds of the formula I wherein
B is C(R4);
R1 is O—CH$_3$, O—CH$_2$CF$_3$ or —O—CHF$_2$;
R2 and R4 are H;
R3 is H or F;
X is O;
V is N;
U is O or S;
W is a bond or —CH$_2$—;
Y is a bond or N(R6);
R5 is CH$_3$;
R6 is CH$_3$;
R5 and R6 together with the nitrogen to which they are bonded form a piperidine ring which is substituted by CF$_3$;
Z is a bond;
A is cyclohexyl;
R7 is 4-CF$_3$;
R8 is H;
R9 is H or ethyl;
R10 is H.

A further embodiment according to the invention are the following compounds:

3-{2-Chloro-4-[4-methyl-2-(1-methyl-cyclohexyl)-oxazol-5-ylmethoxy]-phenyl}-4H-[1,2,4]oxadiazol-5-one 3-[2-Chloro-4-(2-cyclohexyl-4-methyl-oxazol-5-ylmethoxy)-phenyl]-4H-[1,2,4]oxadiazol-5-one 3-{2-Chloro-4-[4-methyl-2-(trans-1,4-trifluoromethyl-cyclohexyl)-oxazol-5-ylmethoxy]-phenyl}-4H-[1,2,4]oxadiazol-5-one 3-{2-Chloro-4-[4-methyl-2-(cis-1,4-trifluoromethyl-cyclohexyl)-oxazol-5-ylmethoxy]-phenyl}-4H-[1,2,4]oxadiazol-5-one 3-{2-Chloro-4-[2-(trans-1,4-methoxy-cyclohexyl)-4-methyl-oxazol-5-ylmethoxy]-phenyl}-4H-[1,2,4]oxadiazol-5-one 3-[2-Chloro-4-(2-cyclohexyl-4-methyl-thiazol-5-ylmethoxy)-phenyl]-4H-[1,2,4]oxadiazol-5-one 3-{2-Chloro-4-[4-methyl-2-(1-trifluoromethanesulfonyl-piperidin-4-yl)-thiazol-5-ylmethoxy]-phenyl}-4H-[1,2,4]oxadiazol-5-one 3-(2-Chloro-4-{4-methyl-2-[1-(2,2,2-trifluoro-ethyl)-piperidin-4-yl]-thiazol-5-ylmethoxy}-phenyl)-4H-[1,2,4]oxadiazol-5-one 3-{2-Chloro-4-[4-methyl-2-(1-phenyl-piperidin-4-yl)-thiazol-5-ylmethoxy]-phenyl}-4H-[1,2,4]oxadiazol-5-one 3-{2-Chloro-4-[2-(4,4-difluoro-cyclohexyl)-4-methoxymethyl-thiazol-5-ylmethoxy]-phenyl}-4H-[1,2,4]oxadiazol-5-one 3-{2-Chloro-4-[2-(2-cyclohexyl-ethyl)-4-methoxymethyl-thiazol-5-ylmethoxy]-phenyl}-4H-[1,2,4]oxadiazol-5-one 3-[2-Chloro-4-(2-cycloheptyl-4-methoxymethyl-thiazol-5-ylmethoxy)-phenyl]-4H-[1,2,4]oxadiazol-5-one 3-(2-Chloro-4-{2-[trans-1,4-(4-chloro-phenyl)-cyclohexyl]-4-methoxymethyl-thiazol-5-ylmethoxy}-phenyl)-4H-[1,2,4]oxadiazol-5-one 3-[2-Chloro-4-(2-cyclopentyl-4-methoxymethyl-oxazol-5-ylmethoxy)-phenyl]-4H-[1,2,4]oxadiazol-5-one 3-{2-Chloro-4-[4-methoxymethyl-2-(6-trifluoromethyl-pyridin-3-yl)-thiazol-5-ylmethoxy]-phenyl}-4H-[1,2,4]oxadiazol-5-one 3-[2-Chloro-4-(2-cyclohexyl-4-ethoxymethyl-oxazol-5-ylmethoxy)-phenyl]-4H-[1,2,4]oxadiazol-5-one 3-[2-Chloro-4-(2-cyclohexyl-4-methoxymethyl-oxazol-5-ylmethoxy)-phenyl]-4H-[1,2,4]oxadiazol-5-one 3-[2-Chloro-4-(2-cycloheptyl-4-methoxymethyl-oxazol-5-ylmethoxy)-phenyl]-4H-[1,2,4]oxadiazol-5-one 3-{2-Chloro-4-[4-methoxymethyl-2-(trans-1,4-trifluoromethyl-cyclohexyl)-oxazol-5-ylmethoxy]-phenyl}-4H-[1,2,4]oxadiazol-5-one 3-{2-Chloro-4-[4-methoxymethyl-2-(cis-1,4-trifluoromethyl-cyclohexyl)-oxazol-5-ylmethoxy]-phenyl}-4H-[1,2,4]oxadiazol-5-one 3-[2-Chloro-4-(2-cyclohexyl-4-morpholin-4-ylmethyl-oxazol-5-ylmethoxy)-phenyl]-4H-[1,2,4]oxadiazol-5-one 3-[2-Chloro-4-(2-cyclohexyl-4-diethylaminomethyl-oxazol-5-ylmethoxy)-phenyl]-4H-[1,2,4]oxadiazol-5-one 3-[2-Chloro-4-(2-cyclohexyl-oxazol-4-ylmethoxy)-phenyl]-4H-[1,2,4]oxadiazol-5-one 3-{2-Chloro-4-[2-(2-cyclohexyl-vinyl)-4-methoxymethyl-thiazol-5-ylmethoxy]-phenyl}-4H-[1,2,4]oxadiazol-5-one 3-{2-Chloro-4-[4-methyl-2-(6-trifluoromethyl-pyridin-3-yl)-thiazol-5-ylmethoxy]-phenyl}-4H-[1,2,4]oxadiazol-5-one 3-(2-Chloro-4-{1-[4-methyl-2-(trans-1,4-trifluoromethyl-cyclohexyl)-thiazol-5-yl]-2-phenyl-ethoxy}-phenyl)-4H-[1,2,4]oxadiazol-5-one 3-{4-[4-(3-Benzyloxy-propyl)-2-(6-trifluoromethyl-pyridin-3-yl)-thiazol-5-ylmethoxy]-2-chloro-phenyl}-4H-[1,2,4]oxadiazol-5-one 3-(2-Chloro-4-{1-[4-methyl-2-(6-trifluoromethyl-pyridin-3-yl)-thiazol-5-yl]-propoxy}-phenyl)-4H-[1,2,4]oxadiazol-5-one 3-(2-Chloro-4-{2-(4-fluoro-phenyl)-1-[4-methyl-2-(6-trifluoromethyl-pyridin-3-yl)-thiazol-5-yl]-ethoxy}-phenyl)-4H-[1,2,4]oxadiazol-5-one 3-(2-Chloro-4-{2,2,2-trifluoro-1-[4-methyl-2-(4-trifluoromethyl-cyclohexyl)-thiazol-5-yl]-ethoxy}-phenyl)-4H-[1,2,4]oxadiazol-5-one 3-(2-Chloro-4-{1-[4-methyl-2-(4-trifluoromethyl-cyclohexyl)-thiazol-5-yl]-2-pyridin-2-yl-ethoxy}-phenyl)-4H-[1,2,4]oxadiazol-5-one 3-(2-Fluoro-4-{2,2,2-trifluoro-1-[4-methyl-2-(trans-1,4-trifluoromethyl-cyclohexyl)-thiazol-5-yl]-ethoxymethyl}-phenyl)-4H-[1,2,4]oxadiazol-5-one 3-(2-Fluoro-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one 3-(4-{2,2,2-Trifluoro-1-[4-methyl-2-(6-trifluoromethyl-pyridin-3-yl)-thiazol-5-yl]-ethoxymethyl}-phenyl)-4H-[1,2,4]oxadiazol-5-one 3-(4-{1-[4-Methyl-2-(6-trifluoromethyl-pyridin-3-yl)-thiazol-5-yl]-propoxymethyl}-2-trifluoromethyl-phenyl)-4H-[1,2,4]oxadiazol-5-one 3-(2-Chloro-4-{2,2,2-trifluoro-1-[4-methyl-2-(trans-1,4-trifluoromethyl-cyclohexyl)-thiazol-5-yl]-ethoxymethyl}-phenyl)-4H-[1,2,4]oxadiazol-5-one 3-(2-Chloro-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one 3-(8-{2,2,2-Trifluoro-1-[4-methyl-2-(6-trifluoromethyl-pyridin-3-yl)-thiazol-5-yl]-ethoxymethyl}-quinolin-5-yl)-4H-[1,2,4]oxadiazol-5-one 3-(2-Chloro-6-{2,2,2-trifluoro-1-[4-methyl-2-(6-trifluoromethyl-pyridin-3-yl)-thiazol-5-yl]-ethoxymethyl}-pyridin-3-yl)-4H-[1,2,4]oxadiazol-5-one 3-(2-Cyclopropyl-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one 3-(2-Cyclopropyl-4-{2,2,2-trifluoro-1-[4-methyl-2-(trans,1,4-trifluoromethyl-cyclohexyl)-thiazol-5-yl]-ethoxymethyl}-phenyl)-4H-[1,2,4]oxadiazol-5-one 3-(4-{2,2-Difluoro-1-[4-methyl-2-(6-trifluoromethyl-pyridin-3-yl)-thiazol-5-yl]-butoxymethyl}-phenyl)-4H-[1,2,4]oxadiazol-5-one 3-(2-Chloro-4-{2,2-difluoro-1-[4-methyl-2-(6-trifluoromethyl-pyridin-3-yl)-thiazol-5-yl]-butoxymethyl}-phenyl)-4H-[1,2,4]oxadiazol-5-one 3-(4-{2,2-Difluoro-1-[4-methyl-2-(6-trifluoromethyl-pyridin-3-yl)-thiazol-5-yl]-butoxymethyl}-naphthalen-1-yl)-4H-[1,2,4]oxadiazol-5-one 3-(8-{2,2-Difluoro-1-[4-methyl-2-(6-trifluoromethyl-pyridin-3-yl)-thiazol-5-yl]-butoxymethyl}-quinolin-5-yl)-4H-[1,2,4]oxadiazol-5-one 3-[4-(2-Benzo[b]thiophen-2-yl-4-methyl-thiazol-5-ylmethoxy)-2-chloro-phenyl]-2H-[1,2,4]oxadiazol-5-one 3-{2-Chloro-4-[4-methyl-2-(1-methyl-1H-pyrazol-4-yl)-thiazol-5-ylmethoxy]-phenyl}-2H-[1,2,4]oxadiazol-5-one 3-[2-Chloro-4-(4-methyl-2-quinolin-8-yl-thiazol-5-ylmethoxy)-phenyl]-2H-[1,2,4]oxadiazol-5-one 3-(2-Methoxy-4-{1-[4-methyl-2-(trans-1,4-trifluoromethyl-cyclohexyl)-oxazol-5-yl]-propoxy}-phenyl)-4H-1,2,4-oxadiazol-5-one 3-{2-Methoxy-4-[4-methyl-2-(trans-1,4-trifluoromethyl-cyclohexyl)-thiazol-5-ylmethoxy]-phenyl}-4H-1,2,4-oxadiazol-5-one 3-(2-Methoxy-4-{1-[4-methyl-2-(trans-1,4-trifluoromethyl-cyclohexyl)-thiazol-5-yl]-propoxy}-phenyl)-4H-1,2,4-oxadiazol-5-one 3-{5-Fluoro-2-methoxy-4-[4-methyl-2-(trans-1,4-trifluoromethyl-cyclohexyl)-thiazol-5-ylmethoxy]-phenyl}-4H-1,2,4-oxadiazol-5-one 3-(5-Fluoro-2-methoxy-4-{1-[4-methyl-2-(trans-1,4-trifluoromethyl-cyclohexyl)-thiazol-5-yl]-propoxy}-phenyl)-4H-1,2,4-oxadiazol-5-one 3-{2-Difluoromethoxy-4-[4-methyl-2-(trans-1,4-trifluoromethyl-cyclohexyl)-thiazol-5-ylmethoxy]-phenyl}-4H-1,2,4-oxadiazol-5-one 3-(2-Difluoromethoxy-4-{1-[4-methyl-2-(trans-1,4-trifluoromethyl-cyclohexyl)-thiazol-5-yl]-propoxy}-phenyl)-4H-1,2,4-oxadiazol-5-one 3-{2-Difluoromethoxy-5-fluoro-4-[4-methyl-2-(trans-1,4-trifluoromethyl-cyclohexyl)-thiazol-5-ylmethoxy]-phenyl}-4H-1,2,4-oxadiazol-5-one 3-(2-Difluoromethoxy-5-fluoro-4-{1-[4-methyl-2-(trans-1,4-trifluoromethyl-cyclohexyl)-thiazol-5-yl]-propoxy}-phenyl)-4H-1,2,4-oxadiazol-5-one 3-{2-Methoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one 3-(2-Methoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one 3-{5-Fluoro-2-methoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one 3-(5-Fluoro-2-methoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one 3-{2-Difluoromethoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one 3-(2-Difluoromethoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one 3-{2-Difluoromethoxy-5-fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one 3-(2-Difluoromethoxy-5-fluoro-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one 3-(5-Fluoro-2-(2,2,2-trifluoro-ethoxy)-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one 3-{2-Fluoro-4-[4-methyl-2-(trans-1,4-trifluoromethyl-cyclohexyl)-thiazol-5-ylmethoxy]-phenyl}-4H-1,2,4-oxadiazol-5-one 3-(2-Fluoro-4-{1-[4-methyl-2-(trans-1,4-trifluoromethyl-cyclohexyl)-thiazol-5-yl]-propoxy}-phenyl)-4H-1,2,4-oxadiazol-5-one 3-{2-Fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one 3-(2-Fluoro-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one 3-[4-[4-Methyl-2-(trans-1,4-trifluoromethyl-cyclohexyl)-thiazol-5-ylmethoxy]-2-(2,2,2-trifluoro-ethoxy)-phenyl]-4H-1,2,4-oxadiazol-5-one This invention also encompasses all combinations of preferred aspects of the invention described herein.

As used herein, the term alkyl is to be understood in the broadest sense to mean saturated hydrocarbon residues which can be linear, i.e. straight-chain, or branched. If not otherwise defined alkyl has 1 to 8 carbon atoms. Examples of "—(C1-C8)-alkyl" are alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. The term "—(C0-C8)-alkyl" is a hydrocarbon residue containing 1, 2, 3, 4, 5, 6, 7 or 8 carbon atoms, in which the term "—CO-alkyl" is a covalent bond. All these statements apply also to the term alkylene.

As used herein, the term alkenyl is to be understood in the broadest sense to mean hydrocarbon residues which has 1 to 4 double bonds and can be linear, i.e. straight-chain, or branched. If not otherwise defined alkenyl has 2 to 8 carbon atoms. Examples of "—(C2-C8)-alkenyl" are alkenyl residues containing 2, 3, 4, 5, 6, 7 or 8 carbon atoms are, for example vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. All these statements apply also to the term alkenylene.

As used herein, the term alkynyl is to be understood in the broadest sense to mean hydrocarbon residues, which has 1 to 4 triple bonds and can be linear, i.e. straight-chain, or branched. If not otherwise defined alkynyl has 2 to 8 carbon atoms. Examples of "—(C2-C8)-alkynyl" are alkynyl residues containing 2, 3, 4, 5, 6, 7 or 8 carbon atoms are, for example ethynyl, 1-propynyl, 2-propynyl (=propargyl) or 2-butynyl. All these statements apply also to the term alkylidene.

All these statements also apply if an alkyl group occurs as a substituent on another residue, for example in an alkyloxy residue, an alkyloxycarbonyl residue or an arylalkyl residue.

If not otherwise defined, alkyl, alkylene, alkenyl, alkenylene, alkynyl and alkynylene are unsubstituted or mono, di- or tri-substituted independently of one another by suitable groups such as, for example: F, Cl, Br, I, CF3, NO2, CN, COOH, CO—O—(C0-C4) alkylene-(C6-C10) aryl, CO—O—(C1-C4) alkyl, CO—O—(C0-C4) alkylene-(C3-C13)cycloalkyl, CO—O—(C0-C4) alkylene-(C3-C15)heterocycle, CO—N((C0-C4) alkylene-H)—(C0-C4) alkylene-(C6-C10) aryl, CO—N((C0-C4) alkylene-H)—(C0-C4) alkylene-H, CO—N((C0-C4) alkylene-H)—(C0-C4) alkylene-(C3-C13)cycloalkyl, CO—N((C0-C4) alkylene-H)—(C0-C4) alkylene-(C3-C15) heterocycle, (C0-C4) alkylene-(C3-C6)cycloalkyl, (C0-C4) alkylene-(C6-C10)aryl, (C0-C4) alkylene-(C3-C15)heterocycle, (C2-C6)-alkenyl, (C2-C6)-alkynyl, O—(C0-C6)-alkyl, O—(C0-C4) alkylene-(C6-C10) aryl, O—(C0-C4) alkylene-(C3-C12)cycloalkyl, O—(C0-C4) alkylene-(C3-C15)heterocycle, O—CO—O—(C0-C4) alkylene-(C6-C10) aryl, O—CO—O—(C1-C4) alkyl, O—CO—O—(C0-C4) alkylene-(C3-C13)cycloalkyl, O—CO—O—(C0-C4) alkylene-(C3-C15)heterocycle, S—(C1-C4)alkyl, S—(C0-C4) alkylene-(C3-C13)cycloalkyl, S—(C0-C4) alkylene-(C6-C10) aryl, S—(C0-C4) alkylene-(C3-C15) heterocycle, SO—(C1-C4)alkyl, SO—(C0-C4) alkylene-(C3-C13)cycloalkyl, SO—(C0-C4) alkylene-(C6-C10) aryl, SO—(C0-C4) alkylene-(C3-C15) heterocycle, SO2-(C1-C4)alkyl, SO2-(C0-C4) alkylene-(C3-C13)cycloalkyl, SO2-(C0-C4) alkylene-(C6-C10) aryl, SO2-(C0-C4) alkylene-(C3-C15) heterocycle, SO2-N((C0-C4) alkylene-H)—(C0-C4)alkylene-(C6-C10)aryl, SO2-N((C0-C4)alkylene-H)—(C0-C4)alkylene-H, SO2-N((C0-C4) alkylene-H)—(C0-C4)alkylene-(C3-C13)cycloalkyl, SO2-N ((C0-C4)alkylene-H)—(C0-C4)alkylene-(C3-C15)heterocycle where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4) alkylene-H)—(C0-C4) alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4) alkylene-H)—CO—(C0-C4)alkylene-(C6-C12)-aryl, N((C0-C4)alkylene-H)—CO—(C0-C4)alkyl, N((C0-C4) alkylene-H)—CO—(C0-C4)alkylene-(C3-C13)cycloalkyl, N((C0-C4)alkylene-H)—CO—(C0-C4)alkylene-(C3-C15) heterocycle, N((C0-C4) alkylene-H)—CO—O—(C0-C4) alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4) alkylene-H)—CO—N((C0-C4)-alkylene-H)—(C0-C4) alkylene-(C6-C12)-aryl, N((C0-C4)alkylene-H)—CO—N ((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl ring or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term cycloalkyl is to be understood to mean saturated hydrocarbon cycle containing from 3 to 13 carbon atoms in a mono- or bicyclic, fused, bridged or spirocyclic ring. Examples of (C3-C13)-cycloalkyl cyclic alkyl residues are cycloalkyl residues containing 3, 4, 5, 6, 7, 8, 9, 10, 11, 12 or 13 ring carbon atoms like cyclopropyl, cyclobutyl, cyclopentyl, cyclohexyl, cycloheptyl, cyclooctyl, cyclononyl, cyclodecyl, cycloundecyl or cyclododecyl. The term cycloalkyl also includes bicyclic groups in which any of the above cycloalkyl ring is fused to a benzene ring, for example indane and 1,2,3,4-tetrahydronaphthalene.

The term cycloalkenyl is to be understood to mean unsaturated hydrocarbon cycle containing from 3 to 8 carbon atoms in a mono- or bicyclic, fused or bridged ring, wherein the one, two or three double bonds are not located within a cyclic alkyl group in such a manner that an aromatic system results. Examples of unsaturated cycloalkenyl groups are cyclopentenyl or cyclohexenyl, which can be bonded via any carbon atom. The term cycloalkenyl also includes bicyclic groups in which any of the above cycloalkenyl ring is fused to a benzene ring, for example 1,2-dihydronaphthalene, 1,4-dihydronaphthalene and 1H-indene.

If not otherwise defined cycloalkyl or cycloalkenyl are unsubstituted or mono-, di- or tri-substituted independently of one another by suitable groups such as, for example: F, Cl, Br, I, CF3, NO2, CN, COOH, CO—O—(C0-C4) alkylene-(C6-C10) aryl, CO—O—(C1-C4) alkyl, CO—O—(C0-C4) alkylene-(C3-C13)cycloalkyl, CO—O—(C0-C4) alkylene-(C3-C15)heterocycle, CO—N((C0-C4) alkylene-H)—(C1-C6) alkylene-H, CO—N((C0-C4) alkylene-H)—(C1-C6) cycloalkyl, CON((C0-C4) alkylene-H)—(C0-C4)alkylene-(C6-C12)-aryl, (C0-C4) alkylene-(C3-C6)cycloalkyl, (C3-C6)alkyl, (C2-C6)-alkenyl, (C2-C6)-alkynyl, (C0-C4) alkylene-(C6-C10)aryl, (C0-C4) alkylene-(C3-C15)heterocycle, O—(C0-C6)-alkyl, (C0-C4) alkylene-O—(C0-C4) alkyl, (C0-C4) alkylene-O—(C0-C4) alkylene-(C3-C13)cycloalkyl, (C0-C4) alkylene-O—(C0-C4) alkylene-(C6-C10) aryl, (C0-C4) alkylene-O—(C0-C4) alkylene-(C3-C15)heterocycle, O—CO—O—(C0-C4) alkylene-(C6-C10) aryl, O—CO—O—(C1-C4) alkyl, O—CO—O—(C0-C4) alkylene-(C3-C13)cycloalkyl, O—CO—O—(C0-C4) alkylene-(C3-C15)heterocycle, O—CO—N((C0-C4) alkylene-H)—(C0-C4) alkylene-(C6-C10) aryl, O—CO—N((C0-C4) alkylene-H)—(C0-C4) alkylene-H, O—CO—N((C0-C4) alkylene-H)—(C0-C4) alkylene-(C3-C13)cycloalkyl, O—CO—N((C0-C4) alkylene-H)—(C0-C4) alkylene-(C3-C15) heterocycle, S—(C1-C4)alkyl, S—(C0-C4) alkylene-(C3-C13)cycloalkyl, S—(C0-C4) alkylene-(C6-C10) aryl, S—(C0-C4) alkylene-(C3-C15) heterocycle, SO—(C1-C4) alkyl, SO—(C0-C4) alkylene-(C3-C13)cycloalkyl, SO—(C0-C4) alkylene-(C6-C10) aryl, SO—(C0-C4) alkylene-(C3-C15) heterocycle, $SO_2$—(C1-C4)alkyl, SO2-(C0-C4) alkylene-(C3-C13)cycloalkyl, SO2-(C0-C4) alkylene-(C6-C10) aryl, SO2-(C0-C4) alkylene-(C3-C15) heterocycle, SO2-N((C0-C4)alkylene-H)—(C0-C4)alkylene-(C6-C10) aryl, SO2-N((C0-C4)alkylene-H)—(C0-C4)alkylene-H, SO2-N((C0-C4) alkylene-H)—(C0-C4)alkylene-(C3-C13) cycloalkyl, SO2-N((C0-C4)alkylene-H)—(C0-C4)alkylene-(C3-C15)heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4) alkylene-H)—(C0-C4)alkylene-H)—(C1-C6)cycloalkyl, N((C0-C4) alkylene-H)—(C0-C4)alkylene-(C6-C12)-aryl, N((C0-C4) alkylene-H)—(C0-C4)alkylene-(C3-C15)heterocycle, N((C0-C4) alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4) alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4) alkylene-H)—CO—O—(C0-C4)alkylene-(C3-C15) heterocycle, N((C0-C4) alkylene-H)—CO—N((C0-C4)-alkylene-H)—(C0-C4)alkylene-(C6-C12)-aryl, N((C0-C4) alkylene-H)—CO—N((C0-C4)-alkylene-H)—(C0-C4) alkyl, N((C0-C4)alkylene-H)—CO—N((C0-C4)-alkylene-H)—(C0-C4)alkylene-(C3-C13)cycloalkyl, N((C0-C4) alkylene-H)—CO—N((C0-C4)-alkylene-H)—(C0-C4) alkylene-(C3-C15)heterocycle, where the aryl or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "aryl" is understood to mean aromatic hydrocarbon ring containing from 6 to 14 carbon atoms in a mono- or bicyclic ring. Examples of (C6-C14)-aryl rings are phenyl, naphthyl, for example 1-naphthyl and 2-naphthyl, biphenyl, for example 2-biphenyl, 3-biphenyl and 4-biphenyl, anthryl or fluorenyl. Biphenyl rings, naphthyl ring and, in particular, phenyl ring are further embodiments of aryl ring.

The terms heterocycle is understood to mean saturated (heterocycloalkyl), partly unsaturated (heterocycloalkenyl) or unsaturated (heteroaryl)hydrocarbon rings containing from 3 to 15 carbon atoms in a mono- or bicyclic, fused, bridged or spirocyclic ring in which 1 to 5 carbon atoms of the 3 to 15 ring carbon atoms are replaced by heteroatoms such as nitrogen, oxygen or sulfur in which further the heteroatoms can be oxidized, for example N=O, S=O, SO2. Examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The heterocyclic rings are unsubstituted or mono-, di- or tri-substituted by suitable groups such as, for example: F, Cl, Br, I, CF3, NO2, CN, COOH, CO—O—(C0-C4) alkylene-(C6-C10) aryl, CO—O—(C1-C4) alkyl, CO—O—(C0-C4) alkylene-(C3-C13)cycloalkyl, CO—O—(C0-C4) alkylene-(C3-C15)heterocycle, CO—N((C0-C4) alkylene-H)—(C1-C6)alkylene-H, CO—N((C0-C4) alkylene-H)—(C1-C6)cycloalkyl, CON((C0-C4) alkylene-H)—(C0-C4)alkylene-(C6-C12)-aryl, (C0-C4) alkylene-(C3-C6)cycloalkyl, (C3-C6)alkyl, (C2-C6)-alkenyl, (C2-C6)-alkynyl, (C0-C4) alkylene-(C6-C10)aryl, (C0-C4) alkylene-(C3-C15)heterocycle, O—(C0-C6)-alkyl, (C0-C4) alkylene-O—(C0-C4) alkyl, (C0-C4) alkylene-O—(C0-C4) alkylene-(C3-C13)cycloalkyl, (C0-C4) alkylene-O—(C0-C4) alkylene-(C6-C10) aryl, (C0-C4) alkylene-O—(C0-C4) alkylene-(C3-C15)heterocycle, O—CO—O—(C0-C4) alkylene-(C6-C10) aryl, O—CO—O—(C1-C4) alkyl, O—CO—O—(C0-C4) alkylene-(C3-C13)cycloalkyl, O—CO—O—(C0-C4) alkylene-(C3-C15)heterocycle, O—CO—N((C0-C4) alkylene-H)—(C0-C4) alkylene-(C6-C10) aryl, O—CO—N((C0-C4) alkylene-H)—(C0-C4) alkylene-H, O—CO—N((C0-C4) alkylene-H)—(C0-C4) alkylene-(C3-C13)cycloalkyl, O—CO—N((C0-C4) alkylene-H)—(C0-C4) alkylene-(C3-C15) heterocycle, S—(C1-C4)alkyl, S—(C0-C4) alkylene-(C3-C13)cycloalkyl, S—(C0-C4) alkylene-(C6-C10) aryl, S—(C0-C4) alkylene-(C3-C15) heterocycle, SO—(C1-C4) alkyl, SO—(C0-C4) alkylene-(C3-C13)cycloalkyl, SO—(C0-C4) alkylene-(C6-C10) aryl, SO—(C0-C4) alkylene-(C3-C15) heterocycle, SO2-(C1-C4)alkyl, SO2-(C0-C4) alkylene-(C3-C13)cycloalkyl, SO2-(C0-C4) alkylene-(C6-C10) aryl, SO2-(C0-C4) alkylene-(C3-C15) heterocycle, SO2-N((C0-C4)alkylene-H)—(C0-C4)alkylene-(C6-C10) aryl, SO2-N((C0-C4)alkylene-H)—(C0-C4)alkylene-H, SO2-N((C0-C4) alkylene-H)—(C0-C4)alkylene-(C3-C13) cycloalkyl, SO2-N((C0-C4)alkylene-H)—(C0-C4)alkylene-(C3-C15)heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4) alkylene-H)—(C0-C4)alkylene-H)—(C1-C6)cycloalkyl, N((C0-C4) alkylene-H)—(C0-C4)alkylene-(C6-C12)-aryl, N((C0-C4) alkylene-H)—(C0-C4)alkylene-(C3-C15)heterocycle, N((C0-C4) alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4) alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4) alkylene-H)—CO—O—(C0-C4)alkylene-(C3-C15) heterocycle, N((C0-C4) alkylene-H)—CO—N((C0-C4)-alkylene-H)—(C0-C4)alkylene-(C6-C12)-aryl, N((C0-C4) alkylene-H)—CO—N((C0-C4)-alkylene-H)—(C0-C4) alkyl, N((C0-C4)alkylene-H)—CO—N((C0-C4)-alkylene-H)—(C0-C4)alkylene-(C3-C13)cycloalkyl, N((C0-C4) alkylene-H)—CO—N((C0-C4)-alkylene-H)—(C0-C4) alkylene-(C3-C15)heterocycle, where the aryl or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "R5 and R6 together with the nitrogen atom to which they are bonded (Y=N(R6)) can form a (C3-C9)-heterocycle which for example can contain additionally 1 to 3 heteroatoms" refer to structures of heterocyclic which can be derived from compounds such as for example pyrrolidine, morpholine, thiomorpholine, piperidine, piperazine, azetidine, 2,3-dihydro-1H-isoindole, piperazin-2-one, azetidine, isoindoline, 2,5-diazabicyclo[2.2.1]heptane, thiomorpholine 1-oxide, thiomorpholine 1,1-dioxide, piperidin-4-one, piperidin-3-one, homopiperidine, homopiperazine, homomorpholine, 2,3,6,7-tetrahydro-(1H)-1,4-diazepin-5(4H)-one, 4-oxazolidine, azetidin-3-one, thiazolidine, thiazolidine 1-oxide, thiazolidine 1,1-dioxide, 4-imidazolidinone, 5,6,7,8-tetrahydro-[1,2,4]triazolo[4,3-a]pyrazine, 1,4-diazabicyclo[4.3.0]nonane, 2-aza-5-oxabicyclo[2.2.1]heptane, 2-oxa-5-azabicyclo[2.2.1]heptane, diazabicyclo[4.4.0]decane, 4,5,6,7-tetrahydrothieno[3,2-c]pyridine, 4,5,6,7-tetrahydro-1H-imidazol[4,5-c]-pyridine, 4,5,6,7-tetrahydro-1H-pyrazolo[4,3-c]pyridine, 3,8-diaza-bicyclo[3.2.1]octane, octahydro-pyrrolo[3,4-c]pyrrole, 2,5-diazabicyclo[2.2.2]octane, 4-spiro-[3-(N-methyl-2-pyrrolidinone)]-piperidine, 2,8-diaza-spiro[5.5]undecane, 2,7-diaza-spiro[4.4]nonane, 3,9-diaza-spiro[5.5]undecane, 2,8-diaza-spiro[4.5]decane, 2,7-diaza-spiro[3.5]nonane, 2,9-diaza-spiro[5.5]undecane, 2,7-diaza-spiro[4.5]decane, 1-oxa-4,9-diaza-spiro[5.5]undecane, 1-oxa-4,8-diaza-spiro[5.5]undecane.

The term "R2 and R3 together with the Carbon atoms to which they are bonded form a (C6-C10) aryl- or a (C5-C10) heteroaryl ring"

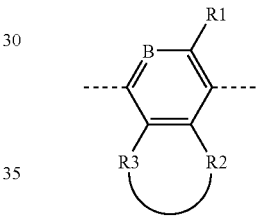

refer to structures of bicyclic aromatic or heteroaryl rings which comprise 10 to 14 (aryl) or 9 to 14 (heteroaryl) ring atoms in total.

The term "oxo-residue" or "=O" refers to residues such as carbonyl (—C(O)—) or nitroso (—N=O).

Halogen is fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The compounds of the formula I may exist in the form of their racemates, racemic mixtures, pure enantiomers, diastereomers and mixtures of diastereomers as well in their tautomeric forms. The present invention encompasses all these isomeric and tautomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Methods of Use

This invention also comprises methods of using the compounds of formula I and their pharmaceutical compositions as peroxisome proliferator activator receptor (PPAR) ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR): structure, mechanisms of activation and diverse functions: Motojima K., Cell Struct Funct., 1993, 18(5), 267-77).

In humans, PPARgamma exists in three variants, PPARgamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog Horm Res., 2001, 56, 239-63; Moller, D. E. and Berger, J. P., Int J Obes Relat Metab Disord., 2003, 27 Suppl 3, 17-21; Ram, V. J., Drugs Today, 2003, 39(8), 609-32).

Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. Sci., 2001, 98, 5306-5311). The dual PPARdelta/PPARalpha agonist YM-16638 significantly lowers plasma lipids in rhesus and cynomolgus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92). More recent publications underline that PPARdelta is an important target for the treatment of dyslipidemia, insulin resistance, type 2 diabetes, atherosclerosis and syndrom X (Wang, Y.-X. et al., Cell, 2003, 113, 159-170; Luquet, S. et al., FASEB J., 2003, 17, 209-226; Tanaka, T. et al., PNAS, 2003, 100, 15924-15929; Holst, D. et al., BioChem. Biophys. Acta, 2003, 1633, 43-50; Dressel, U. et al., Mol. Endocrin., 2003, 17, 2477-2493; Lee, C. H. et al., Science, 2003, 302, 453-457).

Besides its actions as a regulator of the lipid-, glucose- and cholesterol-metabolism PPARdelta is known to play a role in embryonic development, implantation and bone formation (Lim, H. and Dey, S. K., Trends Endocrinol Metab., 2000, 11(4), 137-42; Ding, N. Z. et al., Mol Reprod Dev., 2003, 66(3), 218-24; Mano, H. et al., J Biol Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol Biol., 2003, 85(2-5), 257-65; Tan, N. S. et al., Am J Clin Dermatol., 2003, 4(8), 523-30; Wahli, W., Swiss Med Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33, 194-204). Thus, PPARdelta activators may be of use for the treatment of demyelinating and dysmyelinating diseases. The use of peroxisome proliferator activated receptor delta agonists for the treatment of MS and other demyelinating diseases can be shown as described in WO2005/097098.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299, 1437, 1473-76, 1483).

Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillain-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin forming glial cells are damaged including spinal cord injuries, neuropathies and nerve injury.

The present invention relates to compounds of the formula I suitable for modulating the activity of PPARs, especially the activity of PPARdelta and PPARalpha. Depending on the modulation profile, the compounds of the formula I are suitable for the treatment, control and prophylaxis of the indications described hereinafter, and for a number of other pharmaceutical applications connected thereto (see, for example, Berger, J., et al., Annu. Rev. Med., 2002, 53, 409-435; Wilson, T. et al., J. Med. Chem., 2000, 43(4), 527-550; Kliewer, S. et al., Recent Prog Horm Res., 2001, 56, 239-63; Fruchart, J. C. et al., 2001, Pharmacological Research, 44(5), 345-52; Kersten, S. et al., Nature, 2000, 405, 421-424; Torra, I. P. et al., Curr Opin Lipidol, 2001, 12, 245-254).

Compounds of this type are particularly suitable for the treatment and/or prevention of:

1. Disorders of fatty acid metabolism and glucose utilization disorders.
    Disorders in which insulin resistance is involved
2. Diabetes mellitus, especially type 2 diabetes, including the prevention of the sequelae associated therewith.
    Particular aspects in this connection are
    hyperglycemia,
    improvement in insulin resistance,
    improvement in glucose tolerance,
    protection of the pancreatic β cells
    prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
    high plasma triglyceride concentrations, high postprandial plasma triglyceride concentrations,
    low HDL cholesterol concentrations
    low ApoA lipoprotein concentrations
    high LDL cholesterol concentrations
    small dense LDL cholesterol particles
    high ApoB lipoprotein concentrations
4. Various other conditions which may be associated with the metabolic syndrome, such as:
    obesity (excess weight), including central obesity
    thromboses, hypercoagulable and prothrombotic states (arterial and venous)
    high blood pressure
    heart failure such as, for example (but not restricted thereto), following myocardial infarction, hypertensive heart disease or cardiomyopathy
5. Disorders or conditions in which inflammatory reactions are involved:
    atherosclerosis such as, for example (but not restricted thereto), coronary sclerosis including angina pectoris or myocardial infarction, stroke
    vascular restenosis or reocclusion
    chronic inflammatory bowel diseases such as, for example, Crohn's disease and ulcerative colitis
    asthma
    lupus erythematosus (LE) or inflammatory rheumatic disorders such as, for example, rheumatoid arthritis
    other inflammatory states
6. Disorders of cell cycle or cell differentiation processes:
    adipose cell tumors
    lipomatous carcinomas such as, for example, liposarcomas
    solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
    acute and chronic myeloproliferative disorders and lymphomas
    angiogenesis
7. Demyelinating and other neurodegenerative disorders of the central and peripheral nervous systems including:
    Alzheimer's disease
    multiple sclerosis
    Parkinson's disease
    adrenoleukodystrophy (ALD)
    adrenomyeloneuropathy
    AIDS-vacuolar myelopathy
    HTLV-associated myelopathy
    Leber's hereditary optic atrophy
    progressive multifocal leukoencephalopathy (PML)

subacute sclerosing panencephalitis
Guillain-Barre syndrome
tropical spastic paraparesis
acute disseminated encephalomyelitis (ADEM)
acute viral encephalitis
acute transverse myelitis
spinal cord and brain trauma
Charcot-Marie-Tooth disease
8. Skin disorders and/or disorders of wound healing processes:
  erythemato-squamous dermatoses such as, for example, psoriasis
  acne vulgaris
  other skin disorders and dermatological conditions which are modulated by PPAR
  eczemas and neurodermitis
  dermatitis such as, for example, seborrheic dermatitis or photodermatitis
  keratitis and keratoses such as, for example, seborrheic keratoses, senile keratoses, actinic keratosis, photo-induced keratoses or keratosis follicularis
  keloids and keloid prophylaxis
  warts, including condylomata or condylomata acuminata
  human papilloma viral (HPV) infections such as, for example, venereal papillomata, viral warts such as, for example, molluscum contagiosum, leukoplakia
  papular dermatoses such as, for example, Lichen planus
  skin cancer such as, for example, basal-cell carcinomas, melanomas or cutaneous T-cell lymphomas
  localized benign epidermal tumors such as, for example, keratoderma, epidermal naevi
  chilblains
  wound healing
9. Other disorders
  high blood pressure
  pancreatitis
  syndrome X
  polycystic ovary syndrome (PCOS)
  asthma
  osteoarthritis
  lupus erythematosus (LE) or inflammatory rheumatic disorders such as, for example, rheumatoid arthritis
  vasculitis
  wasting (cachexia)
  gout
  ischemia/reperfusion syndrome
  acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and atheriosclerosis and the diverse sequalae thereof.

Combinations with Other Medicaments

The compounds of the invention can be administered alone or in combination with one or more further pharmacologically active substances. In particular, the compounds of the invention can be administered in combination with active ingredients having a similar pharmacological action. For example, they can be administered in combination with active ingredients which have favorable effects on metabolic disturbances or disorders frequently associated therewith. Examples of such medicaments are
  1. medicaments which lower blood glucose, anti-diabetics,
  2. active ingredients for the treatment of dyslipidemias,
  3. anti-atherosclerotic medicaments,
  4. anti-obesity agents,
  5. anti-inflammatory active ingredients
  6. active ingredients for the treatment of malignant tumors
  7. anti-thrombotic active ingredients
  8. active ingredients for the treatment of high blood pressure
  9. active ingredients for the treatment of heart failure and
  10. active ingredients for the treatment and/or prevention of complications caused by diabetes or associated with diabetes.
  11. active ingredients for the treatment of neurodegenerative diseases
  12. active ingredients for the treatment of disorders of the central nervous system
  13. active ingredients for the treatment of drug, nicotine and alcohol addiction
  14. analgesics They can be combined with the compounds of the invention of the formula I in particular for a synergistic enhancement of activity. Administration of the active ingredient combination can take place either by separate administration of the active ingredients to the patient or in the form of combination products in which a plurality of active ingredients are present in one pharmaceutical preparation.

Particularly suitable further active ingredients for the combination preparations are: All anti-diabetics mentioned in the Rote Liste 2006, Chapter 12; all slimming agents/appetite suppressants mentioned in the Rote Liste 2006, Chapter 1; all lipid-lowering agents mentioned in the Rote Liste 2006, Chapter 58. They can be combined with the compound of the formula I according to the invention in particular for a synergistic enhancement of activity. The active compound combination can be administered either by separate administration of the active compounds to the patient or in the form of combination preparations in which a plurality of active compounds are present in a pharmaceutical preparation. Most of the active compounds listed below are disclosed in USP Dictionary of USAN and International Drug Names, US Pharmacopeia, Rockville 2001.

Anti-diabetics include insulin and insulin derivatives, such as, for example, Lantus® (see www.lantus.com) or HMR 1964 or those described in WO2005005477 (Novo Nordisk), fast-acting insulins (see U.S. Pat. No. 6,221,633), inhalable insulins, such as, for example, Exubera® or oral insulins, such as, for example, IN-105 (Nobex) or Oral-Iyn™ (Generex Biotechnology), GLP-1 derivatives, such as, for example, Exenatide, Liraglutide or those disclosed in WO 98/08871 or WO2005027978 by Novo Nordisk A/S, in WO 01/04156 by Zealand or in WO 00/34331 by Beaufour-Ipsen, pramlintide acetate (Symlin; Amylin Pharmaceuticals), and also orally effective hypoglycemic active ingredients.

The active compounds preferably include
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of the glucose transporter 4 (GLUT4),
inhibitors of glutamine:fructose-6-phosphate amidotransferase (GFAT), GLP-1 agonists,
potassium channel openers, such as, for example, those disclosed in WO 97/26265 and WO 99/03861 by Novo Nordisk A/S,
inhibitors of dipeptidylpeptidase IV (DPP-IV),
insulin sensitizers,
inhibitors of liver enzymes involved in the stimulation of gluconeogenesis and/or glycogenolysis,
modulators of glucose uptake, glucose transport and glucose backresorption,
inhibitors of 11β-HSD1,
inhibitors of protein tyrosine phosphatase 1B (PTP1B),
modulators of the sodium/glucose cotransporter 1 or 2 (SGLT1, SGLT2),
compounds which alter lipid metabolism, such as antihyperlipidemic active ingredients and antilipidemic active ingredients,
compounds which reduce food intake or food absorption,
compounds which increase thermogenesis,
PPAR and RXR modulators and
active ingredients which act on the ATP-dependent potassium channel of the beta cells.

In one embodiment of the invention, the compound of the formula I is administered in combination with a HMGCoA reductase inhibitor, such as simvastatin, fluvastatin, pravastatin, lovastatin, atorvastatin, cerivastatin, rosuvastatin or L-659699.

In one embodiment of the invention, the compound of the formula I is administered in combination with a cholesterol resorption inhibitor, such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, the compound of the formula I is administered in combination with a PPAR gamma agonist, such as, for example, rosiglitazone, pioglitazone, JTT-501, G1262570, R-483 or CS-011 (rivoglitazone).

In one embodiment of the invention, the compound of the formula I is administered in combination with a PPAR alpha agonist, such as, for example, GW9578, GW-590735, K-111, LY-674, KRP-101 or DRF-10945.

In one embodiment of the invention, the compound of the formula I is administered in combination with a mixed PPAR alpha/gamma agonist, such as, for example, muraglitazar, tesaglitazar, naveglitazar, LY-510929, ONO-5129, E-3030 or as described in WO00/64888, WO00/64876, WO03/020269, WO2004075891, WO2004076402, WO2004075815, WO2004076447, WO2004076428, WO2004076401, WO2004076426, WO2004076427, WO2006018118, WO2006018115, and WO2006018116 or in J. P. Berger et al., TRENDS in Pharmacological Sciences 28(5), 244-251, 2005.

In one embodiment of the invention, the compound of the formula I is administered in combination with a PPAR delta agonist, such as, for example, GW-501516 or as described in WO2005097762, WO2005097786, WO2005097763, and WO2006029699.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate, such as, for example, fenofibrate, clofibrate or bezafibrate.

In one embodiment of the invention, the compound of the formula I is administered in combination with an MTP inhibitor, such as, for example, implitapide, BMS-201038, R-103757 or those described in WO2005085226.

In one embodiment of the invention, the compound of the formula I is administered in combination with a CETP inhibitor, such as, for example, torcetrapib or JTT-705.

In one embodiment of the invention, the compound of the formula I is administered in combination with a bile acid resorption inhibitor (see, for example, U.S. Pat. No. 6,245,744, U.S. Pat. No. 6,221,897 or WO00/61568), such as, for example, HMR 1741 or those described in DE 10 2005 033099.1 and DE 10 2005 033100.9.

In one embodiment of the invention, the compound of the formula I is administered in combination with a polymeric bile acid adsorber, such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those described in WO2005097738.

In one embodiment, the compound of the formula I is administered in combination with Omacor® (omega-3 fatty acids; highly concentrated ethyl esters of eicosapentaenoic acid and docosahexaenoic acid).

In one embodiment of the invention, the compound of the formula I is administered in combination with an ACAT inhibitor, such as, for example, avasimibe.

In one embodiment of the invention, the compound of the formula I is administered in combination with an antioxidant, such as, for example, OPC-14117, probucol, tocopherol, ascorbic acid, β-carotene or selenium.

In one embodiment of the invention, the compound of the formula I is administered in combination with a vitamin, such as, for example, vitamin B6 or vitamin B12.

In one embodiment of the invention, the compound of the formula I is administered in combination with a lipoprotein lipase modulator, such as, for example, ibrolipim (NO-1886).

In one embodiment of the invention, the compound of the formula I is administered in combination with an ATP-citrate lyase inhibitor, such as, for example, SB-204990.

In one embodiment of the invention, the compound of the formula I is administered in combination with a squalene synthetase inhibitor, such as, for example, BMS-188494 or as described in WO2005077907.

In one embodiment of the invention, the compound of the formula I is administered in combination with a lipoprotein (a) antagonist, such as, for example, gemcabene (CI-1027).

In one embodiment of the invention, the compound of the formula I is administered in combination with an HM74A receptor agonists, such as, for example, nicotinic acid.

In one embodiment of the invention, the compound of the formula I is administered in combination with a lipase inhibitor, such as, for example, orlistat or cetilistat (ATL-962).

In one embodiment of the invention, the compound of the formula I is administered in combination with insulin.

In one embodiment of the invention, the compound of the formula I is administered in combination with a sulfonylurea, such as, for example, tolbutamide, glibenciamide, glipizide or glimepiride.

In one embodiment of the invention, the compound of the formula I is administered in combination with a biguanide, such as, for example, metformin.

In another embodiment of the invention, the compound of the formula I is administered in combination with a meglitinide, such as, for example, repaglinide or nateglinide.

In one embodiment of the invention, the compound of the formula I is administered in combination with a thiazolidinedione, such as, for example, troglitazone, ciglitazone, pioglitazone, rosiglitazone or the compounds disclosed in WO 97/41097 by Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with an α-glucosidase inhibitor, such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the compounds mentioned above, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those described in WO2003084922, WO2004007455, WO2005073229-31 or WO2005067932.

In one embodiment of the invention, the compound of the formula I is administered in combination with glucagon receptor antagonists, such as, for example, A-770077, NNC-25-2504 or such as in WO2004100875 or WO2005065680.

In one embodiment of the invention, the compound of the formula I is administered in combination with activators of glucokinase, such as, for example, RO-4389620, LY-2121260 (WO2004063179), PSN-105, PSN-110, GKA-50 or those described, for example, by Prosidion in WO2004072031, WO2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, US 04067939 or WO 04052869, by Novo Nordisk in EP 1532980, WO 03055482, WO 04002481, WO 05049019, WO 05066145 or WO 05123132, by Merck/Banyu in WO 03080585, WO03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of the glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine:fructose-6-phosphate amidotransferase (GFAT), as described, for example, in WO2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964× or as described in WO2003074500, WO2003106456, WO200450658, WO2005058901, WO2005012312, WO2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase-1 (11β-HSD1), such as, for example, BVT-2733 or those described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment of the invention, the compound of the formula I is administered in combination with inhibitors of protein tyrosine phosphatase 1B (PTP1B), as described, for example, in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment of the invention, the compound of the formula I is administered in combination with modulators of the sodium/glucose cotransporter 1 or 2 (SGLT1, SGLT2), such as, for example, KGA-2727, T-1095 and SGL-0010 or as described, for example, in WO2004007517, WO200452903, WO200452902, WO2005121161, WO2005085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL), such as those described, for example, in WO01/17981, WO01/66531, WO2004035550, WO2005073199 or WO03/051842.

In one embodiment of the invention, the compound of the formula I is administered in combination with inhibitors of acetyl-CoA carboxylase (ACC) such as those described, for example, in WO199946262, WO200372197, WO2003072197 or WO2005044814.

In one embodiment of the invention, the compound of the formula I is administered in combination with an inhibitor of phosphoenolpyruvate carboxykinase (PEPCK), such as those described, for example, in WO2004074288.

In one embodiment of the invention, the compound of the formula I is administered in combination with an inhibitor of glycogen synthase kinase-3 beta (GSK-3 beta), such as those described, for example, in US2005222220, WO2004046117, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin-A receptor antagonist, such as, for example, avosentan (SPP-301).

In one embodiment of the invention, the compound of the formula I is administered in combination with inhibitors of "I-kappaB kinase" (IKK inhibitors), such as those described, for example, in WO2001000610, WO2001030774, WO2004022553 or WO2005097129.

In one embodiment of the invention, the compound of the formula I is administered in combination with modulators of the glucocorticoid receptor as described, for example, in WO2005090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, {4-[(4-aminoquinazolin-2-ylamino)methyl]-cyclohexylmethyl}naphthalene-1-sulfonamide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those described in WO2005080424;

cannabinoid receptor 1 antagonists, such as, for example, rimonabant, SR147778 or those described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897;

MC4 agonists (for example [2-(3a-benzyl-2-methyl-3-oxo-2,3,3a,4,6,7-hexahydro-pyrazolo[4,3-c]pyridin-5-yl)-1-(4-chlorophenyl)-2-oxoethyl]-1-amino-1,2,3,4-tetrahydro-naphthalene-2-carboxamide; (WO 01/91752)) or LB53280, LB53279, LB53278 or THIQ, MB243, RY764, CHIR-785, PT-141 or those described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077 or WO2006024390;

orexin receptor antagonists (for example 1-(2-methylbenzoxazol-6-yl)-3-[1,5]naphthyridin-4-ylurea hydrochloride (SB-334867-A) or those described, for example, in WO200196302, WO200185693, WO2004085403 or WO2005075458);

histamine H3 receptor agonists (for example 3-cyclohexyl-1-(4,4-dimethyl-1,4,6,7-tetrahydroimidazo[4,5-c]pyridin-5-yl)-propan-1-one oxalic acid salt (WO 00/63208) or those described in WO200064884, WO2005082893);

CRF antagonists (for example [2-methyl-9-(2,4,6-trimethylphenyl)-9H-1,3,9-triazafluoren-4-yl]dipropylamine (WO 00/66585));

CRF BP antagonists (for example urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or those compounds described in WO2003/15769, WO2005085200, WO2005019240, WO2004011438, WO2004012648, WO2003015769, WO2004072025, WO2005070898, WO2005070925, WO2006018280, WO2006018279, WO2004039780, WO2003033476, WO2002006245, WO2002002744, WO2003004027 or FR2868780);

CCK-A agonists (such as, for example, {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (for example dexfenfluramine);

mixed serotonin- and noradrenergic compounds (for example WO 00/71549);

5-HT receptor agonists, for example 1-(3-ethylbenzofuran-7-yl)piperazine oxalic acid salt (WO 01/09111);

5-HT2C receptor agonists (such as, for example, APD-356, BVT-933 or those described in WO200077010, WO20077001-02, WO2005019180, WO2003064423, WO200242304 or WO2005082859);

5-HT6 receptor antagonists, such as described, for example, in WO2005058858;

bombesin receptor agonists (BRS-3 agonists);

galanin receptor antagonists;

growth hormone (for example human growth hormone or AOD-9604);

growth hormone releasing compounds (tert-butyl 6-benzyloxy-1-(2-diisopropylamino-ethylcarbamoyl)-3,4-dihydro-1H-isoquinoline-2-carboxylate (WO 01/85695));

growth hormone secretagog receptor antagonists (ghrelin antagonists) such as, for example, A-778193 or those described in WO2005030734;

TRH agonists (see, for example, EP 0 462 884);

uncoupling protein 2 or 3 modulators;

leptin agonists (see for example Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (as described, for example, in WO 00/40569);

inhibitors of diacylglycerol O-acyltransferases (DGATs) such as described, for example, in US2004/0224997, WO2004094618, WO200058491, WO2005044250, WO2005072740, JP2005206492 or WO2005013907;

inhibitors of fatty acid synthase (FAS) such as, for example, C75 or those described in WO2004005277;

oxyntomodulin;

oleoyl-estrone or thyroid hormone receptor agonists, such as, for example, KB-2115 or those described in WO20058279, WO200172692, WO200194293, WO2003084915, WO2004018421 or WO2005092316.

In one embodiment of the invention, the further active ingredient is leptin; see for example "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindol or phentermine.

In another embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE (phosphodiesterase) inhibitors, as described, for example, in WO2003/077949 or WO2005012485.

In one embodiment of the invention, the compound of the formula I is administered in combination with NAR-1 (nicotinic acid receptor) agonists as described, for example, in WO2004094429.

In one embodiment of the invention, the compound of the formula I is administered in combination with CB2 (cannabinoid receptor) agonists as described, for example, in US2005/143448.

In one embodiment of the invention, the compound of the formula I is administered in combination with histamine 1 agonists as described, for example, in WO2005101979.

In one embodiment of the invention, the compound of the formula I is administered in combination with bupropion, as described in WO2006017504.

In one embodiment of the invention, the compound of the formula I is administered in combination with opioid antagonists as described, for example, in WO2005107806 or WO2004094429.

In one embodiment of the invention, the compound of the formula I is administered in combination with neutral endopeptidase inhibitors as described, for example, in WO200202513, WO2002/06492, WO 2002040008, WO2002040022 or WO2002047670.

In one embodiment of the invention, the compound of the formula I is administered in combination with NPY inhibitors (neuropeptide Y) as described, for example, in WO2002047670.

In one embodiment of the invention, the compound of the formula I is administered in combination with sodium/hydrogen exchange inhibitors as described, for example, in WO2003092694.

In one embodiment of the invention, the compound of the formula I is administered in combination with modulators of the glucocorticoid receptor as described, for example, in WO2005090336.

In one embodiment of the invention, the compound of the formula I is administered in combination with nicotine receptor agonists as described, for example, in WO2004094429.

In one embodiment of the invention, the compound of the formula I is administered in combination with NRIs (norepinephrine reuptake inhibitors) as described, for example, in WO2002053140.

In one embodiment of the invention, the compound of the formula I is administered in combination with MOA (E-beta-methoxyacrylate), such as, for example, segeline, or as described, for example, in WO2002053140.

In one embodiment of the invention, the compound of the formula I is administered in combination with antithrombotic active ingredients, such as, for example, clopidogrel.

It is to be understood that each suitable combination of the compounds according to the invention with one or more of the compounds mentioned above and optionally one or more further pharmacologically active substances is meant to be included in the scope of the present invention.

The formulae for some of the development codes mentioned above are given below.

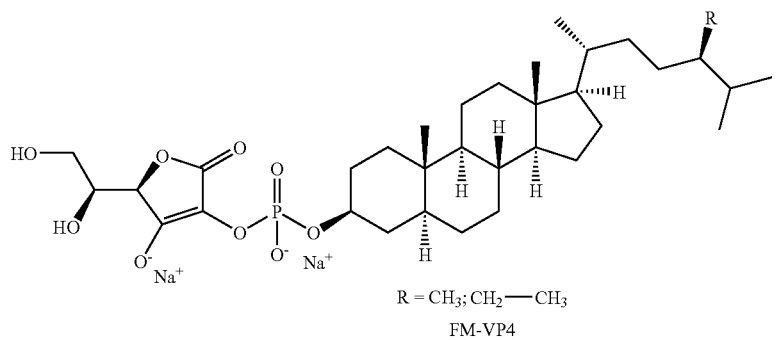

R = CH₃; CH₂—CH₃

FM-VP4

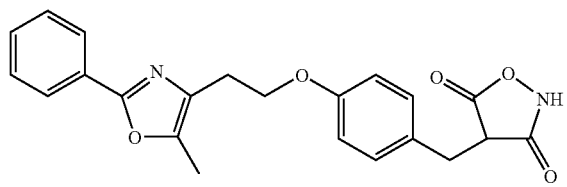

JTT-501

-continued
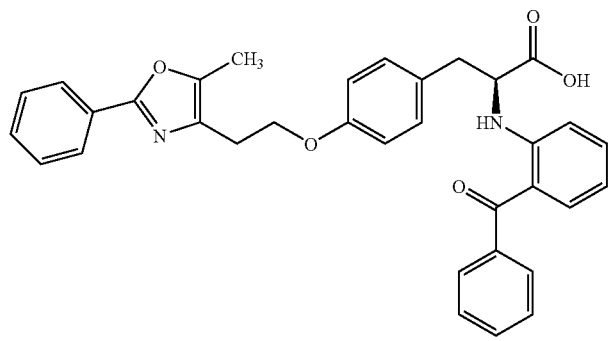
GI 262570
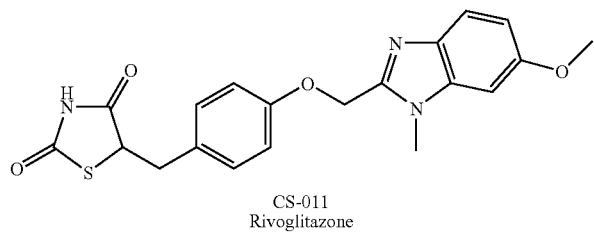
CS-011
Rivoglitazone
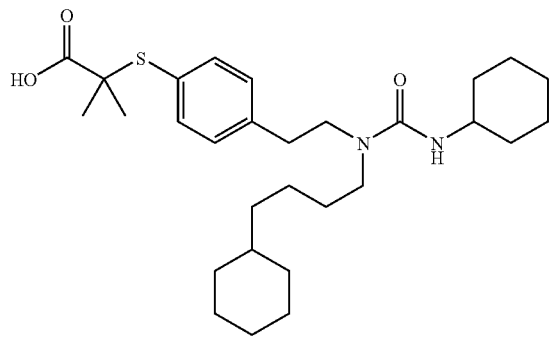
GW-9578
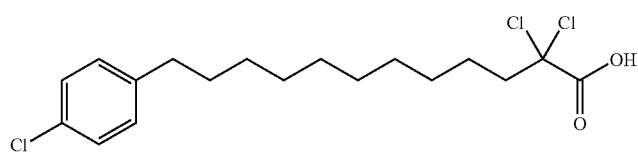
K-111
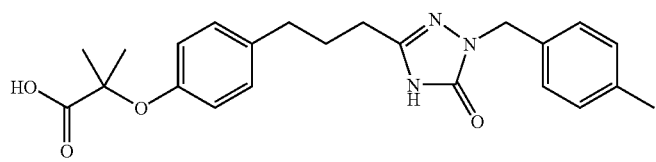
LY-674
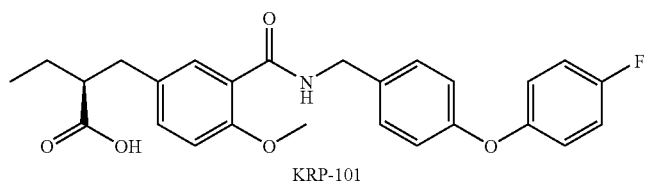
KRP-101

-continued
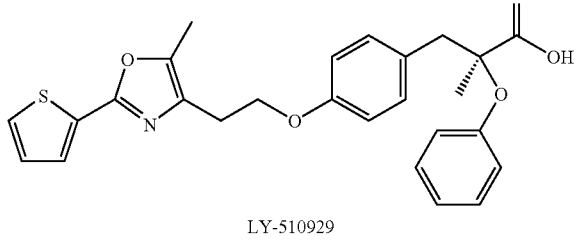
LY-510929
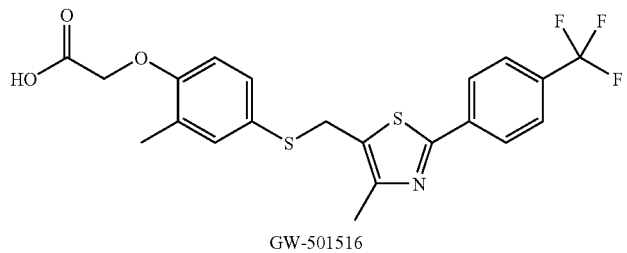
GW-501516
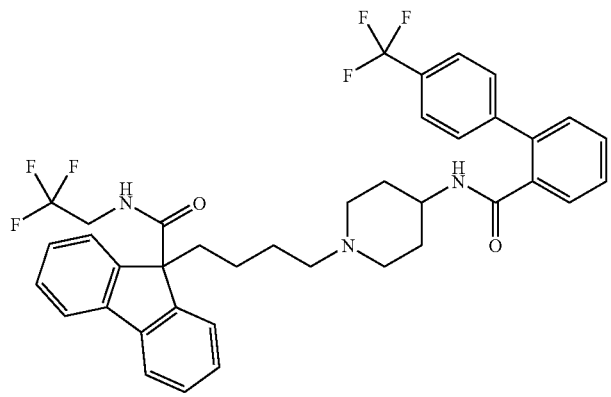
BMS-201038
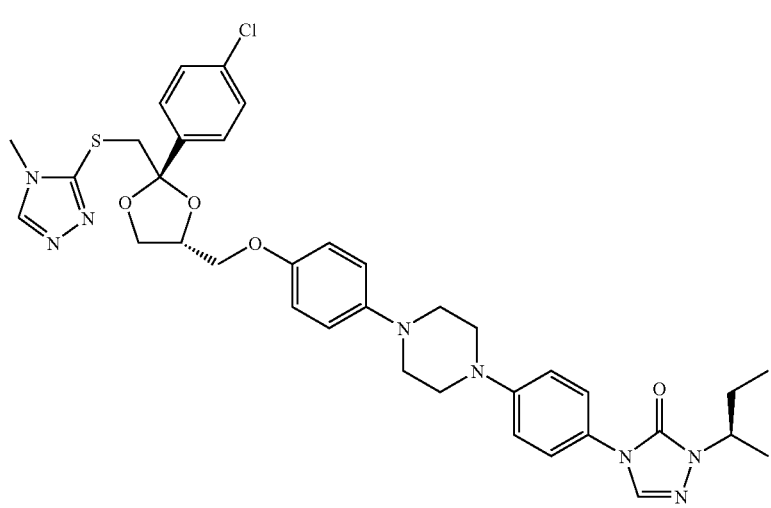
R-103757
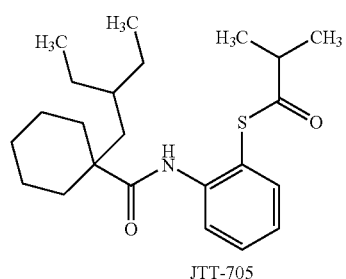
JTT-705

-continued
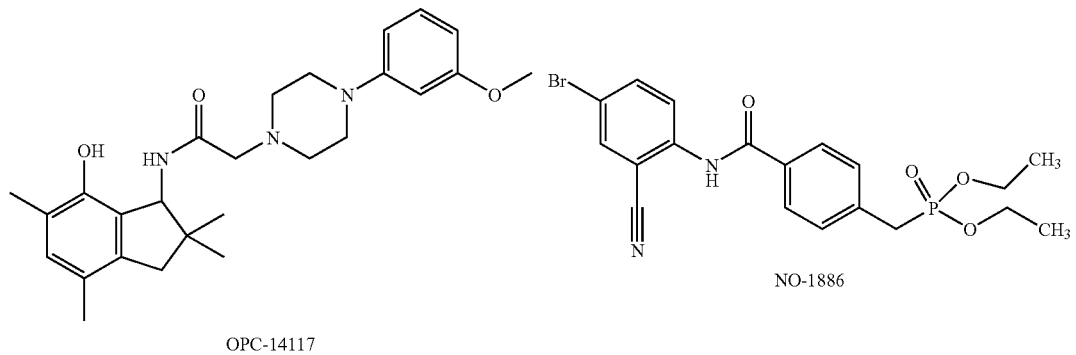
OPC-14117    NO-1886
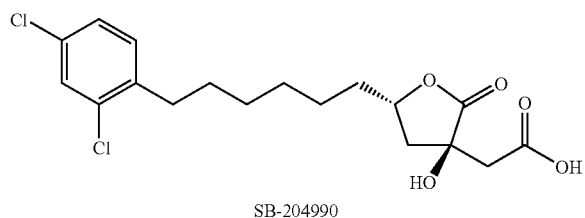
SB-204990
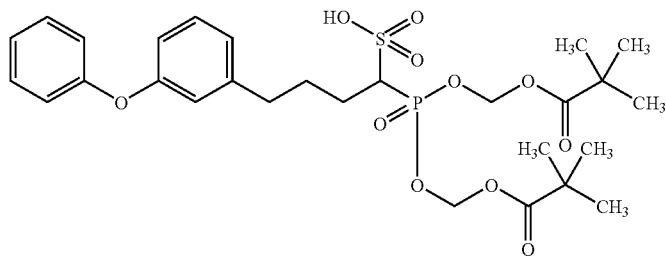
BMS-188494
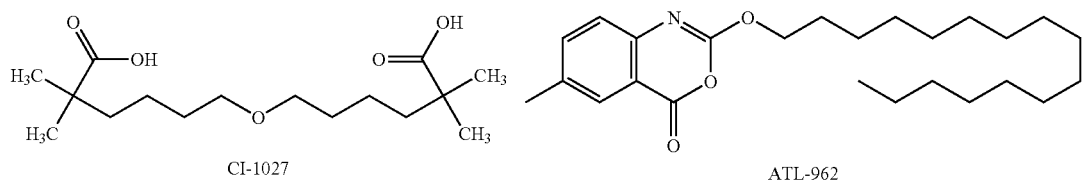
CI-1027    ATL-962
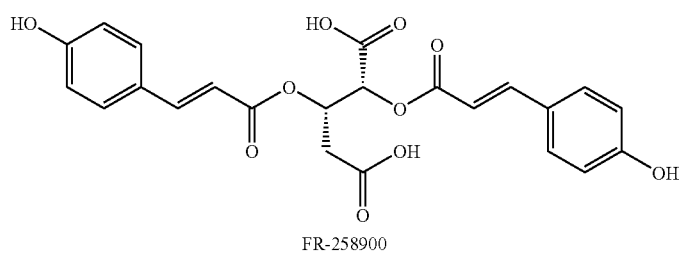
FR-258900

-continued
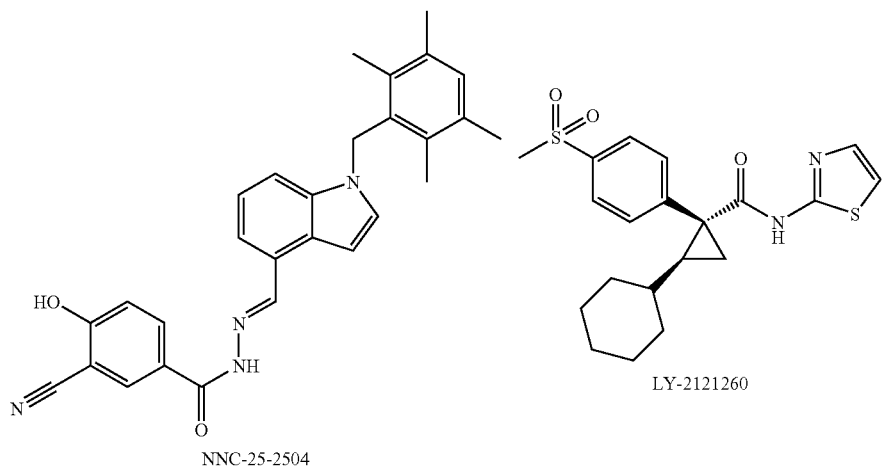
NNC-25-2504
LY-2121260
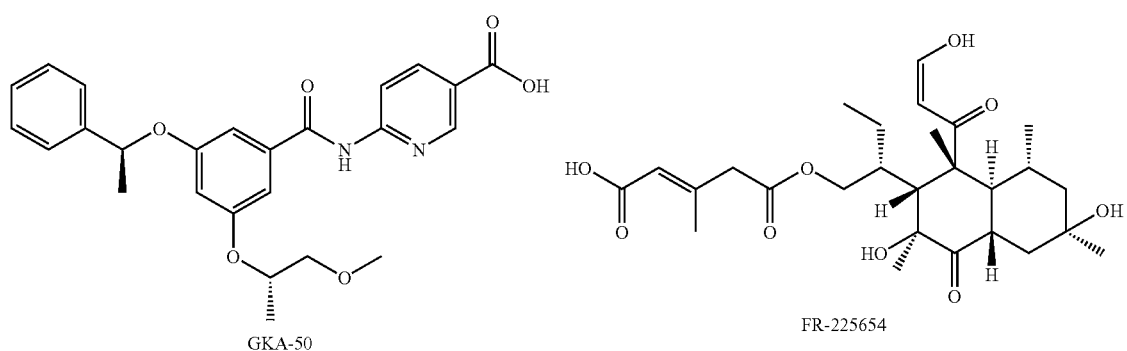
GKA-50
FR-225654
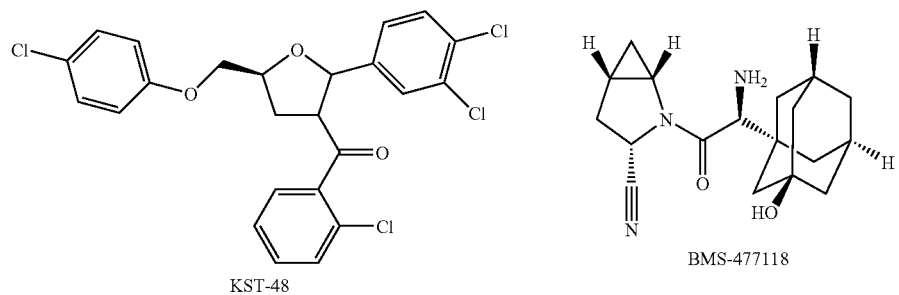
KST-48
BMS-477118
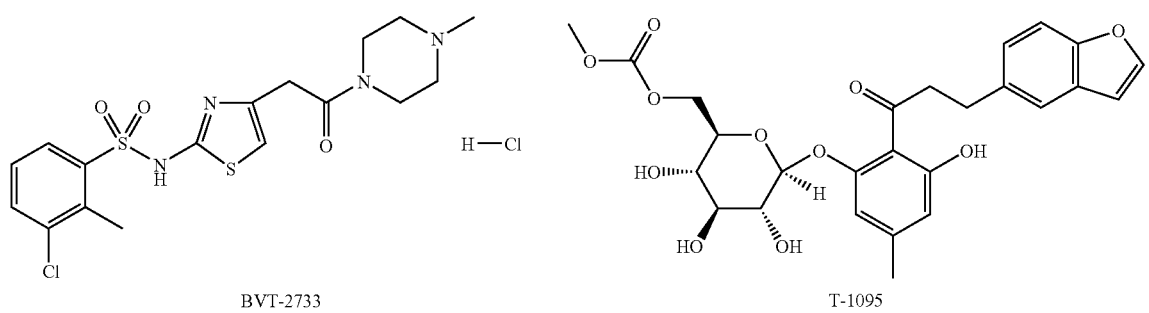
BVT-2733
T-1095

-continued
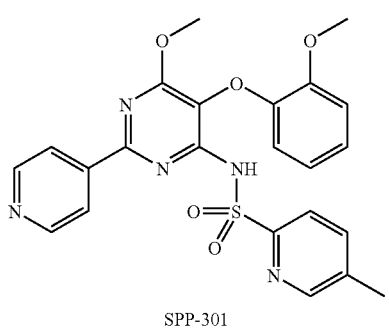
SPP-301
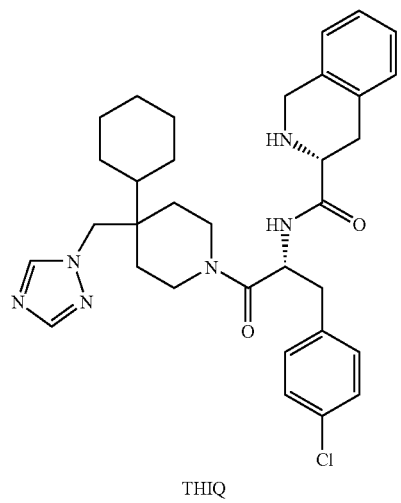
THIQ
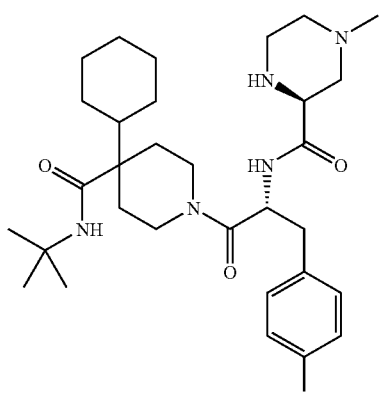
MB243
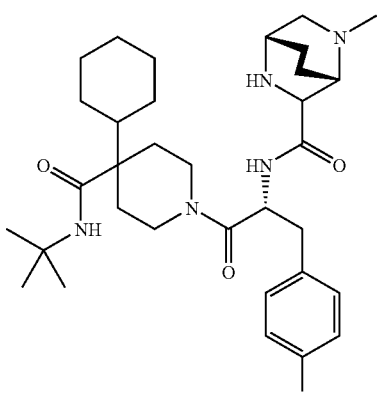
RY764
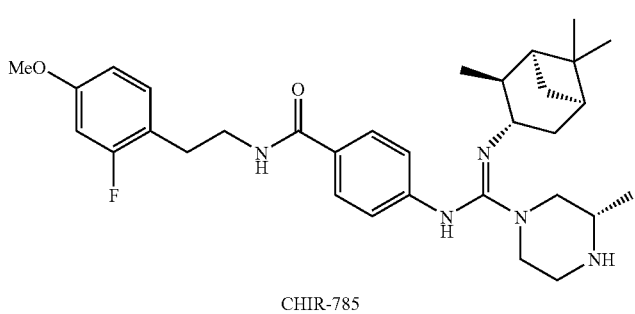
CHIR-785
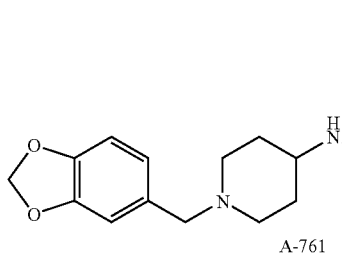
A-761
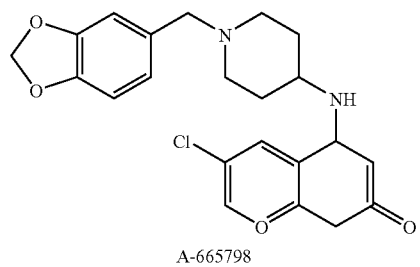
A-665798

-continued
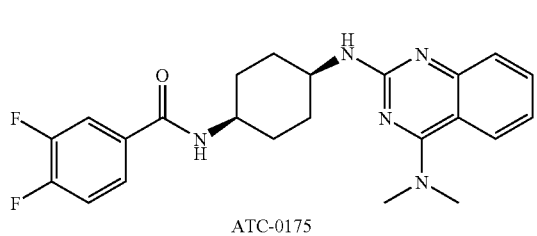
ATC-0175
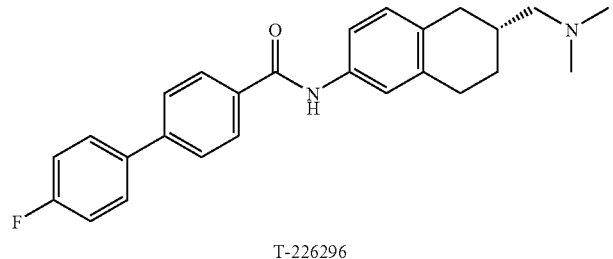
T-226296
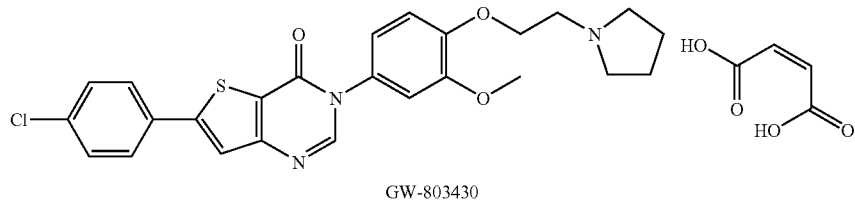
GW-803430
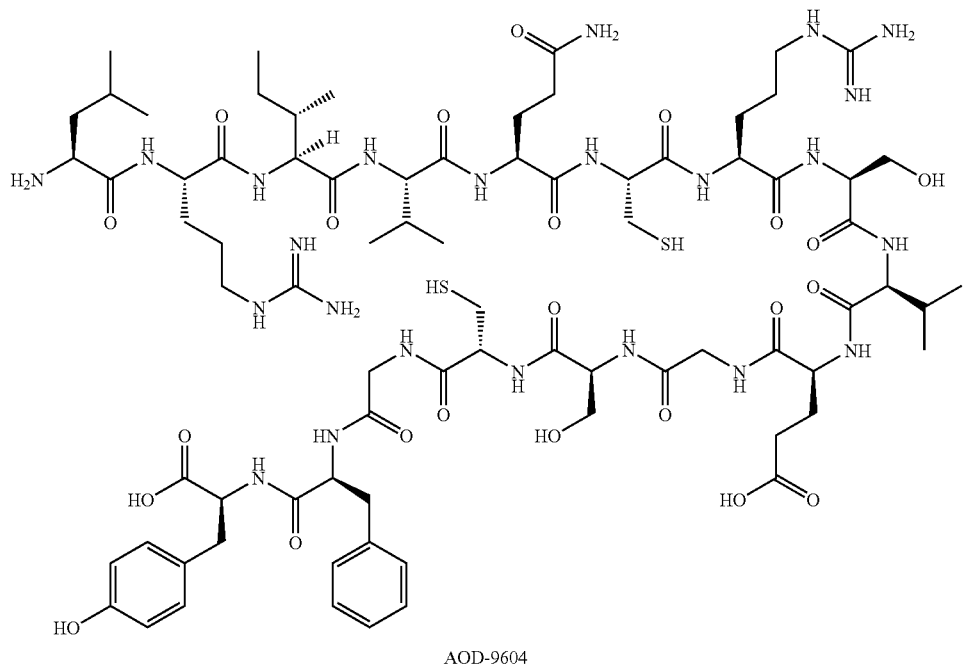
AOD-9604
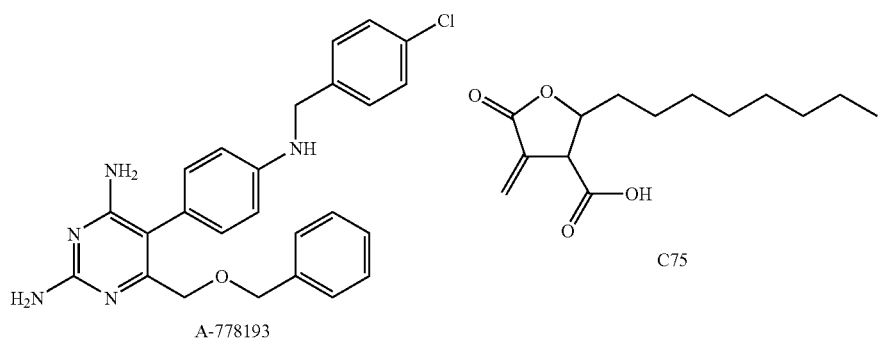
A-778193    C75

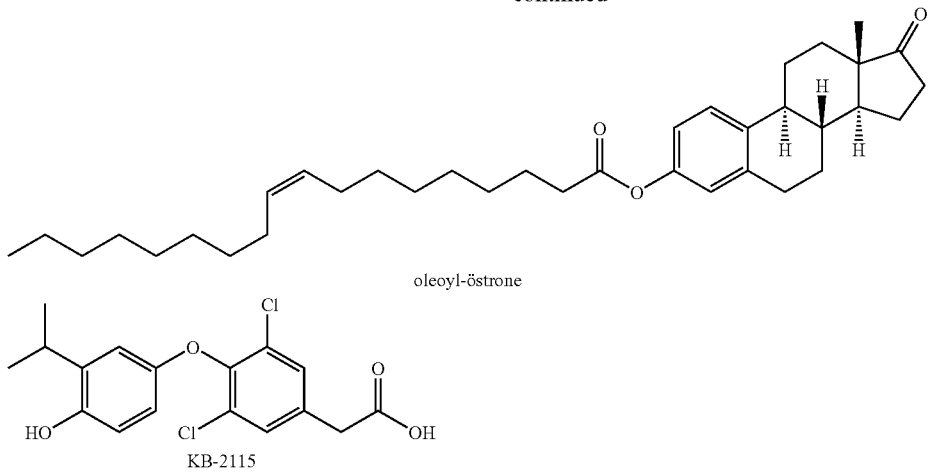

oleoyl-östrone

KB-2115

Determination of EC50 Values of PPAR Agonists in the Cellular PPARalpha Assay

The activity of the compounds was tested as follows. The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fatty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession # AF264724) were cloned in 5'-upstream of a 68 bp-long minimal MMTV promoter (Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete Photinus pyralis gene (Accession # M15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARalpha receptor (amino acids S167-Y468; Accession # S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (#

353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin).

Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Gio reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

The raw data from the luminometer are transferred into a Microsoft Excel file. Dose-effect plots and EC50 values of PPAR agonists are calculated using the XL.Fit program as specified by the manufacturer (IDBS). The PPARalpha EC50 values for the compounds of Examples 1 to 69 in this assay are in the range from 10 nM to >33 µM. Compounds of the invention of the formula I activate the PPARalpha receptor. Determination of EC50 values of PPAR agonists in the cellular PPARdelta assay The potency of substances which bind to human PPARdelta and activate it in an agonistic manner is analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanPPARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

Construction of the PPARdelta Reporter Cell Line

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARdelta receptor (amino acids S139-Y441; Accession # L07592) was cloned in at the 3'-end of this GR-GAL4 construct. The fusion construct prepared in this way (GR-GAL4-humanPPARdelta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

The activity of PPARdelta agonists is determined in a 3-day assay in exact analogy to the procedure already described for the PPARalpha reporter cell line except that the PPARdelta reporter cell line and a specific PPARdelta agonist was used as a standard to control test efficacy. PPARdelta EC50 values in the range from 0.3 nM to >10 µM were measured for the PPAR agonists of Examples 1 to 69 described in this application. Compounds of the invention of the formula I activate the PPARdelta receptor.

It will be appreciated that every suitable combination of the compounds of the invention with one or more of the aforementioned compounds and optionally one or more other pharmacologically active substances is regarded as falling within the protection conferred by the present invention. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow. The examples given in Table I serve to illustrate the invention, and should not be construed as limiting it.

TABLE I
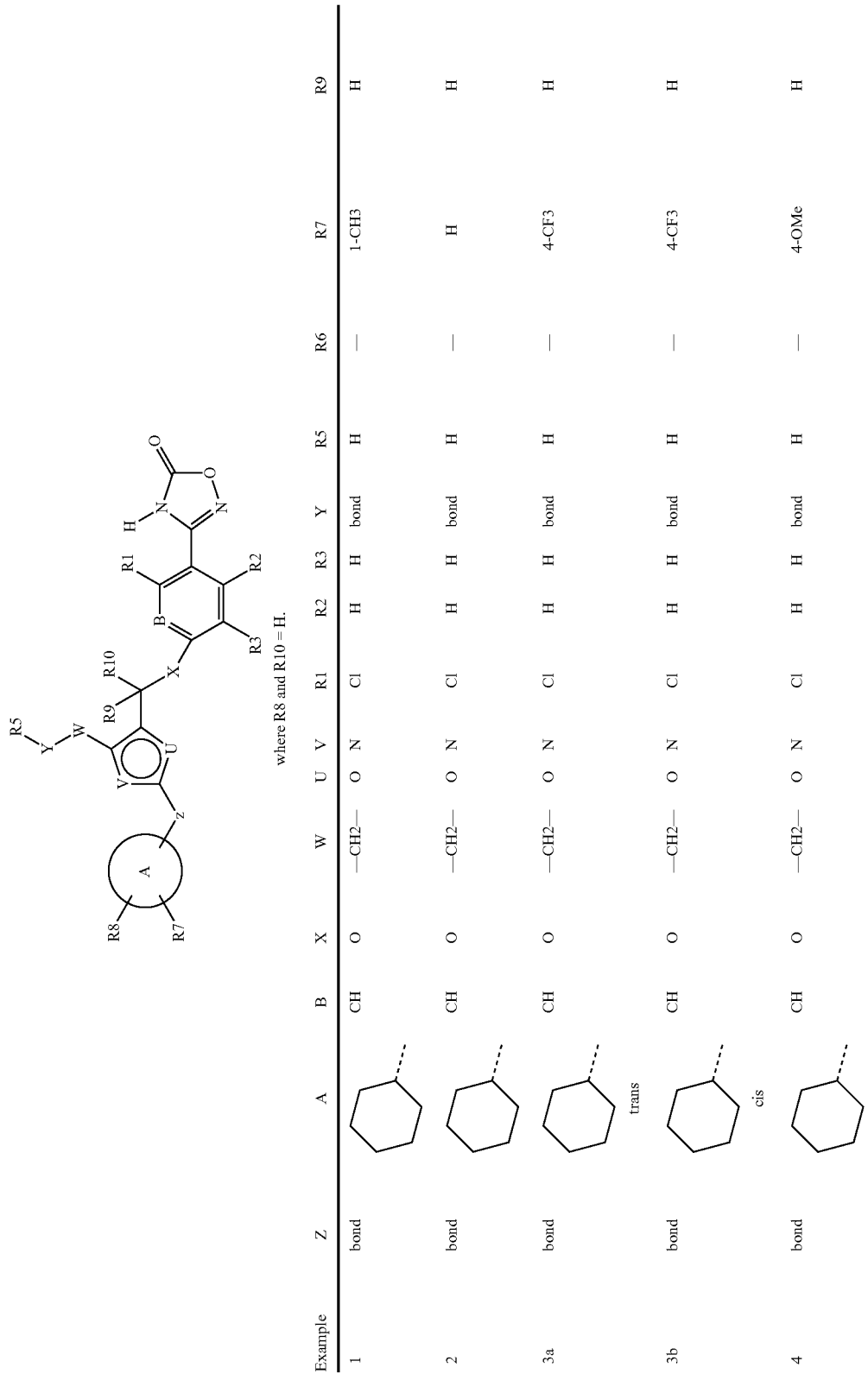
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 1 | bond | cyclohexyl | CH | O | —CH2— | O | N | Cl | H | H | bond | H | — | 1-CH3 | H |
| 2 | bond | cyclohexyl | CH | O | —CH2— | O | N | Cl | H | H | bond | H | — | H | H |
| 3a | bond | cyclohexyl trans | CH | O | —CH2— | O | N | Cl | H | H | bond | H | — | 4-CF3 | H |
| 3b | bond | cyclohexyl cis | CH | O | —CH2— | O | N | Cl | H | H | bond | H | — | 4-CF3 | H |
| 4 | bond | cyclohexyl | CH | O | —CH2— | O | N | Cl | H | H | bond | H | — | 4-OMe | H |

TABLE I-continued where R8 and R10 = H.

| Example | Z | A | B | X | W | U | V | R1 | R2 | R3 | Y | R5 | R6 | R7 | R9 |
|---------|---|---|---|---|---|---|---|----|----|----|---|----|----|----|----|
| 5 | bond | cyclohexyl | CH | O | —CH2— | S | N | Cl | H | H | bond | H | — | H | H |
| 6 | bond | piperidyl | CH | O | —CH2— | S | N | Cl | H | H | bond | H | — | N—SO2CF3 | H |
| 7 | bond | piperidyl | CH | O | —CH2— | S | N | Cl | H | H | bond | H | — | N—CH2CF3 | H |
| 8 | bond | piperidyl | CH | O | —CH2— | S | N | Cl | H | H | bond | H | — | N-Ph | H |
| 9 | bond | cyclohexyl | CH | O | —CH2— | S | N | Cl | H | H | O | —CH3 | — | 4-F | H |
| 10 | —CH2CH2— | cyclohexyl | CH | O | —CH2— | S | N | Cl | H | H | O | —CH3 | — | H | H |

TABLE I-continued
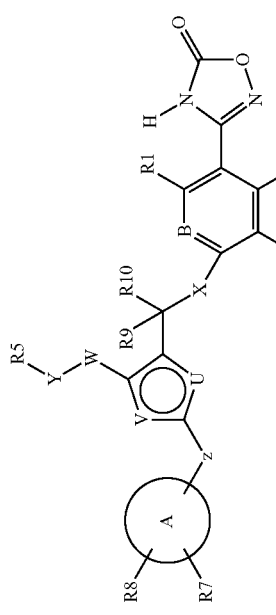
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 11 | bond | cycloheptyl | CH | O | —CH2— | S | N | Cl | H | H | O | —CH3 | — | H | H |
| 12 | bond | cyclohexyl (trans) | CH | O | —CH2— | S | N | Cl | H | H | O | —CH3 | — | 4-(4-Chlorophenyl) | H |
| 13 | bond | cyclopentyl | CH | O | —CH2— | O | N | Cl | H | H | O | —CH3 | — | H | H |
| 14 | bond | pyridyl | CH | O | —CH2— | S | N | Cl | H | H | O | —CH3 | — | 6-CF3 | H |
| 15 | bond | cyclohexyl | CH | O | —CH2— | O | N | Cl | H | H | O | —CH2CH3 | — | H | H |
| 16 | bond | cyclohexyl | CH | O | —CH2— | O | N | Cl | H | H | O | —CH3 | — | H | H |

TABLE I-continued
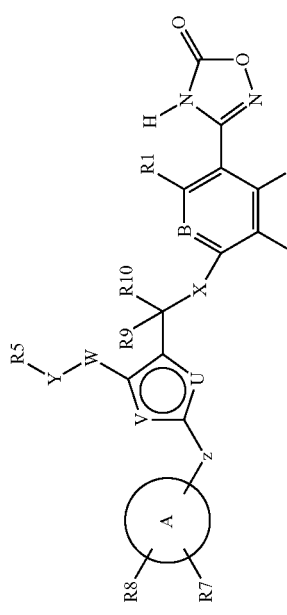
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 17 | bond | cycloheptyl | CH | O | —CH2— | O | N | Cl | H | H | O | —CH3 | — | H | H |
| 18a | bond | cyclohexyl trans | CH | O | —CH2— | O | N | Cl | H | H | O | —CH3 | — | 4-CF3 | H |
| 18b | bond | cyclohexyl cis | CH | O | —CH2— | O | N | Cl | H | H | O | —CH3 | — | 4-CF3 | H |
| 19 | bond | cyclohexyl | CH | O | —CH2— | O | N | Cl | H | H | N | H | H | H | H |
| 20 | bond | cyclohexyl | CH | O | —CH2— | O | N | Cl | H | H | N | —CH2CH3 | —CH2CH3 | H | H |
| 21 | bond | cyclohexyl | CH | O | bond | O | N | Cl | H | H | bond | H | — | H | H |

TABLE 1-continued
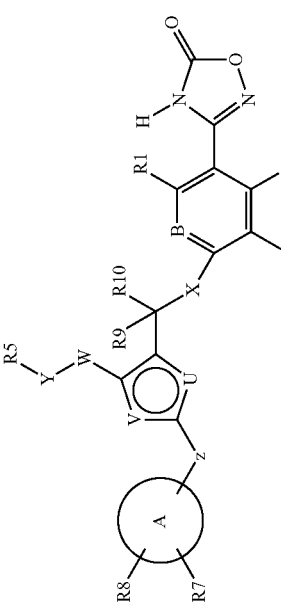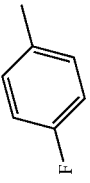
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 22 | —CHCH— | cyclohexyl | CH | O | —CH2— | S | N | Cl | H | H | O | —CH3 | — | H | H |
| 23 | bond | pyridyl | CH | O | —CH2— | S | N | Cl | H | H | bond | H | — | 6-CF3 | H |
| 24 | bond | cyclohexyl trans | CH | O | —CH2— | S | N | Cl | H | H | bond | H | — | 4-CF3 | —CH2Ph |
| 25 | bond | pyridyl | CH | O | —(CH2)3— | S | N | Cl | H | H | O | —CH2Ph | — | 6-CF3 | H |
| 26 | bond | pyridyl | CH | O | —CH2— | S | N | Cl | H | H | bond | H | — | 6-CF3 | —CH2CH3 |
| 27 | bond | pyridyl | CH | O | —CH2— | S | N | Cl | H | H | bond | H | — | 6-CF3 | 4-fluorophenyl-methyl |

TABLE I-continued
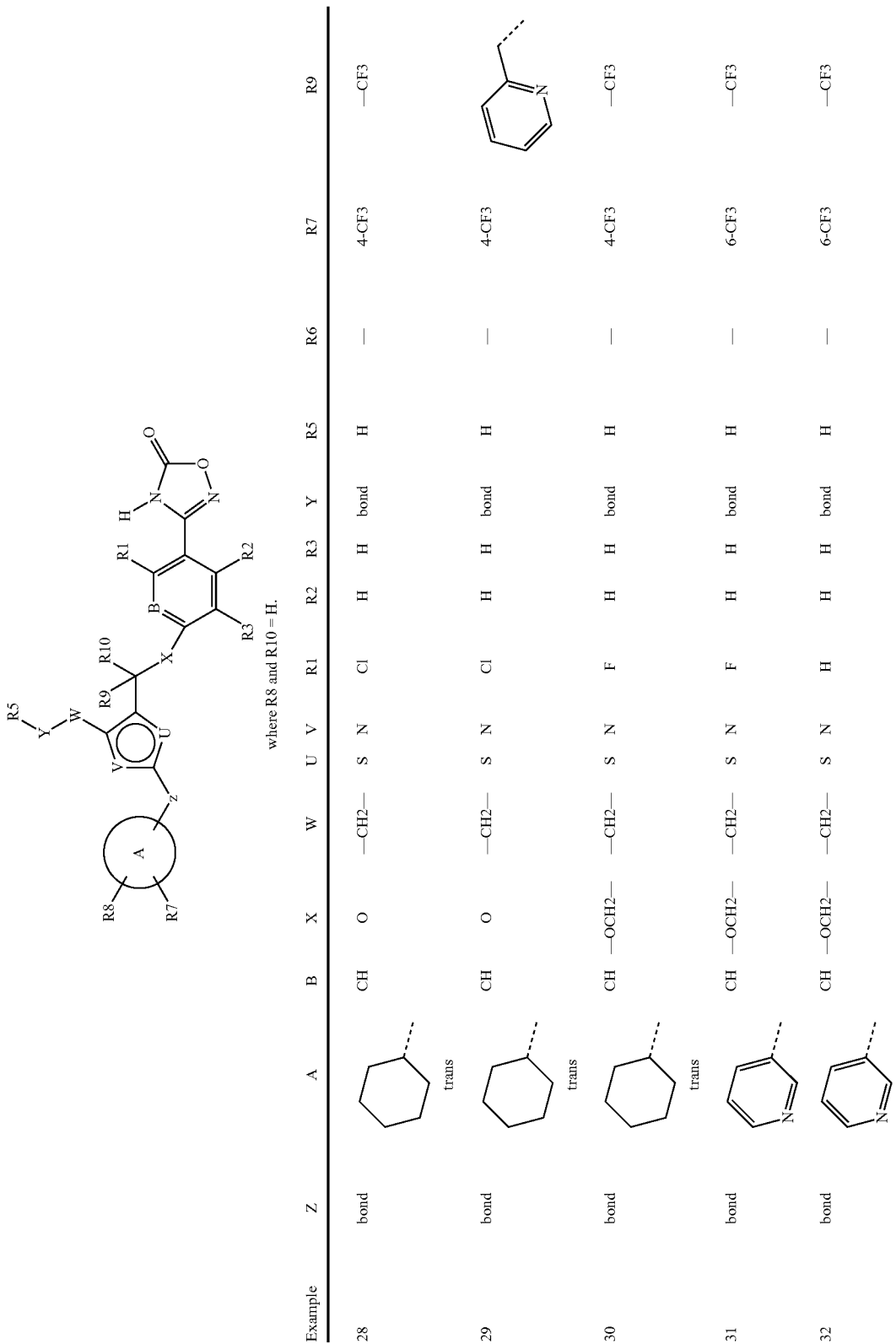
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 28 | bond | cyclohexyl trans | CH | O | —CH2— | S | N | Cl | H | H | bond | H | — | 4-CF3 | —CF3 |
| 29 | bond | cyclohexyl trans | CH | O | —CH2— | S | N | Cl | H | H | bond | H | — | 4-CF3 | 2-pyridylmethyl |
| 30 | bond | cyclohexyl trans | CH | —OCH2— | —CH2— | S | N | F | H | H | bond | H | — | 4-CF3 | —CF3 |
| 31 | bond | pyridyl | CH | —OCH2— | —CH2— | S | N | F | H | H | bond | H | — | 6-CF3 | —CF3 |
| 32 | bond | pyridyl | CH | —OCH2— | —CH2— | S | N | H | H | H | bond | H | — | 6-CF3 | —CF3 |

TABLE 1-continued where R8 and R10 = H.

| Example | Z | A | B | X | W | U | V | R1 | R2 | R3 | Y | R5 | R6 | R7 | R9 |
|---|---|---|---|---|---|---|---|---|---|---|---|---|---|---|---|
| 33 | bond | pyridine | CH | —OCH2— | —CH2— | S | N | —CF3 | H | H | bond | H | — | 6-CF3 | —CH2CH3 |
| 34 | bond | cyclohexane trans | CH | —OCH2— | —CH2— | S | N | Cl | H | H | bond | H | — | 4-CF3 | —CF3 |
| 35 | bond | pyridine | CH | —OCH2— | —CH2— | S | N | Cl | H | H | bond | H | — | 6-CF3 | —CF3 |
| 36 | bond | pyridine | CH | —OCH2— | —CH2— | S | N | H | pyridyl | pyridyl | H | bond | — | 6-CF3 | —CF3 |
| 37 | bond | pyridine | N | —OCH2— | —CH2— | S | N | Cl | H | H | bond | H | — | 6-CF3 | —CF3 |
| 38 | bond | pyridine | CH | —OCH2— | —CH2— | S | N | H | H | H | bond | H | cyclopropyl | 6-CF3 | —CF3 |

TABLE I-continued
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 39 | bond | cyclohexyl trans | CH | —OCH2— | —CH2— | S | N | cyclopropyl | H | H | bond | H | — | 4-CF3 | —CF3 |
| 40 | bond | pyridyl | CH | —OCH2— | —CH2— | S | N | H | H | H | bond | H | — | 6-CF3 | —CF2—CH3 |
| 41 | bond | pyridyl | CH | —OCH2— | —CH2— | S | N | Cl | H | H | bond | H | — | 6-CF3 | —CF2—CH3 |
| 42 | bond | pyridyl | CH | —OCH2— | —CH2— | S | N | H | phenyl | | H | bond | — | 6-CF3 | —CF2—CH3 |
| 43 | bond | pyridyl | CH | —OCH2— | —CH2— | S | N | H | pyridyl | | H | bond | — | 6-CF3 | —CF2—CH3 |

TABLE I-continued
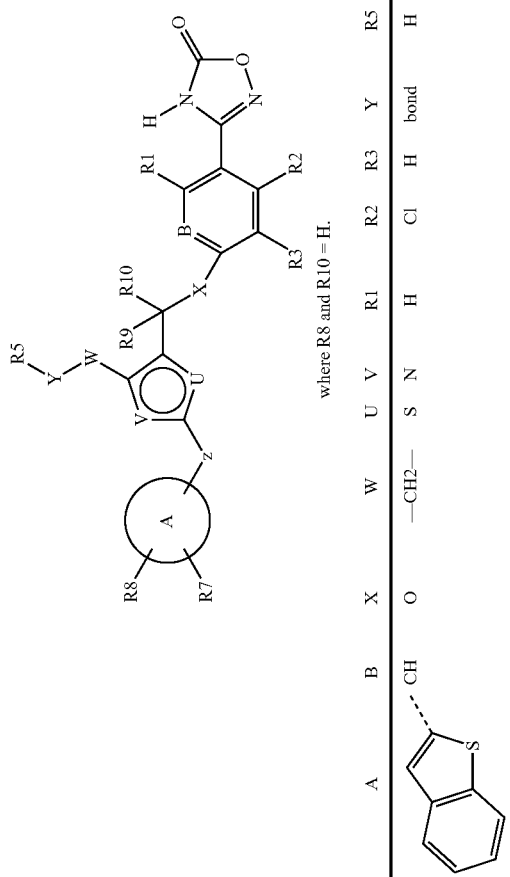
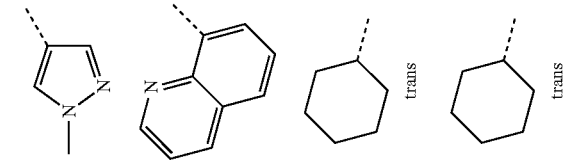
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 44 | bond | benzothiophen-2-yl | CH | O | —CH2— | S | N | H | Cl | H | bond | H | — | H | H |
| 45 | bond | 1-methylpyrazol-4-yl | CH | O | —CH2— | S | N | H | Cl | H | bond | H | — | H | H |
| 46 | bond | quinolin-8-yl | CH | O | —CH2— | S | N | H | Cl | H | bond | H | — | H | H |
| 47 | bond | cyclohexyl trans | CH | O | —CH2— | O | N | —OCH3 | H | H | bond | H | — | 4-CF3 | —CH2CH3 |
| 48 | bond | cyclohexyl trans | CH | O | —CH2— | S | N | —OCH3 | H | H | bond | H | — | 4-CF3 | H |

TABLE I-continued
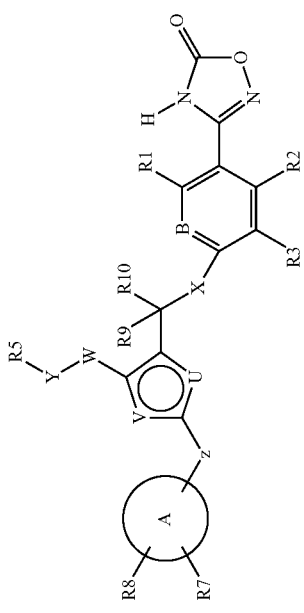
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 49 | bond | cyclohexyl trans | CH | O | —CH2— | S | N | —OCH3 | H | H | bond | H | — | 4-CF3 | —CH2CH3 |
| 50 | bond | cyclohexyl trans | CH | O | —CH2— | S | N | —OCH3 | H | H | bond | H | — | 4-CF3 | H |
| 51 | bond | cyclohexyl trans | CH | O | —CH2— | S | N | —OCH3 | H | H | bond | H | — | 4-CF3 | —CH2CH3 |
| 52 | bond | cyclohexyl trans | CH | O | —CH2— | S | N | —OCHF2 | H | H | bond | H | — | 4-CF3 | H |
| 53 | bond | cyclohexyl trans | CH | O | —CH2— | S | N | —OCHF2 | H | H | bond | H | — | 4-CF3 | —CH2CH3 |

TABLE I-continued

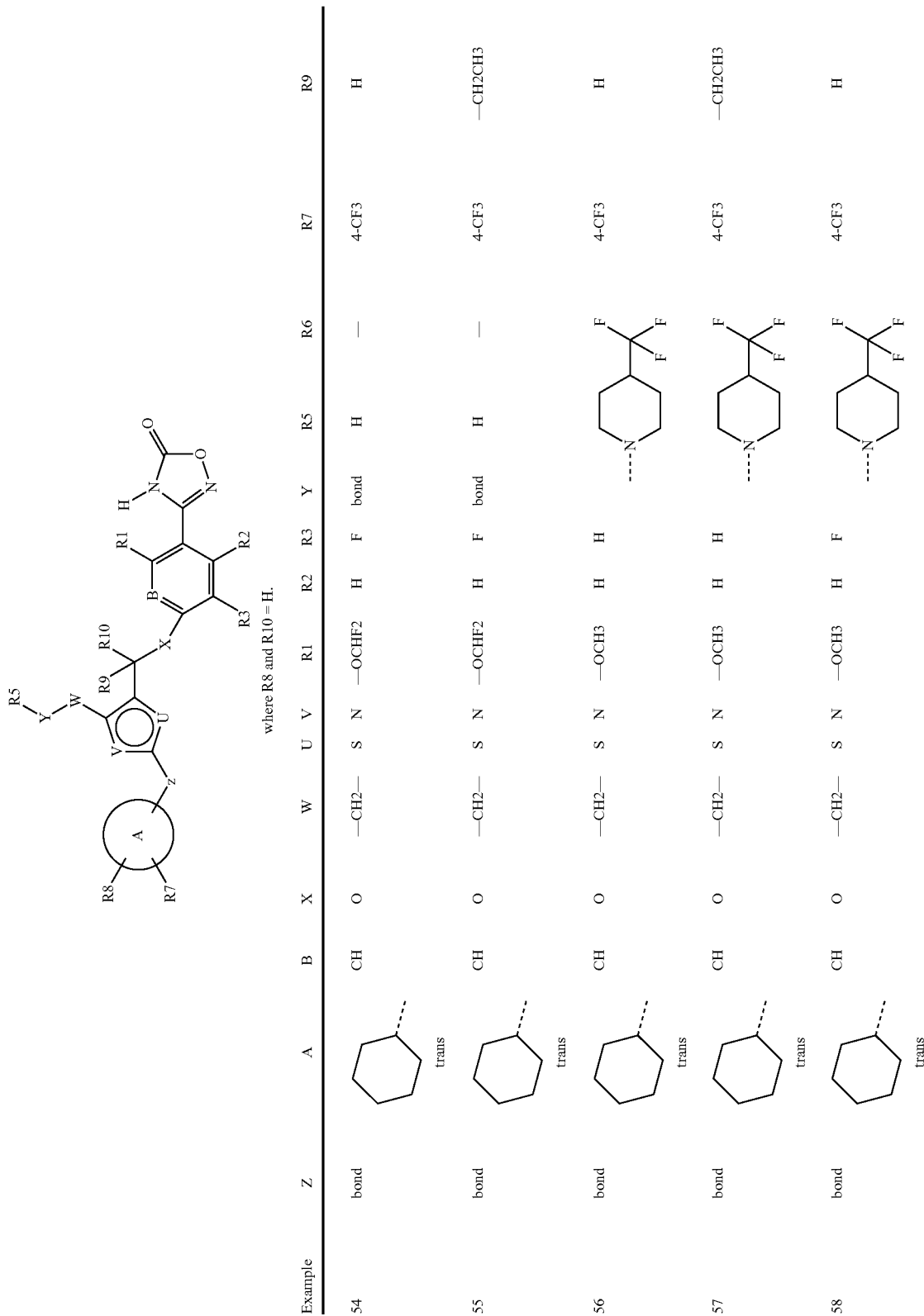

where R8 and R10 = H.

| Example | Z | A | B | X | W | V | U | R1 | R2 | R3 | Y | R5 | R6 | R7 | R9 |
|---|---|---|---|---|---|---|---|---|---|---|---|---|---|---|---|
| 54 | bond | cyclohexyl trans | CH | O | —CH2— | S | N | —OCHF2 | H | F | bond | H | — | 4-CF3 | H |
| 55 | bond | cyclohexyl trans | CH | O | —CH2— | S | N | —OCHF2 | H | F | bond | H | — | 4-CF3 | —CH2CH3 |
| 56 | bond | cyclohexyl trans | CH | O | —CH2— | S | N | —OCH3 | H | H | F | N-methyl-4-(trifluoromethyl)piperidine | | 4-CF3 | H |
| 57 | bond | cyclohexyl trans | CH | O | —CH2— | S | N | —OCH3 | H | H | F | N-methyl-4-(trifluoromethyl)piperidine | | 4-CF3 | —CH2CH3 |
| 58 | bond | cyclohexyl trans | CH | O | —CH2— | S | N | —OCH3 | H | F | F | N-methyl-4-(trifluoromethyl)piperidine | | 4-CF3 | H |

TABLE I-continued

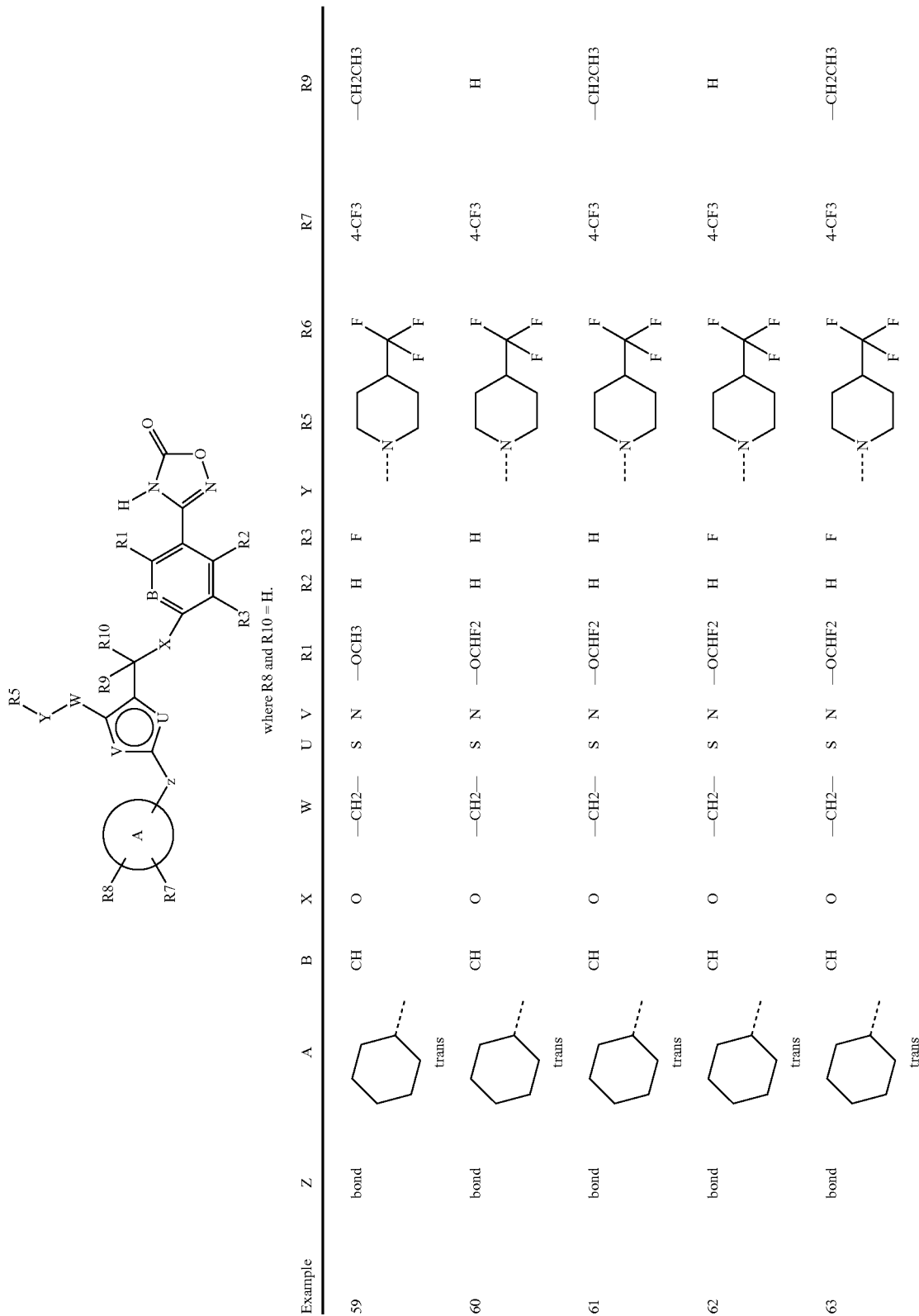

where R8 and R10 = H.

| Example | Z | A | B | X | W | U | V | R1 | R2 | R3 | Y | R5 | R6 | R7 | R9 |
|---|---|---|---|---|---|---|---|---|---|---|---|---|---|---|---|
| 59 | bond | cyclohexyl trans | CH | O | —CH2— | S | N | —OCH3 | H | F | | N-piperidinyl-CF3 | | 4-CF3 | —CH2CH3 |
| 60 | bond | cyclohexyl trans | CH | O | —CH2— | S | N | —OCHF2 | H | H | | N-piperidinyl-CF3 | | 4-CF3 | H |
| 61 | bond | cyclohexyl trans | CH | O | —CH2— | S | N | —OCHF2 | H | H | | N-piperidinyl-CF3 | | 4-CF3 | —CH2CH3 |
| 62 | bond | cyclohexyl trans | CH | O | —CH2— | S | N | —OCHF2 | H | F | | N-piperidinyl-CF3 | | 4-CF3 | H |
| 63 | bond | cyclohexyl trans | CH | O | —CH2— | S | N | —OCHF2 | H | F | | N-piperidinyl-CF3 | | 4-CF3 | —CH2CH3 |

TABLE I-continued
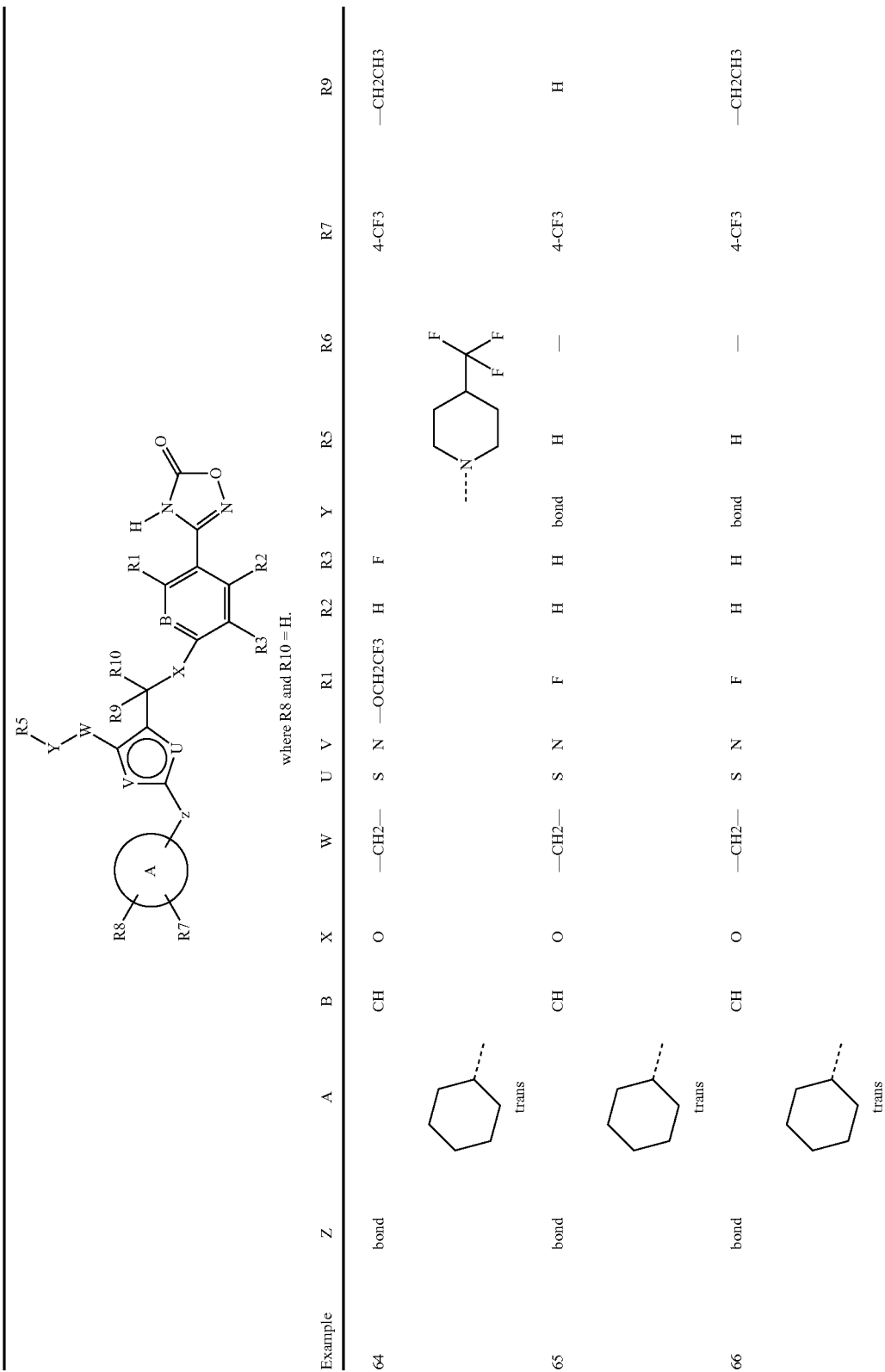
where R8 and R10 = H.
| Example | Z | A | B | X | W | U | V | R1 | R2 | R3 | Y | R5 | R6 | R7 | R9 |
|---|---|---|---|---|---|---|---|---|---|---|---|---|---|---|---|
| 64 | bond | cyclohexyl trans | CH | O | —CH2— | S | N | —OCH2CF3 | H | F | F | | 1-methyl-4-(trifluoromethyl)piperidinyl | 4-CF3 | —CH2CH3 |
| 65 | bond | cyclohexyl trans | CH | O | —CH2— | S | N | F | H | H | bond | H | — | 4-CF3 | H |
| 66 | bond | cyclohexyl trans | CH | O | —CH2— | S | N | F | H | H | bond | H | — | 4-CF3 | —CH2CH3 |

TABLE I-continued where R8 and R10 = H.

| Example | Z | A | B | X | W | U | V | R1 | R2 | R3 | Y | R5 | R6 | R7 | R9 |
|---------|------|---------------|----|---|------|---|---|----|----|----|------|----|----------------------|-------|---------|
| 67 | bond | cyclohexyl trans | CH | O | —CH2— | S | N | F | H | H | | N-methyl piperidine | 4-CF3 CF3 | 4-CF3 | H |
| 68 | bond | cyclohexyl trans | CH | O | —CH2— | S | N | F | H | H | | N-methyl piperidine | 4-CF3 CF3 | 4-CF3 | —CH2CH3 |
| 69 | bond | cyclohexyl trans | CH | O | —CH2— | S | N | —OCH2CF3 | H | H | bond | H | — | 4-CF3 | H |

A dotted line means the point of attachment.

The potency of some of the described examples are indicated in the following table:
| Example | PPARalpha EC50 (μM) | PPARdelta EC50 (μM) |
|---|---|---|
| 5 | 1.26 | 0.23 |
| 10 | 0.53 | 0.07 |
| 11 | 1.25 | 0.13 |
| 12 | 0.80 | 0.01 |
| 18a | 2.5 | 0.04 |
| 25 | 0.075 | 0.0003 |
| 31 | >33 | 0.014 |
| 37 | >33 | 0.059 |
| 39 | 5.44 | 0.086 |
| 46 | 4.33 | 7.39 |
-continued
| Example | PPARalpha EC50 (μM) | PPARdelta EC50 (μM) |
|---|---|---|
| 51 | 0.335 | 0.007 |
| 61 | >33 | 0.007 |
| 62 | >33 | 0.052 |
| 66 | 0.304 | 0.011 |
| 68 | >33 | 0.130 |
Processes
The compounds of the general formula I according to the invention can be obtained as outlined to the reaction schemes below:
Process A
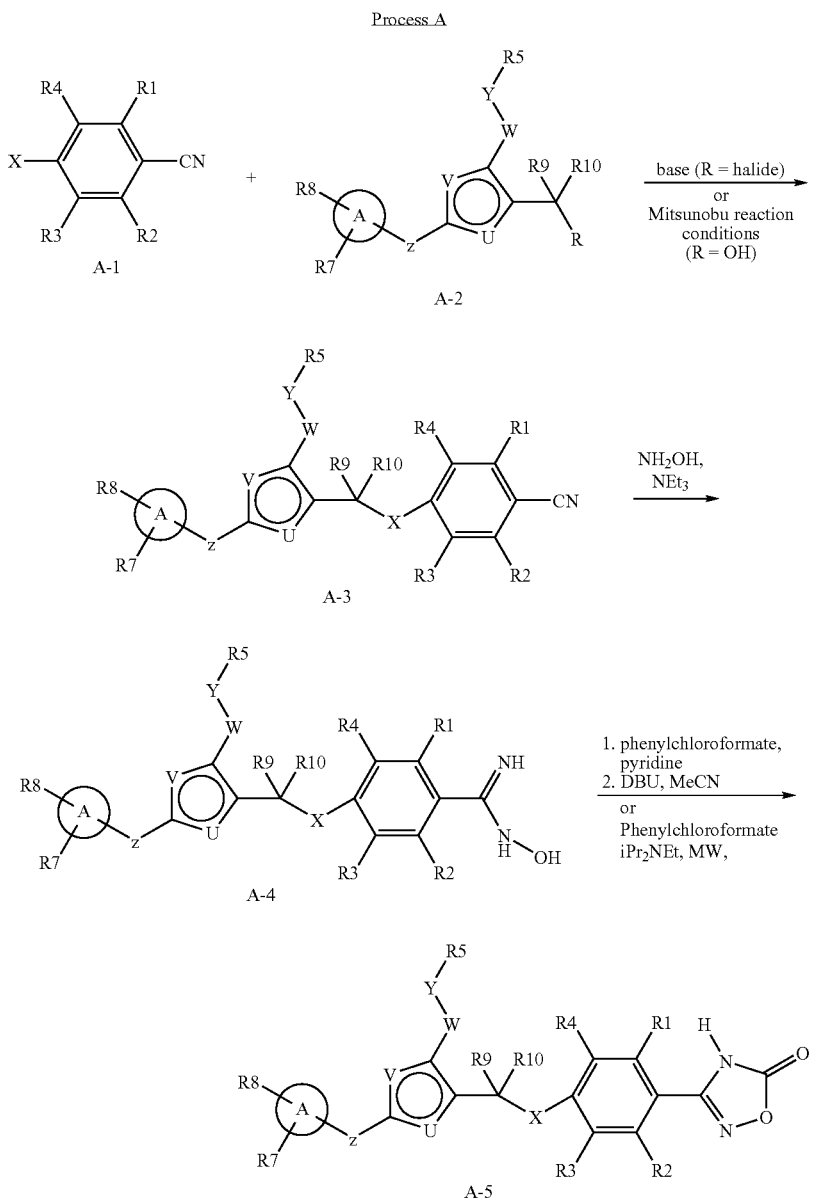

A compound of the general formula A-1 where X is —OH or —SH and R1, R2, R3 and R4 are as defined is either reacted with an halide of general formula A-2 where R=halide and U, V, W, Y, Z, A, R5, R6, R7, R8, R9 and R10 are as defined in the presence of a base as cesium carbonate or sodium hydride in a solvent as dimethylformamide or with an alcohol of general formula A-2 where R=OH and U, V, W, Y, Z, A, R5, R6, R7, R8, R9 and R are as defined under Mitsunobu reaction conditions (triphenylphosphine, diethylazodicarboxylate for instance) in solvent as dichloromethane or tetrahydrofuran to give a compound of the general formula A-3. If X=S in the compound of the general formula A-3, the sulfur atom can be oxidized (X=SO or X=SO2) by methods known in the art, e.g. with a oxidizing agent as meta-chloroperbenzoic acid in an apolar solvent as dichloromethane. The compound of the general formula A-3 is reacted with hydroxylamine hydrochloride in the presence of a base as triethylamine in a solvent as tetrahydrofuran and methanol to obtain a compound of the general formula A-4. This reaction can be facilitated by heating the reaction mixture under microwave irradiation. This compound of general formula A-4 is converted to the product of general formula A-5 by reaction with phenylchloroformate in the presence of a base as pyridine or diisopropylethylamine followed by heating the reaction mixture with microwave irradiation to allow cyclization or alternatively isolating the resulting intermediate and treating it with a base as 1,8-diazabicyclo[5.4.0]undec-7-ene in a solvent as acetonitrile.

Examples 1-24, 65-68 were obtained according to process A.

Other compounds can be obtained accordingly or by known processes.

Process B:

This process is used for synthesizing the building blocks B-5, which corresponds to general formula A-2 of process A, where R=OH, R9 and R10=H, V is N and A, W, Y, Z, R5, R6, R7 and R8 are as defined above and to general formula D-2 of process D, where R9 and R10=H, V is N and A, W, Y, Z, R5, R6, R7 and R8 are as defined above and to general formula E-2 of process E, where R9 and R10=H, V is N and A, W, Y, Z, R5, R6, R7 and R8 are as defined above and B-6, which corresponds to general formula A-2 of process A, where R=Cl and R9 and R10=H, V is N and A, W, Y, Z, R5, R6, R7 and R8 are as defined above.

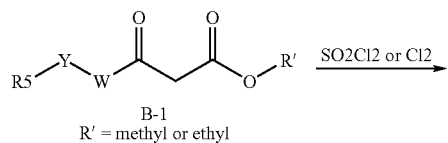

B-1
R' = methyl or ethyl

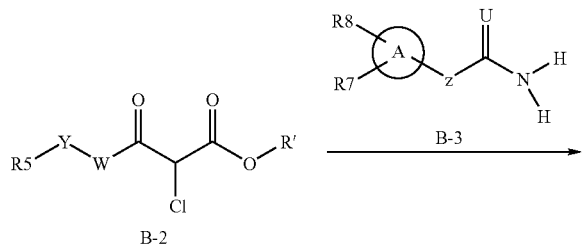

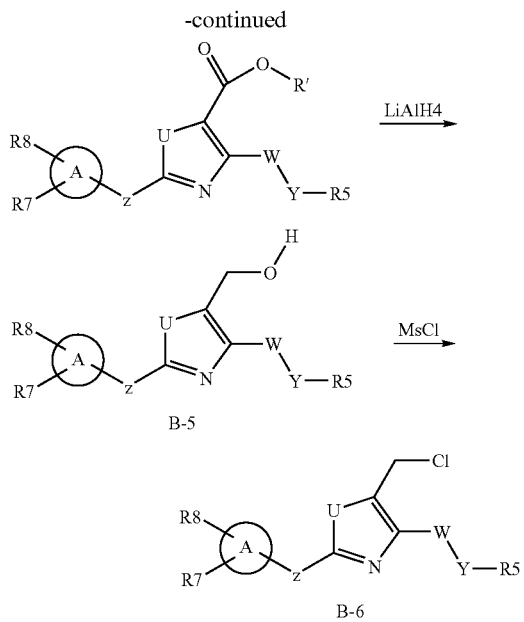

A 3-Oxo-butyric acid methyl- or ethyl ester of general formula B-1 where W, Y and R5 are as defined above is reacted with sulfuryl chloride or chlorine to a chlorine substituted compound of general formula B-2. This compound of general formula B-2 is reacted with an amide or thioamide of general formula B-3, where A, Z U, R7 and R8 are as defined to obtain an oxazole or thiazole ester of general formula B-4. The ester of general formula B-4 is reduced with a reducing agent, e.g. lithium aluminum hydride, to the alcohol of general formula B-5. The alcohol of general formula B-5 is reacted with methanesulfonyl chloride in the presence of a base as triethylamine in a solvent as dichloromethane to obtain the building block of general formula B-6.

Process C:

This process is used for synthesizing the building blocks C-4, which corresponds to general formula A-2 of process A, where R=OH, V is N, W is CH2, R9 and R10 are H, Z is bond, (C2-C6) alkyl, —CH=CH—, —C≡C— and A, Y, R6, R7 and R8 are as defined and, C-5 which corresponds to general formula A-2 of process A, where R=Cl, V is N, W is CH2, R9 and R10 are H, Z is bond, (C2-C6) alkyl, —CH=CH—, —C≡C— and A, Y, R6, R7 and R8 are as defined.

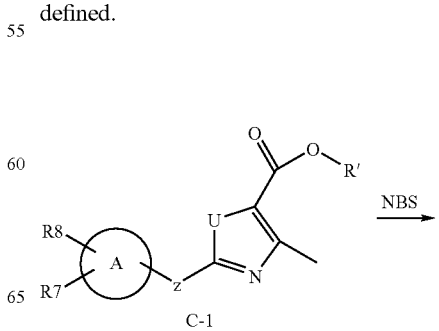

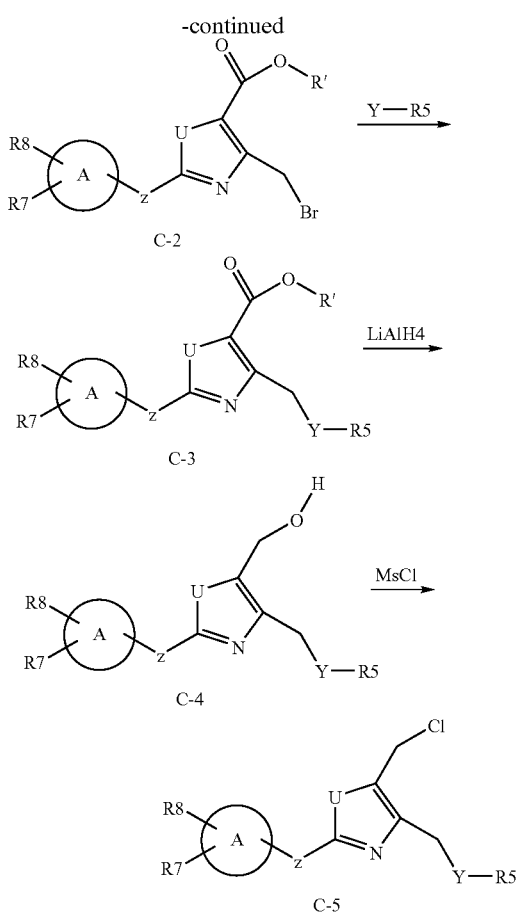

The oxazole or thiazole ester of general formula C-1 (which corresponds to the general formula B-4 of process B, where Z is a bond, (C2-C6) alkyl, —CH═CH— or —C≡C—, W is CH2, V is N, Y is a bond, R5 is H and U, A, R7 and R8 are as defined), is brominated by the treatment with N-bromosuccinimide in refluxing tetrachloromethane in the presence of a radical initiator like AIBN to yield the brominated product of general formula C-2. In case Z is (C2-C6) alkyl or in case Z is a bond and ring A is an aliphatic carbocycle or aliphatic heterocycle where R7 and R8 are not bonded to the same carbon atom and the atom of ring A directly attached to the oxazole or thiazole moiety is a carbon atom and bears a hydrogen atom, the carbon atom directly attached to the oxazole or thiazole ring is brominated as well. The brominated product of general formula C-2 is reacted with a nucleophile Y—R5 where Y is OH or Y is NH(R6) in a polar solvent like tetrahydrofuran in the presence of a base like DBU to obtain a compound of general formula C-3. In case the carbon atom directly attached to the oxazole or thiazole ring of the compound of general formula C-2 was brominated as well, this will eliminate under the reaction conditions to yield a double bond. This double bond can be hydrogenated with hydrogen in the presence of a palladium catalyst in a polar solvent, such as ethanol or methanol.

The ester of general formula C-3 is reduced with a reducing agent, e.g. lithium aluminum hydride, to the alcohol of general formula C-4. The alcohol of general formula C-4 is reacted with methanesulfonyl chloride in the presence of a base as triethylamine in a solvent as dichloromethane to obtain the building block of general formula C-5.

Other compounds can be obtained accordingly or by known processes.

Process D

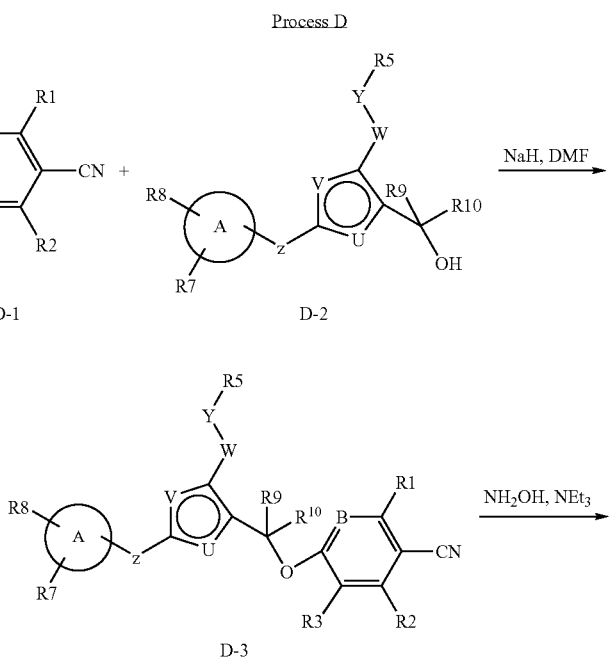

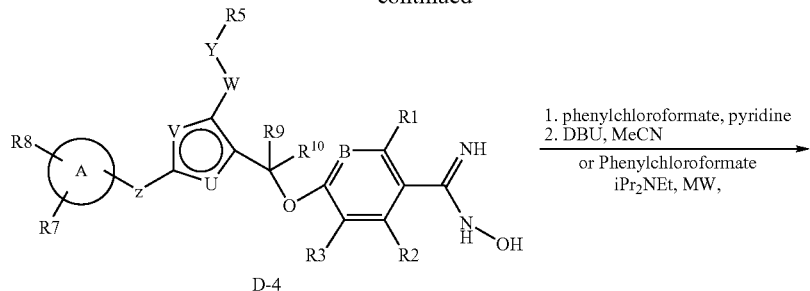

D-4

D-5

A compound of general formula D-2 where R5, R7, R8, R9, R10, A, U, V, W, Y and Z are as defined above is reacted with a fluoro-nitrile of general formula D-1 where B, R1, R2, R3 and R4 are as defined above in the presence of a base such as sodium hydride in a solvent such as dimethylformamide to give a compound of general formula D-3. As described in process A, compound D-3 is treated with hydroxylamine hydrochloride in the presence of a base such as triethylamine in a solvent as tetrahydrofuran and methanol to obtain a compound of general formula D-4. This reaction can be facilitated by heating the reaction mixture under microwave irradiation. Compound D-4 is converted to the product of general formula B-5 by reaction with phenylchloroformate in the presence of a base as pyridine or diisopropylethylamine followed by heating the reaction mixture under microwave irradiation to allow cyclization or alternatively isolating the resulting intermediate and treating it with a base as 1,8-diazabicyclo[5.4.0]undec-7-ene in a solvent as acetonitrile.

Examples 25-29, 47-64 were obtained according to process D.

Process E

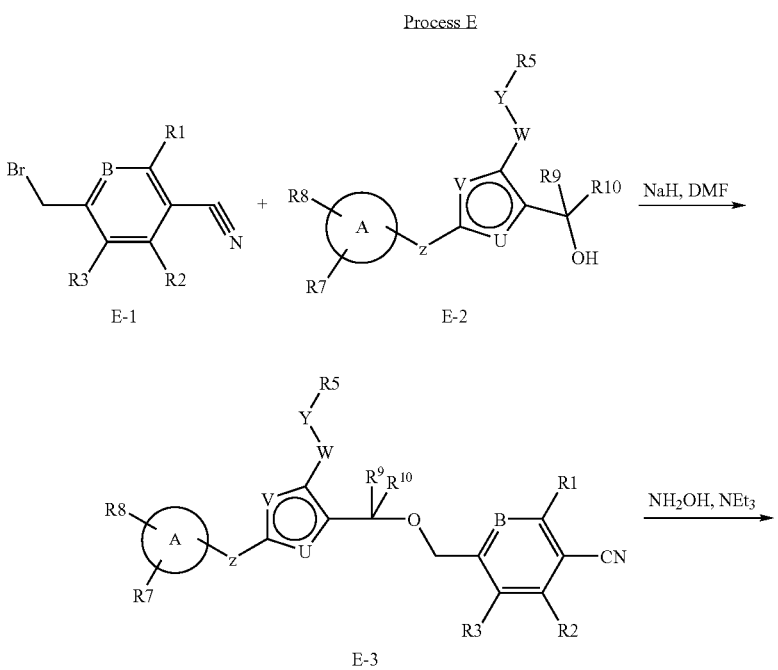

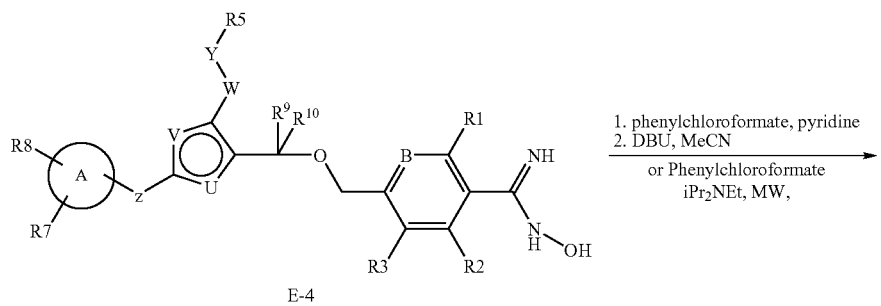

E-4

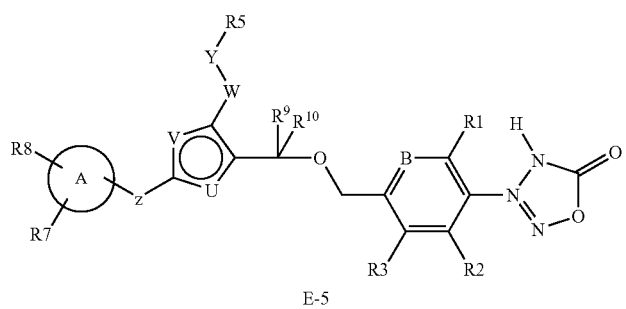

E-5

A compound of general formula E-2 where R5, R7, R8, R9, R10, A, U, V, W, Y and Z are as defined above is reacted with a benzylic bromide of general formula E-1 where B, R1, R2, R3 and R4 are as defined above in the presence of a base such as sodium hydride in a solvent such as dimethylformamide to give a compound of general formula E-3. As described in process A, compound E-3 is treated with hydroxylamine hydrochloride in the presence of a base such as triethylamine in a solvent as tetrahydrofuran and methanol to obtain a compound of general formula E-4. This reaction can be facilitated by heating the reaction mixture under microwave irradiation. Compound E-4 is converted to the product of general formula E-5 by reaction with phenylchloroformate in the presence of a base as pyridine or diisopropylethylamine followed by heating the reaction mixture under microwave irradiation to allow cyclization or alternatively isolating the resulting intermediate and treating it with a base as 1,8-diazabicyclo[5.4.0]undec-7-ene in a solvent as acetonitrile.

Examples 30-43 were obtained according to process E.

Process F:

This process is used for synthesizing the building blocks F-3, which corresponds to general formula A-2 of process A, where R=OH, R10=H, V is N and A, W, Y, Z, R5, R6, R7, R8 and R9 are as defined above and to general formula D-2 of process D, where R10=H, V is N and A, W, Y, Z, R5, R6, R7, R8 and R9 are as defined above and to general formula E-2 of process E, where R10=H, V is N and A, W, Y, Z, R5, R6, R7, R8 and R9 are as defined above.

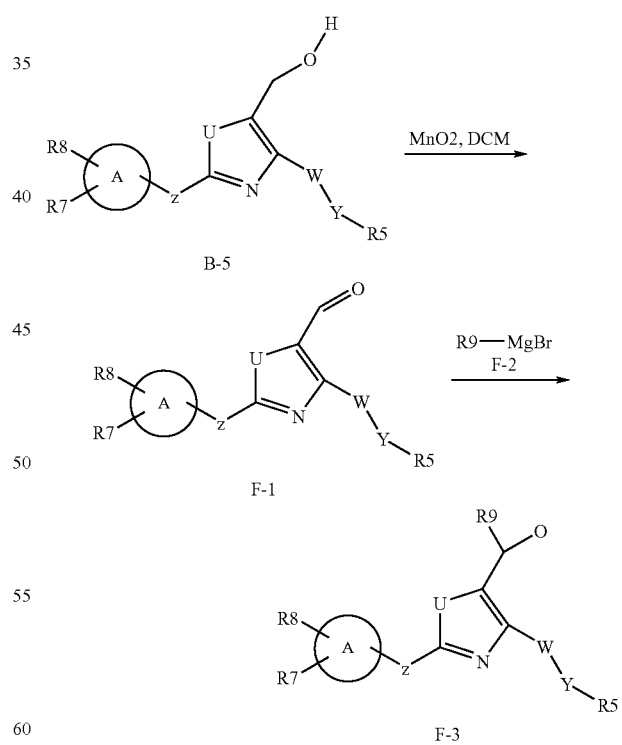

A compound of general formula B-5 (derived from process B) is treated with an oxidizing agent as manganese dioxide in an apolar solvent as dichloromethane to obtain an aldehyde of general formula F-1 where W, Y, U, Z, A, R5, R7 and R8 are as defined. The aldehyde of general formula F-1 is reacted with a Grignard reagent of general formula F-2, where R9 is as defined to obtain an secondary alcohol of general formula F-3.

Other compounds can be obtained accordingly or by known processes.

Process G:

This process is used for synthesizing the building blocks G-3, which corresponds to general formula A-2 of process A, where R=OH, R9 is —CF2R", R10=H, V is N and A, W, Y, Z, R5, R6, R7 and R8 are as defined above and to general formula D-2 of process D, where R9 is —CF2R", R10=H, V is N and A, W, Y, Z, R5, R6, R7 and R8 are as defined above and to general formula E-2 of process E, where R9 is —CF2R", R10=H, V is N and A, W, Y, Z, R5, R6, R7 and R8 are as defined above.

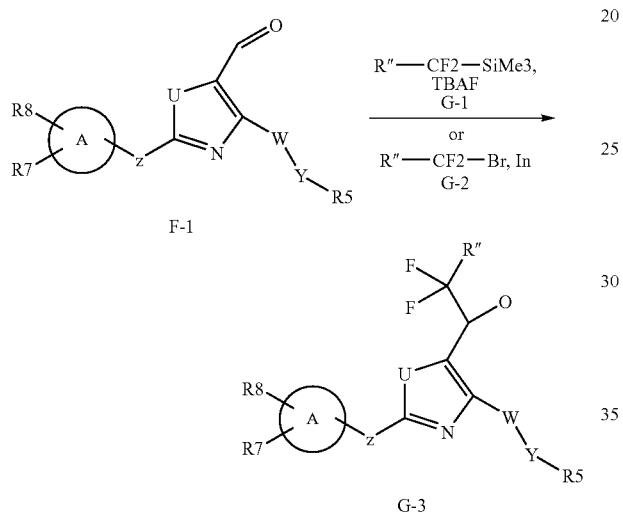

A compound of general formula F-1 (derived from process F) is treated with a difluorotrimethylsilyl reagent of general formula G-1 in a polar solvent as tetrahydrofuran with catalytic amounts of a fluoride ion source as KF or tetrabutyl ammonium fluoride or alternatively with a bromodifluoromethyl reagent of general formula G-2 in the presence of indium in a polar solvent, such as tetrahydrofuran in an ultrasonic bath to obtain to obtain an secondary alcohol of general formula G-3.

Other compounds can be obtained accordingly or by known processes.

Process H:

This process is used for synthesizing the building blocks H-3, which corresponds to general formula E-1 of process E.

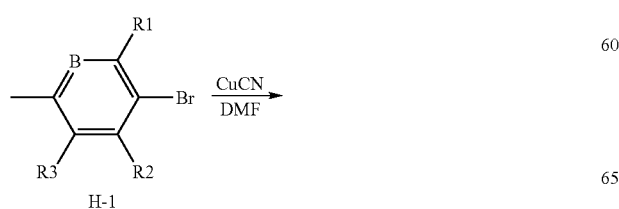

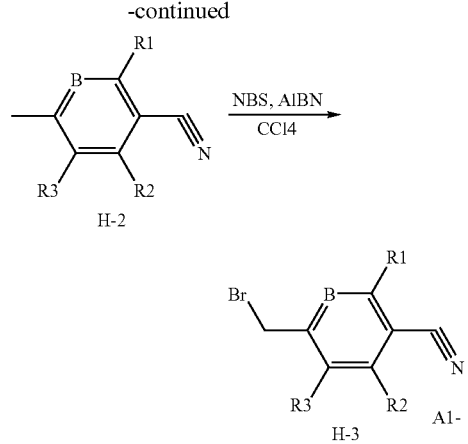

Bromo-4-methyl-benzene of general formula H-1, where B, R1, R2, R3 and R4 are as defined above is reacted with copper cyanide in a polar solvent as dimethylformamide at elevated temperature to obtain the 4-methyl-benzonitrile of general formula H-2. The 4-methyl-benzonitrile of general formula H-2 is brominated by the treatment with N-bromo-succinimide in refluxing tetrachloromethane in the presence of a radical initiator like AIBN to obtain the 4-Bromomethyl-benzonitrile of general formula H-3.

Process I:

This process is used for synthesizing the compounds of general formula I-7.

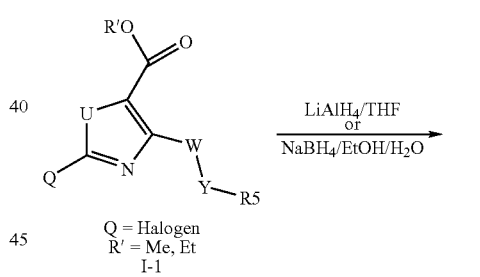

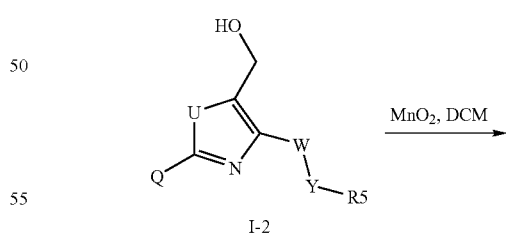

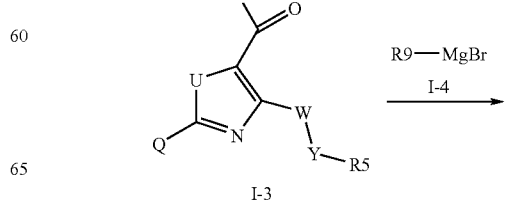

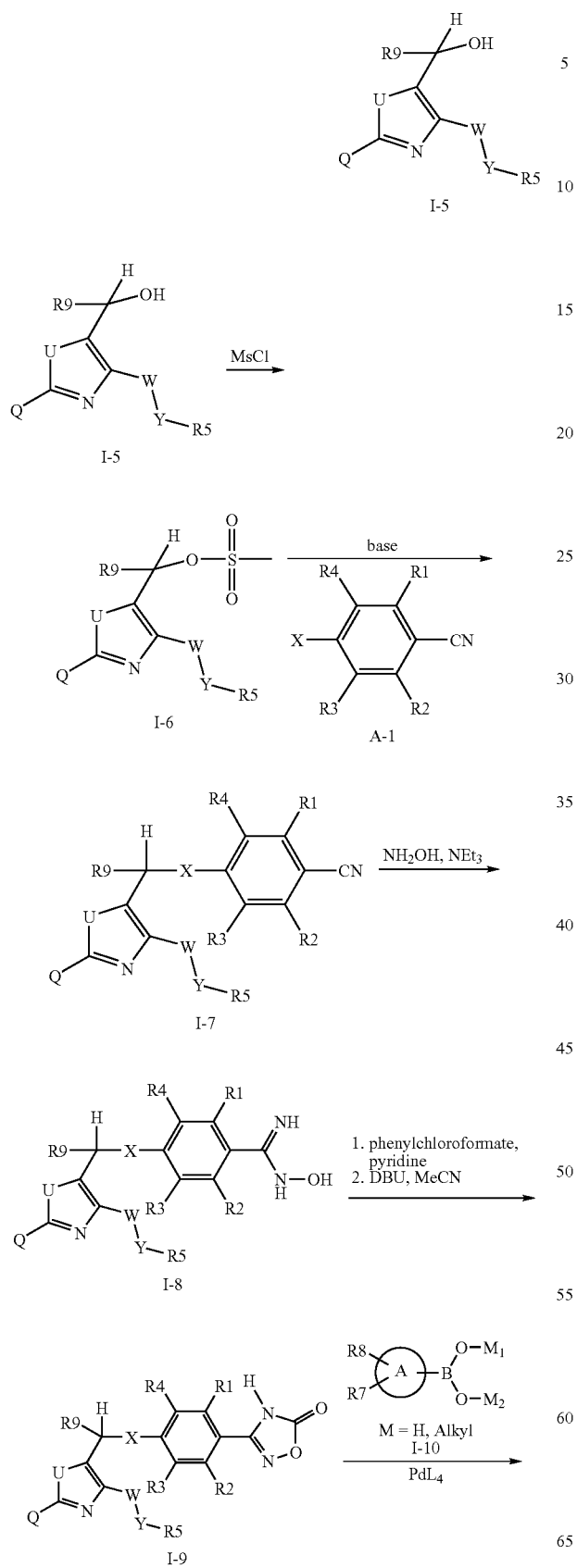

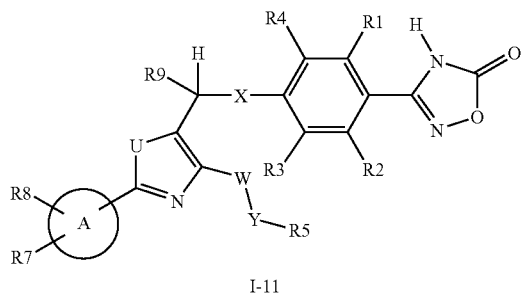

A compound of general formula I-1, where Q=Halogen, R'=CH3 or CH2CH3 and U, W, Y, R5 are as defined above is converted to I-2 using a reducing agent as for example LiAlH₄ in a solvent as THF or with NaBH₄ in a solvent as ethanol/water. The alcohol of general formula I-2 can be oxidized in aldehyde of general formula I-3 by treatment with an oxidizing agent as manganese dioxide in an apolar solvent as dichloromethane. The aldehyde of general formula I-3 is reacted with a Grignard reagent of general formula I-4, where X is Cl or Br and R9 is as defined above (except H), to obtain a secondary alcohol of general formula I-5. The building block I-5 (or I-2 when R9=H) is reacted with methanesulfonyl chloride in the presence of a base as triethylamine in a solvent as dichloromethane to obtain the building block of general formula I-6. A compound of the general formula A-1 where X is —OH or —SH and R1, R2, R3 and R4 are as defined is reacted with a compound of general formula I-6 in the presence of a base as cesium carbonate or sodium hydride in a solvent as dimethylformamide to give a compound of the general formula I-7. If X=S in the compound of the general formula I-7, the sulfur atom can be oxidized (X=SO or X=SO2) by methods known in the art, e.g with a oxidizing agent as meta-chloroperbenzoic acid in an apolar solvent as dichloromethane. The compound of the general formula I-7 is reacted with hydroxylamine hydrochloride in the presence of a base as triethylamine in a solvent as tetrahydrofuran and methanol to obtain a compound of the general formula I-8. A compound of the general formula I-8 is converted to the product of general formula I-9 by reaction with phenylchloroformate in the presence of a base as pyridine and treating this intermediate with a base as 1,8-diazabicyclo[5.4.0]undec-7-ene in a solvent as acetonitrile. A compound of general formula I-9 is converted to a compound of the general formula I-11 by reacting with a boronic acid or a boronic ester of general formula I-10, where M1 & M2 can be independently hydrogen or alkyl (in the case of alkyl, M1/M2 can form a ring system) and A, R7 and R8 are as defined above, using a catalytic amount of a transition metal as for example palladium and a ligand as for example triphenylphosphine in the presence of a base as for example Cs₂CO₃ in a solvent as for example DMF/water.

Compound 44-46 were obtained acording this process 1.

Process J:

Process J:

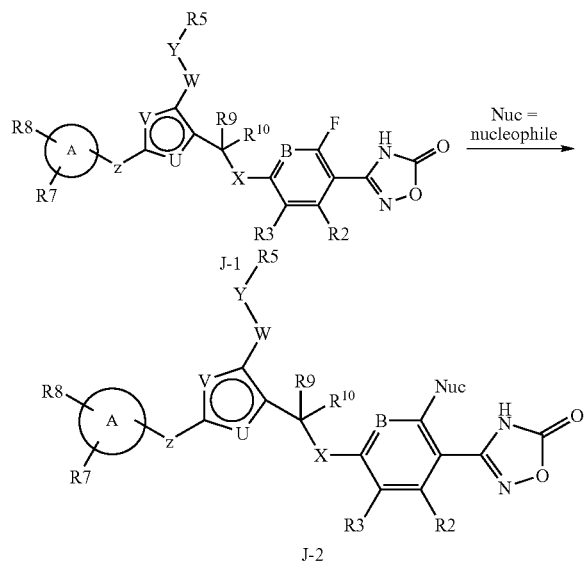

Process K:

A compound of general formula J-1 where R1=F and B, R2, R3, R5, R7, R8, U, V, X, W, Y and Z are as defined above is reacted with a nucleophile, such as sodium methylate, or an alcohol in presence of a base such as potassium tert-butoxide under microwave irradiation to obtain a compound of general formula J-2.

Example 69 was obtained according to process J.

Process K:

This process is used for synthesizing the building blocks K-6, K-7, K-9 and K-10, which corresponds to general formula A-2 of process A, where R=OH, general formula D-2 of process D and general formula E-2 of process E, where Y=N, W=CH2 or C(O), R10=H, A, Z, U, R5, R7 and R8 are as defined above and R9=H or another substituent as defined above.

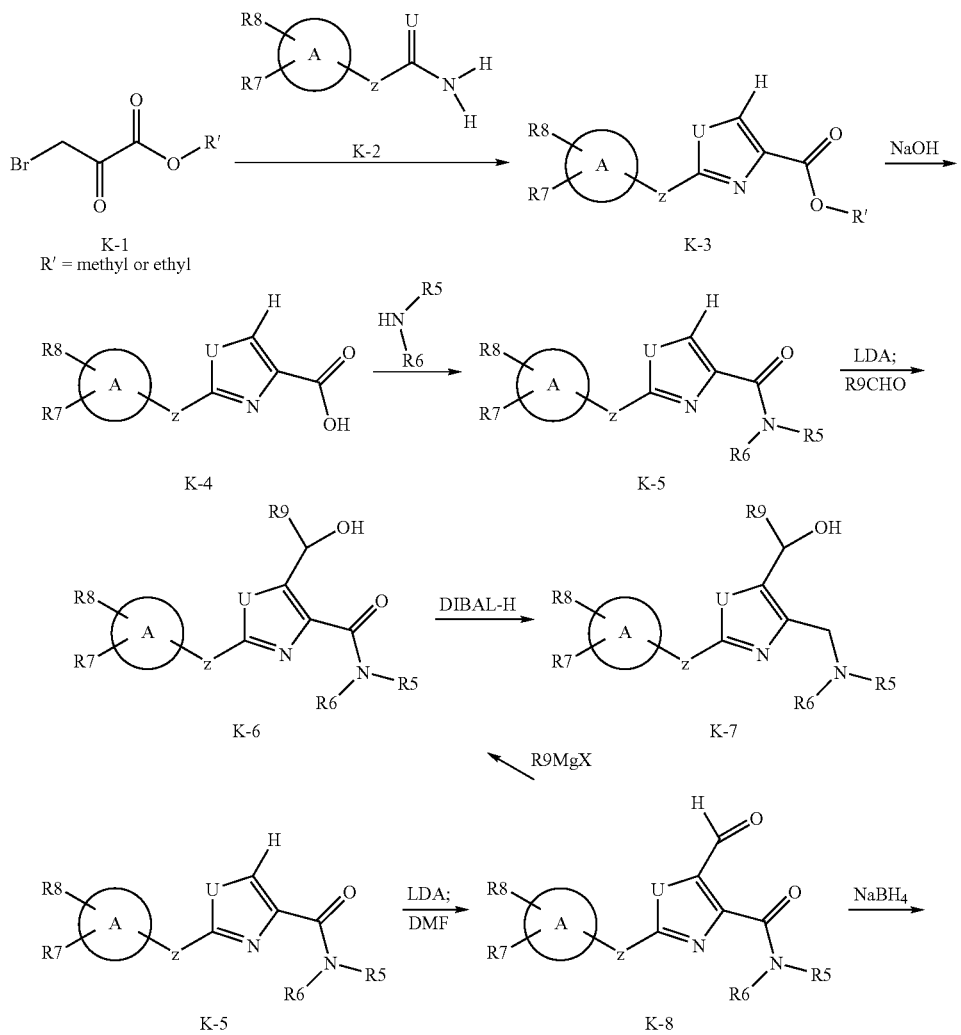

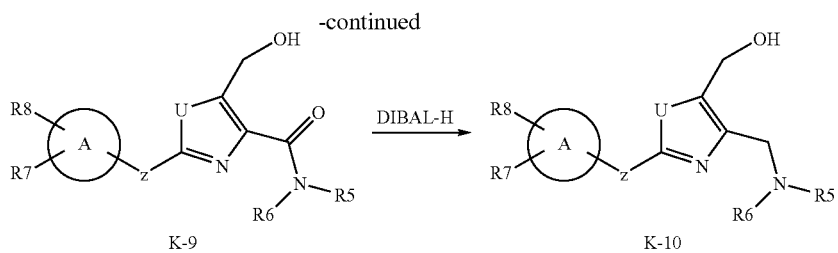

Methyl- or ethyl bromo pyruvate of formula K-1 is reacted with an amide or thioamide of general formula K-2 where A, Z, U, R7 and R8 are as defined above to give an oxazole or thiazole ester of general formula K-3. The ester of general formula K-3 is saponified, with sodium hydroxide for instance, to the carboxylic acid of general formula K-4 then coupled with an amine of general formula R5R6NH where R5 and R6 are as defined above under reaction conditions known by the person skilled in the art to yield the amide of general formula K-5. Alternatively, the amide of general formula K-5 can be directly obtained from the ester of general formula K-3 by treatment with an amine of general formula R5R6NH in presence of trimethylaluminum in refluxing toluene. Compound of general formula K-5 is reacted with a strong base such as lithium diisopropyl amide (LDA) followed by an aldehyde of general formula R9CHO where R9 is as defined above to obtain secondary alcohol of general formula K-6. Alternatively, the compound of general formula K-5 is reacted with a strong base such as lithium diisopropyl amide (LDA) followed by dimethylformamide (DMF) to provide the aldehyde of general formula K-8 which is be derived to secondary alcohol of general formula K-6 by treatment with a Grignard reagent of general formula R9MgX where X is Cl or Br and R9 is as defined above. The amide of general formula K-6 is reduced to the amine of general formula K-7 with a reducing agent such as diisobutyl aluminum hydride (DIBAL-H).

The aldehyde of general formula K-8 can be reduced to the primary alcohol of general formula K-9 with a mild reducing agent such sodium borohydride. The amide of general formula K-9 is then reduced to the amine of general formula K-10 with a stronger reducing agent such as diisobutyl aluminum hydride (DIBAL-H).

Process L:

This process is used for synthesizing the building blocks L-3, which corresponds to general formula B-2 of process B, where B=C(R4), R1=OR, R is (C1-C4)alkyl or (C0-C2)alkylene-(C3-C6)cycloalkyl wherein alkyl and alkylene are unsubstituted or mono, di- or trisubstituted by F, and where R2, R3 and R4 are as defined above.

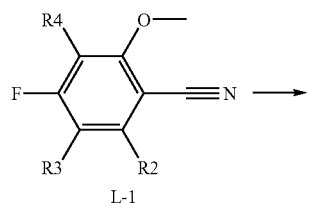

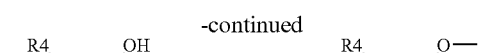

The aryl methyl ether of general formula L-1 where R2, R3 and R4 are as defined above, is demethylated by the treatment with aluminum trichloride in refluxing dichloroethane to give the phenol of general formula L-2. The phenol of general formula L-2 is reacted with an electrophile RX where X is a leaving group such as halide or a sulfonate in a polar solvent like dimethylformamide in the presence of a base like potassium carbonate to obtain a compound of general formula L-3. When methyl chlorodifluororacetate is used as electrophile and the reaction mixture is heated to 60-120° C. in a solvent such as dimethylformamide or dimethylacetamide, the compound of general formula L-3 where R is CHF2 is obtained.

Other compounds can be obtained accordingly or by known processes.

| | List of abbreviation: |
|---|---|
| Ac | acetyl |
| AIBN | 2,2'-Azobis(2-methylpropionitrile) |
| Bn | benzyl |
| iBu | isobutyl |
| tBu | tert-Butyl |
| BuLi | n-butyllithium |
| Bz | benzoyl |
| Cy | cyclohexyl |
| DBU | 1,8-Diazabicyclo[5.4.0]undec-7-ene |
| DCI | Direct chemical ionization (MS) |
| DCM | dichloromethane |
| DMAP | N,N-dimethylaminopyridine |
| DMF | N,N-dimethylformamide |
| DMSO | dimethylsulfoxide |
| EE | ethyl acetate |
| eq | equivalents |
| ESI | electrospray-Ionisation (MS) |
| FG | Leaving group |
| Hal | halogen |
| HPLC | High performance liquid chromatography |
| LC-MS | liquid chromatography coupled with mass-spectroscopy |
| Me | methyl |
| MS | mass-spectroscopy |
| MsCl | Methansulfonylchloride |
| NBS | N-Bromosuccinimide |
| NMR | Nuclear magnetic resonance |
| p | para |
| Pd/C | palladium on carbon |
| iPr | isopropyl |

-continued

List of abbreviation:

| | |
|---|---|
| nPr | n-propyl |
| Rf | retention factor (TLC) |
| tert | Tertiary |
| TBAF | Tetrabutyl ammonium fluoride |
| TFA | Trifluoroacetic acid |
| TLC | Thin layer chromatography |

Further compounds of the formula I can be prepared correspondingly or by known processes.

The experimental procedures for preparing the examples mentioned above are described below:

Building Block Synthesis According to Process B:

5-Chloromethyl-4-methyl-2-(1-methyl-cyclohexyl)-oxazole

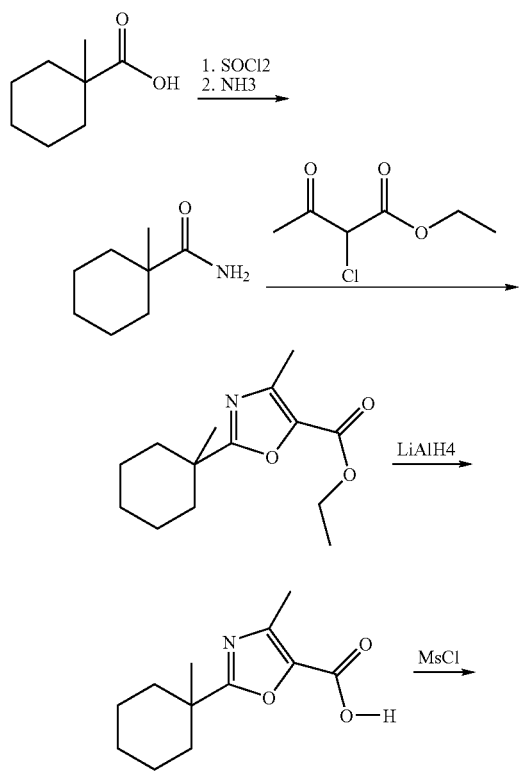

1-Methyl-cyclohexanecarboxylic acid amide

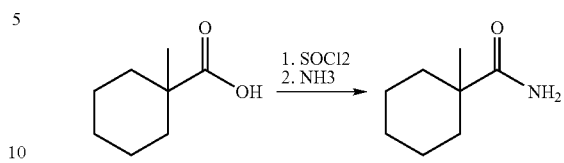

25.0 g 1-Methyl-cyclohexanecarboxylic acid was refluxed in 200 ml thionylchloride for three hours. The cooled reaction mixture was evaporated in vacuo. The residue was dissolved in 200 ml tetrahydrofuran and added dropwise to 300 ml of an ice cooled 33% ammonia solution. After completion of the addition the mixture was evaporated in vacuo, the residue dissolved in 200 ml water and extracted five times with portions of 200 ml of ethyl acetate. The combined organic layers were dried over MgSO4 and the solvent removed under reduced pressure to provide 25.0 g 1-Methyl-cyclohexanecarboxylic acid amide as an oil.

C8H15NO (141.21), MS (ESI): 142.2 (M+H+).

4-Methyl-2-(1-methyl-cyclohexyl)-oxazole-5-carboxylic acid ethyl ester

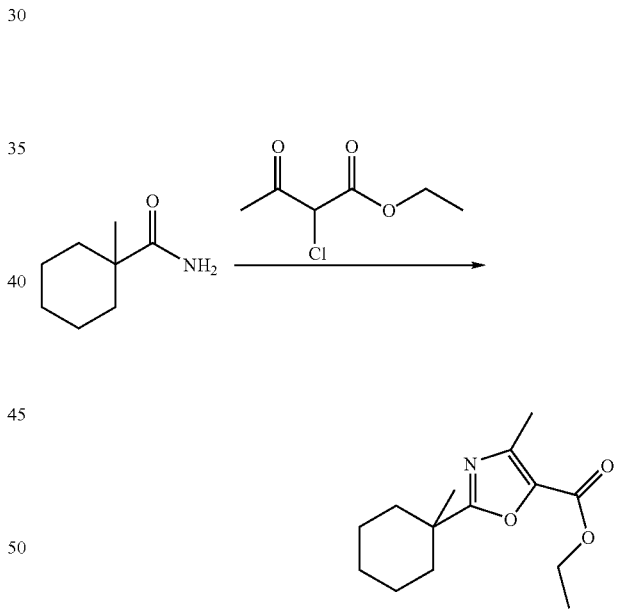

25.0 g 1-Methyl-cyclohexanecarboxylic acid amide was suspended in 40 ml ethanol and warmed to 50° C. At this temperature 29.0 ml Ethyl 2-chloroacetoacetate were added and the reaction mixture heated under reflux overnight. The cooled reaction mixture was evaporated under reduced pressure and the resulting residue was purified by chromatography with the eluent petroleum ether:ethyl acetate=4:1 to obtain 21.0 g 4-Methyl-2-(1-methyl-cyclohexyl)-oxazole-5-carboxylic acid ethyl ester as an oil which solidifies upon standing.

C14H21NO3 (251.33), MS (ESI): 252.2 (M+H+).

[4-Methyl-2-(1-methyl-cyclohexyl)-oxazol-5-yl]-methanol

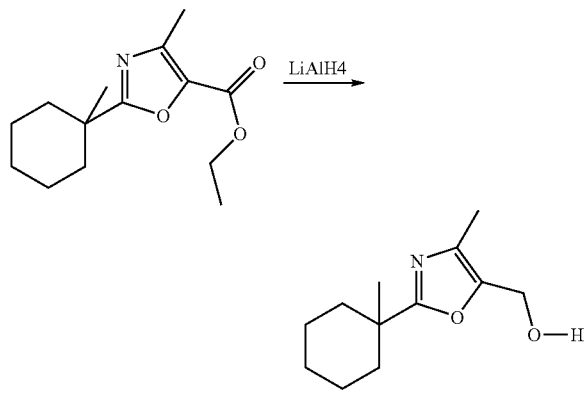

0.30 g Lithium aluminum hydride was dissolved in 10 ml dry tetrahydrofuran. 2.0 g 4-Methyl-2-(1-methyl-cyclohexyl)-oxazole-5-carboxylic acid ethyl ester, dissolved in 20 ml tetrahydrofuran, were added. The reaction mixture was stirred at room temperature over a period of one hour, then 50 ml ethyl acetate and 50 ml saturated ammonium chloride solution were added to the ice cooled mixture. The reaction mixture was extracted five times with portions of 60 ml of ethyl acetate. The combined organic layers were dried over MgSO4 and the solvent removed under reduced pressure to provide 1.54 g [4-Methyl-2-(1-methyl-cyclohexyl)-oxazol-5-yl]-methanol as an oil.

C12H19NO2 (209.29), MS (ESI): 210.2 (M+H+).

5-Chloromethyl-4-methyl-2-(1-methyl-cyclohexyl)-oxazole

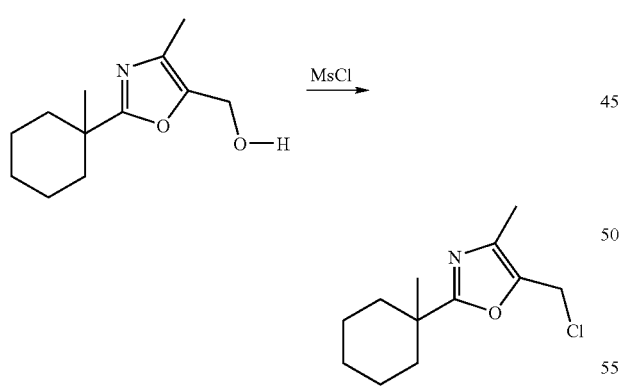

1.54 g [4-Methyl-2-(1-methyl-cyclohexyl)-oxazol-5-yl]-methanol were dissolved in 10 ml dichloromethane, 1.53 ml triethylamine and 0.68 ml methanesulfonyl chloride were added. The reaction mixture was stirred at room temperature overnight. Then 40 ml of dichloromethane were added and the reaction mixture washed with 50 ml water and 50 ml brine. The organic layer was dried over MgSO4 and the solvent removed under reduced pressure. This provided 1.68 g 5-Chloromethyl-4-methyl-2-(1-methyl-cyclohexyl)-oxazole as an oil.

C12H18ClNO (227.74), MS (ESI): 228.2 (M+H+), Rf (n-heptane:ethyl acetate=1:1)=0.73.

5-Chloromethyl-2-cyclohexyl-4-methyl-oxazole

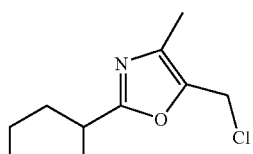

According to the method described for 5-Chloromethyl-4-methyl-2-(1-methyl-cyclohexyl)-oxazole, 5-Chloromethyl-2-cyclohexyl-4-methyl-oxazole was obtained from commercially available cyclohexanecarboxamide and Ethyl 2-chloroacetoacetate.

C11H16ClNO (213.71), MS (ESI): 214.1 (M+H+), Rf (n-heptane:ethyl acetate=1:1)=0.64.

5-Chloromethyl-4-methyl-2-(cis/trans-1,4-trifluoromethyl-cyclohexyl)-oxazole

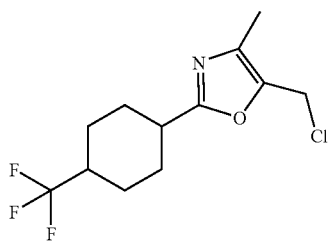

According to the method described for 5-Chloromethyl-4-methyl-2-(1-methyl-cyclohexyl)-oxazole, a mixture of cis and trans 5-Chloromethyl-4-methyl-2-(4-trifluoromethyl-cyclohexyl)-oxazole was obtained from commercially available cis/trans-4-(Trifluoromethyl)cyclohexanecarboxylic acid and Ethyl 2-chloroacetoacetate.

C12H15ClF3NO (281.71), MS (ESI): 282.1 (M+H+), Rf (n-heptane:ethyl acetate=1:1)=0.64.

5-Chloromethyl-2-(trans-1,4-methoxy-cyclohexyl)-4-methyl-oxazole

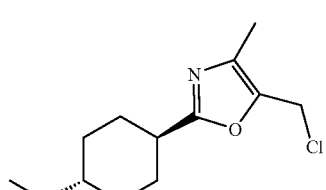

According to the method described for 5-Chloromethyl-4-methyl-2-(1-methyl-cyclohexyl)-oxazole, 5-Chloromethyl-2-(trans-1,4-methoxy-cyclohexyl)-4-methyl-oxazole was obtained from commercially available 4-Methoxycyclohexanecarboxylic acid and Ethyl 2-chloroacetoacetate.

C12H18ClNO2 (243.74), MS (ESI): 244.1 (M+H+), Rf (n-heptane:ethyl acetate=1:1)=0.31.

5-Chloromethyl-2-cyclohexyl-4-methyl-thiazole

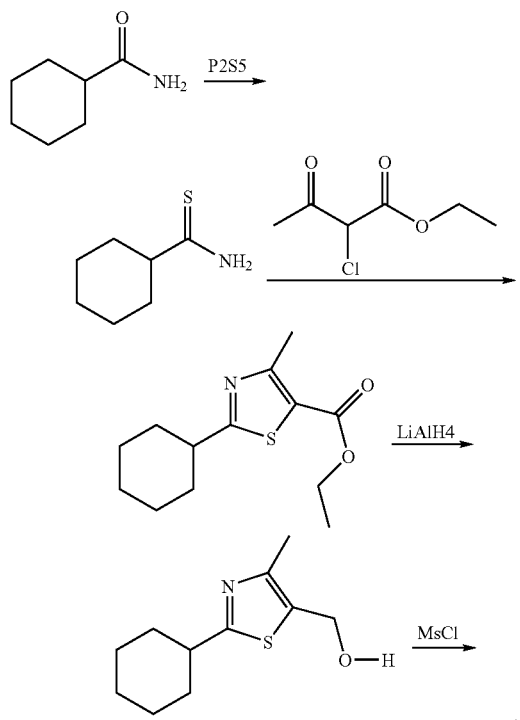

Cyclohexanecarbothioic acid amide

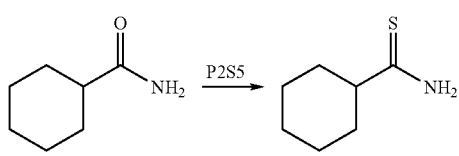

25.0 g Cyclohexanecarboxamide were dissolved in 200 ml toluene. 8.74 g phosphorus pentasulfide were added, followed by the addition of 33.0 g sodium bicarbonate. The reaction mixture was warmed to 115° C. and stirred overnight. The reaction mixture was filtered over a celite pad, washed with dichloromethane. The filtrate evaporated under reduced pressure. The residue was dissolved in 250 ml dichloromethane and the organic layer was washed three times with 100 ml water and twice with 100 ml brine. The aqueous layer was extracted five times with 100 ml dichloromethane. The combined organic layers were dried over MgSO4 and the solvent removed under reduced pressure. The resulting residue was purified by chromatography with the eluent dichloromethane:ethyl acetate=1:1 to obtain 7.92 g Cyclohexanecarbothioic acid amide as a yellow solid.

C7H13NS (143.25), MS (ESI): 144.2 (M+H+).

5-Chloromethyl-2-cyclohexyl-4-methyl-thiazole

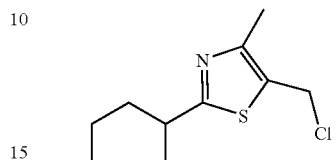

According to the method described for 5-Chloromethyl-4-methyl-2-(1-methyl-cyclohexyl)-oxazole, 5-Chloromethyl-2-cyclohexyl-4-methyl-thiazole was obtained from Cyclohexanecarbothioic acid amide and Ethyl 2-chloroacetoacetate.

C11H16ClNS (229.77), MS (ESI): 230.1 (M+H$^+$), Rf (n-heptane:ethyl acetate=1:1)=0.74.

4-(5-Chloromethyl-4-methyl-thiazol-2-yl)-piperidine-1-carboxylic acid tert-butyl ester

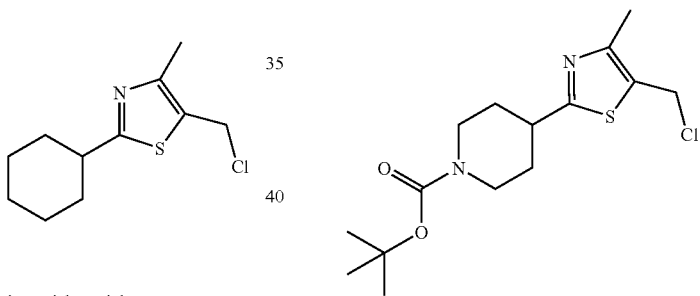

According to the method described for 5-Chloromethyl-4-methyl-2-(1-methyl-cyclohexyl)-oxazole, 4-(5-Chloromethyl-4-methyl-thiazol-2-yl)-piperidine-1-carboxylic acid tert-butyl ester was obtained from commercially available 4-Thiocarbamoyl-piperidine-1-carboxylic acid tert-butyl ester and Ethyl 2-chloroacetoacetate.

C15H23ClN2O2S (330.88), MS (ESI): 331.1 (M+H$^+$).

1-Phenyl-piperidine-4-carboxylic acid amide

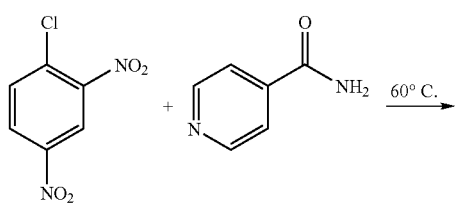

4-Carbamoyl-1-(2,4-dinitro-phenyl)-pyridinium hydrochloride

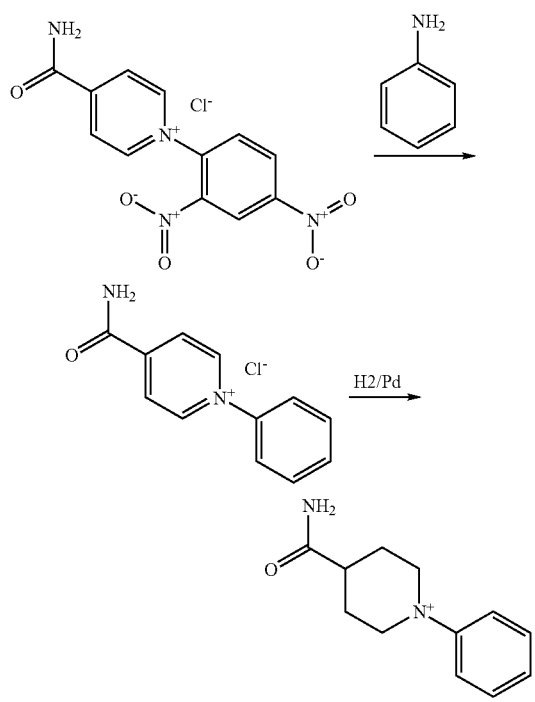

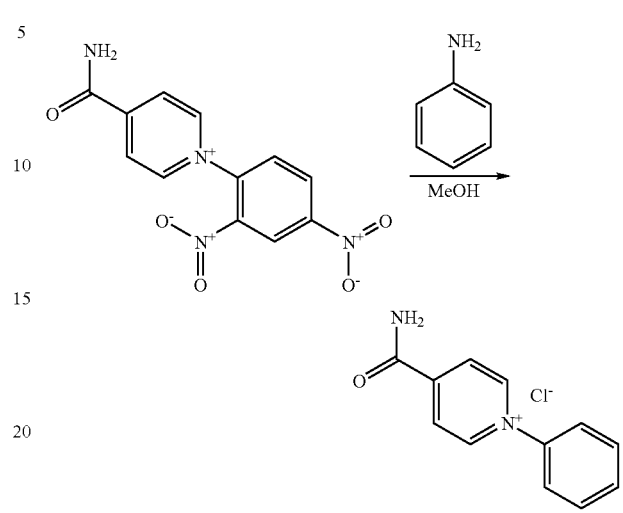

A mixture of 113.4 g 1-chloro-2,4-dinitrobenzene and 57.0 g isonicotinamide were stirred at 105° C. for one hour and thirty minutes. The cooled reaction mixture was diluted by the addition of 300 ml methanol. The suspension was warmed and filtered. The insoluble residue was washed with methanol, collected and dried in vacuo to obtain 99.4 g 4-Carbamoyl-1-(2,4-dinitro-phenyl)-pyridinium as hydrochloride salt as white solid.

C12H9N4O5. Cl (324.68).

4-Carbamoyl-1-phenyl-pyridinium hydrochloride

A suspension of 30.0 g 4-Carbamoyl-1-(2,4-dinitro-phenyl)-pyridinium hydrochloride and 22.4 g aniline in 600 ml methanol was stirred at room temperature for four days. The suspension was warmed to 55° C. and stirred at this temperature for one hour. The resulting solution was cooled and the solvent removed in vacuo. The resulting residue was suspended in 300 ml propan-2-one and stirred at room temperature. The insoluble residue was filtered and dried in vacuo to obtain 27.3 g 4-Carbamoyl-1-phenyl-pyridinium hydrochloride.

C12H11N2O. Cl (234.69), MS (ESI): 199.1 (M+H$^+$).

1-Phenyl-piperidine-4-carboxylic acid amide

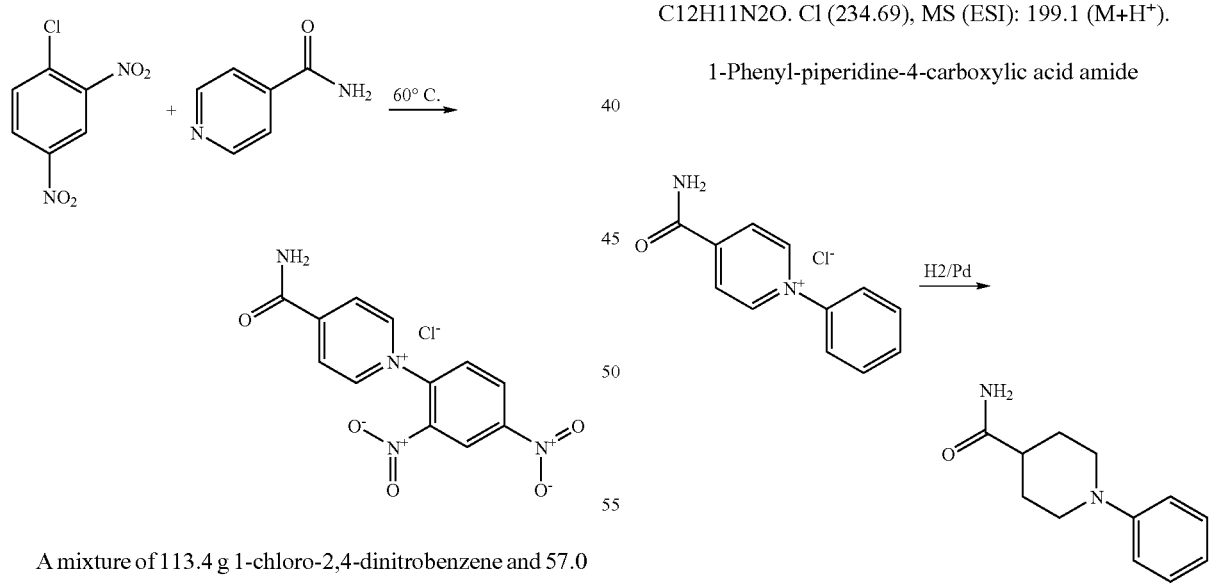

2.0 g palladium on charcoal (10%) were added to a solution of 22.7 g 4-Carbamoyl-1-phenyl-pyridinium hydrochloride in 500 ml ethanol EtOH. The reaction mixture was stirred at room temperature under an atmosphere of hydrogen at 3 bar for one hour. The catalyst was filtered off through a pad of celite and washed with ethanol. The filtrate was evaporated in vacuo. The resulting residue was purified by flash chromatography on silica gel with the eluent ethyl acetate:methanol=9:1=>4:1 to obtain 6.9 g 1-Phenyl-piperidine-4-carboxylic acid amide as a solid.

C12H16N2O (204.27), MS (ESI): 205.0 (M+H⁺).

4-(5-Chloromethyl-4-methyl-thiazol-2-yl)-1-phenyl-piperidine

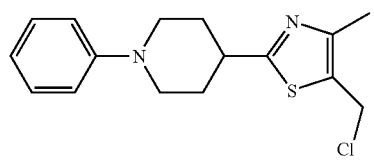

According to the method described for 5-Chloromethyl-4-methyl-2-(1-methyl-cyclohexyl)-oxazole, 4-(5-Chloromethyl-4-methyl-thiazol-2-yl)-1-phenyl-piperidine was obtained from 1-Phenyl-piperidine-4-carboxylic acid amide and Ethyl 2-chloroacetoacetate.

C16H19ClN2S (306.86), MS (ESI): 307.0 (M+H+).

5-Chloromethyl-2-(4,4-difluoro-cyclohexyl)-4-methoxymethyl-thiazole

2-Chloro-4-methoxy-3-oxo-butyric acid methyl ester

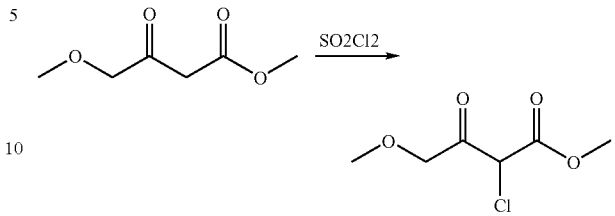

46.0 g Methyl 4-methoxyacetoacetate were dissolved in 500 ml dichloromethane. 28.1 ml Sulfuryl chloride were added in one portion. The reaction mixture was stirred overnight at room temperature. The solvent was removed under reduced pressure, the resulting residue was dissolved in 300 ml ethyl acetate and washed with 100 ml water and 100 ml brine. The organic layer was dried over MgSO4 and the solvent removed under reduced pressure. The resulting residue was purified by chromatography on silica gel with the eluent n-heptane:ethyl acetate=5:1=>2:1 to obtain 45.0 g 2-Chloro-4-methoxy-3-oxo-butyric acid methyl ester as a yellow oil.

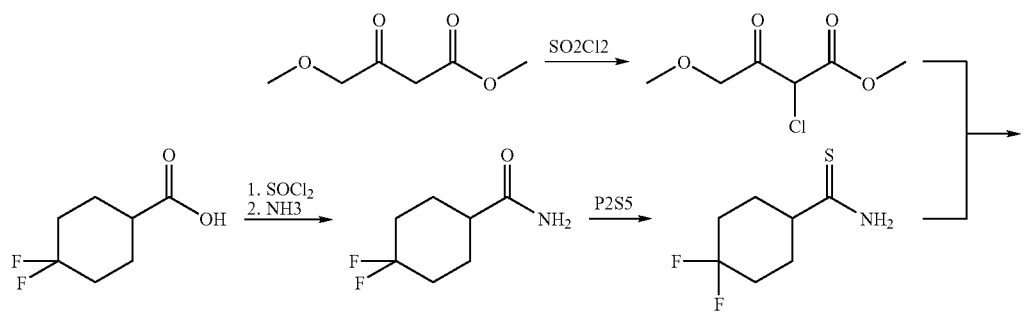

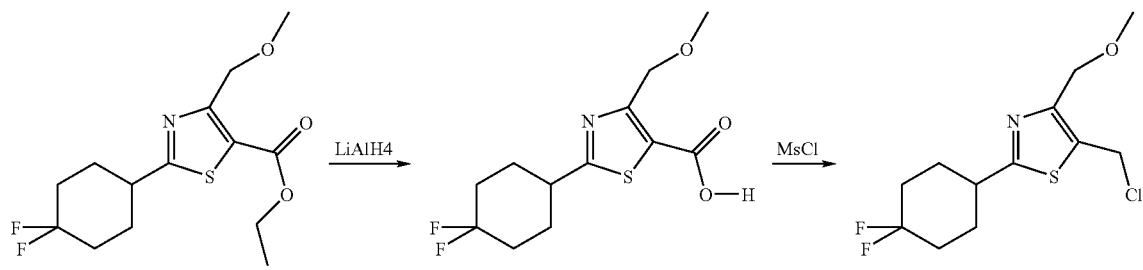

107

C6H9ClO4 (180.59), MS (ESI): 181.2 (M+H+), Rf (n-heptane:ethyl acetate=2:1)=0.31

4,4-Difluoro-cyclohexanecarbothioic acid amide

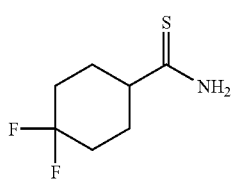

According to the method described for 1-Methyl-cyclohexanecarboxylic acid amide and Cyclohexanecarbothioic acid amide 4,4-Difluoro-cyclohexanecarbothioic acid amide was obtained from commercially available 4,4-Difluoro-cyclohexanecarboxylic acid.

C7H11F2NS (179.23), MS (ESI): 180.1 (M+H+).

2-(4,4-Difluoro-cyclohexyl)-4-methoxymethyl-thiazole-5-carboxylic acid methyl ester

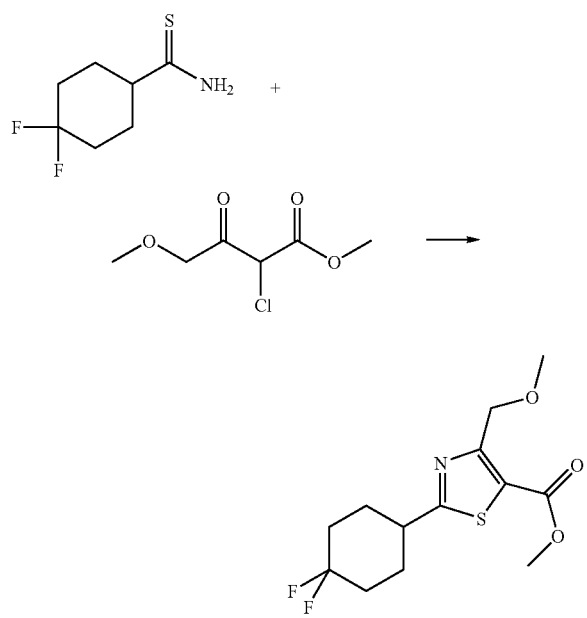

7.0 g 4,4-Difluoro-cyclohexanecarbothioic acid amide and 8.46 g 2-Chloro-4-methoxy-3-oxo-butyric acid methyl ester were dissolved in 70 ml ethanol and heated under reflux overnight. The cooled reaction mixture was evaporated under reduced pressure and the resulting residue was purified by silica chromatography with the eluent n-heptane:ethyl acetate=4:1=>2:1 to obtain 4.0 g 2-(4,4-Difluoro-cyclohexyl)-4-methoxymethyl-thiazole-5-carboxylic acid methyl ester as an oil.

C13H17F2NO3S (305.35), MS (ESI): 306.2 (M+H+),+), Rf (n-heptane:ethyl acetate=4:1)=0.14.

108

5-Chloromethyl-2-(4,4-difluoro-cyclohexyl)-4-methoxymethyl-thiazole

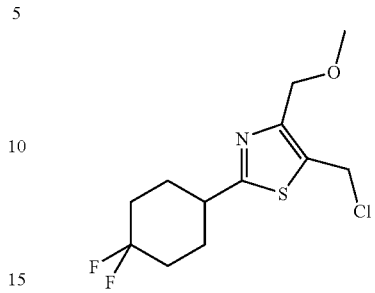

According to the method described for 5-Chloromethyl-4-methyl-2-(1-methyl-cyclohexyl)-oxazole, 5-Chloromethyl-2-(4,4-difluoro-cyclohexyl)-4-methoxymethyl-thiazole was obtained from 2-(4,4-Difluoro-cyclohexyl)-4-methoxymethyl-thiazole-5-carboxylic acid methyl ester.

C12H16ClF2NOS (295.78), MS (ESI): 296.2 (M+H+), Rf (n-heptane:ethyl acetate=1:1)=0.60.

5-Chloromethyl-2-(2-cyclohexyl-ethyl)-4-methoxymethyl-thiazole

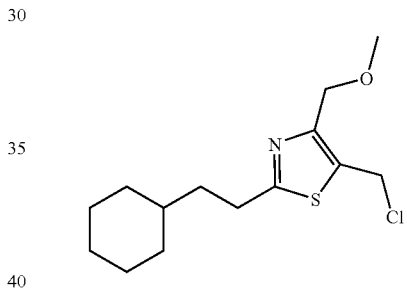

According to the method described for 5-Chloromethyl-4-methyl-2-(1-methyl-cyclohexyl)-oxazole and 5-Chloromethyl-2-(4,4-difluoro-cyclohexyl)-4-methoxymethyl-thiazole, 5-Chloromethyl-2-(2-cyclohexyl-ethyl)-4-methoxymethyl-thiazole was obtained from 2-Chloro-4-methoxy-3-oxo-butyric acid methyl ester and 3-Cyclohexyl-propionic acid.

C14H22ClNOS (287.85), MS (ESI): 288.0 (M+H+).

5-Chloromethyl-2-cycloheptyl-4-methoxymethyl-thiazole

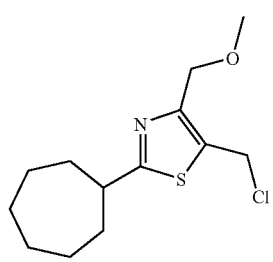

According to the method described for 5-Chloromethyl-4-methyl-2-(1-methyl-cyclohexyl)-oxazole and 5-Chloromethyl-2-(4,4-difluoro-cyclohexyl)-4-methoxymethyl-thiazole, 5-Chloromethyl-2-cycloheptyl-4-methoxymethyl-thiazole was obtained from 2-Chloro-4-methoxy-3-oxo-butyric acid methyl ester and Cycloheptanecarboxylic acid.

C13H20ClNOS (273.83), MS (ESI): 274.0 (M+H+), Rf (n-heptane:ethyl acetate=1:1)=0.71.

5-Chloromethyl-2-[trans-1,4-(4-chloro-phenyl)-cyclohexyl]-4-methoxymethyl-thiazole

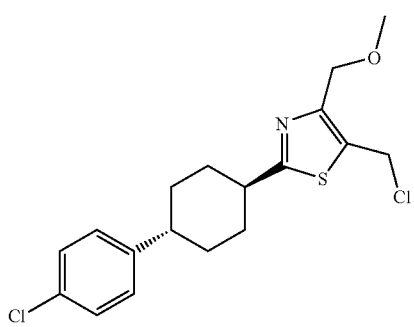

According to the method described for 5-Chloromethyl-4-methyl-2-(1-methyl-cyclohexyl)-oxazole and 5-Chloromethyl-2-(4,4-difluoro-cyclohexyl)-4-methoxymethyl-thiazole, 5-Chloromethyl-2-[trans-1,4-(4-chloro-phenyl)-cyclohexyl]-4-methoxymethyl-thiazole was obtained from 2-Chloro-4-methoxy-3-oxo-butyric acid methyl ester and 4-(4-Chloro-phenyl)-cyclohexanecarboxylic acid.

C18H21Cl2NOS (370.34), MS (ESI): 370.0 (M+H+), Rf (n-heptane:ethyl acetate=1:1)=0.68.

5-Chloromethyl-2-cyclopentyl-4-methoxymethyl-oxazole

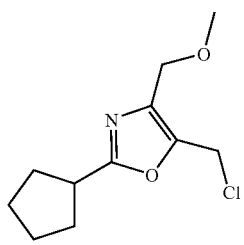

According to the method described for 5-Chloromethyl-4-methyl-2-(1-methyl-cyclohexyl)-oxazole and 5-Chloromethyl-2-(4,4-difluoro-cyclohexyl)-4-methoxymethyl-thiazole, 5-Chloromethyl-2-cyclopentyl-4-methoxymethyl-oxazole was obtained from 2-Chloro-4-methoxy-3-oxo-butyric acid methyl ester and Cyclopentanecarboxylic acid.

C11H16ClNO2 (229.71), MS (ESI): 230.1 (M+H+).

4-Methoxymethyl-2-(6-trifluoromethyl-pyridin-3-yl)-thiazole-5-carboxylic acid methyl ester 10.5 g 6-Trifluoromethyl-thionicotinamide (derived from 6-Trifluoromethyl-nicotinic acid according to the method described for 5-Chloromethyl-4-methyl-2-(1-methyl-cyclohexyl)-oxazole and 5-Chloromethyl-2-(4,4-difluoro-cyclohexyl)-4-methoxymethyl-thiazole) and 10.0 g 2-Chloro-4-methoxy-3-oxo-butyric acid methyl ester were dissolved in 100 ml ethanol and heated under reflux overnight. The cooled reaction mixture was evaporated under reduced pressure and the resulting residue was purified by RP-HPLC to obtain 1.9 g 4-Methoxymethyl-2-(6-trifluoromethyl-pyridin-3-yl)-thiazole-5-carboxylic acid methyl ester.

C13H11F3N2O3S (332.30), MS (ESI): 333.0 (M+H+).

5-(5-Chloromethyl-4-methoxymethyl-thiazol-2-yl)-2-trifluoromethyl-pyridine

According to the method described for 5-Chloromethyl-4-methyl-2-(1-methyl-cyclohexyl)-oxazole and, 5-(5-Chloromethyl-4-methoxymethyl-thiazol-2-yl)-2-trifluoromethyl-pyridine was obtained from 4-Methoxymethyl-2-(6-trifluoromethyl-pyridin-3-yl)-thiazole-5-carboxylic acid methyl ester.

C12H10ClF3N2OS (322.74), MS (ESI): 322.9 (M+H+).

111

[4-Methyl-2-(6-trifluoromethyl-pyridin-3-yl)-thiazol-5-yl]-methanol

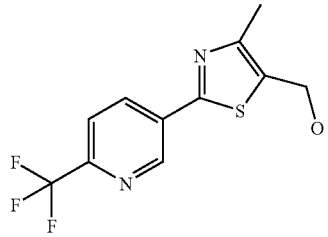

According to the method described for [4-Methyl-2-(1-methyl-cyclohexyl)-oxazol-5-yl]-methanol, [4-Methyl-2-(6-trifluoromethyl-pyridin-3-yl)-thiazol-5-yl]-methanol was obtained from 6-Trifluoromethyl-thionicotinamide (derived from 6-(Trifluoromethyl)nicotinamide according to the method described for and Cyclohexanecarbothioic acid amide) and Ethyl 2-chloroacetoacetate.

C11H9F3N2OS (274.27), MS (ESI): 275.1 (M+H+).

[4-(3-Benzyloxy-propyl)-2-(6-trifluoromethyl-pyridin-3-yl)-thiazol-5-yl]-methanol

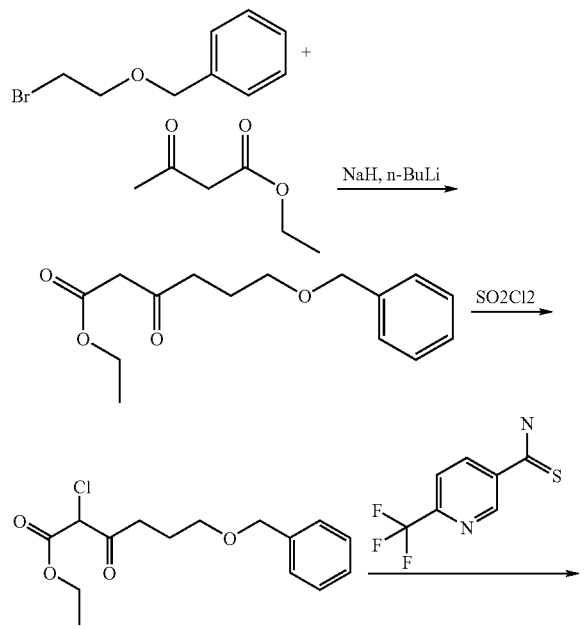

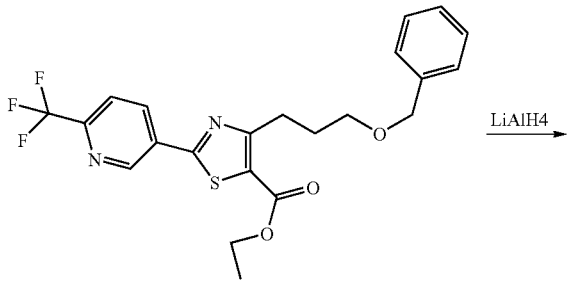

112

-continued

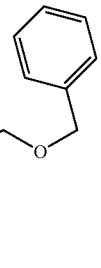

6-Benzyloxy-3-oxo-hexanoic acid ethyl ester

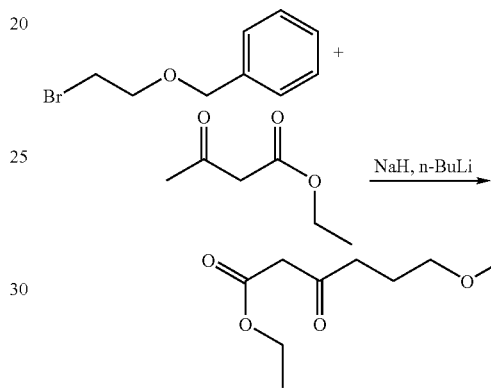

To a stirred suspension of 2.44 g sodium hydride (55% in oil) in 80 ml tetrahydrofuran were added 7.0 ml ethyl acetoacetate dissolved in 25 ml tetrahydrofuran at −40° C. The resulting mixture was stirred at −20° C. for thirty minutes. The reaction mixture became clear. Then 22.0 ml n-butyllithium (2.5 M in n-heptane) were added and the reaction mixture was stirred at 0° C. for fifteen minutes. Then 7.3 ml benzyl 2-bromoethylether, dissolved in 25 ml tetrahydrofuran, were added. The reaction mixture was stirred at 0° C. for two hours and then at room temperature overnight.

200 ml saturated NH4Cl solution was added and the mixture extracted three times with portions of 150 ml ethyl acetate. The combined organic layers were washed with water, dried over MgSO4 and then the solvent was evaporated in vacuo to obtain 13.9 g of crude 6-Benzyloxy-3-oxo-hexanoic acid ethyl ester as a yellow oil. This material was used in the next step without purification.

C15H20O4 (264.32), Rf (n-heptane:ethyl acetate=4:1) =0.23.

6-Benzyloxy-2-chloro-3-oxo-hexanoic acid ethyl ester

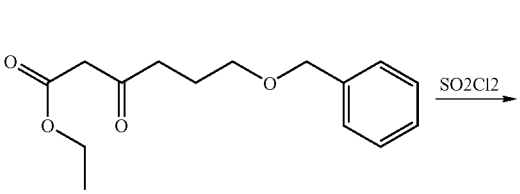

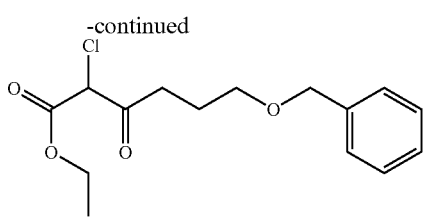

To a stirred solution of 13.9 g of crude 6-Benzyloxy-3-oxo-hexanoic acid ethyl ester in 50 ml dichloromethane were added dropwise 4.3 ml sulfuryl chloride. The reaction mixture was stirred at 0° C. and then at room temperature for thirty minutes. The reaction mixture was poured on ice and extracted three times with portions of 150 ml dichloromethane. The combined organic layers were washed with water, dried over MgSO4 and then the solvent was evaporated in vacuo to obtain 14.9 g of crude 6-Benzyloxy-2-chloro-3-oxo-hexanoic acid ethyl ester as a yellow oil.

C15H19ClO4 (298.77), Rf (n-heptane:ethyl acetate=9:1) =0.16.

[4-(3-Benzyloxy-propyl)-2-(6-trifluoromethyl-pyridin-3-yl)-thiazol-5-yl]-methanol

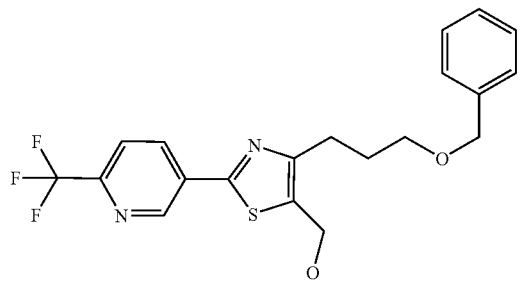

According to the method described for [4-Methyl-2-(1-methyl-cyclohexyl)-oxazol-5-yl]-methanol, [4-(3-Benzyloxy-propyl)-2-(6-trifluoromethyl-pyridin-3-yl)-thiazol-5-yl]-methanol was obtained from 6-Trifluoromethyl-thionicotinamide (derived from 6-(Trifluoromethyl) nicotinamide according to the method described for and Cyclohexanecarbothioic acid amide) and 6-Benzyloxy-2-chloro-3-oxo-hexanoic acid ethyl ester.

C20H19F3N2O2S (408.45), MS (ESI): 409.2 (M+H+).

5-Chloromethyl-2-(2-cyclohexyl-vinyl)-4-methoxymethyl-thiazole

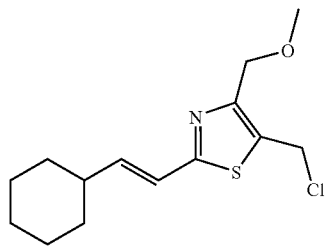

According to the method described for 5-Chloromethyl-4-methyl-2-(1-methyl-cyclohexyl)-oxazole and 5-Chloromethyl-2-(4,4-difluoro-cyclohexyl)-4-methoxymethyl-thiazole, 5-Chloromethyl-2-(2-cyclohexyl-vinyl)-4-methoxymethyl-thiazole was obtained from 2-Chloro-4-methoxy-3-oxo-butyric acid methyl ester and 3-cyclohexyl-acrylic acid.

C14H20ClNOS (285.84), MS (ESI): 286.1 (M+H+).

[4-Methyl-2-(trans-1,4-trifluoromethyl-cyclohexyl)-thiazol-5-yl]-methanol

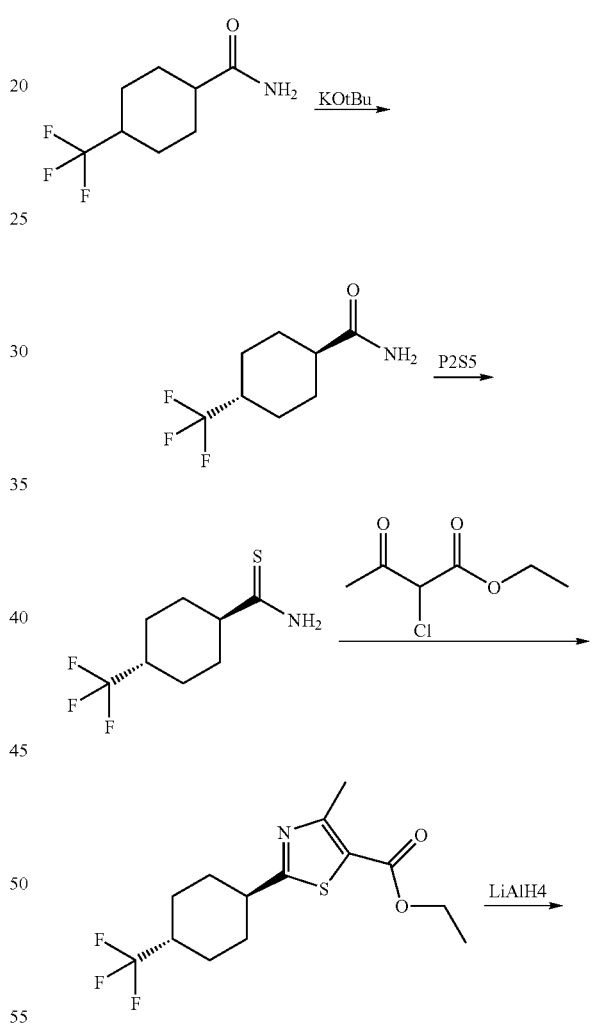

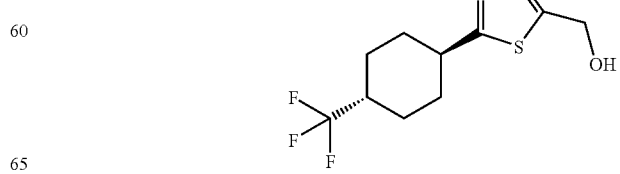

115 trans-1,4-Trifluoromethyl-cyclohexanecarboxylic acid amide

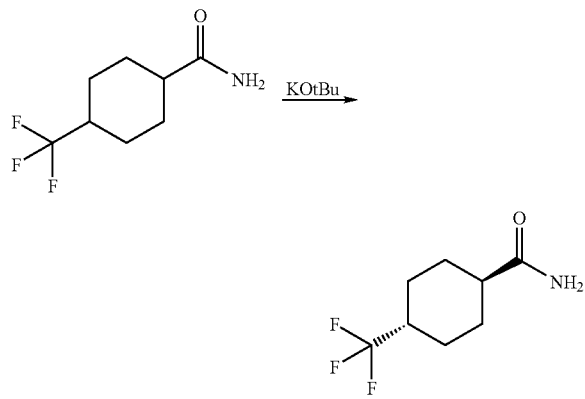

14.0 g 4-Trifluoromethyl-cyclohexanecarboxylic acid amide (mixture of cis and trans, obtained from commercially available 4-(trifluoromethyl)cyclohexylcarboxylic acid according to the method described for 1-Methyl-cyclohexanecarboxylic acid amide) was dissolved in 140 ml methanol and separated in 10 portions. To each portion was added 2.4 g potassium tert.-butoxide and each mixture heated under microwave irradiation at 90° C. for thirty minutes. The portions were then combined, the solvent evaporated in vacuo and the residue dissolved in 100 ml ethyl acetate and 100 ml water. The aqueous phase was extracted three times with portions of 100 ml ethyl acetate. The combined organic layers were dried over MgSO4. The solvent was removed in vacuo to obtain 12.68 g trans-1,4-Trifluoromethyl-cyclohexanecarboxylic acid amide as a solid.

=C8H12F3NO (195.19), MS (ESI): 196.2 (M+H+).

[4-Methyl-2-(trans-1,4-trifluoromethyl-cyclohexyl)-thiazol-5-yl]-methanol

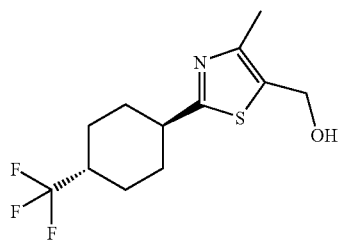

According to the method described for [4-Methyl-2-(1-methyl-cyclohexyl)-oxazol-5-yl]-methanol, [4-Methyl-2-(trans-1,4-trifluoromethyl-cyclohexyl)-thiazol-5-yl]-methanol was obtained from trans-1,4-Trifluoromethyl-cyclohexanecarbothioic acid amide (derived from trans-1,4-Trifluoromethyl-cyclohexanecarboxylic acid amide according to the method described for Cyclohexanecarbothioic acid amide) and Ethyl 2-chloroacetoacetate.

C12H16F3NOS (279.33), MS (ESI): 280.1 (M+H+).

116

[4-Methyl-2-(4-trifluoromethyl-cyclohexyl)-oxazol-5-yl]-methanol

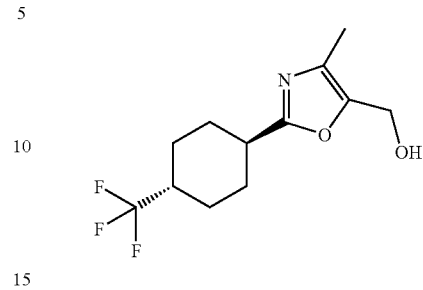

According to the method described for [4-methyl-2-(1-methyl-cyclohexyl)-oxazol-5-yl]-methanol, [4-methyl-2-(4-trifluoromethyl-cyclohexyl)-oxazol-5-yl]-methanol was obtained from trans-1,4-trifluoromethyl-cyclohexanecarboxylic acid amide and ethyl 2-chloroacetoacetate.

C12H16F3NO2 (263.26), MS (ESI): 264.2 (M+H+).

Building Block Synthesis According to Process C:

5-Chloromethyl-2-cyclohexyl-4-ethoxymethyl-oxazole

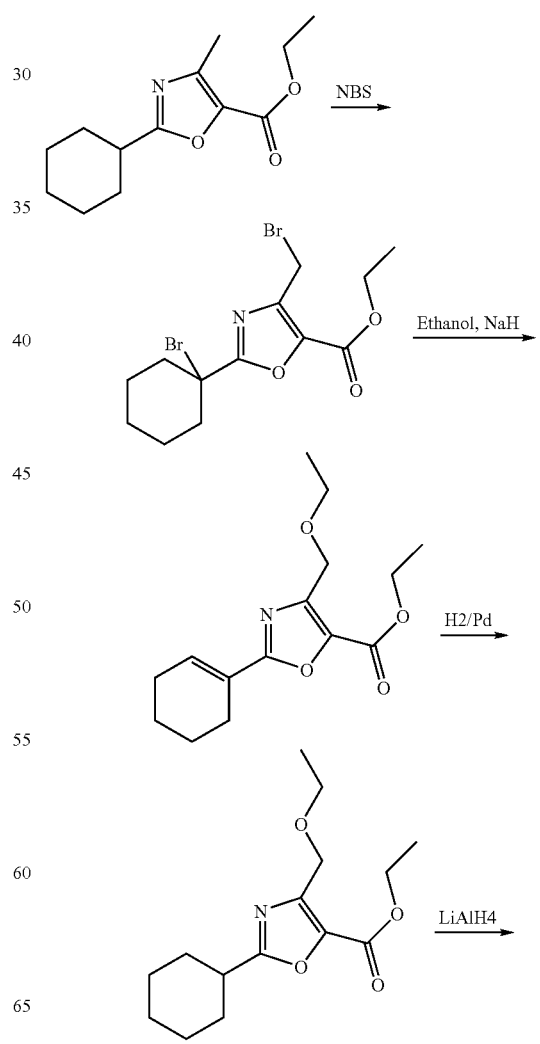

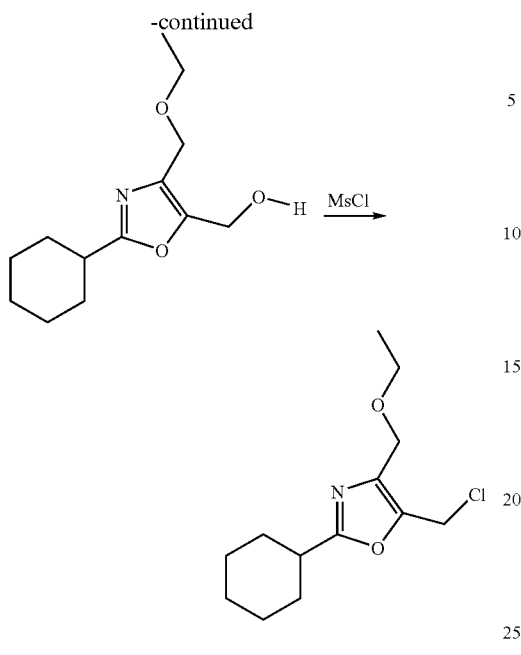

2-(1-Bromo-cyclohexyl)-4-bromomethyl-oxazole-5-carboxylic acid ethyl ester

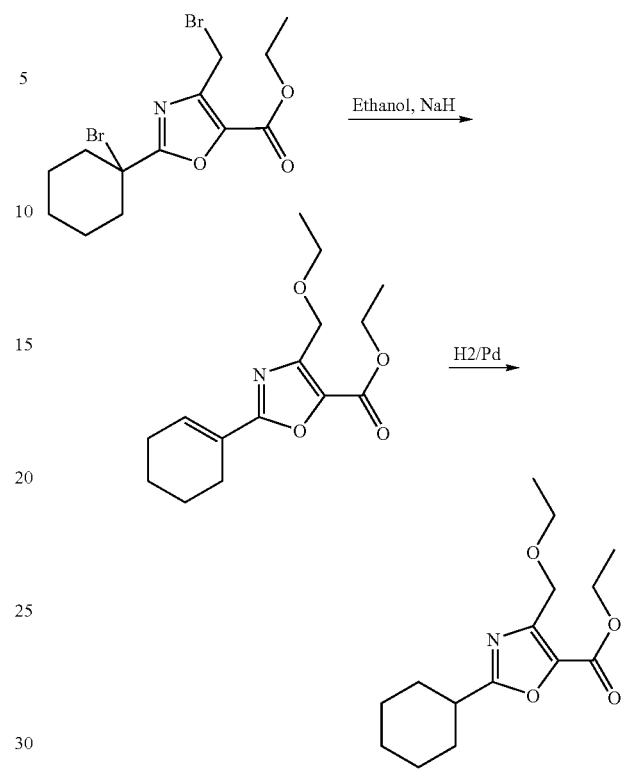

2-Cyclohexyl-4-ethoxymethyl-oxazole-5-carboxylic acid ethyl ester

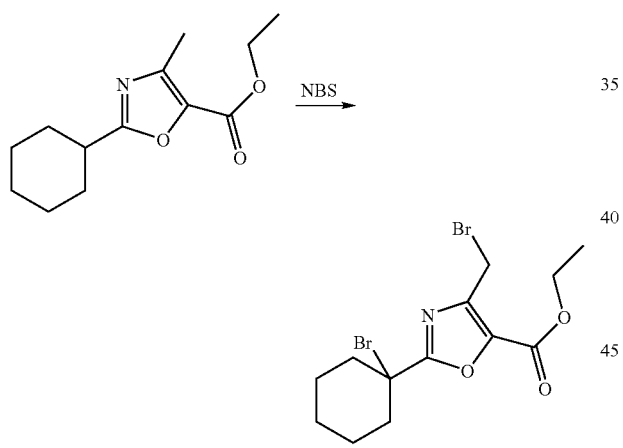

To a refluxing mixture of 5.0 g 2-Cyclohexyl-4-methyl-oxazole-5-carboxylic acid ethyl ester (derived from commercially available cyclohexanecarboxamide and Ethyl 2-chloroacetoacetate according to the method described for 5-Chloromethyl-4-methyl-2-(1-methyl-cyclohexyl)-oxazole) in 150 ml tetrachloro-methane were added portionwise a mixture of 9.38 g N-bromosuccinimide and 2.77 g 2,2'-Azobis(2-methylpropionitrile). The reaction mixture was heated under reflux for three hours. The cooled reaction mixture was filtered over a celite pad, the filtrate was evaporated in vacuo and the resulting residue was purified by chromatography on silica gel with the eluent n-heptane:ethyl acetate=20:1=>5:1 to provide 5.0 g 2-(1-Bromo-cyclohexyl)-4-bromomethyl-oxazole-5-carboxylic acid ethyl ester as an oil.

C13H17Br2NO3 (395.09), MS (ESI): 394.0, 396.0, 397.9 (M+H+), Rf (n-heptane:ethyl acetate=2:1)=0.50.

1.25 g 2-(1-Bromo-cyclohexyl)-4-bromomethyl-oxazole-5-carboxylic acid ethyl ester was dissolved in 15 ml ethanol. 176 mg sodium hydride were added and the reaction mixture stirred at 65° C. for one hour. The cooled reaction mixture was neutralized by the addition of acetic acid (pH~6). 50 mg palladium on charcoal (10%) were added and the reaction mixture was stirred under an atmosphere of hydrogen for one hour. The catalyst was filtered off through a pad of celite, the filtrate was evaporated in vacuo and the resulting crude material was purified by reversed phase HPLC to obtain 370 mg 2-Cyclohexyl-4-ethoxymethyl-oxazole-5-carboxylic acid ethyl ester as an oil.

C15H23NO4 (281.35), MS (ESI): 282.2 (M+H+).

5-Chloromethyl-2-cyclohexyl-4-ethoxymethyl-oxazole

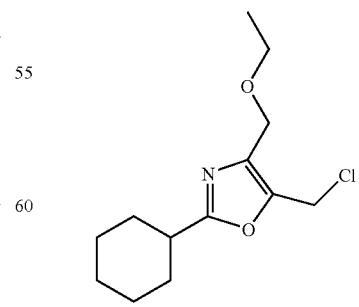

According to the method described for 5-Chloromethyl-4-methyl-2-(1-methyl-cyclohexyl)-oxazole, 5-Chloromethyl- 2-cyclohexyl-4-ethoxymethyl-oxazole was obtained from 2-Cyclohexyl-4-ethoxymethyl-oxazole-5-carboxylic acid ethyl ester.

C13H20ClNO2 (257.76), MS (ESI): 258.2 (M+H+).

5-Chloromethyl-2-cyclohexyl-4-methoxymethyl-oxazole

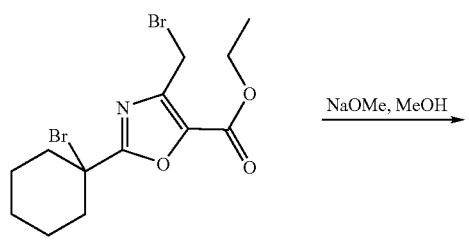

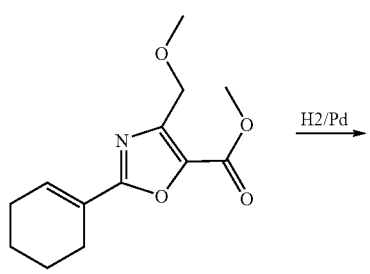

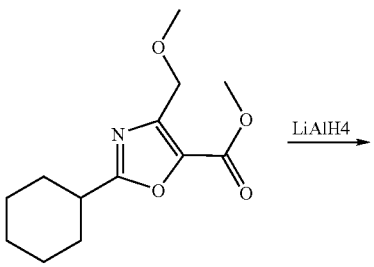

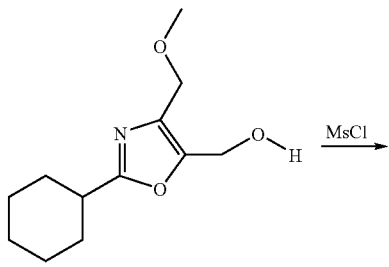

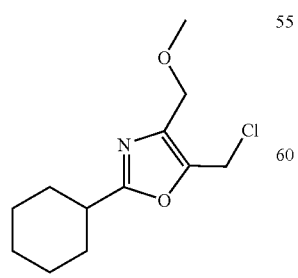

2-Cyclohex-1-enyl-4-methoxymethyl-oxazole-5-carboxylic acid methyl ester

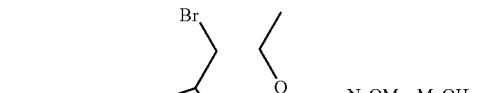

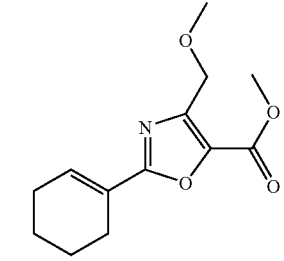

14.7 g 2-(1-Bromo-cyclohexyl)-4-bromomethyl-oxazole-5-carboxylic acid ethyl ester were dissolved in 150 ml methanol. 6.03 g sodium methylate were added and the reaction mixture stirred at 65° C. for one hour. The cooled reaction mixture was acidified by addition of acetic acid (pH~6). The solvent was removed in vacuo. The residue was dissolved in 250 ml ethyl acetate and washed with 80 ml water and brine, dried over MgSO4 and then the solvent was removed in vacuo. The residue was purified by reversed phase HPLC to obtain 5.30 g 2-Cyclohex-1-enyl-4-methoxymethyl-oxazole-5-carboxylic acid methyl ester as an oil.

C13H17NO4 (251.28), MS (ESI): 252.2 (M+H+), Rf (n-heptane:ethyl acetate=4:1)=0.14.

2-Cyclohexyl-4-methoxymethyl-oxazole-5-carboxylic acid methyl ester

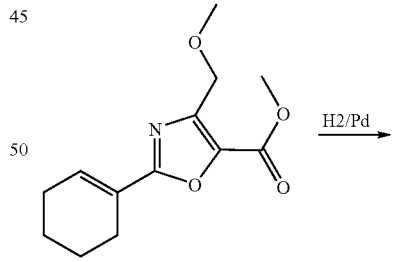

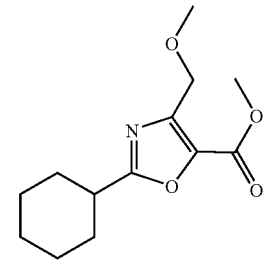

5.30 g 2-Cyclohex-1-enyl-4-methoxymethyl-oxazole-5-carboxylic acid methyl ester were dissolved in 40 ml methanol. 500 mg palladium on charcoal (10%) were added and the reaction mixture was stirred under an atmosphere of hydrogen overnight. The catalyst was filtered off through a pad of celite, the filtrate was evaporated in vacuo to obtain 4.70 g 2-Cyclohexyl-4-methoxymethyl-oxazole-5-carboxylic acid methyl ester as an oil.

C13H19NO4 (253.30), MS (ESI): 254.3 (M+H+).

5-Chloromethyl-2-cyclohexyl-4-methoxymethyl-oxazole

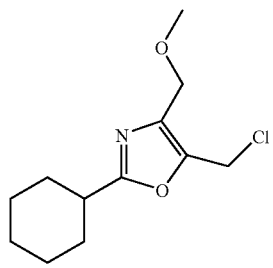

According to the method described for 5-Chloromethyl-4-methyl-2-(1-methyl-cyclohexyl)-oxazole, 5-Chloromethyl-2-cyclohexyl-4-methoxymethyl-oxazole was obtained from 2-Cyclohexyl-4-methoxymethyl-oxazole-5-carboxylic acid methyl ester.

C12H18ClNO2 (243.74), MS (ESI): 245.2 (M+H+), Rf (n-heptane:ethyl acetate=1:1)=0.69.

5-Chloromethyl-2-cycloheptyl-4-methoxymethyl-oxazole

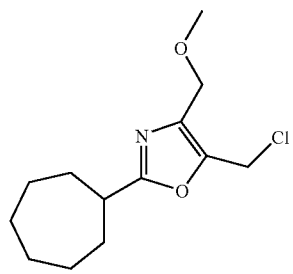

According to the method described for 5-Chloromethyl-2-cyclohexyl-4-methoxymethyl-oxazole, 5-Chloromethyl-2-cycloheptyl-4-methoxymethyl-oxazole was obtained from 2-Cycloheptyl-4-methyl-oxazole-5-carboxylic acid ethyl ester (derived from commercially available cycloheptanecarboxylic acid and Ethyl 2-chloroacetoacetate according to the method described for 5-Chloromethyl-4-methyl-2-(1-methyl-cyclohexyl)-oxazole).

C13H20ClNO2 (257.76), MS (ESI): 258.2 (M+H+).

Cis/trans-5-Chloromethyl-4-methoxymethyl-2-(4-trifluoromethyl-cyclohexyl)-oxazole

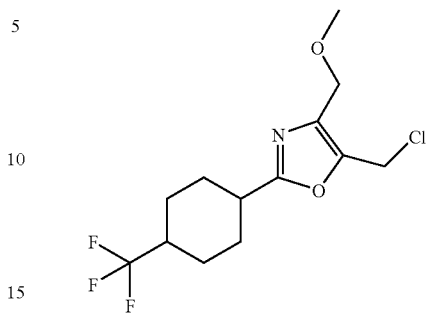

According to the method described for 5-Chloromethyl-2-cyclohexyl-4-methoxymethyl-oxazole, a mixture of cis and trans 5-Chloromethyl-4-methoxymethyl-2-(4-trifluoromethyl-cyclohexyl)-oxazole was obtained from cis/trans-4-Methyl-2-(4-trifluoromethyl-cyclohexyl)-oxazole-5-carboxylic acid ethyl ester (derived from commercially available 4-Trifluoromethyl-cyclohexanecarboxylic acid and Ethyl 2-chloroacetoacetate according to the method described for 5-Chloromethyl-4-methyl-2-(1-methyl-cyclohexyl)-oxazole).

C13H17ClF3NO2 (311.73), MS (ESI): 312.1 (M+H+).

4-(5-Chloromethyl-2-cyclohexyl-oxazol-4-ylmethyl)-morpholine

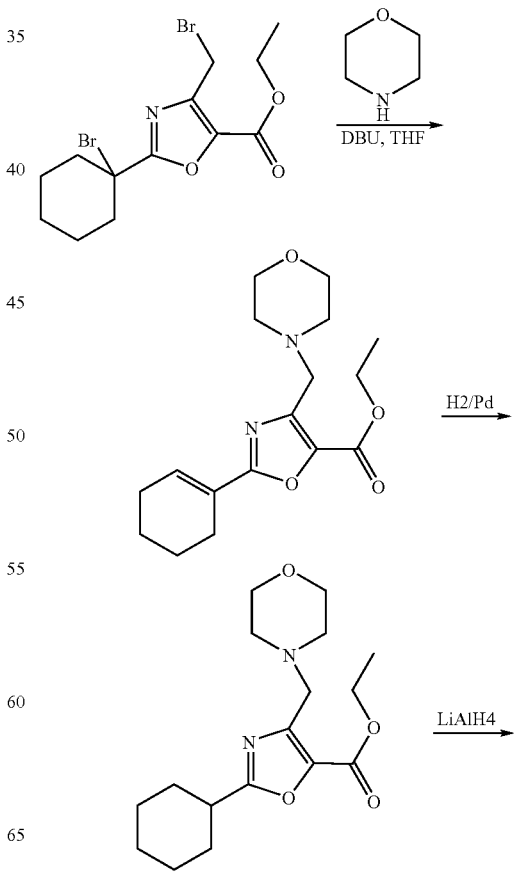

123

-continued

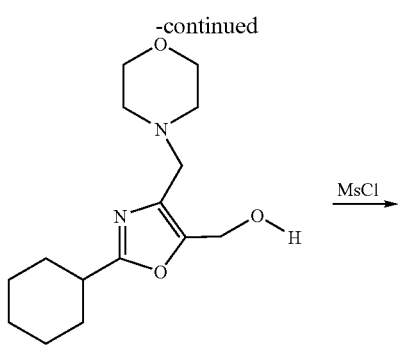

MsCl →

2-Cyclohex-1-enyl-4-morpholin-4-ylmethyl-oxazole-5-carboxylic acid ethyl ester

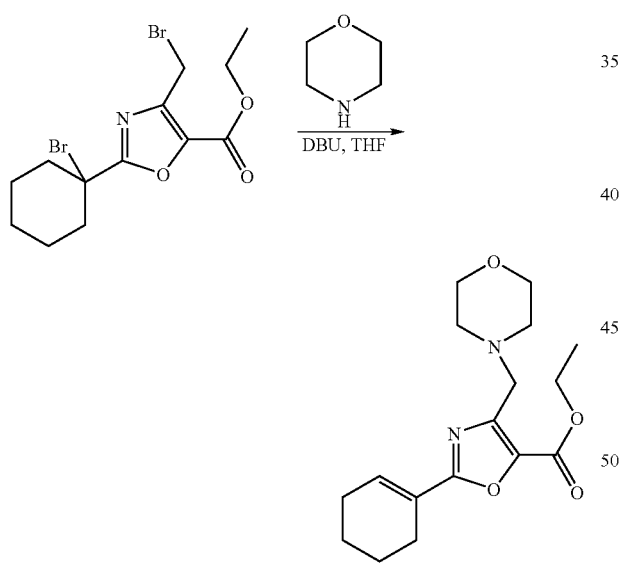

1.25 g 2-(1-Bromo-cyclohexyl)-4-bromomethyl-oxazole-5-carboxylic acid ethyl ester was dissolved in 15 ml tetrahydrofuran. 1.38 ml morpholine and 0.5 ml DBU were added and the reaction mixture stirred at 65° C. for three hours. The solvent was removed in vacuo and the resulting crude material was purified by reversed phase HPLC. The lyophilisate was dissolved in ethyl acetate and washed with saturated NaHCO3 and 2N NaOH solution the organic layer was dried over MgSO4. The solvent was removed in vacuo to obtain 580 mg 2-Cyclohex-1-enyl-4-morpholin-4-ylmethyl-oxazole-5-carboxylic acid ethyl ester as an oil.

C17H24N2O4 (320.39), MS (ESI): 321.2 (M+H+).

124

2-Cyclohexyl-4-morpholin-4-ylmethyl-oxazole-5-carboxylic acid ethyl ester

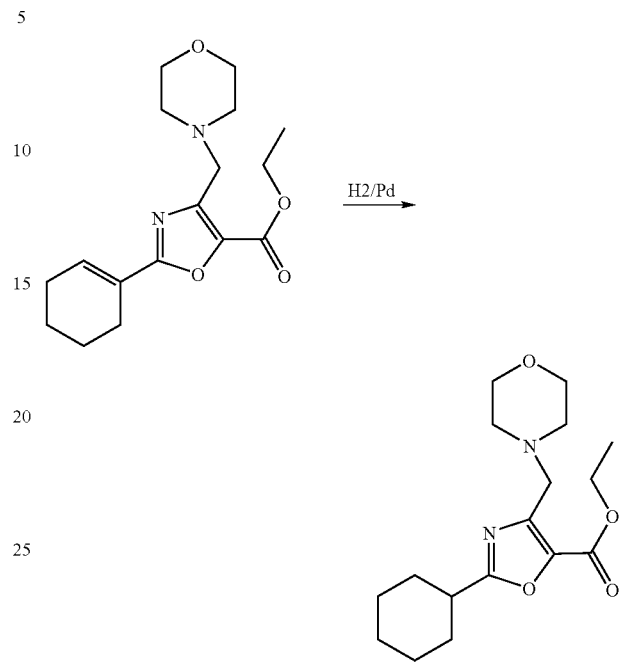

580 mg 2-Cyclohex-1-enyl-4-morpholin-4-ylmethyl-oxazole-5-carboxylic acid ethyl ester were dissolved in 15 ml methanol. 50 mg palladium on charcoal (10%) were added and the reaction mixture was stirred under an atmosphere of hydrogen for one hour. The catalyst was filtered off through a pad of celite, the filtrate was evaporated in vacuo to obtain 570 mg 2-Cyclohexyl-4-morpholin-4-ylmethyl-oxazole-5-carboxylic acid ethyl ester as an oil.

C17H26N2O4 (322.41), MS (ESI): 323.3 (M+H+).

4-(5-Chloromethyl-2-cyclohexyl-oxazol-4-ylmethyl)-morpholine

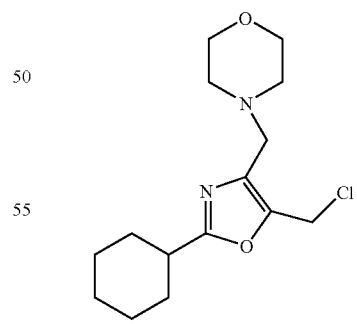

According to the method described for 5-Chloromethyl-4-methyl-2-(1-methyl-cyclohexyl)-oxazole, 4-(5-Chloromethyl-2-cyclohexyl-oxazol-4-ylmethyl)-morpholine was obtained from 2-Cyclohexyl-4-morpholin-4-ylmethyl-oxazole-5-carboxylic acid ethyl ester.

C15H23ClN2O2 (298.82), MS (ESI): 299.2 (M+H+).

125

(5-Chloromethyl-2-cyclohexyl-oxazol-4-ylmethyl)-diethyl-amine

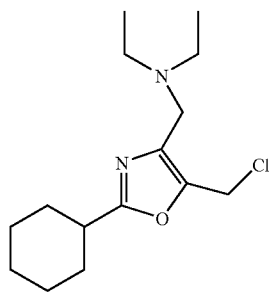

According to the method described for 4-(5-Chloromethyl-2-cyclohexyl-oxazol-4-ylmethyl)-morpholine and 5-Chloromethyl-4-methyl-2-(1-methyl-cyclohexyl)-oxazole, (5-Chloromethyl-2-cyclohexyl-oxazol-4-ylmethyl)-diethyl-amine was obtained from 2-(1-Bromo-cyclohexyl)-4-bromomethyl-oxazole-5-carboxylic acid ethyl ester and diethylamine.

C15H25ClN2O (284.83), MS (ESI): 285.2 (M+H+).

Building Block Synthesis According to Process F:

4-Methyl-2-(trans-1,4-trifluoromethyl-cyclohexyl)-thiazole-5-carbaldehyde

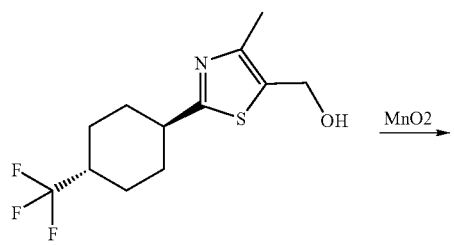

1.0 g [4-Methyl-2-(trans-1,4-trifluoromethyl-cyclohexyl)-thiazol-5-yl]-methanol were dissolved in 30 ml dichloromethane. 4.29 g manganese (IV) dioxide were added and the resulting mixture heated under reflux for four hours. The cooled reaction mixture was filtered through a Celite pad. The filtrate was evaporated to obtain 600 mg 4-Methyl-2-(trans-1,4-trifluoromethyl-cyclohexyl)-thiazole-5-carbaldehyde as a yellow oil.

C12H14F3NOS (277.31), MS (ESI): 278.1 (M+H+).

126

1-[4-Methyl-2-(trans-1,4-trifluoromethyl-cyclohexyl)-thiazol-5-yl]-2-phenyl-ethanol

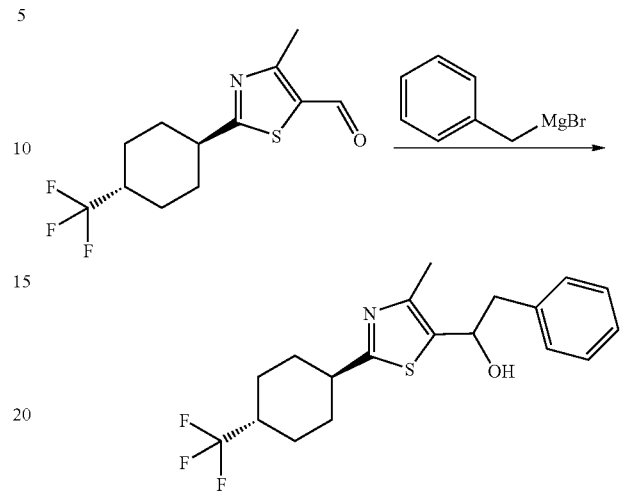

In an argon flushed flask were placed 107 mg magnesium. A small crystal of iodine were added. After ten minutes 20 ml diethylether were added. 0.1 ml benzyl bromide were added. When the reaction started the brown color of the iodine vanished. Then 680 mg of benzyl bromide were added. The reaction temperature was raised to 35° C. When the reaction temperature decreased to room temperature it was stirred for additional thirty minutes. Then 600 mg 4-Methyl-2-(trans-1,4-trifluoromethyl-cyclohexyl)-thiazole-5-carbaldehyde, dissolved in 10 ml diethylether, were added and stirred at room temperature for fifteen minutes. The reaction mixture was then cooled in an ice bath and quenched by addition of 20 ml water. The mixture was extracted three times with portions of 50 ml ethyl acetate. The combined organic layers were dried over MgSO4. The solvent was evaporated in vacuo to obtain 1.10 g 1-[4-Methyl-2-(trans-1,4-trifluoromethyl-cyclohexyl)-thiazol-5-yl]-2-phenyl-ethanol as a yellow oil.

C19H22F3NOS (369.45), MS (ESI): 370.2 (M+H+), Rf (n-heptane:ethyl acetate=2.1)=0.18.

1-[4-Methyl-2-(trans-1,4-trifluoromethyl-cyclohexyl)-thiazol-5-yl]-2-pyridin-2-yl-ethanol

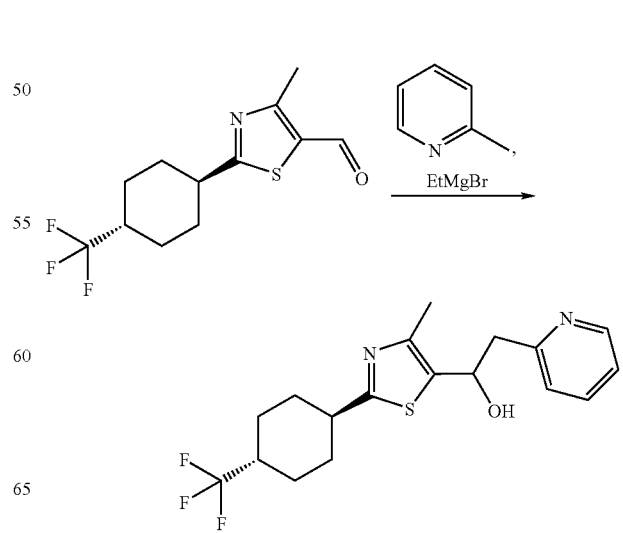

4.3 ml of a 1M solution of ethylmagnesiumbromide was added to a solution of 0.43 ml 2-picoline in 40 ml dibutylether. The reaction mixture was stirred at 140° C. for forty minutes. Then an argon current was bubbled through the reaction mixture for ten minutes. The mixture was cooled to 70° C. 1.0 g 4-Methyl-2-(trans-1,4-trifluoromethyl-cyclohexyl)-thiazole-5-carbaldehyde, dissolved in 50 ml tetrahydrofuran, were added and stirred at room temperature for thirty minutes. The reaction mixture was pored on ice and extracted three times with portions of 80 ml ethyl acetate. The combined organic layers were dried over MgSO4. The solvent was evaporated in vacuo. The resulting residue was purified on silica gel with the eluent n-heptane:ethyl acetate=40:1=>1:10 to obtain 580 mg 1-[4-Methyl-2-(trans-1,4-trifluoromethyl-cyclohexyl)-thiazol-5-yl]-2-pyridin-2-yl-ethanol as a yellow oil.

C18H21F3N2OS (370.44), MS (ESI): 371.2 (M+H+), Rf (n-heptane:ethyl acetate=1.1)=0.06.

2-(4-Fluoro-phenyl)-1-[4-methyl-2-(6-trifluoromethyl-pyridin-3-yl)-thiazol-5-yl]-ethanol

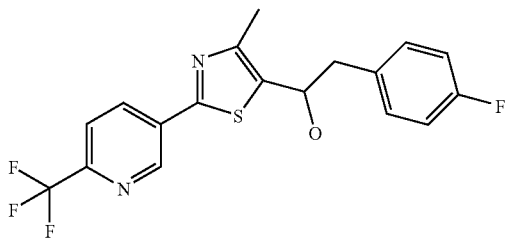

According to the method described for 1-[4-Methyl-2-(trans-1,4-trifluoromethyl-cyclohexyl)-thiazol-5-yl]-2-phenyl-ethanol, 2-(4-Fluoro-phenyl)-1-[4-methyl-2-(6-trifluoromethyl-pyridin-3-yl)-thiazol-5-yl]-ethanol was obtained from 4-Methyl-2-(6-trifluoromethyl-pyridin-3-yl)-thiazole-5-carbaldehyde (derived from [4-Methyl-2-(6-trifluoromethyl-pyridin-3-yl)-thiazol-5-yl]-methanol according to the method described for 4-Methyl-2-(trans-1,4-trifluoromethyl-cyclohexyl)-thiazole-5-carbaldehyde) and 4-fluorbenzylmagnesiumbromide.

C18H14F4N2OS (382.38), MS (ESI): 383.1 (M+H+).

1-[4-Methyl-2-(6-trifluoromethyl-pyridin-3-yl)-thiazol-5-yl]-propan-1-ol

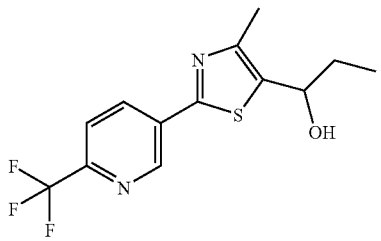

According to the method described for 1-[4-Methyl-2-(trans-1,4-trifluoromethyl-cyclohexyl)-thiazol-5-yl]-2-phenyl-ethanol, 1-[4-Methyl-2-(6-trifluoromethyl-pyridin-3-yl)-thiazol-5-yl]-propan-1-ol was obtained from 4-Methyl-2-(6-trifluoromethyl-pyridin-3-yl)-thiazole-5-carbaldehyde (derived from [4-Methyl-2-(6-trifluoromethyl-pyridin-3-yl)-thiazol-5-yl]-methanol according to the method described for 4-Methyl-2-(trans-1,4-trifluoromethyl-cyclohexyl)-thiazole-5-carbaldehyde) and ethylmagnesiumbromide.

C13H13F3N2OS (302.32), MS (ESI): 303.1 (M+H+).

1-[4-Methyl-2-(trans-1,4-trifluoromethyl-cyclohexyl)-thiazol-5-yl]-propan-1-ol

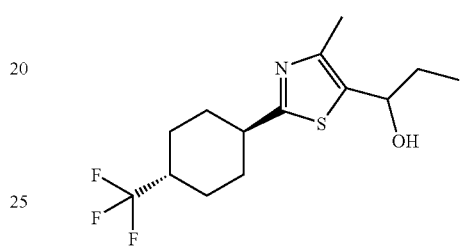

According to the method described for 1-[4-methyl-2-(trans-1,4-trifluoromethyl-cyclohexyl)-thiazol-5-yl]-2-phenyl-ethanol, 1-[4-methyl-2-(trans-1,4-trifluoromethyl-cyclohexyl)-thiazol-5-yl]-propan-1-ol was obtained from 4-methyl-2-(trans-1,4-trifluoromethyl-cyclohexyl)-thiazole-5-carbaldehyde and ethylmagnesiumbromide.

C14H20F3NOS (307.38), MS (ESI): 308 (M+H⁺).

1-[4-Methyl-2-(4-trifluoromethyl-cyclohexyl)-oxazol-5-yl]-propan-1-ol

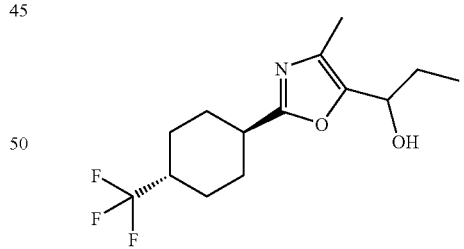

According to the method described for 1-[4-methyl-2-(trans-1,4-trifluoromethyl-cyclohexyl)-thiazol-5-yl]-2-phenyl-ethanol, 1-[4-methyl-2-(4-trifluoromethyl-cyclohexyl)-oxazol-5-yl]-propan-1-ol was obtained from 4-methyl-2-(4-trifluoromethyl-cyclohexyl)-oxazole-5-carbaldehyde (derived from [4-methyl-2-(4-trifluoromethyl-cyclohexyl)-oxazol-5-yl]-methanol according to the method described for 4-methyl-2-(trans-1,4-trifluoromethyl-cyclohexyl)-thiazole-5-carbaldehyde) and ethylmagnesiumbromide.

C14H20F3NO2 (291.32), MS (ESI): 292.2 (M+H⁺).

Building Block Synthesis According to Process G:

2,2,2-Trifluoro-1-[4-methyl-2-(6-trifluoromethyl-pyridin-3-yl)-thiazol-5-yl]-ethanol

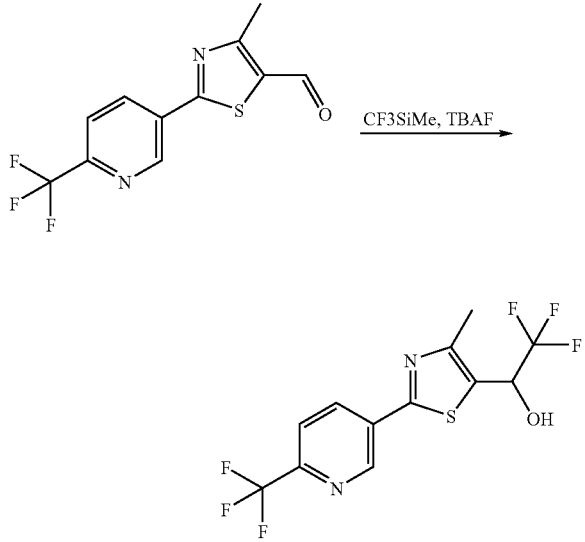

To an ice cooled solution of 2.0 g 4-Methyl-2-(6-trifluoromethyl-pyridin-3-yl)-thiazole-5-carbaldehyde (derived from [4-Methyl-2-(6-trifluoromethyl-pyridin-3-yl)-thiazol-5-yl]-methanol according to the method described for 4-Methyl-2-(trans-1,4-trifluoromethyl-cyclohexyl)-thiazole-5-carbaldehyde) and 1.09 ml (trifluoromethyl)trimethylsilane in 10 ml tetrahydrofuran were added 100 mg tetrabutylammoniumfluoride. The reaction mixture was stirred at room temperature for thirty minutes. Then 20 ml 2N HCL were added and the mixture stirred at room temperature for thirty minutes. The mixture was extracted three times with portions of 50 ml ethyl acetate. The combined organic layers were dried over MgSO4. The solvent was evaporated in vacuo to obtain 1.5 g 2,2,2-Trifluoro-1-[4-methyl-2-(6-trifluoromethyl-pyridin-3-yl)-thiazol-5-yl]-ethanol as a solid.

C12H8F6N2OS (342.26), MS (ESI): 343.1 (M+H+).

2,2,2-Trifluoro-1-[trans-1,4-methyl-2-(4-trifluoromethyl-cyclohexyl)-thiazol-5-yl]-ethanol

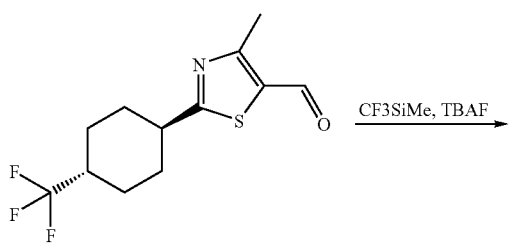

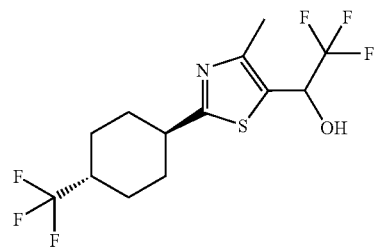

According to the method described for 2,2,2-Trifluoro-1-[4-methyl-2-(6-trifluoromethyl-pyridin-3-yl)-thiazol-5-yl]-ethanol, 2,2,2-Trifluoro-1-[trans-1,4-methyl-2-(4-trifluoromethyl-cyclohexyl)-thiazol-5-yl]-ethanol was obtained from 4-Methyl-2-(trans-1,4-trifluoromethyl-cyclohexyl)-thiazole-5-carbaldehyde and (trifluoromethyl)trimethylsilane.

C13H15F6NOS (347.33), MS (ESI): 348.1 (M+H+).

2,2-Difluoro-1-[4-methyl-2-(6-trifluoromethyl-pyridin-3-yl)-thiazol-5-yl]-but-3-en-1-ol

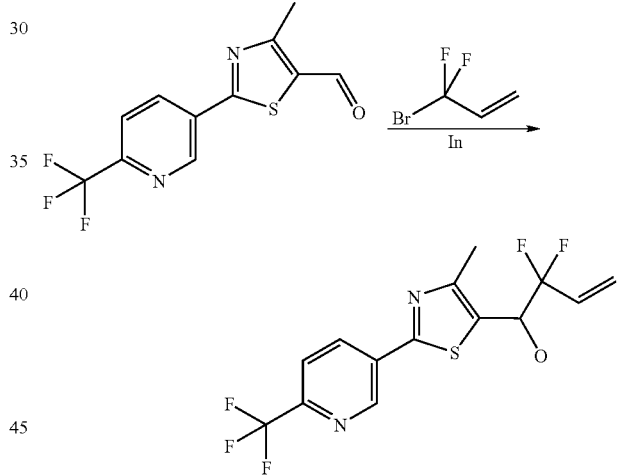

To a solution of 5.0 g 4-Methyl-2-(6-trifluoromethyl-pyridin-3-yl)-thiazole-5-carbaldehyde (derived from [4-Methyl-2-(6-trifluoromethyl-pyridin-3-yl)-thiazol-5-yl]-methanol according to the method described for 4-Methyl-2-(trans-1,4-trifluoromethyl-cyclohexyl)-thiazole-5-carbaldehyde) and 4.33 g 3-bromo-3,3-difluorpropene in 25 ml dimethylformamide. 2.11 g Indium were added and the resulting suspension was stirred in an ultrasonic bath for three hours. Then 20 ml 1N HCL were added and the mixture stirred at room temperature for thirty minutes. The mixture was extracted three times with portions of 50 ml ethyl acetate. The combined organic layers were dried over MgSO4. The solvent was evaporated in vacuo. The resulting residue was purified by reversed phase HPLC to obtain 4.67 g 2,2-Difluoro-1-[4-methyl-2-(6-trifluoromethyl-pyridin-3-yl)-thiazol-5-yl]-but-3-en-1-ol as a colorless lyophilisate.

C14H11F5N2OS (350,31), MS (ESI): 351.1 (M+H+).

2,2-Difluoro-1-[4-methyl-2-(6-trifluoromethyl-pyridin-3-yl)-thiazol-5-yl]-butan-1-ol

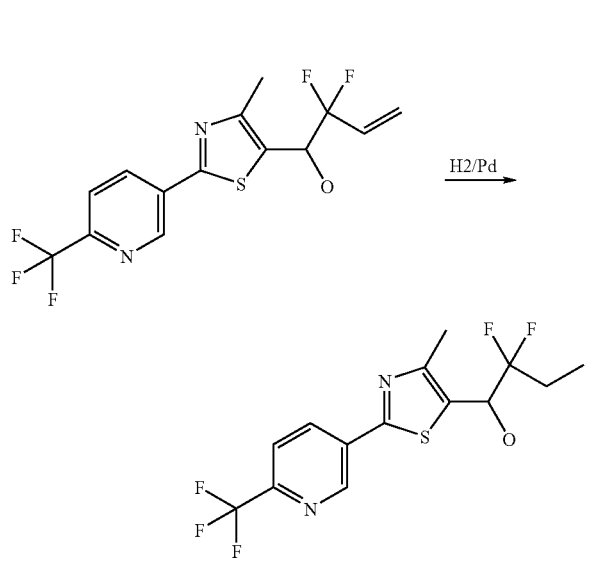

500 mg 2,2-Difluoro-1-[4-methyl-2-(6-trifluoromethyl-pyridin-3-yl)-thiazol-5-yl]-but-3-en-1-ol were dissolved in 50 ml ethyl acetate. 50 mg palladium (5% on charcoal) were added and the reaction mixture stirred at room temperature under a hydrogen atmosphere. After three hours the catalyst was filtered off and the filtrate evaporated in vacuo to obtain 490 mg 2,2-Difluoro-1-[4-methyl-2-(6-trifluoromethyl-pyridin-3-yl)-thiazol-5-yl]-butan-1-ol as a white solid.

C14H13F5N2OS (352.33), MS (ESI): 353.1 (M+H+).

Building Block Synthesis According to Process H:

4-Bromomethyl-2-chloro-benzonitrile

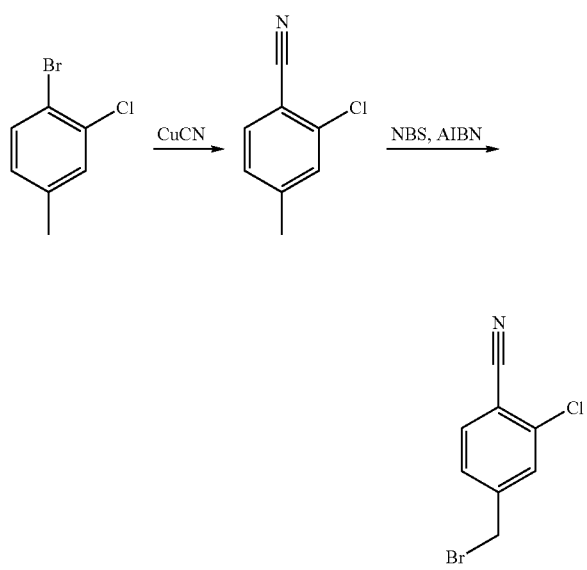

2-Chloro-4-methyl-benzonitrile

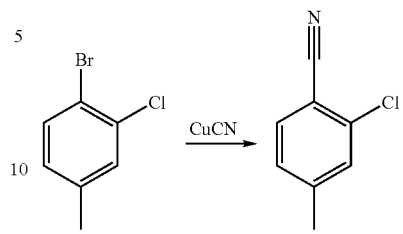

25.0 g 4-bromo-3-chlorotoluene and 21.8 g copper (I) cyanide were dissolved in 200 ml dimethylformamide and stirred at 150° C. for three hours. The cooled reaction mixture was diluted by addition of 300 ml ethyl acetate and washed three times with portions of 150 ml saturated NH4Cl solution. The precipitates were filtered off and the filtrate dried over MgSO4 and then reduced in vacuo to obtain 17.3 g 2-Chloro-4-methyl-benzonitrile. This material was used without purification in the next step.

C8H6ClN (151.60).

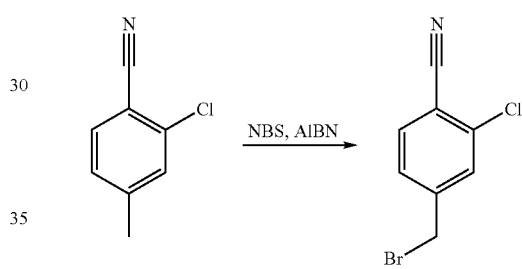

4-Bromomethyl-2-chloro-benzonitrile 17.3 g 2-Chloro-4-methyl-benzonitrile were dissolved in 50 ml tetrachloromethane and heated to reflux. A mixture of 24.3 g N-bromosuccinimide and 7.48 g 2,2'-azobis(2-methylpropionitrile) were added in five portions over a period of one hour. The reaction mixture was heated under reflux for additional three hours. The cooled reaction mixture was then filtered through a celite pad. The filtrate was washed with 100 ml saturated NaHCO3 solution, dried over MgSO4 and the solvent was removed in vacuo. The resulting residue was dissolved in 200 ml tetrahydrofuran and cooled in an ice bath to 0° C. 88.0 ml Diethyl phosphite were added, followed by the addition of 117.0 ml N,N-Diisopropylethylamine. The cooling bath was removed and the reaction mixture stirred at room temperature for four hours. The reaction mixture was poured in 400 ml 50% NaHCO3 solution and extracted with 400 ml diethylether. The organic layer was separated and washed with 200 ml 50% NaHCO3 solution and 200 ml water and then dried over MgSO4. The solvent was removed in vacuo. The resulting residue was purified on silica gel with the eluent n-heptane ethyl acetate=19:1 to obtain 13.0 g 4-Bromomethyl-2-chloro-benzonitrile as a solid.

C8H5BrClN (230.49), Rf (n-heptane:ethyl acetate= 4:1)=0.31.

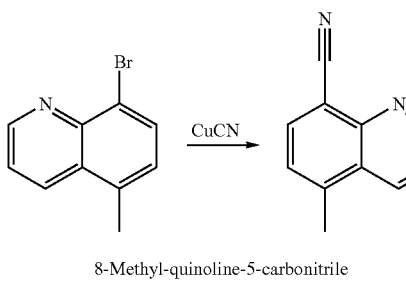

8-Methyl-quinoline-5-carbonitrile 4.0 g 8-Bromo-5-methyl-quinoline and 1.69 g copper (I) cyanide were dissolved in 16 ml dimethylformamide and stirred at 200° C. for thirty minutes under microwave irradiation. The cooled reaction mixture was poured in 50 ml 2N HCL and extracted with 100 ml ethyl acetate. The organic layer was washed with 50 ml 2N HCl and 30 ml brine and then dried over MgSO4. The solvent was removed in vacuo. The resulting residue was purified on silica gel with the eluent n-heptane ethyl acetate=2:1 to obtain 3.0 g 8-Methyl-quinoline-5-carbonitrile.

C11H8N2 (168.20), Rf (n-heptane:ethyl acetate=4:1)=0.20.

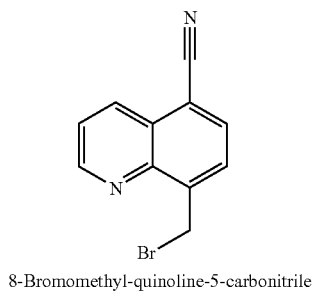

8-Bromomethyl-quinoline-5-carbonitrile

According to the method described for 4-Bromomethyl-2-chloro-benzonitrile, 8-Bromomethyl-quinoline-5-carbonitrile was obtained from 8-Methyl-quinoline-5-carbonitrile.

C11H7BrN2 (247.10), Rf (n-heptane:ethyl acetate=4:1)=0.24.

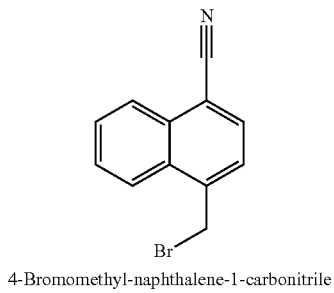

4-Bromomethyl-naphthalene-1-carbonitrile

According to the method described for 4-Bromomethyl-2-chloro-benzonitrile, 4-Bromomethyl-naphthalene-1-carbonitrile was obtained from commercially available 1-cyano-4-metylnaphthalene.

C12H8BrN (246.11), Rf (n-heptane:ethyl acetate=4:1)=0.38.

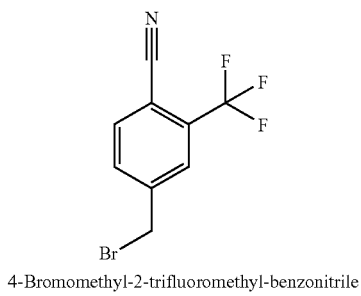

4-Bromomethyl-2-trifluoromethyl-benzonitrile

According to the method described for 4-Bromomethyl-2-chloro-benzonitrile, 4-Bromomethyl-2-trifluoromethyl-benzonitrile was obtained from commercially available 4-methyl-2-(trifluoromethyl)-benzonitrile.

C9H5BrF3N (264.05), Rf (n-heptane:ethyl acetate=4:1)=0.25.

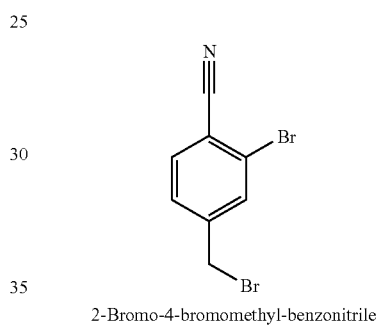

2-Bromo-4-bromomethyl-benzonitrile

According to the method described for 4-Bromomethyl-2-chloro-benzonitrile, 2-Bromo-4-bromomethyl-benzonitrile was obtained from commercially available 2-Bromo-4-methyl-benzonitrile.

C8H5Br2N (274.94), Rf (n-heptane:ethyl acetate=4:1)=0.30.

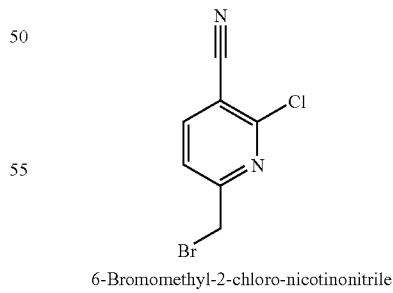

6-Bromomethyl-2-chloro-nicotinonitrile

According to the method described for 4-Bromomethyl-2-chloro-benzonitrile, 6-Bromomethyl-2-chloro-nicotinonitrile was obtained from commercially available 2-Chloro-6-methyl-nicotinonitrile.

C7H4BrClN2 (231.48), Rf (n-heptane:ethyl acetate=1:1)=0.48.

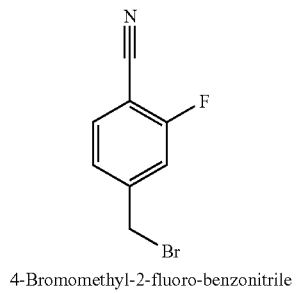

4-Bromomethyl-2-fluoro-benzonitrile

According to the method described for 4-Bromomethyl-2-chloro-benzonitrile, 4-Bromomethyl-2-fluoro-benzonitrile was obtained from commercially available 2-Fluoro-4-methyl-benzonitrile.

C8H5BrFN (214.04), Rf (n-heptane:ethyl acetate=4:1) =0.25.

Building Block Synthesis According to Process K:

[5-Hydroxymethyl-2-(trans-1,4-trifluoromethyl-cyclohexyl)-thiazol-4-yl]-(4-trifluoromethyl-piperidin-1-yl)-methanone

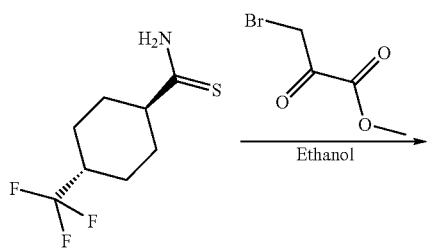

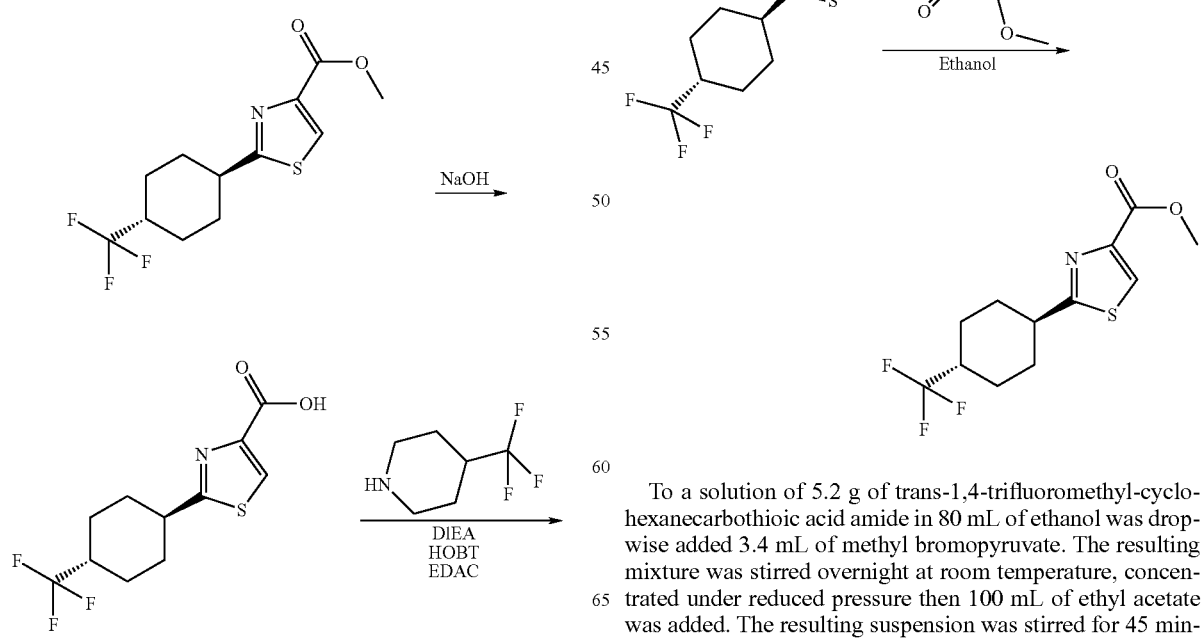

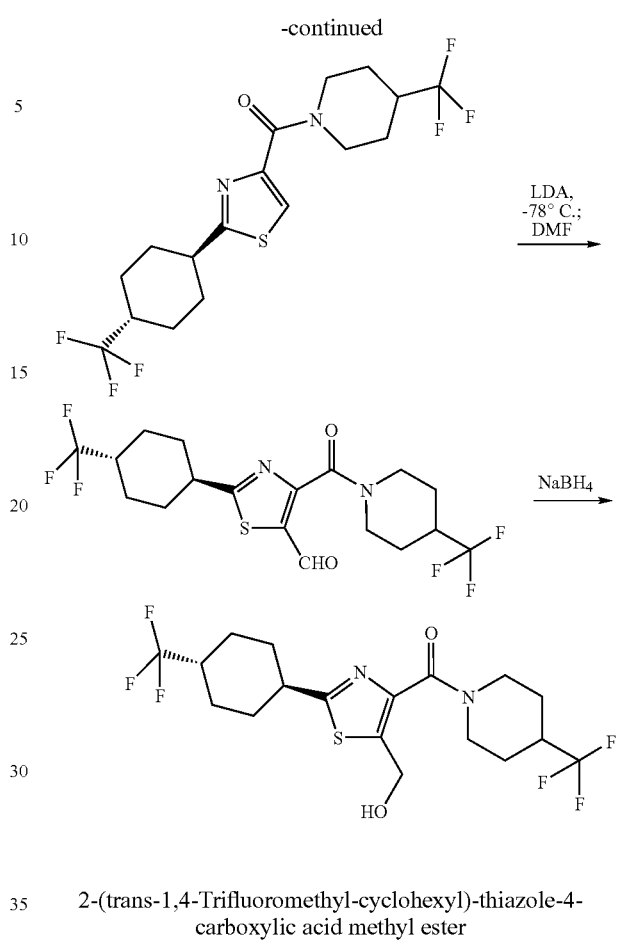

2-(trans-1,4-Trifluoromethyl-cyclohexyl)-thiazole-4-carboxylic acid methyl ester To a solution of 5.2 g of trans-1,4-trifluoromethyl-cyclohexanecarbothioic acid amide in 80 mL of ethanol was dropwise added 3.4 mL of methyl bromopyruvate. The resulting mixture was stirred overnight at room temperature, concentrated under reduced pressure then 100 mL of ethyl acetate was added. The resulting suspension was stirred for 45 minutes at 0° C. and the solid was filtered, washed with heptane and diisopropyl ether to give 5.7 g of 2-(trans-1,4-trifluoromethyl-cyclohexyl)-thiazole-4-carboxylic acid methyl ester as a white solid.

C12H14F3NO2S (293.31), MS (ESI): 294 (M+H⁺).

2-(trans-1,4-Trifluoromethyl-cyclohexyl)-thiazole-4-carboxylic acid

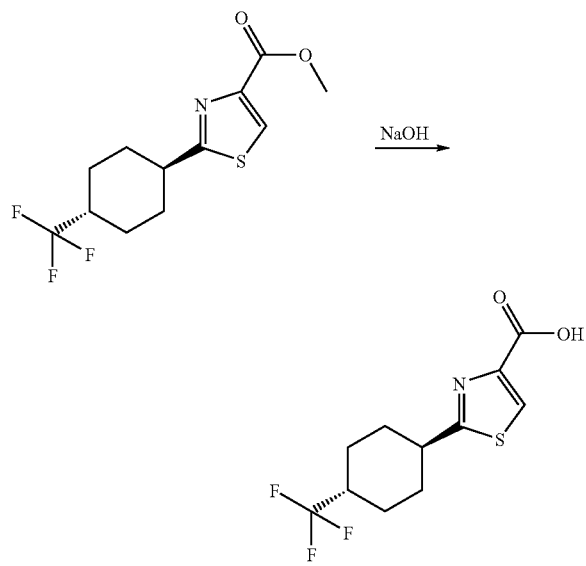

To a solution of 6.2 g of 2-(trans-1,4-trifluoromethyl-cyclohexyl)-thiazole-4-carboxylic acid methyl ester in 70 mL of ethanol at 0° C. was added 32 mL of a 1M aqueous solution of sodium hydroxide. The resulting mixture was stirred for 1 hour allowing the temperature to warm up to room temperature. Additional 5 mL of a 1M aqueous solution of sodium hydroxide was added and the mixture was stirred for 15 minutes at room temperature. 150 mL of water was added and the reaction mixture was extracted with 20 mL of ethyl acetate. The aqueous layer was acidified with a saturated aqueous solution of KHSO4 and extracted several times with ethyl acetate. The combined organic extracts were dried over magnesium sulfate, filtered and concentrated under reduced pressure to give 4.6 g of 2-(trans-1,4-trifluoromethyl-cyclohexyl)-thiazole-4-carboxylic acid as a beige solid.

C11H12F3NO2S (279.28), MS (EI): 279 (M⁺).

[2-(trans-1,4-Trifluoromethyl-cyclohexyl)-thiazol-4-yl]-(4-trifluoromethyl-piperidin-1-yl)-methanone

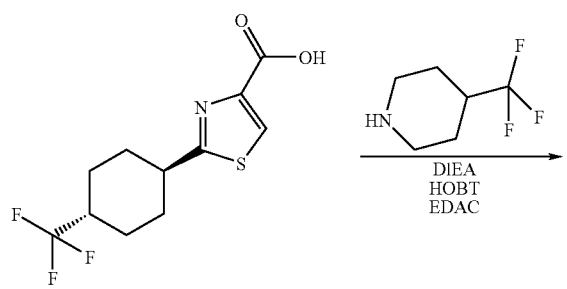

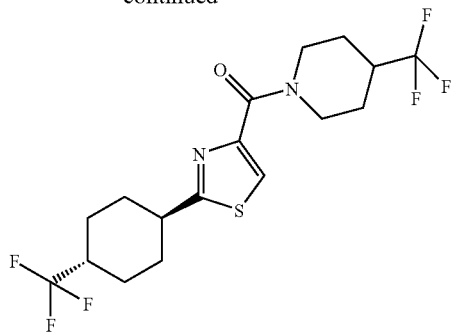

To a solution of 17.8 g of 2-(trans-1,4-trifluoromethyl-cyclohexyl)-thiazole-4-carboxylic acid in 700 mL of dichloromethane was added 12.1 g of 4-trifluoromethylpiperidine hydrochloride, 33 mL of N,N-diisopropylethylamine, 16 g of 1-(3-dimethylaminopropyl)-3-ethylcarbodiimide hydrochloride and 1.3 g of 1-hydroxybenzotriazole. The resulting mixture was stirred for 7 hours at room temperature. The reaction volume was reduced to half under reduced pressure and the mixture was poured onto water and extracted with dichloromethane. The combined organic extracts were dried over magnesium sulfate, filtered and concentrated under reduced pressure. The crude product was purified by column chromatography on silica gel (gradient from heptane 100 to heptane 50/ethyl acetate 50) to give 22 g of 2-(trans-1,4-trifluoromethyl-cyclohexyl)-thiazole-4-carboxylic acid as a white solid.

C17H2OF6N2OS (414.42), MS (ESI): 415 (M+H⁺).

2-(trans-1,4-Trifluoromethyl-cyclohexyl)-4-(4-trifluoromethyl-piperidine-1-carbonyl)-thiazole-5-carbaldehyde

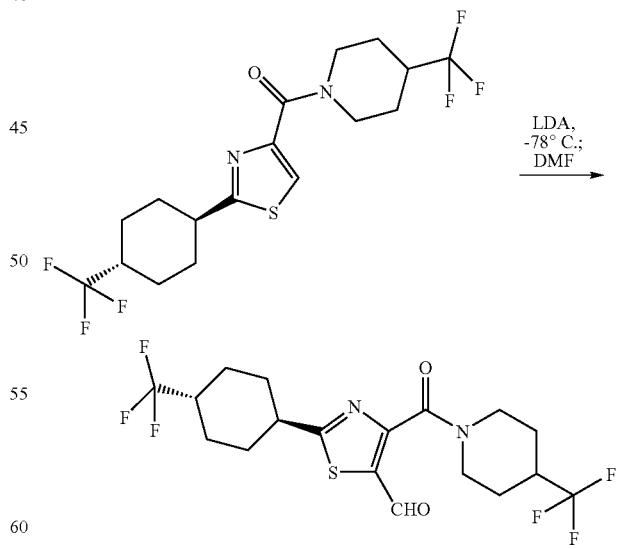

To a solution of 22 g of 2-(trans-1,4-trifluoromethyl-cyclohexyl)-thiazole-4-carboxylic acid in 300 mL of tetrahydrofuran at −78° C. was dropwise added 47.8 mL of a 2M solution of lithium diisopropyl amide in tetrahydrofuran/heptane. The resulting mixture was stirred for 5 minutes at −78° C. and 11.7 mL of anhydrous dimethylformamide was added. The resulting mixture was stirred for 15 minutes at −78° C. 5 mL of ethyl acetate and 2 mL of water were added and the temperature was allowed to warm up to room temperature. The reaction mixture was poured onto water and extracted with ethyl acetate. The combined organic extracts were dried over magnesium sulfate, filtered and concentrated under reduced pressure. The crude product was purified by column chromatography on silica gel (gradient from heptane 100 to heptane 50/ethyl acetate 50) to give 16.8 g of 2-(trans-1,4-trifluoromethyl-cyclohexyl)-4-(4-trifluoromethyl-piperidine-1-carbonyl)-thiazole-5-carbaldehyde as a white solid.

C18H20F6N2O2S (442.43), MS (ESI): 443 (M+H$^+$).

[5-Hydroxymethyl-2-(trans-1,4-trifluoromethyl-cyclohexyl)-thiazol-4-yl]-(4-trifluoromethyl-piperidin-1-yl)-methanone

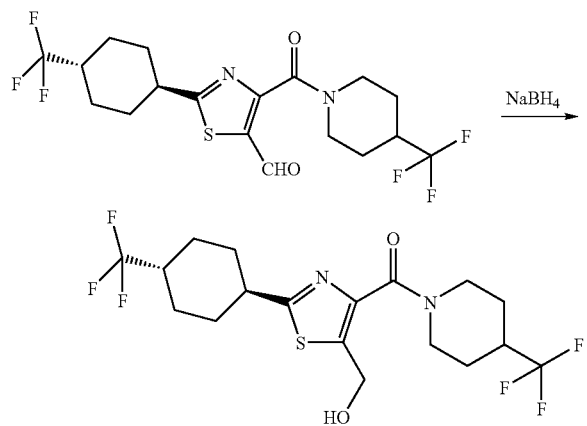

To a solution of 5 g of 2-(trans-1,4-trifluoromethyl-cyclohexyl)-4-(4-trifluoromethyl-piperidine-1-carbonyl)-thiazole-5-carbaldehyde in 90 mL of methanol at 0° C. was added 427 mg of sodium borohydride. The resulting mixture was stirred for 15 minutes at 0° C. and ethyl acetate/water were added. The reaction mixture was extracted three times with ethyl acetate. The combined organic extracts were dried over magnesium sulfate, filtered and concentrated under reduced pressure to give 5 g of [5-hydroxymethyl-2-(trans-1,4-trifluoromethyl-cyclohexyl)-thiazol-4-yl]-(4-trifluoromethyl-piperidin-1-yl)-methanone as a colorless gum.

C18H22F6N2O2S (444.41), MS (ESI): 445.0 (M+H$^+$).

[2-(trans-1,4-Trifluoromethyl-cyclohexyl)-4-(4-trifluoromethyl-piperidin-1-ylmethyl)-thiazol-5-yl]-methanol

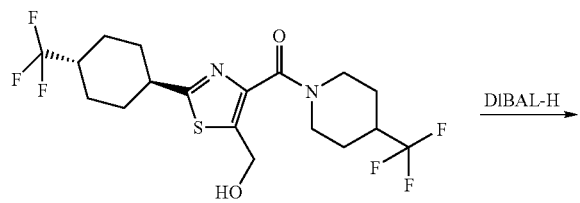

-continued

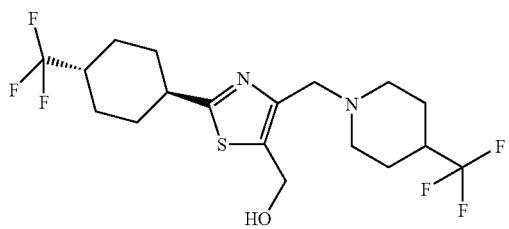

To a solution of 5 g of [5-hydroxymethyl-2-(trans-1,4-trifluoromethyl-cyclohexyl)-thiazol-4-yl]-(4-trifluoromethyl-piperidin-1-yl)-methanone in 50 mL of tetrahydrofuran at room temperature was added 10 mL of a 1M solution of diisobutyl aluminum hydride in tetrahydrofuran. The resulting mixture was stirred for 30 minutes at room temperature. Additional 11.5 mL of a 1M solution of diisobutyl aluminum hydride in tetrahydrofuran was added and the mixture was stirred for 45 minutes at room temperature. Since there is remaining starting material, additional 23 mL of a 1M solution of diisobutyl aluminum hydride was added and the mixture was stirred for 1 hour at room temperature. Since there is remaining starting material, additional 10 mL of a 1M solution of diisobutyl aluminum hydride was added and the mixture was stirred for 30 minutes at room temperature. The solvent was partially removed under reduced pressure and the mixture was poured onto cold aqueous solution of NaHSO4 and dichloromethane. The reaction mixture was extracted with dichloromethane. The combined organic extracts were dried over magnesium sulfate, filtered and concentrated under reduced pressure; The residue was triturated in diisopropyl ether/heptane and filtered to give 1.75 g of [2-(trans-1,4-trifluoromethyl-cyclohexyl)-4-(4-trifluoromethyl-piperidin-1-ylmethyl)-thiazol-5-yl]-methanol as a white solid.

C18H24F6N2OS (430.46), MS (ESI): 431.1 (M+H$^+$).

1-[2-(trans-1,4-Trifluoromethyl-cyclohexyl)-4-(4-trifluoromethyl-piperidin-1-ylmethyl)-thiazol-5-yl]-propan-1-ol

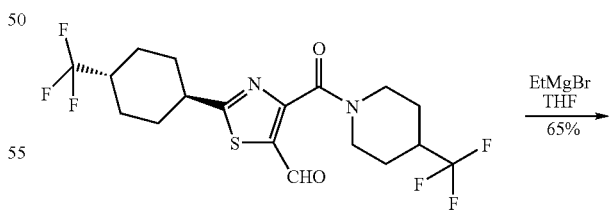

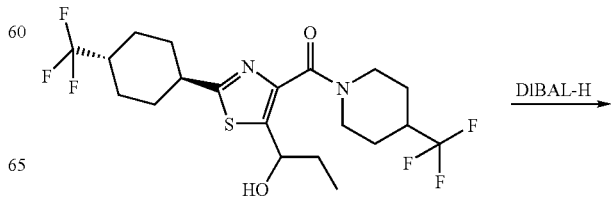

-continued

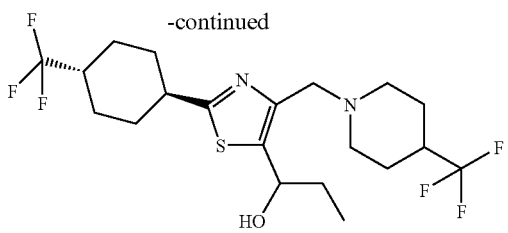

[5-(1-Hydroxy-propyl)-2-(trans-1,4-trifluoromethyl-cyclohexyl)-thiazol-4-yl]-(4-trifluoromethyl-piperidin-1-yl)-methanone

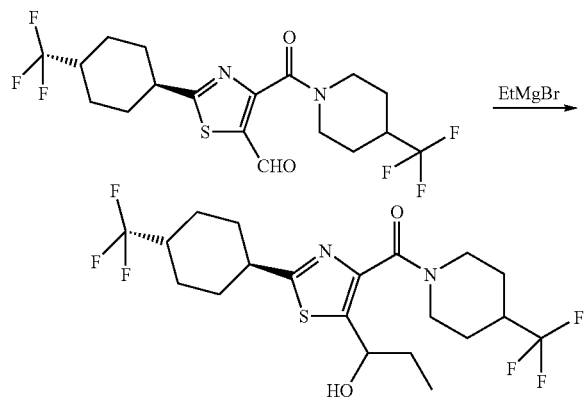

To a solution of 0.67 g of 2-(trans-1,4-trifluoromethyl-cyclohexyl)-4-(4-trifluoromethyl-piperidine-1-carbonyl)-thiazole-5-carbaldehyde in 6 mL of tetrahydrofuran at 0° C. was added 1.5 mL of a 1M solution of ethyl magnesium bromide. The resulting mixture was stirred for 35 minutes at 0° C. Additional 0.5 mL of a 1M solution of ethyl magnesium bromide was added. After 10 minutes at 0° C., the reaction mixture was poured onto ethyl acetate/saturated aqueous ammonium chloride and extracted with ethyl acetate. The combined organic extracts were dried over magnesium sulfate, filtered and concentrated under reduced pressure. The crude product was purified by column chromatography on silica gel (gradient from heptane 99/ethyl acetate 1 to heptane 50/ethyl acetate 50) to give 0.5 g of [5-(1-hydroxy-propyl)-2-(trans-1,4-trifluoromethyl-cyclohexyl)-thiazol-4-yl]-(4-trifluoromethyl-piperidin-1-yl)-methanone as a colorless gum.

C20H26F6N2O2S (472.50), MS (ESI): 473.2 (M+H$^+$).

1-[2-(trans-1,4-Trifluoromethyl-cyclohexyl)-4-(4-trifluoromethyl-piperidin-1-ylmethyl)-thiazol-5-yl]-propan-1-ol

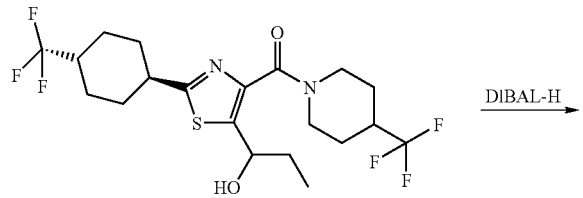

-continued

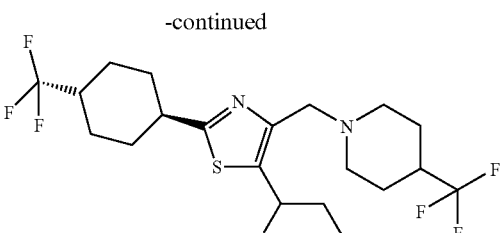

To a solution of 5.9 g of [5-(1-hydroxy-propyl)-2-(trans-1,4-trifluoromethyl-cyclohexyl)-thiazol-4-yl]-(4-trifluoromethyl-piperidin-1-yl)-methanone in 60 mL of tetrahydrofuran at room temperature was added 15 mL of a 1M solution of diisobutyl aluminum hydride in tetrahydrofuran. The resulting mixture was stirred for 30 minutes at room temperature. Additional 5 mL of a 1M solution of diisobutyl aluminum hydride in tetrahydrofuran was added and the mixture was stirred for 1 hour at room temperature. Since there is remaining starting material, additional 5 mL of a 1M solution of diisobutyl aluminum hydride was added and the mixture was stirred for 30 minutes at room temperature. The mixture was poured onto an aqueous solution of NaHSO4 and dichloromethane and extracted with dichloromethane. The combined organic extracts were dried over magnesium sulfate, filtered and concentrated under reduced pressure. The residue was purified by column chromatography on silica gel (gradient from heptane 90/ethyl acetate 10 to heptane 50/ethyl acetate 50) to give 3.5 g of 1-[2-(trans-1,4-trifluoromethyl-cyclohexyl)-4-(4-trifluoromethyl-piperidin-1-ylmethyl)-thiazol-5-yl]-propan-1-ol.

C20H28F6N2OS (458.51), MS (ESI): 459.1 (M+H$^+$).

Building Block Synthesis According to Process L:

2-Difluoromethoxy-4-fluoro-benzonitrile

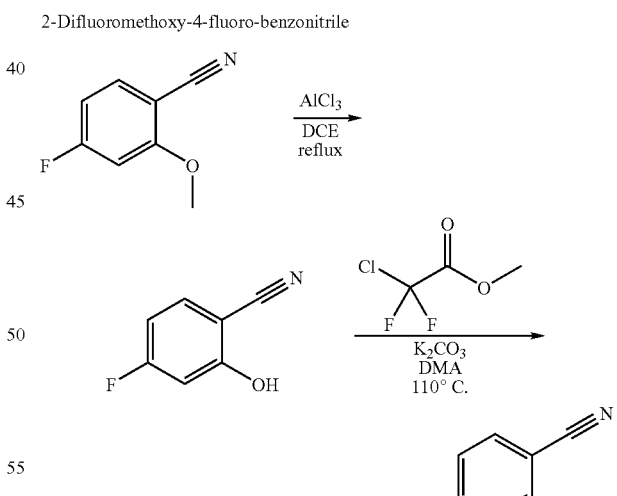

4-Fluoro-2-methoxy-benzonitrile was prepared according to a previous publication:[1]

To a solution of 1 g of 4-fluoro-2-methoxy-benzonitrile in 15 mL of dichloroethane was added 1.1 g of aluminum trichloride. The resulting mixture was refluxed for 1 day then poured slowly into water and extracted with ethyl acetate. The organic extracts were washed twice with 10% aqueous solution of sodium hydroxide. The combined basic layers were washed twice with ethyl acetate, acidified with concentrated aqueous solution of hydrochloric acid and extracted three times with ethyl acetate. The combined organic extracts were washed with water, with brine, dried over magnesium sulfate, filtered and concentrated under reduced pressure to give 0.78 g of 4-fluoro-2-hydroxy-benzonitrile as a white solid.

C7H4FNO (137.11), MS (ESI): 138.17 (M+H⁺).

To a solution of 4.6 g of 4-fluoro-2-hydroxy-benzonitrile in 15 mL of anhydrous dimethylacetamide were added 6.8 g of methyl chlorodifluororacetate and 6.5 g of potassium carbonate. The resulting mixture was degassed by bubbling argon through it and heated to 110° C. for 2 h then an additional 6.5 g of methyl chlorodifluororacetate and 6.5 g of potassium carbonate were added. The resulting mixture was heated to 110° C. for another hour then concentrated under reduced pressure. The residue was taken into ethyl acetate, washed twice with a molar aqueous solution of sodium hydroxide, with water and brine, dried over magnesium sulfate, filtered and concentrated under reduced pressure. The crude product was purified by column chromatography on silica gel (gradient from heptane 100 to heptane 80/ethyl acetate 20) to give 4.78 g of 2-difluoromethoxy-4-fluoro-benzonitrile as a yellowish liquid.

C8H4F3NO (187.12), MS (ESI): 188.0 (M+H⁺).

2-Difluoromethoxy-4,5-difluoro-benzonitrile

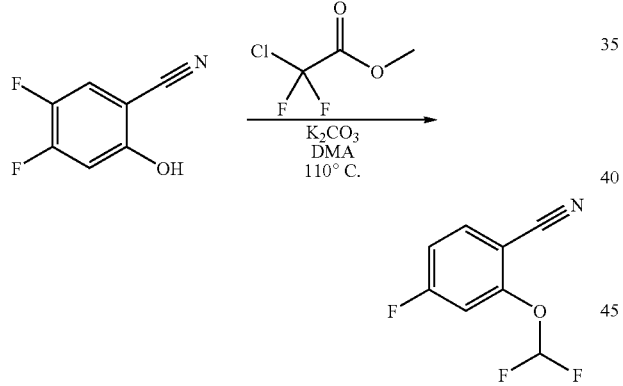

To a solution of 1 g of commercially available 4,5-difluoro-2-hydroxy-benzonitrile in 5 mL of anhydrous dimethylacetamide were added 1.3 g of methyl chlorodifluororacetate and 1.28 g of potassium carbonate. The resulting mixture was degassed by bubbling argon through it and heated to 110° C. for 1.5 h then concentrated under reduced pressure. The residue was taken into ethyl acetate, washed twice with a molar aqueous solution of sodium hydroxide, with water and brine, dried over magnesium sulfate, filtered and concentrated under reduced pressure. The crude product was purified by column chromatography on silica gel (gradient from heptane 100 to heptane 80/ethyl acetate 20) to give 0.42 g of 2-difluoromethoxy-4,5-difluoro-benzonitrile as a yellowish liquid.

C8H3F4NO (205.11), MS (EI): 205 (M⁺).

The following examples were prepared according to process A:

EXAMPLE 1

3-{2-Chloro-4-[4-methyl-2-(1-methyl-cyclohexyl)-oxazol-5-ylmethoxy]-phenyl}-4H-[1,2,4]oxadiazol-5-one

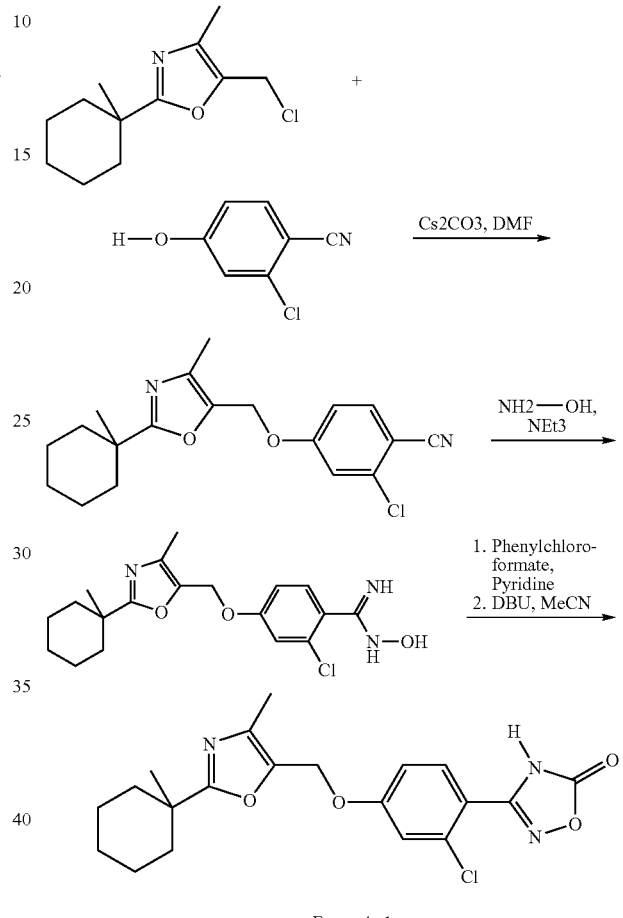

Example 1

2-Chloro-4-[4-methyl-2-(1-methyl-cyclohexyl)-oxazol-5-ylmethoxy]-benzonitrile

To a solution of 1.70 g 2-Chloro-4-hydroxy-benzonitrile in 25 ml dimethylformamide

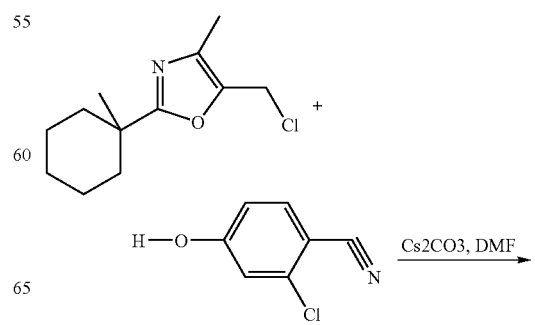

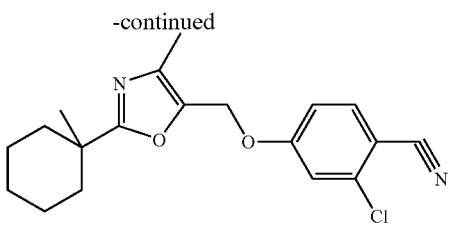

were added 1.68 g 5-Chloromethyl-4-methyl-2-(1-methyl-cyclohexyl)-oxazole and 4.80 g cesium carbonate. The mixture was stirred at room temperature overnight. Then 100 ml of ethyl acetate were added, the mixture washed with 40 ml water and brine and then dried over MgSO4. The solvent was removed in vacuo. The resulting crude material was purified by reversed phase HPLC to obtain 1.24 g of 2-Chloro-4-[4-methyl-2-(1-methyl-cyclohexyl)-oxazol-5-ylmethoxy]-benzonitrile as amorphous lyophilisate.

$C_{19}H_{21}ClN_2O_2$ (344.84), MS (ESI): 345.2 (M+H$^+$).

2-Chloro-N-hydroxy-4-[4-methyl-2-(1-methyl-cyclohexyl)-oxazol-5-ylmethoxy]-benzamidine

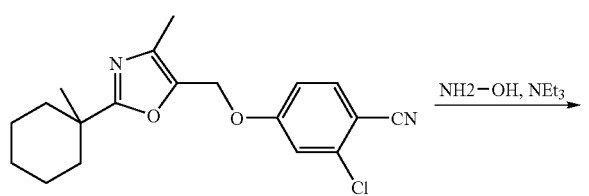

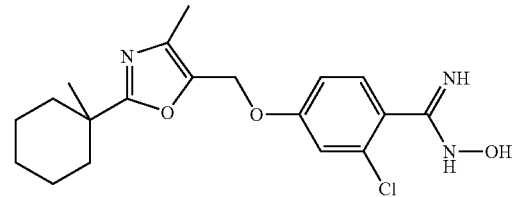

1.24 g 2-Chloro-4-[4-methyl-2-(1-methyl-cyclohexyl)-oxazol-5-ylmethoxy]-benzonitrile were dissolved in a mixture of 20 ml tetrahydrofuran and 20 ml methanol. 5.0 g hydroxylamine hydrochloride were added followed by the addition of 10.0 ml triethylamine. The reaction mixture was stirred at 65° C. overnight. The solvents were removed in vacuo and the resulting residue poured into water and extracted five times with ethylacetate. The combined organic extracts were washed with brine, dried over MgSO4 and the solvent was evaporated in vacuo to obtain 1.39 g 2-Chloro-N-hydroxy-4-[4-methyl-2-(1-methyl-cyclohexyl)-oxazol-5-ylmethoxy]-benzamidine as an oil.

$C_{19}H_{24}ClN_3O_3$ (377.87), MS (ESI): 378.2 (M+H$^+$).

3-{2-Chloro-4-[4-methyl-2-(1-methyl-cyclohexyl)-oxazol-5-ylmethoxy]-phenyl}-4H-[1,2,4]oxadiazol-5-one

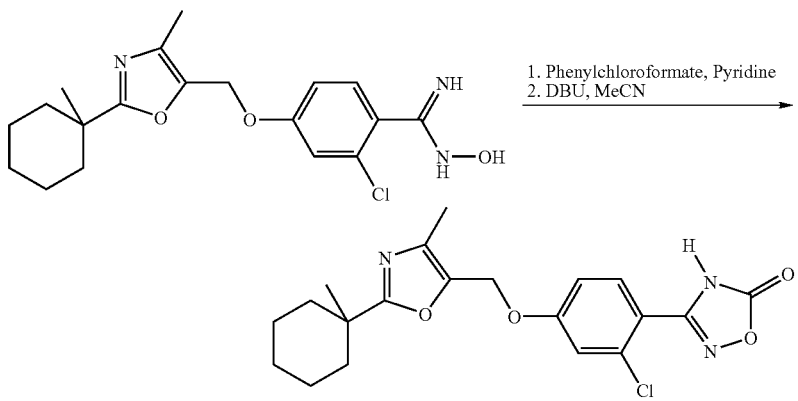

Example 1

1.39 g 2-Chloro-N-hydroxy-4-[4-methyl-2-(1-methyl-cyclohexyl)-oxazol-5-ylmethoxy]-benzamidine were dissolved in 10 ml dichloromethane. 0.36 ml pyridine and 0.56 ml phenylchloroformate were added and the mixture stirred at room temperature for ten minutes. The mixture was diluted by the addition of 30 ml acetonitrile and 2.75 ml 1,8-Diazabicyclo[5.4.0]undec-7-ene were added. The mixture was stirred at room temperature for 10 minutes. The mixture was evaporated in vacuo and the resulting crude material was purified by reversed phase HPLC to obtain 950 mg 3-{2-Chloro-4-[4-methyl-2-(1-methyl-cyclohexyl)-oxazol-5-ylmethoxy]-phenyl}-4H-[1,2,4]oxadiazol-5-one as an amorphous lyophilisate.

C20H22ClN3O4 (403.87), MS (ESI): 404.1 (M+H$^+$).

EXAMPLE 2

3-[2-Chloro-4-(2-cyclohexyl-4-methyl-oxazol-5-ylmethoxy)-phenyl]-4H-[1,2,4]oxadiazol-5-one

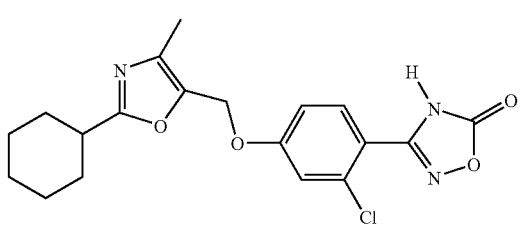

According to the method described in Example 1 3-[2-Chloro-4-(2-cyclohexyl-4-methyl-oxazol-5-ylmethoxy)-phenyl]-4H-[1,2,4]oxadiazol-5-one was obtained from 5-Chloromethyl-2-cyclohexyl-4-methyl-oxazole and commercially available 2-Chloro-4-hydroxy-benzonitrile.

$C_{19}H_{20}ClN_3O_4$ (389.84), MS (ESI): 390.2 (M+H$^+$).

EXAMPLE 3

3-{2-Chloro-4-[4-methyl-2-(trans-1,4-trifluoromethyl-cyclohexyl)-oxazol-5-ylmethoxy]-phenyl}-4H-[1,2,4]oxadiazol-5-one 3a and 3-{2-Chloro-4-[4-methyl-2-(cis-1,4-trifluoromethyl-cyclohexyl)-oxazol-5-ylmethoxy]-phenyl}-4H-[1,2,4]oxadiazol-5-one 3b example 3a

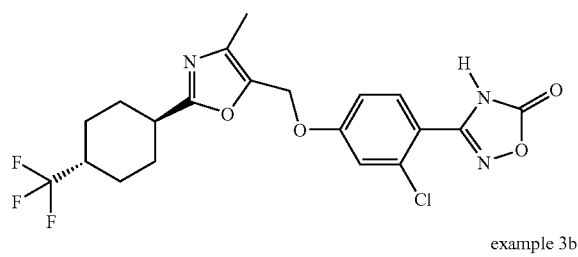

example 3b

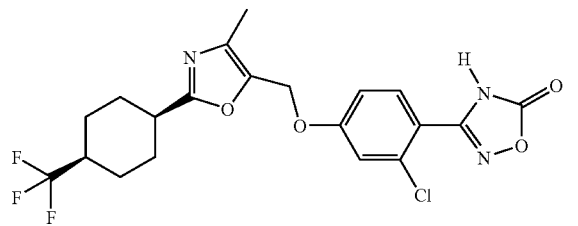

According to the method described in Example 1 a mixture of cis and trans 3-[2-Chloro-4-(2-cyclohexyl-4-methyl-oxazol-5-ylmethoxy)-phenyl]-4H-[1,2,4]oxadiazol-5-one was obtained from 5-Chloromethyl-4-methyl-2-(cis/trans-1,4-trifluoromethyl-cyclohexyl)-oxazole. The diastereoisomers were separated by chromatography on a chiral phase Chiralpak AD-H/45, n-heptane:ethanol:methanol=10:1:1+0.1% trifluoro acetic acid to obtain 3-{2-Chloro-4-[trans-1,4-methyl-2-(4-trifluoromethyl-cyclohexyl)-oxazol-5-ylmethoxy]-phenyl}-4H-[1,2,4]oxadiazol-5-one 3a [C20H19ClF3N3O4 (457.84), MS (ESI): 458.1 (M+H$^+$), Rt=48.4 min] and 3-{2-Chloro-4-[4-methyl-2-(cis-1,4-trifluoromethyl-cyclohexyl)-oxazol-5-ylmethoxy]-phenyl}-4H-[1,2,4]oxadiazol-5-one 3b [$C_{20}H_{19}ClF_3N_3O_4$ (457.84), MS (ESI): 458.1 (M+H$^+$), Rt=8.6 min].

EXAMPLE 4

3-{2-Chloro-4-[2-(trans-1,4-methoxy-cyclohexyl)-4-methyl-oxazol-5-ylmethoxy]-phenyl}-4H-[1,2,4]oxadiazol-5-one

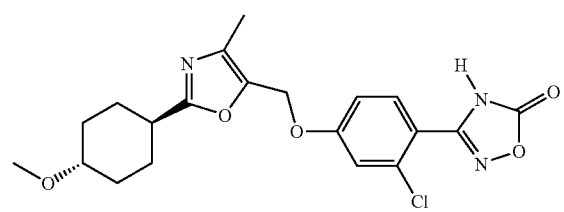

According to the method described in Example 1 3-{2-Chloro-4-[2-(trans-1,4-methoxy-cyclohexyl)-4-methyl-oxazol-5-ylmethoxy]-phenyl}-4H-[1,2,4]oxadiazol-5-one was obtained from 5-Chloromethyl-2-(trans-1,4-methoxy-cyclohexyl)-4-methyl-oxazole and commercially available 2-Chloro-4-hydroxy-benzonitrile.

$C_{20}H_{22}ClN_3O_5$ (419.87), MS (ESI): 420.1 (M+H$^+$).

EXAMPLE 5

3-[2-Chloro-4-(2-cyclohexyl-4-methyl-thiazol-5-ylmethoxy)-phenyl]-4H-[1,2,4]oxadiazol-5-one

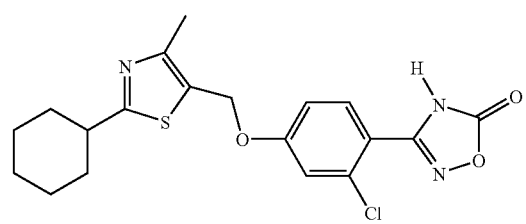

According to the method described in Example 1 3-[2-Chloro-4-(2-cyclohexyl-4-methyl-thiazol-5-ylmethoxy)-phenyl]-4H-[1,2,4]oxadiazol-5-one was obtained from 5-Chloromethyl-2-cyclohexyl-4-methyl-thiazole and commercially available 2-Chloro-4-hydroxy-benzonitrile.

$C_{19}H_{20}ClN_3O3_S$ (405.91), MS (ESI): 406.1 (M+H+).

EXAMPLE 6

3-{2-Chloro-4-[4-methyl-2-(1-trifluoromethane-sulfonyl-piperidin-4-yl)-thiazol-5-ylmethoxy]-phenyl}-4H-[1,2,4]oxadiazol-5-one

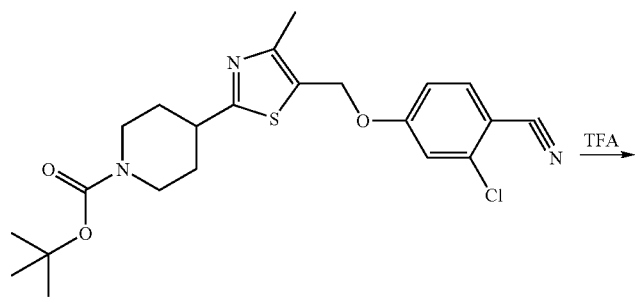

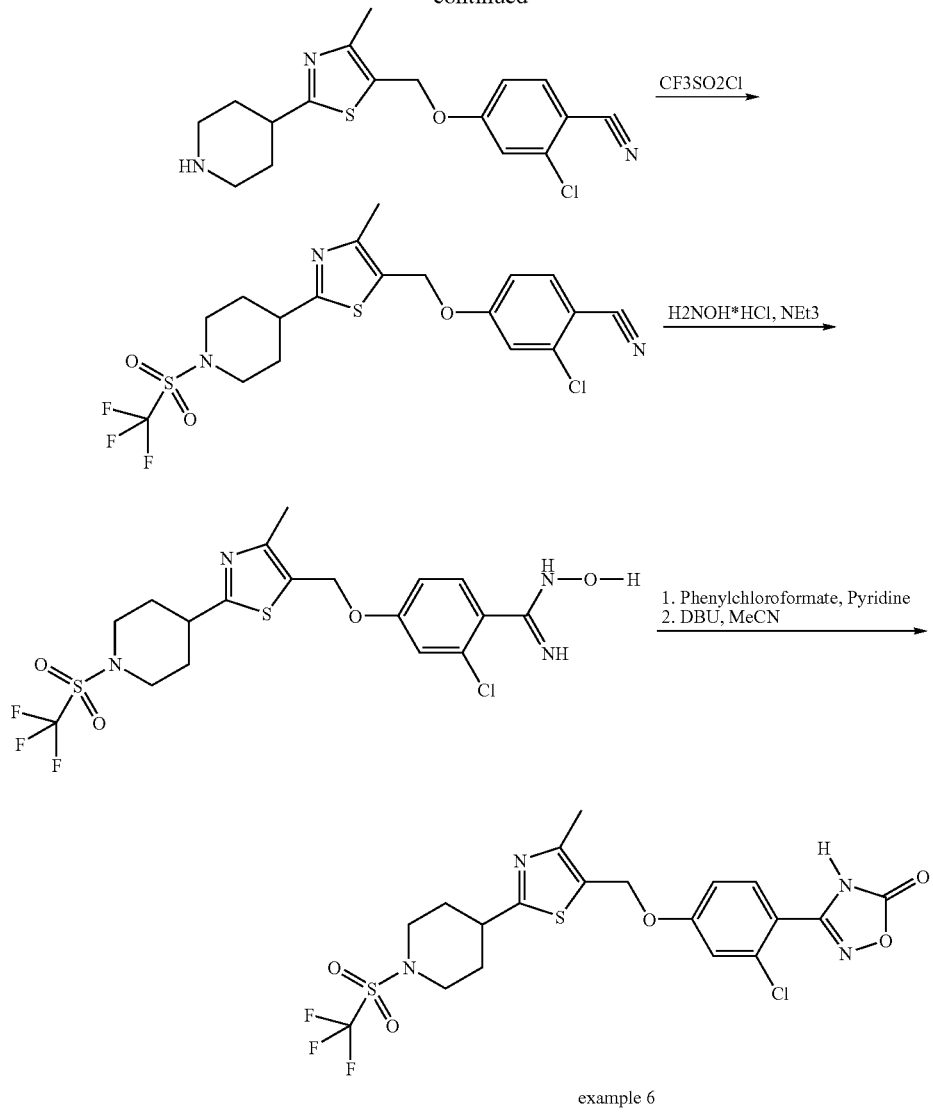

example 6

2-Chloro-4-(4-methyl-2-piperidin-4-yl-thiazol-5-ylmethoxy)-benzonitrile

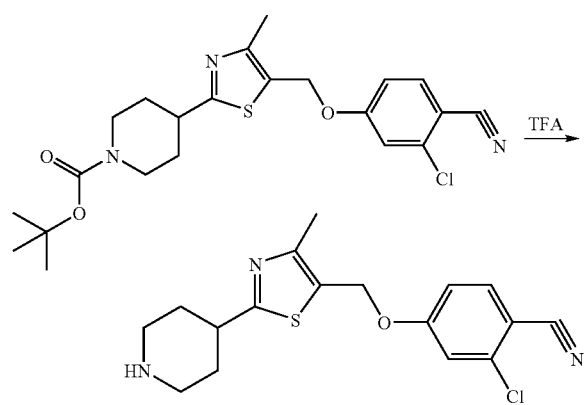

4.5 g 4-[5-(3-Chloro-4-cyano-phenoxymethyl)-4-methyl-thiazol-2-yl]-piperidine-1-carboxylic acid tert-butyl ester (derived from 4-(5-Chloromethyl-4-methyl-thiazol-2-yl)-piperidine-1-carboxylic acid tert-butyl ester and commercially available 2-Chloro-4-hydroxy-benzonitrile according to the method described in Example 1) was dissolved in 100 ml dichloromethane. 20 ml trifluoroacetic acid were added and the reaction mixture stirred at room temperature for one hour. The solvent was removed in vacuo and the residue was dissolved in 200 ml ethyl acetate, washed three times with saturated NaHCO3 solution and then dried over MgSO4. The solvent was removed in Vacuo to obtain 3.5 g 2-Chloro-4-(4-methyl-2-piperidin-4-yl-thiazol-5-ylmethoxy)-benzonitrile as colorless solid.

$C_{17}H_{18}ClN_3OS$ (347.87), MS (ESI): 348.0 (M+H$^+$).

151

2-Chloro-4-[4-methyl-2-(1-trifluoromethanesulfonyl-piperidin-4-yl)-thiazol-5-ylmethoxy]-benzonitrile

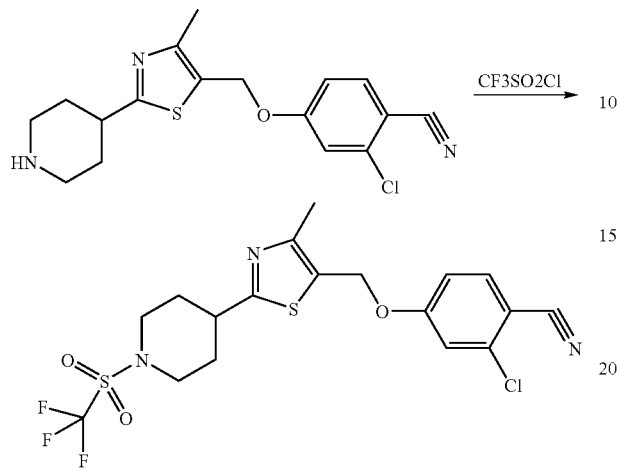

500 mg 2-Chloro-4-(4-methyl-2-piperidin-4-yl-thiazol-5-ylmethoxy)-benzonitrile was dissolved in 20 ml dichloromethane. 0.25 ml N,N-Diisopropylethylamine and 50 mg dimethylaminopyridine were added. Then 0.26 ml trifluoromethanesulfonylchloride were added to the ice cooled reaction mixture. The cooling bath was removed and the reaction mixture stirred at room temperature overnight. The reaction mixture was washed with 10 ml saturated NaHCO3 solution and then dried over MgSO4. The solvent was removed in Vacuo. The resulting crude material was purified by reversed phase HPLC to obtain 350 mg 2-Chloro-4-[4-methyl-2-(1-trifluoromethanesulfonyl-piperidin-4-yl)-thiazol-5-ylmethoxy]-benzonitrile as amorphous solid.

$C_{18}H_{18}ClF_3N_4O_5S_2$ (479.93), MS (ESI): 479.9 (M+H$^+$).

3-{2-Chloro-4-[4-methyl-2-(1-trifluoromethanesulfonyl-piperidin-4-yl)-thiazol-5-ylmethoxy]-phenyl}-4H-[1,2,4]oxadiazol-5-one

example 6

According to the method described in Example 1 3-{2-Chloro-4-[4-methyl-2-(1-trifluoromethanesulfonyl-piperidin-4-yl)-thiazol-5-ylmethoxy]-phenyl}-4H-[1,2,4]oxadiazol-5-one was obtained from 2-Chloro-4-[4-methyl-2-(1-trifluoromethanesulfonyl-piperidin-4-yl)-thiazol-5-ylmethoxy]-benzonitrile.

$C_{19}H_{18}ClF_3N_4O_5S_2$ (538.96), MS (ESI): 539.3 (M+H$^+$).

EXAMPLE 7

3-(2-Chloro-4-{4-methyl-2-[1-(2,2,2-trifluoro-ethyl)-piperidin-4-yl]-thiazol-5-ylmethoxy}-phenyl)-4H-[1,2,4]oxadiazol-5-one

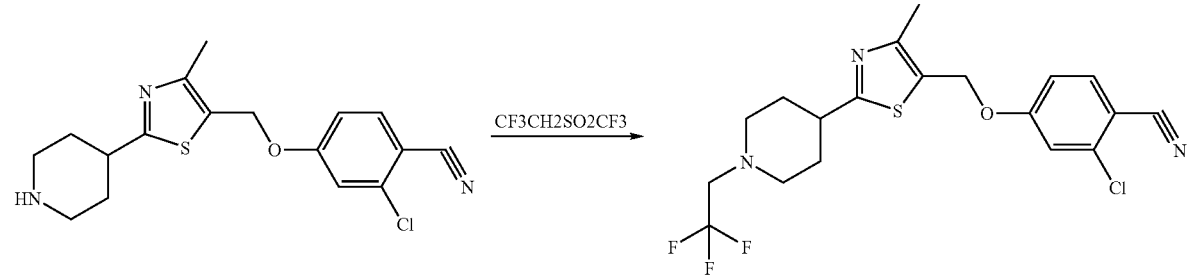

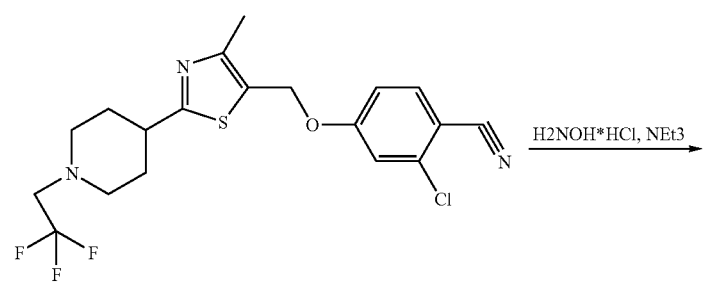

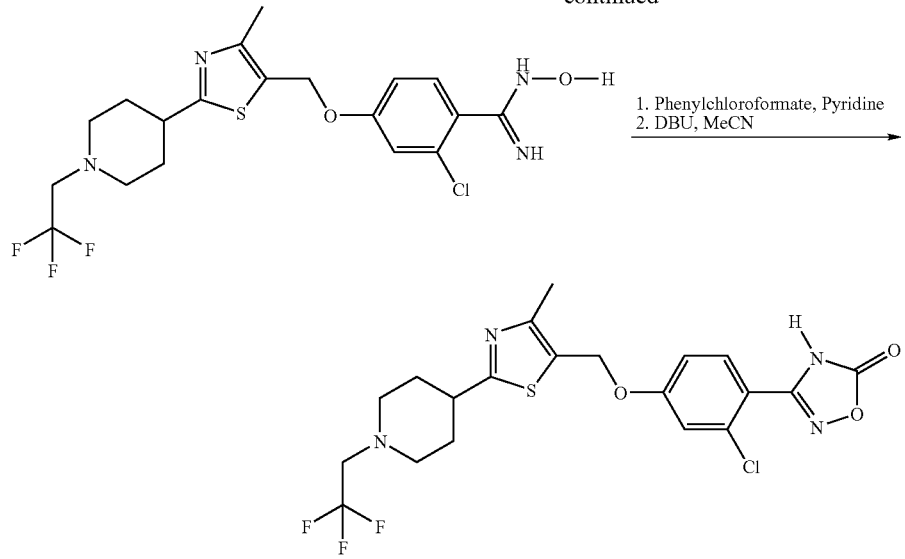

2-Chloro-4-{4-methyl-2-[1-(2,2,2-trifluoro-ethyl)-piperidin-4-yl]-thiazol-5-ylmethoxy}-benzonitrile 3-(2-Chloro-4-{4-methyl-2-[1-(2,2,2-trifluoro-ethyl)-piperidin-4-yl]-thiazol-5-ylmethoxy}-phenyl)-4H-[1,2,4]oxadiazol-5-one example 7

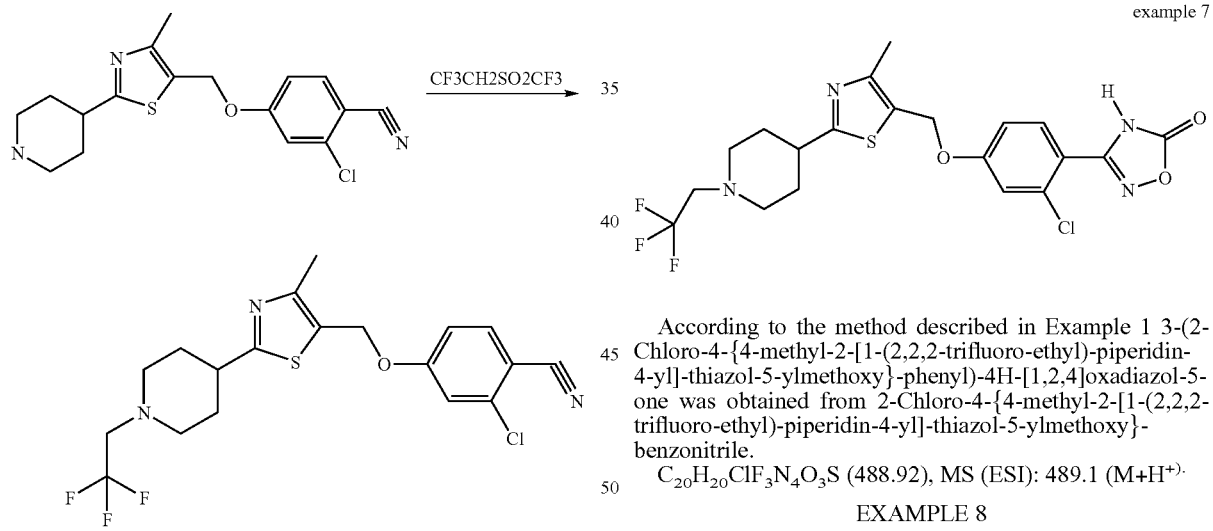

710 mg 2-Chloro-4-(4-methyl-2-piperidin-4-yl-thiazol-5-ylmethoxy)-benzonitrile were dissolved in 20 ml tetrahydrofuran. 0.55 ml N,N-Diisopropylethylamine and 710 mg 2,2,2-Trifluoroethyl-trifluoromethanesulfonate were added and the reaction mixture heated under reflux for two hours. The cooled reaction mixture was diluted by addition of 100 ml ethyl acetate, washed with 20 ml water and brine then dried over MgSO4. The solvent was removed in vacuo to obtain 1.0 g crude 2-Chloro-4-{4-methyl-2-[1-(2,2,2-trifluoro-ethyl)-piperidin-4-yl]-thiazol-5-ylmethoxy}-benzonitrile.

$C_{19}H_{19}ClF_3N_3OS$ (429.89), MS (ESI): 430.0 (M+H$^+$).

According to the method described in Example 1 3-(2-Chloro-4-{4-methyl-2-[1-(2,2,2-trifluoro-ethyl)-piperidin-4-yl]-thiazol-5-ylmethoxy}-phenyl)-4H-[1,2,4]oxadiazol-5-one was obtained from 2-Chloro-4-{4-methyl-2-[1-(2,2,2-trifluoro-ethyl)-piperidin-4-yl]-thiazol-5-ylmethoxy}-benzonitrile.

$C_{20}H_{20}ClF_3N_4O_3S$ (488.92), MS (ESI): 489.1 (M+H$^+$).

EXAMPLE 8

3-{2-Chloro-4-[4-methyl-2-(1-phenyl-piperidin-4-yl)-thiazol-5-yl methoxy]-phenyl}-4H-[1,2,4]oxadiazol-5-one

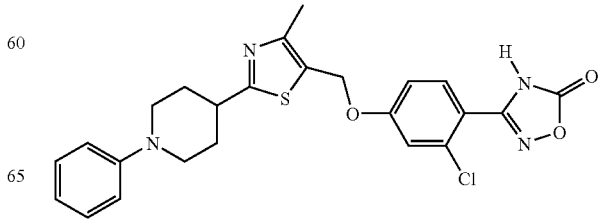

According to the method described in Example 1 3-{2-Chloro-4-[4-methyl-2-(1-phenyl-piperidin-4-yl)-thiazol-5-ylmethoxy]-phenyl}-4H-[1,2,4]oxadiazol-5-one was obtained from 4-(5-Chloromethyl-4-methyl-thiazol-2-yl)-1-phenyl-piperidine and commercially available 2-Chloro-4-hydroxy-benzonitrile.

$C_{24}H_{23}ClN_4O_3S$ (482.99), MS (ESI): 483.4 (M+H$^+$).

EXAMPLE 9

3-{2-Chloro-4-[2-(4,4-difluoro-cyclohexyl)-4-methoxymethyl-thiazol-5-ylmethoxy]-phenyl}-4H-[1,2,4]oxadiazol-5-one

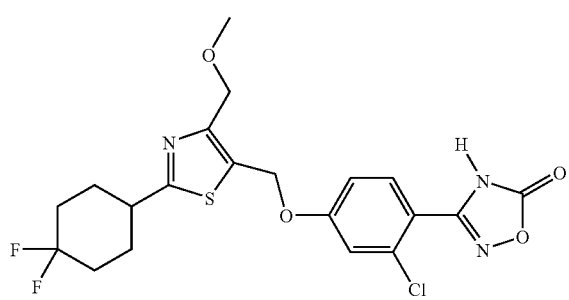

According to the method described in Example 1 3-{2-Chloro-4-[2-(4,4-difluoro-cyclohexyl)-4-methoxymethyl-thiazol-5-ylmethoxy]-phenyl}-4H-[1,2,4]oxadiazol-5-one was obtained from 5-Chloromethyl-2-(4,4-difluoro-cyclohexyl)-4-methoxymethyl-thiazole and commercially available 2-Chloro-4-hydroxy-benzonitrile.

$C_{20}H_{20}ClF_2N_3O_4S$ (471.91), MS (ESI): 472.4 (M+H$^+$).

EXAMPLE 10

3-{2-Chloro-4-[2-(2-cyclohexyl-ethyl)-4-methoxymethyl-thiazol-5-ylmethoxy]-phenyl}-4H-[1,2,4]oxadiazol-5-one

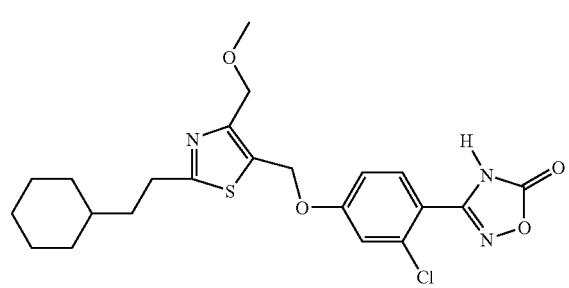

According to the method described in Example 1 3-{2-Chloro-4-[2-(2-cyclohexyl-ethyl)-4-methoxymethyl-thiazol-5-ylmethoxy]-phenyl}-4H-[1,2,4]oxadiazol-5-one was obtained from 5-Chloromethyl-2-(2-cyclohexyl-ethyl)-4-methoxymethyl-thiazole and commercially available 2-Chloro-4-hydroxy-benzonitrile.

$C_{22}H_{26}ClN_3O_4S$ (463.99), MS (ESI): 464.4 (M+H$^+$).

EXAMPLE 11

3-[2-Chloro-4-(2-cycloheptyl-4-methoxymethyl-thiazol-5-ylmethoxy)-phenyl]-4H-[1,2,4]oxadiazol-5-one

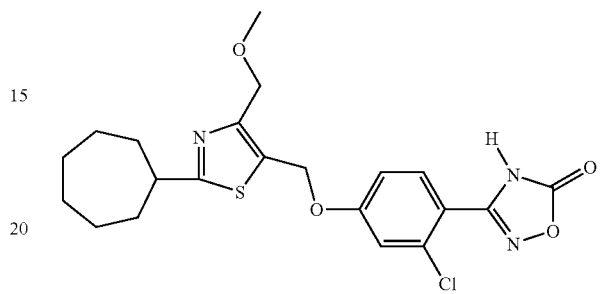

According to the method described in Example 1 3-[2-Chloro-4-(2-cycloheptyl-4-methoxymethyl-thiazol-5-ylmethoxy)-phenyl]-4H-[1,2,4]oxadiazol-5-one was obtained from 5-Chloromethyl-2-cycloheptyl-4-methoxymethyl-thiazole and commercially available 2-Chloro-4-hydroxy-benzonitrile.

$C_{21}H_{24}ClN_3O_4S$ (449.96), MS (ESI): 450.5 (M+H$^+$).

EXAMPLE 12

Trans-3-(2-Chloro-4-{2-[4-(4-chloro-phenyl)-cyclohexyl]-4-methoxymethyl-thiazol-5-ylmethoxy}-phenyl)-4H-[1,2,4]oxadiazol-5-one

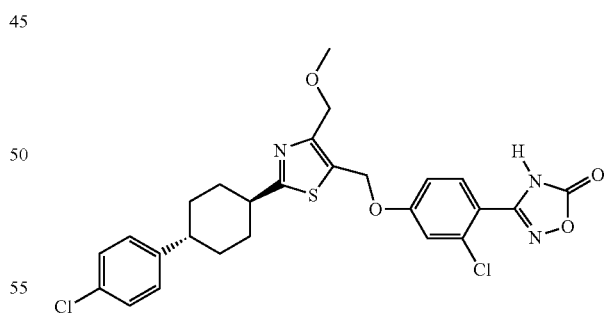

According to the method described in Example 1 trans-3-(2-Chloro-4-{2-[4-(4-chloro-phenyl)-cyclohexyl]-4-methoxymethyl-thiazol-5-ylmethoxy}-phenyl)-4H-[1,2,4]oxadiazol-5-one was obtained from trans-5-Chloromethyl-2-[4-(4-chloro-phenyl)-cyclohexyl]-4-methoxymethyl-thiazole and commercially available 2-Chloro-4-hydroxy-benzonitrile.

$C_{26}H_{25}Cl_2N_3O_4S$ (546.48), MS (ESI): 546.4 (M+H$^+$).

EXAMPLE 13

3-[2-Chloro-4-(2-cyclopentyl-4-methoxymethyl-oxazol-5-ylmethoxy)-phenyl]-4H-[1,2,4]oxadiazol-5-one

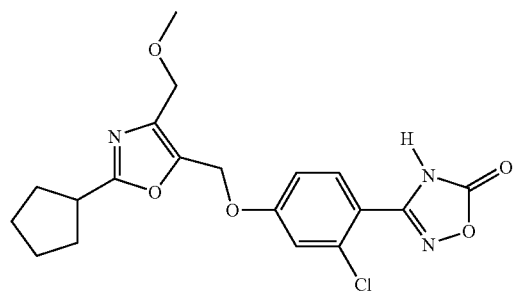

According to the method described in Example 1 3-[2-Chloro-4-(2-cyclopentyl-4-methoxymethyl-oxazol-5-yl-methoxy)-phenyl]-4H-[1,2,4]oxadiazol-5-one was obtained from 5-Chloromethyl-2-cyclopentyl-4-methoxymethyl-oxazole and commercially available 2-Chloro-4-hydroxy-benzonitrile.

$C_{19}H_{20}ClN_3O_5$ (405.84), MS (ESI): 406.1 (M+H$^+$).

EXAMPLE 14

3-{2-Chloro-4-[4-methoxymethyl-2-(6-trifluoromethyl-pyridin-3-yl)-thiazol-5-ylmethoxy]-phenyl}-4H-[1,2,4]oxadiazol-5-one

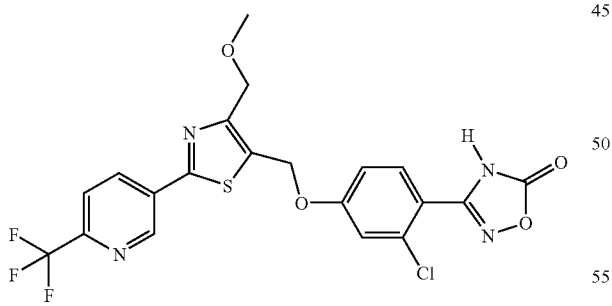

According to the method described in Example 1 3-{2-Chloro-4-[4-methoxymethyl-2-(6-trifluoromethyl-pyridin-3-yl)-thiazol-5-ylmethoxy]-phenyl}-4H-[1,2,4]oxadiazol-5-one was obtained from 5-(5-Chloromethyl-4-methoxymethyl-thiazol-2-yl)-2-trifluoromethyl-pyridine and commercially available 2-Chloro-4-hydroxy-benzonitrile.

$C_{20}H_{14}ClF_3N_4O_4S$ (498.87), MS (ESI): 499.3 (M+H$^+$).

EXAMPLE 15

3-[2-Chloro-4-(2-cyclohexyl-4-ethoxymethyl-oxazol-5-ylmethoxy)-phenyl]-4H-[1,2,4]oxadiazol-5-one

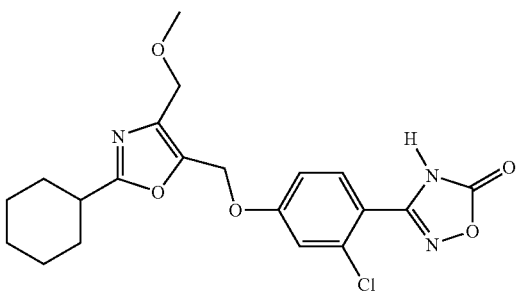

According to the method described in Example 1 3-[2-Chloro-4-(2-cyclohexyl-4-ethoxymethyl-oxazol-5-yl-methoxy)-phenyl]-4H-[1,2,4]oxadiazol-5-one was obtained from 5-Chloromethyl-2-cyclohexyl-4-ethoxymethyl-oxazole and commercially available 2-Chloro-4-hydroxy-benzonitrile.

$C_{21}H_{24}ClN_3O_5$ (433.90), MS (ESI): 434.2 (M+H$^+$).

EXAMPLE 16

3-[2-Chloro-4-(2-cyclohexyl-4-methoxymethyl-oxazol-5-ylmethoxy)-phenyl]-4H-[1,2,4]oxadiazol-5-one

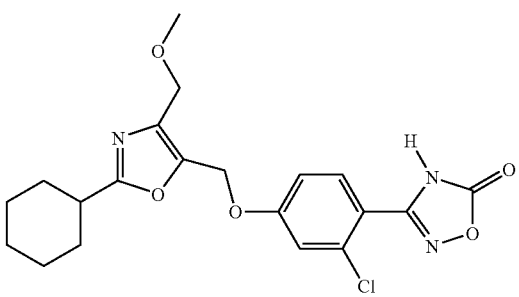

According to the method described in Example 1 3-[2-Chloro-4-(2-cyclohexyl-4-methoxymethyl-oxazol-5-yl-methoxy)-phenyl]-4H-[1,2,4]oxadiazol-5-one was obtained from 5-Chloromethyl-2-cyclohexyl-4-methoxymethyl-oxazole and commercially available 2-Chloro-4-hydroxy-benzonitrile.

$C_{18}H_{22}ClN_3O_5$ (419.87), MS (ESI): 420.1 (M+H$^+$).

EXAMPLE 17

3-[2-Chloro-4-(2-cycloheptyl-4-methoxymethyl-oxazol-5-ylmethoxy)-phenyl]-4H-[1,2,4]oxadiazol-5-one

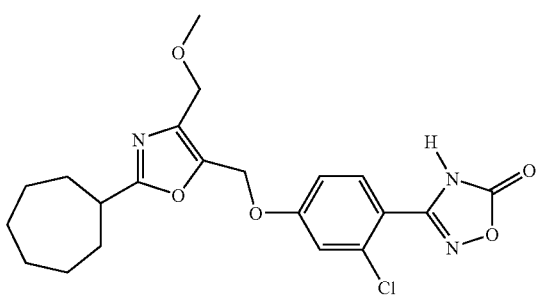

According to the method described in Example 1 3-[2-Chloro-4-(2-cycloheptyl-4-methoxymethyl-oxazol-5-ylmethoxy)-phenyl]-4H-[1,2,4]oxadiazol-5-one was obtained from 5-Chloromethyl-2-cycloheptyl-4-methoxymethyl-oxazole and commercially available 2-Chloro-4-hydroxy-benzonitrile.

$C_{21}H_{24}ClN_3O_5$ (433.90), MS (ESI): 434.1 (M+H$^+$).

EXAMPLE 18

Trans-3-{2-Chloro-4-[4-methoxymethyl-2-(4-trifluoromethyl-cyclohexyl)-oxazol-5-ylmethoxy]-phenyl}-4H-[1,2,4]oxadiazol-5-one 18a and cis-3-{2-Chloro-4-[4-methoxymethyl-2-(4-trifluoromethyl-cyclohexyl)-oxazol-5-ylmethoxy]-phenyl}-4H-[1,2,4]oxadiazol-5-one 18b example 18a

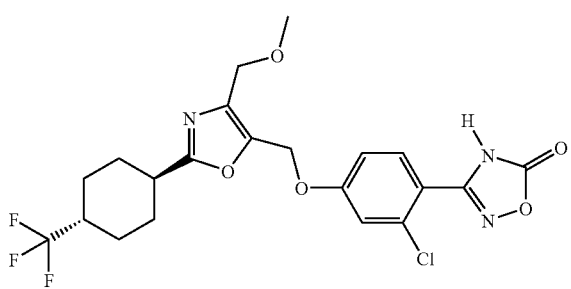

example 18b

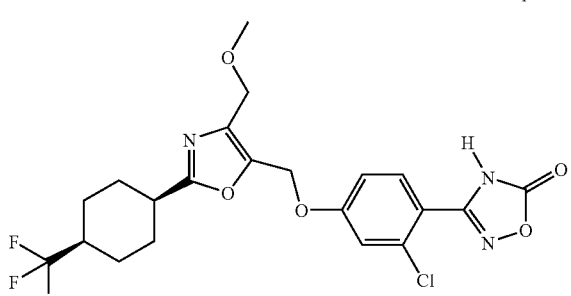

According to the method described in Example 1 a mixture of cis and trans 3-{2-Chloro-4-[4-methoxymethyl-2-(4-trifluoromethyl-cyclohexyl)-oxazol-5-ylmethoxy]-phenyl}-4H-[1,2,4]oxadiazol-5-one was obtained from cis/trans-5-Chloromethyl-4-methoxymethyl-2-(4-trifluoromethyl-cyclohexyl)-oxazole. The diastereoisomers were separated by chromatography on a chiral phase Chiralpak AD-H/45 n-heptane:methanol:ethanol=10:1:1+0.1% trifluoro acetic acid to obtain trans-3-{2-Chloro-4-[4-methoxymethyl-2-(4-trifluoromethyl-cyclohexyl)-oxazol-5-ylmethoxy]-phenyl}-4H-[1,2,4]oxadiazol-5-one 18a [$C_{21}H_{21}ClF_3N_3O_5$ (487.87), MS (ESI): 488.2 (M+H$^+$), Rt=24.5 min] and cis-3-{2-Chloro-4-[4-methoxymethyl-2-(4-trifluoromethyl-cyclohexyl)-oxazol-5-ylmethoxy]-phenyl}-4H-[1,2,4]oxadiazol-5-one 18b [$C_{21}H_{21}ClF_3N_3O_5$ (487.87), MS (ESI): 488.2 (M+H$^+$), Rt=8.0 min].

EXAMPLE 19

3-[2-Chloro-4-(2-cyclohexyl-4-morpholin-4-ylmethyl-oxazol-5-ylmethoxy)-phenyl]-4H-[1,2,4]oxadiazol-5-one

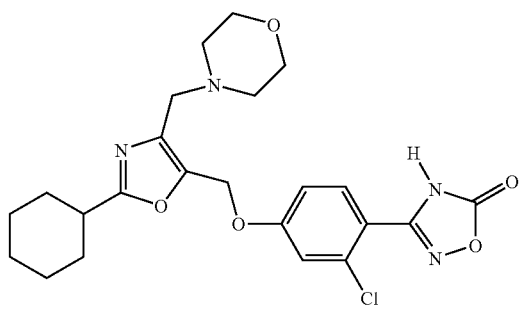

According to the method described in Example 1 3-[2-Chloro-4-(2-cyclohexyl-4-morpholin-4-ylmethyl-oxazol-5-ylmethoxy)-phenyl]-4H-[1,2,4]oxadiazol-5-one was obtained from 4-(5-Chloromethyl-2-cyclohexyl-oxazol-4-ylmethyl)-morpholine and commercially available 2-Chloro-4-hydroxy-benzonitrile.

$C_{23}H_{27}ClN_4O_5$ (474.95), MS (ESI): 475.22 (M+H$^+$).

EXAMPLE 20

3-[2-Chloro-4-(2-cyclohexyl-4-diethylaminomethyl-oxazol-5-ylmethoxy)-phenyl]-4H-[1,2,4]oxadiazol-5-one

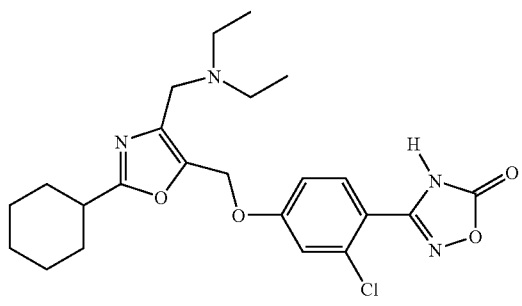

According to the method described in Example 1 3-[2-Chloro-4-(2-cyclohexyl-4-diethylaminomethyl-oxazol-5-ylmethoxy)-phenyl]-4H-[1,2,4]oxadiazol-5-one was obtained from (5-Chloromethyl-2-cyclohexyl-oxazol-4-ylmethyl)-diethyl-amine and commercially available 2-Chloro-4-hydroxy-benzonitrile.

$C_{23}H_{29}ClN_4O_4$ (460.96), MS (ESI): 461.2 (M+H$^+$).

EXAMPLE 21

3-[2-Chloro-4-(2-cyclohexyl-oxazol-4-ylmethoxy)-phenyl]-4H-[1,2,4]oxadiazol-5-one

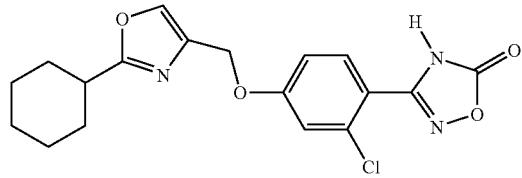

According to the method described in Example 1 3-[2-Chloro-4-(2-cyclohexyl-oxazol-4-ylmethoxy)-phenyl]-4H-[1,2,4]oxadiazol-5-one was obtained from 2-Cyclohexyl-4-iodomethyl-oxazole[2] and commercially available 2-Chloro-4-hydroxy-benzonitrile.

$C_{18}H_{18}ClN_3O_4$ (375.81), MS (ESI): 376.1 (M+H$^+$).

EXAMPLE 22

3-{2-Chloro-4-[2-(2-cyclohexyl-vinyl)-4-methoxymethyl-thiazol-5-ylmethoxy]-phenyl}-4H-[1,2,4]oxadiazol-5-one

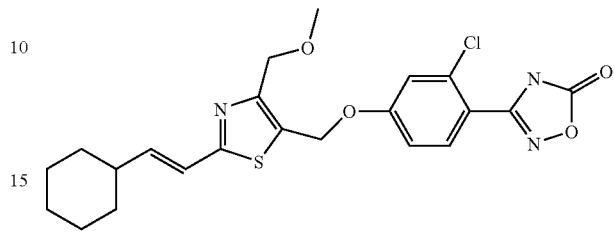

According to the method described in Example 1 3-{2-Chloro-4-[2-(2-cyclohexyl-vinyl)-4-methoxymethyl-thiazol-5-ylmethoxy]-phenyl}-4H-[1,2,4]oxadiazol-5-one was obtained from 5-Chloromethyl-2-(2-cyclohexyl-vinyl)-4-methoxymethyl-thiazole and commercially available 2-Chloro-4-hydroxy-benzonitrile.

C22H24ClN3O4S (461.97), MS (ESI): 462.1 (M+H$^+$).

EXAMPLE 23

3-{2-Chloro-4-[4-methyl-2-(6-trifluoromethyl-pyridin-3-yl)-thiazol-6-ylmethoxy]-phenyl}-4H-[1,2,4]oxadiazol-5-one

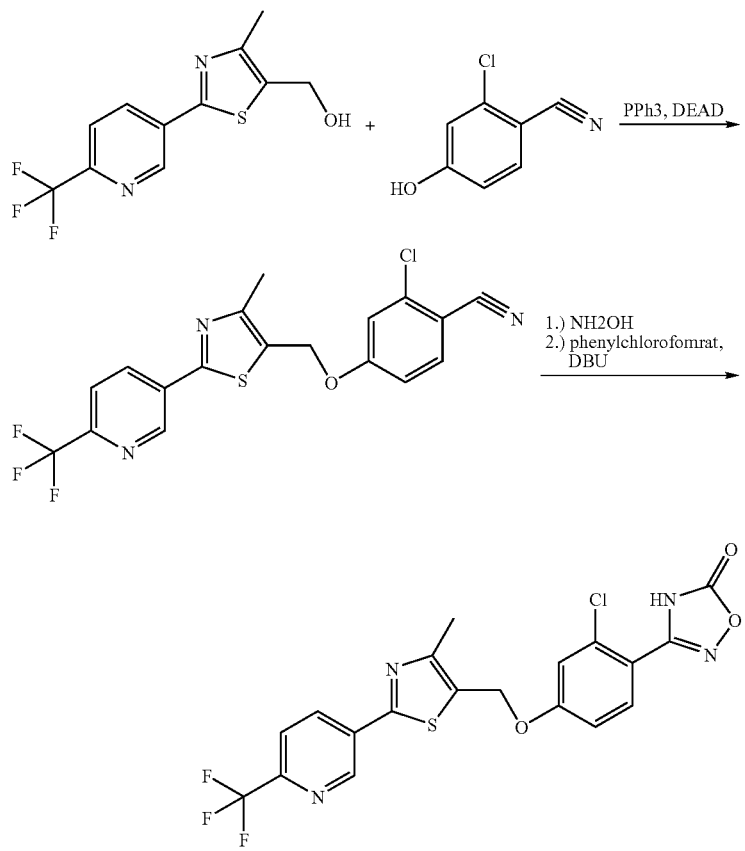

163

2-Chloro-4-[4-methyl-2-(6-trifluoromethyl-pyridin-3-yl)-thiazol-5-ylmethoxy]-benzonitrile

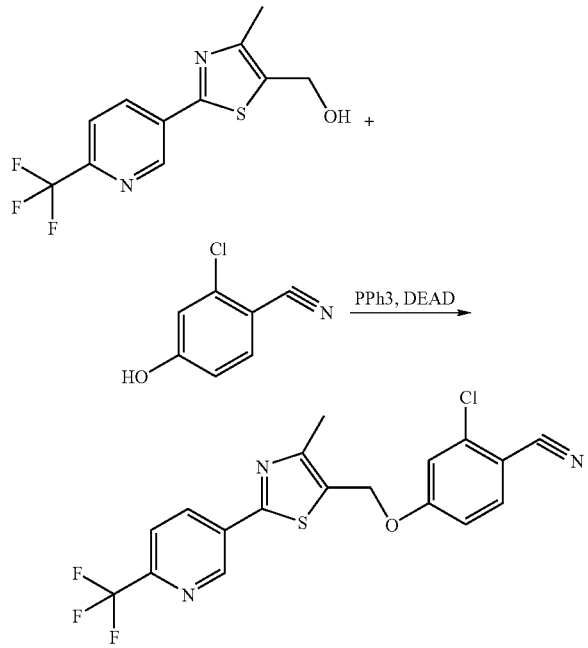

To an ice cooled solution of 2.76 g [4-Methyl-2-(6-trifluoromethyl-pyridin-3-yl)-thiazol-5-yl]-methanol, 2.06 g 2-chloro-4-hydroxybenzonitrile and 3.03 g triphenylphosphine in 30 ml tetrahydrofuran were added 1.74 ml diethylazodicarboxyate. The reaction mixture was stirred at room temperature overnight. 0.56 ml 30% H2O2 were added and the reaction mixture diluted by addition of 200 ml diethylether. The organic layer was washed with 50 ml 1N NaOH and 50 ml water, dried over MgSO4. The solvent was removed in vacuo. The resulting residue was purified by reversed phase HPLC to obtain 2.02 g 2-Chloro-4-[4-methyl-2-(6-trifluoromethyl-pyridin-3-yl)-thiazol-5-ylmethoxy]-benzonitrile as a lyophilisate.

$C_{18}H_{11}ClF3N3OS$ (409.82), MS (ESI): 410.1 (M+H$^+$).

3-{2-Chloro-4-[4-methyl-2-(6-trifluoromethyl-pyridin-3-yl)-thiazol-5-ylmethoxy]-phenyl}-4H-[1,2,4]oxadiazol-5-one

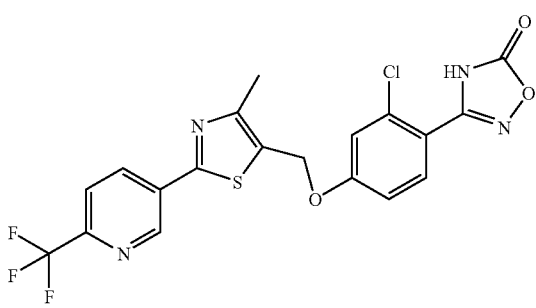

164

According to the method described in Example 1 3-{2-Chloro-4-[4-methyl-2-(6-trifluoromethyl-pyridin-3-yl)-thiazol-5-ylmethoxy]-phenyl}-4H-[1,2,4]oxadiazol-5-one was obtained from 2-Chloro-4-[4-methyl-2-(6-trifluoromethyl-pyridin-3-yl)-thiazol-5-ylmethoxy]-benzonitrile.

$C_{19}H_{12}ClF_3N_4O_3S$ (468.84), MS (ESI): 469.2 (M+H$^+$).

EXAMPLE 24

3-(2-Chloro-4-{1-[4-methyl-2-(trans-1,4-trifluoromethyl-cyclohexyl)-thiazol-5-yl]-2-phenyl-ethoxy}-phenyl)-4H-[1,2,4]oxadiazol-5-one

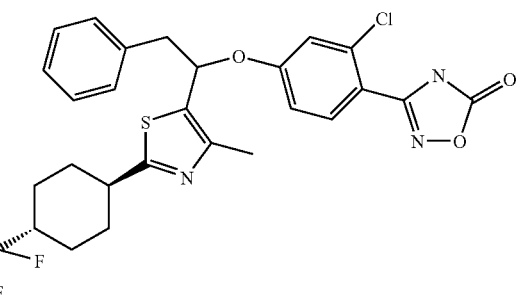

According to the method described in Example 1 3-(2-Chloro-4-{1-[4-methyl-2-(trans-1,4-trifluoromethyl-cyclohexyl)-thiazol-5-yl]-2-phenyl-ethoxy}-phenyl)-4H-[1,2,4]oxadiazol-5-one was obtained from 2-Chloro-4-{1-[4-methyl-2-(4-trifluoromethyl-cyclohexyl)-thiazol-5-yl]-2-phenyl-ethoxy}-benzonitrile (derived from 1-[4-Methyl-2-(trans-1,4-trifluoromethyl-cyclohexyl)-thiazol-5-yl]-2-phenyl-ethanol and 2-chloro-4-hydroxybenzonitrile according to the method described in example 23).

The racemic mixture was separated into its enantiomers by chromatography on chiral phase (Chiralpak AD-H/39) with the eluent n-heptane:propanol:ethanol=8:1:1, Rt=7.13 min and 9.94 min.

$C_{27}H_{25}ClF_3N_3O_3S$ (564.03), MS (ESI): 564.33 (M+H$^+$).

The following examples were prepared according to process D:

EXAMPLE 25
3-{4-[4-(3-Benzyloxy-propyl)-2-(6-trifluoromethyl-pyridin-3-yl)-thiazol-5-ylmethoxy]-2-chloro-phenyl}-4H-[1,2,4]oxadiazol-5-one
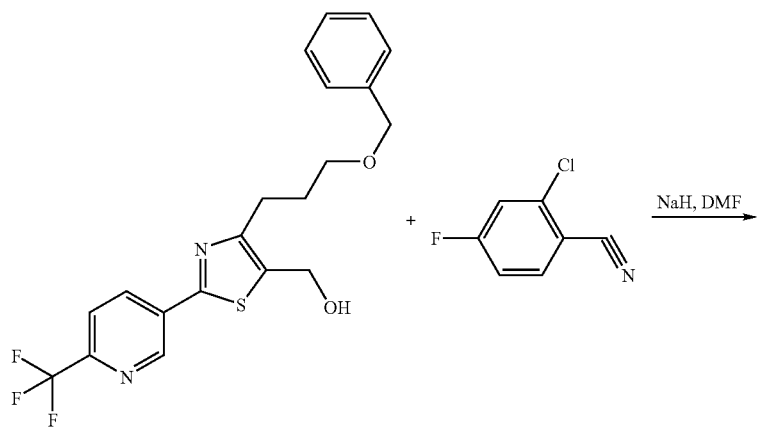
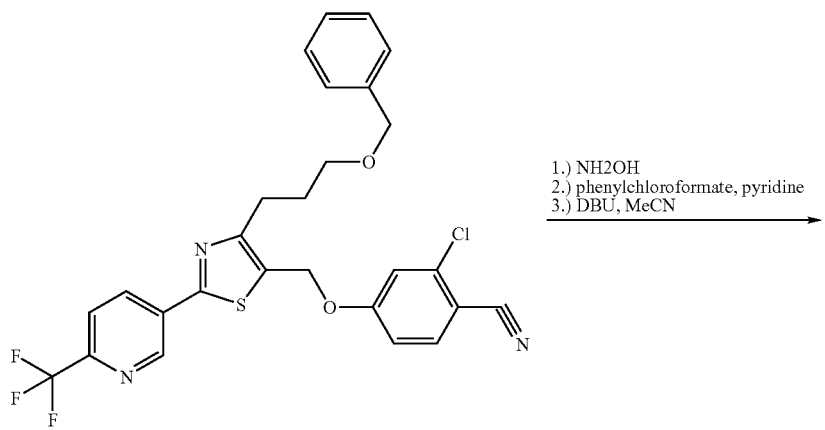
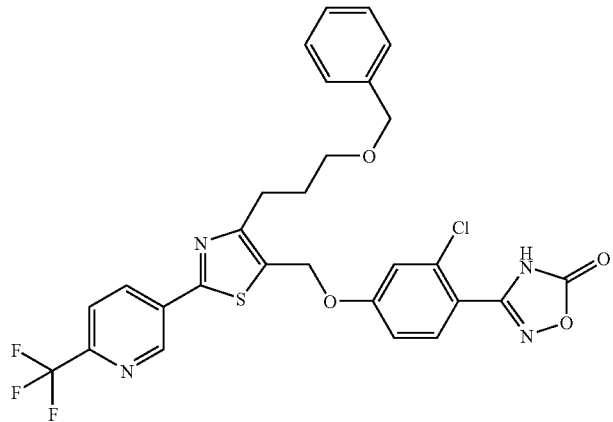

167

4-[4-(3-Benzyloxy-propyl)-2-(6-trifluoromethyl-pyridin-3-yl)-thiazol-5-ylmethoxy]-2-chloro-benzonitrile

168

3-{4-[4-(3-Benzyloxy-propyl)-2-(6-trifluoromethyl-pyridin-3-yl)-thiazol-5-ylmethoxy]-2-chloro-phenyl}-4H-[1,2,4]oxadiazol-5-one

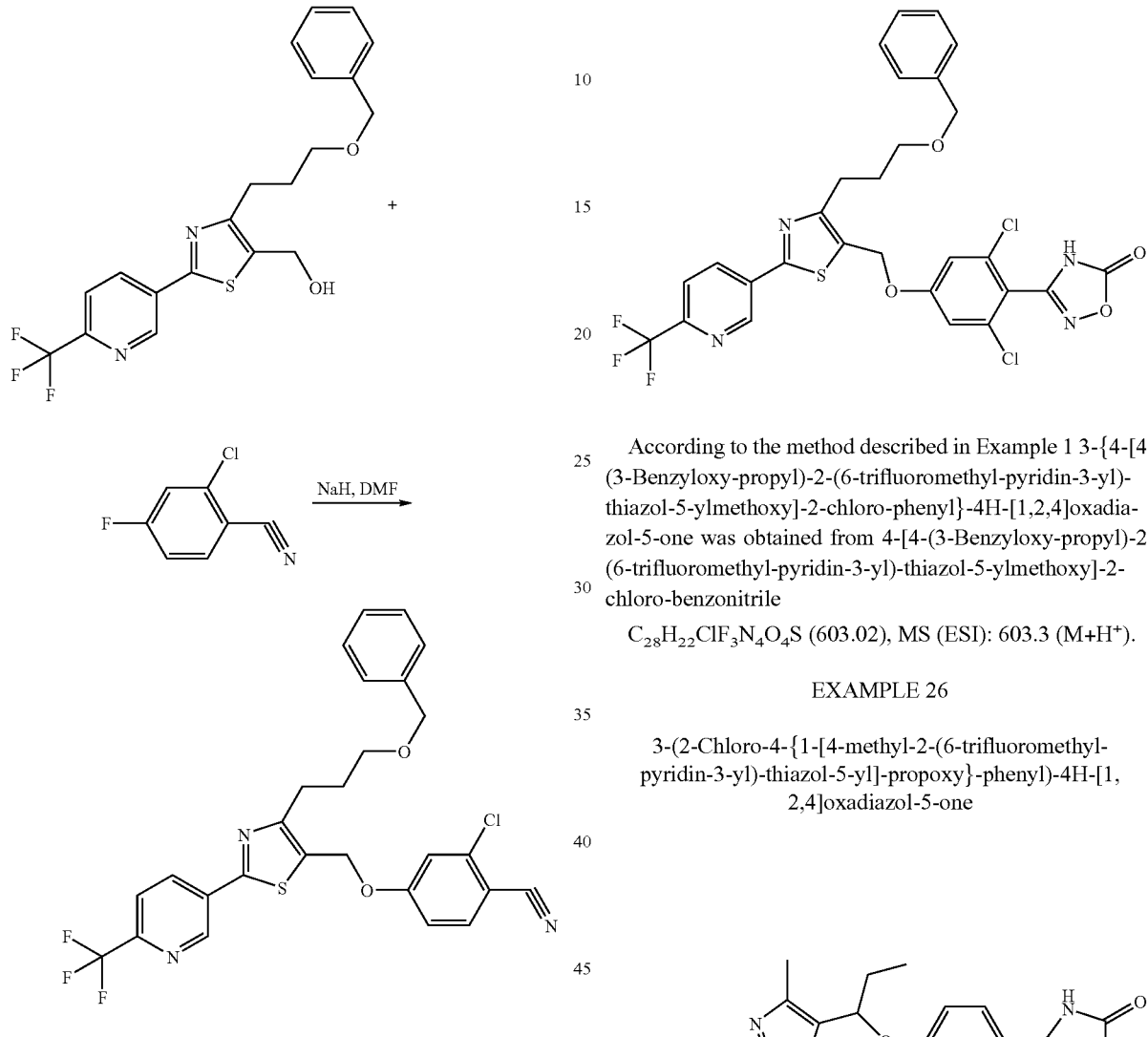

According to the method described in Example 1 3-{4-[4-(3-Benzyloxy-propyl)-2-(6-trifluoromethyl-pyridin-3-yl)-thiazol-5-ylmethoxy]-2-chloro-phenyl}-4H-[1,2,4]oxadiazol-5-one was obtained from 4-[4-(3-Benzyloxy-propyl)-2-(6-trifluoromethyl-pyridin-3-yl)-thiazol-5-ylmethoxy]-2-chloro-benzonitrile $C_{28}H_{22}ClF_3N_4O_4S$ (603.02), MS (ESI): 603.3 (M+H$^+$).

EXAMPLE 26

3-(2-Chloro-4-{1-[4-methyl-2-(6-trifluoromethyl-pyridin-3-yl)-thiazol-5-yl]-propoxy}-phenyl)-4H-[1,2,4]oxadiazol-5-one 1.44 g [4-(3-Benzyloxy-propyl)-2-(6-trifluoromethyl-pyridin-3-yl)-thiazol-5-yl]-methanol were dissolved in 15 ml dimethylformamide. 231 mg sodium hydride (95%) were added and the reaction mixture stirred at room temperature. After thirty minutes 549 mg 2-chloro-4-fluorobenzonitrile were added and the reaction mixture stirred at room temperature for one hour. Then the reaction was quenched by the addition of 20 ml water and extracted three times with portions of 50 ml methyltertbutylether. The combined organic phases were dried over MgSO4. The solvent was removed in vacuo. The resulting residue was purified by reversed phase HPLC to obtain 641 mg 4-[4-(3-Benzyloxy-propyl)-2-(6-trifluoromethyl-pyridin-3-yl)-thiazol-5-ylmethoxy]-2-chloro-benzonitrile as yellow lyophilisate.

$C_{27}H_{21}ClF_3N_3O_2S$ (544.0), MS (ESI): 544.2 (M+H$^+$), Rf (n-heptane:ethyl acetate=1:1) 0.66.

According to the method described in Example 1 3-(2-Chloro-4-{1-[4-methyl-2-(6-trifluoromethyl-pyridin-3-yl)-thiazol-5-yl]-propoxy}-phenyl)-4H-[1,2,4]oxadiazol-5-one was obtained from 2-Chloro-4-{1-[4-methyl-2-(6-trifluoromethyl-pyridin-3-yl)-thiazol-5-yl]-propoxy}-benzonitrile (derived from 1-[4-Methyl-2-(6-trifluoromethyl-pyridin-3-yl)-thiazol-5-yl]-propan-1-ol and 2-chloro-4-fluorobenzonitrile according to the method described in example 25).

$C_{21}H_{16}ClF_3N_4O_3S$ (496.90), MS (ESI): 497.1 (M+H$^+$).

EXAMPLE 27

3-(2-Chloro-4-{2-(4-fluoro-phenyl)-1-[4-methyl-2-(6-trifluoromethyl-pyridin-3-yl)-thiazol-5-yl]-ethoxy}-phenyl)-4H-[1,2,4]oxadiazol-5-one

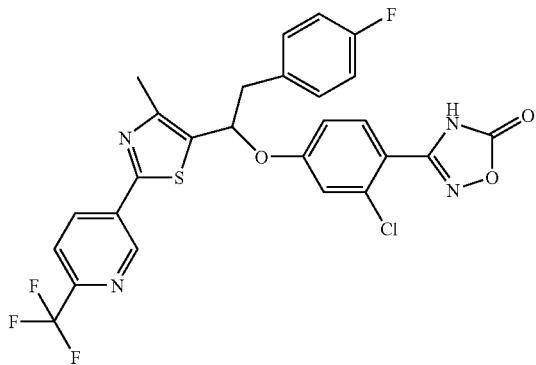

According to the method described in Example 1 3-(2-Chloro-4-{2-(4-fluoro-phenyl)-1-[4-methyl-2-(6-trifluoromethyl-pyridin-3-yl)-thiazol-5-yl]-ethoxy}-phenyl)-4H-[1,2,4]oxadiazol-5-one was obtained from 2-Chloro-4-{2-(4-fluoro-phenyl)-1-[4-methyl-2-(6-trifluoromethyl-pyridin-3-yl)-thiazol-5-yl]-ethoxy}-benzonitrile (derived from 2-(4-Fluoro-phenyl)-1-[4-methyl-2-(6-trifluoromethyl-pyridin-3-yl)-thiazol-5-yl]-ethanol and 2-chloro-4-fluorobenzonitrile according to the method described in example 25).

$C_{26}H_{17}ClF_4N_4O_3S$ (576,96), MS (ESI): 577.0 (M+H$^+$).

EXAMPLE 28

3-(2-Chloro-4-{2,2,2-trifluoro-1-[4-methyl-2-(4-trifluoromethyl-cyclohexyl)-thiazol-5-yl]-ethoxy}-phenyl)-4H-[1,2,4]oxadiazol-5-one

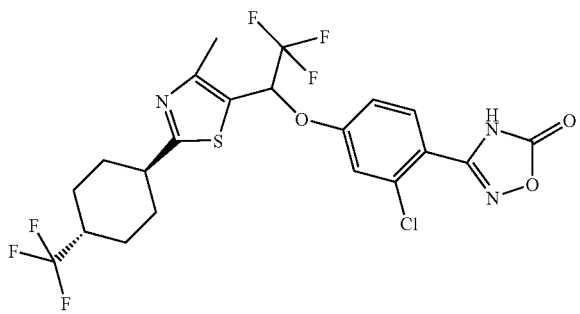

According to the method described in Example 1 3-(2-Chloro-4-{2,2,2-trifluoro-1-[4-methyl-2-(4-trifluoromethyl-cyclohexyl)-thiazol-5-yl]-ethoxy}-phenyl)-4H-[1,2,4]oxadiazol-5-one was obtained from 2-Chloro-4-{2,2,2-trifluoro-1-[4-methyl-2-(4-trifluoromethyl-cyclohexyl)-thiazol-5-yl]-ethoxy}-benzonitrile (derived from 2,2,2-Trifluoro-1-[4-methyl-2-(4-trifluoromethyl-cyclohexyl)-thiazol-5-yl]-ethanol and 2-chloro-4-fluorobenzonitrile according to the method described in example 25).

$C_{21}H_{18}ClF_6N_3O_3S$ (541,90), MS (ESI): 542.1 (M+H$^+$).

EXAMPLE 29

3-(2-Chloro-4-{1-[4-methyl-2-(4-trifluoromethyl-cyclohexyl)-thiazol-5-yl]-2-pyridin-2-yl-ethoxy}-phenyl)-4H-[1,2,4]oxadiazol-5-one

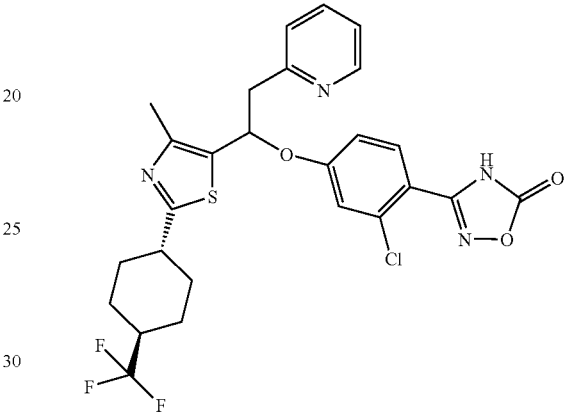

According to the method described in Example 1 3-(2-Chloro-4-{1-[4-methyl-2-(4-trifluoromethyl-cyclohexyl)-thiazol-5-yl]-2-pyridin-2-yl-ethoxy}-phenyl)-4H-[1,2,4]oxadiazol-5-one was obtained from 2-Chloro-4-{1-[4-methyl-2-(4-trifluoromethyl-cyclohexyl)-thiazol-5-yl]-2-pyridin-2-yl-ethoxy}-benzonitrile (derived from 1-[4-Methyl-2-(4-trifluoromethyl-cyclohexyl)-thiazol-5-yl]-2-pyridin-2-yl-ethanol and 2-chloro-4-fluorobenzonitrile according to the method described in example 25).

$C_{26}H_{24}ClF_3N_4O_3S$ (565.02), MS (ESI): 565.2 (M+H$^+$).

The following examples were prepared according to process E:

EXAMPLE 30

3-(2-Fluoro-4-{2,2,2-trifluoro-1-[4-methyl-2-(trans-1,4-trifluoromethyl-cyclohexyl)-thiazol-5-yl]-ethoxymethyl}-phenyl)-4H-[1,2,4]oxadiazol-5-one

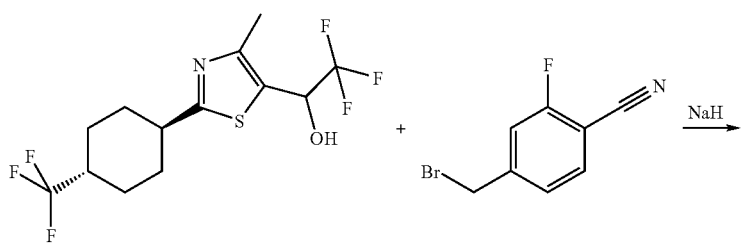

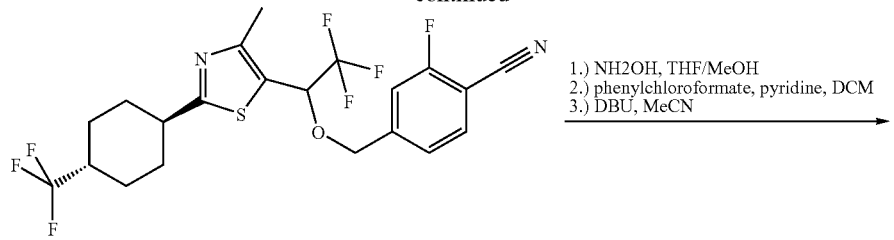

2-Fluoro-4-{2,2,2-trifluoro-1-[4-methyl-2-(trans-1,4-trifluoromethyl-cyclohexyl)-thiazol-5-yl]-ethoxymethyl}-benzonitrile

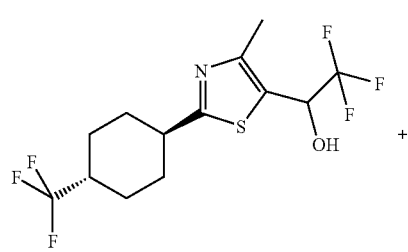

800 mg 2,2,2-Trifluoro-1-[4-methyl-2-(trans-1,4-trifluoromethyl-cyclohexyl)-thiazol-5-yl]-ethanol and 493 mg 4-Bromomethyl-2-fluoro-benzonitrile were dissolved in 25 ml dimethylformamide and cooled in an ice bath. At 0° C. 116 mg sodium hydride (95%) were added. The cooling bath was removed and the reaction mixture was stirred at room temperature for one hour. Then 10 ml water were added and the reaction extracted three times with portions of 30 ml ethyl acetate. The combined organic layers were dried over MgSO4. The solvent was removed in vacuo. The resulting residue was purified by reversed phase HPLC to obtain 550 mg 2-Fluoro-4-{2,2,2-trifluoro-1-[4-methyl-2-(trans-1,4-trifluoromethyl-cyclohexyl)-thiazol-5-yl]-ethoxymethyl}-benzonitrile.

$C_{21}H_{19}F_7N_2OS$ (480.45), MS (ESI): 481.2 (M+H$^+$).

3-(2-Fluoro-4-{2,2,2-trifluoro-1-[4-methyl-2-(trans-1,4-trifluoromethyl-cyclohexyl)-thiazol-5-yl]-ethoxymethyl}-phenyl)-4H-[1,2,4]oxadiazol-5-one

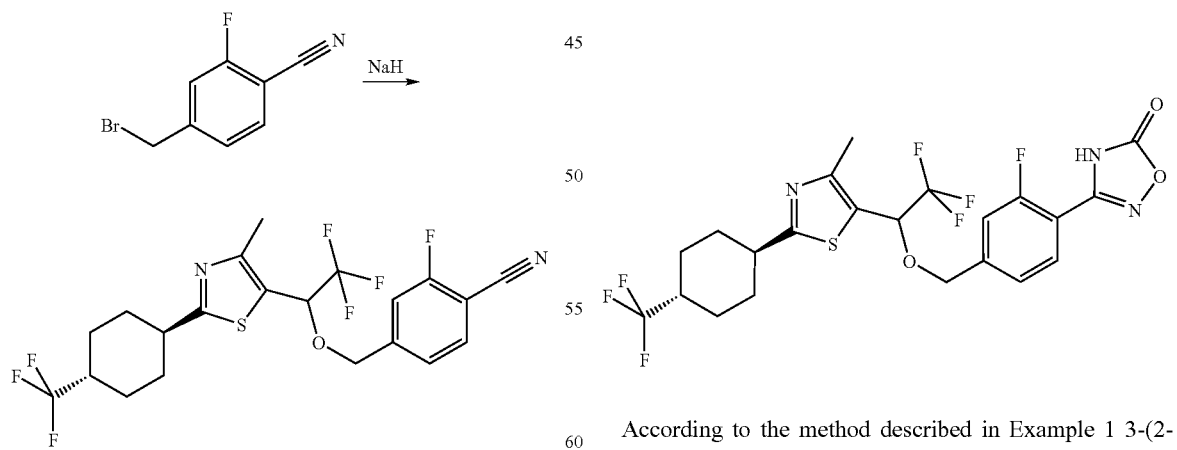

According to the method described in Example 1 3-(2-Fluoro-4-{2,2,2-trifluoro-1-[4-methyl-2-(trans-1,4-trifluoromethyl-cyclohexyl)-thiazol-5-yl]-ethoxymethyl}-phenyl)-4H-[1,2,4]oxadiazol-5-one was obtained from 2-Fluoro-4-{2,2,2-trifluoro-1-[4-methyl-2-(trans-1,4-trifluoromethyl-cyclohexyl)-thiazol-5-yl]-ethoxymethyl}-benzonitrile.

$C_{22}H_{20}F_7N_3O_3S$ (539.48), MS (ESI): 540.2 (M+H$^+$).

EXAMPLE 31

3-(2-Fluoro-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one

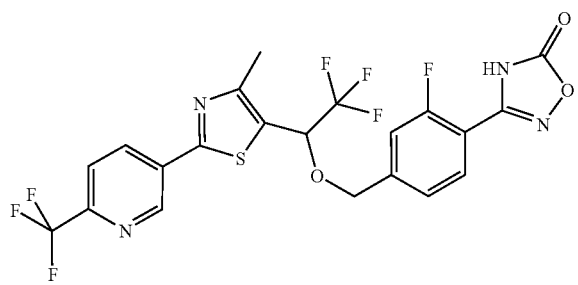

According to the method described in Example 1 3-(2-Fluoro-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one was obtained from 2-Fluoro-4-{2,2,2-trifluoro-1-[4-methyl-2-(6-trifluoromethyl-pyridin-3-yl)-thiazol-5-yl]-ethoxymethyl}-benzonitrile (derived from 2,2,2-Trifluoro-1-[4-methyl-2-(6-trifluoromethyl-pyridin-3-yl)-thiazol-5-yl]-ethanol and 4-Bromomethyl-2-fluoro-benzonitrile according to the method described in example 30). The racemic mixture was separated into its enantiomers by chromatography on chiral phase (Chiralpak AD-H/44) with the eluent n-heptane:propanol:ethanol=8:1:1 (preconditioning of the column with 0.1% trifluoroacetic acid), Rt=9.51 min and 11.49 min.

$C_{21}H_{13}F_7N_4O_3S$ (534.42), MS (ESI): 535.2 (M+H$^+$).

EXAMPLE 32

3-(4-{2,2,2-Trifluoro-1-[4-methyl-2-(6-trifluoromethyl-pyridin-3-yl)-thiazol-5-yl]-ethoxymethyl}-phenyl)-4H-[1,2,4]oxadiazol-5-one

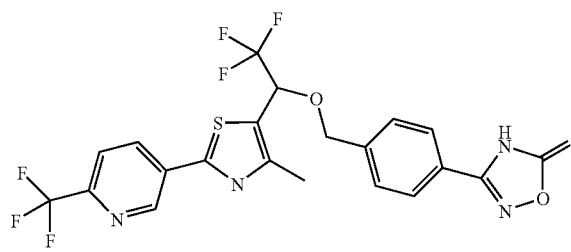

According to the method described in Example 1 3-(4-{2,2,2-Trifluoro-1-[4-methyl-2-(6-trifluoromethyl-pyridin-3-yl)-thiazol-5-yl]-ethoxymethyl}-phenyl)-4H-[1,2,4]oxadiazol-5-one was obtained from 4-{2,2,2-Trifluoro-1-[4-methyl-2-(6-trifluoromethyl-pyridin-3-yl)-thiazol-5-yl]-ethoxymethyl}-benzonitrile (derived from 2,2,2-Trifluoro-1-[4-methyl-2-(6-trifluoromethyl-pyridin-3-yl)-thiazol-5-yl]-ethanol and commercially available 4-Bromomethyl-benzonitrile according to the method described in example 30).

$C_{21}H_{14}F_6N_4O_3S$ (516.43), MS (ESI): 517.1 (M+H$^+$).

EXAMPLE 33

3-(4-{1-[4-Methyl-2-(6-trifluoromethyl-pyridin-3-yl)-thiazol-5-yl]-propoxymethyl}-2-trifluoromethyl-phenyl)-4H-[1,2,4]oxadiazol-5-one

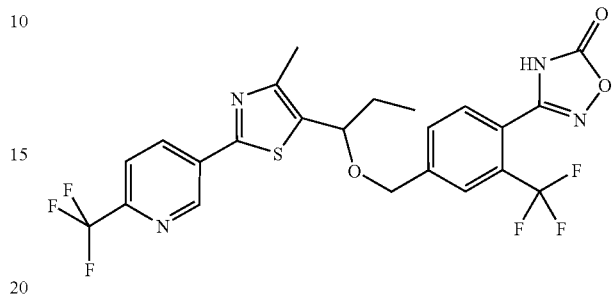

According to the method described in Example 1 3-(4-{1-[4-Methyl-2-(6-trifluoromethyl-pyridin-3-yl)-thiazol-5-yl]-propoxymethyl}-2-trifluoromethyl-phenyl)-4H-[1,2,4]oxadiazol-5-one was obtained from 4-{1-[4-Methyl-2-(6-trifluoromethyl-pyridin-3-yl)-thiazol-5-yl]-propoxymethyl}-2-trifluoromethyl-benzonitrile (derived from 1-[4-Methyl-2-(6-trifluoromethyl-pyridin-3-yl)-thiazol-5-yl]-propan-1-ol and 4-Bromomethyl-2-trifluoromethyl-benzonitrile according to the method described in example 30).

$C_{12}H_{18}F_6N_4O_3S$ (544.48), MS (ESI): 545.1 (M+H$^+$).

EXAMPLE 34

3-(2-Chloro-4-{2,2,2-trifluoro-1-[4-methyl-2-(trans-1,4-trifluoromethyl-cyclohexyl)-thiazol-5-yl]-ethoxymethyl}-phenyl)-4H-[1,2,4]oxadiazol-5-one

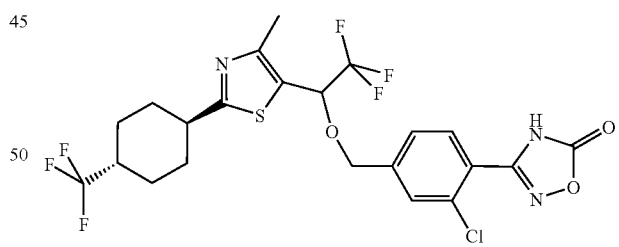

According to the method described in Example 1 3-(2-Chloro-4-{2,2,2-trifluoro-1-[4-methyl-2-(trans-1,4-trifluoromethyl-cyclohexyl)-thiazol-5-yl]-ethoxymethyl}-phenyl)-4H-[1,2,4]oxadiazol-5-one was obtained from 2-Chloro-4-{2,2,2-trifluoro-1-[4-methyl-2-(4-trifluoromethyl-cyclohexyl)-thiazol-5-yl]-ethoxymethyl}-benzonitrile (derived from 2,2,2-Trifluoro-1-[4-methyl-2-(trans-1,4-trifluoromethyl-cyclohexyl)-thiazol-5-yl]-ethanol and 4-Bromomethyl-2-chloro-benzonitrile according to the method described in example 30).

$C_{22}H_{20}ClF_6N_3O_3S$ (555.93), MS (ESI): 556.0 (M+H$^+$).

EXAMPLE 35

3-(2-Chloro-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one

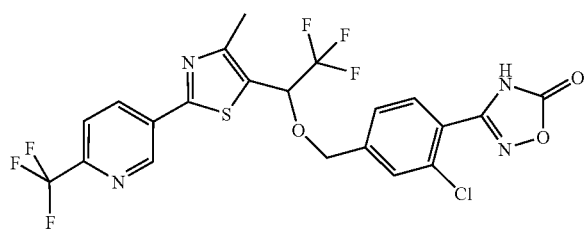

According to the method described in Example 1 3-(2-Chloro-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one was obtained from 2-Chloro-4-{2,2,2-trifluoro-1-[4-methyl-2-(6-trifluoromethyl-pyridin-3-yl)-thiazol-5-yl]-ethoxymethyl}-benzonitrile (derived from 2,2,2-Trifluoro-1-[4-methyl-2-(6-trifluoromethyl-pyridin-3-yl)-thiazol-5-yl]-ethanol and 4-Bromomethyl-2-chloro-benzonitrile according to the method described in example 30).

$C_{21}H_{13}ClF_6N_4O_3S$ (550.87), MS (ESI): 550.97 (M+H$^+$).

EXAMPLE 36

3-(8-{2,2,2-Trifluoro-1-[4-methyl-2-(6-trifluoromethyl-pyridin-3-yl)-thiazol-5-yl]-ethoxymethyl}-quinolin-5-yl)-4H-[1,2,4]oxadiazol-5-one

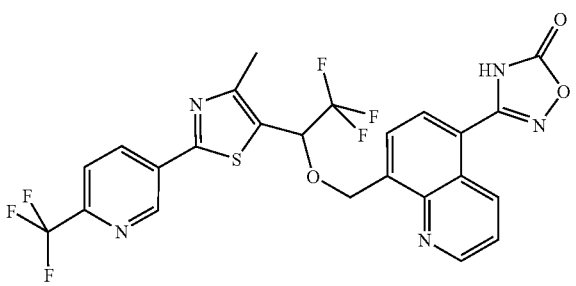

According to the method described in Example 1 3-(8-{2,2,2-Trifluoro-1-[4-methyl-2-(6-trifluoromethyl-pyridin-3-yl)-thiazol-5-yl]-ethoxymethyl}-quinolin-5-yl)-4H-[1,2,4]oxadiazol-5-one was obtained from 8-{2,2,2-Trifluoro-1-[4-methyl-2-(6-trifluoromethyl-pyridin-3-yl)-thiazol-5-yl]-ethoxymethyl}-quinoline-5-carbonitrile (derived from 2,2,2-Trifluoro-1-[4-methyl-2-(6-trifluoromethyl-pyridin-3-yl)-thiazol-5-yl]-ethanol and 8-Bromomethyl-quinoline-5-carbonitrile according to the method described in example 30).

$C_{24}H_{15}F_6N_5O_3S$ (567.47), MS (ESI): 568.0 (M+H$^+$).

EXAMPLE 37

3-(2-Chloro-6-{2,2,2-trifluoro-1-[4-methyl-2-(6-trifluoromethyl-pyridin-3-yl)-thiazol-5-yl]-ethoxymethyl}-pyridin-3-yl)-4H-[1,2,4]oxadiazol-5-one

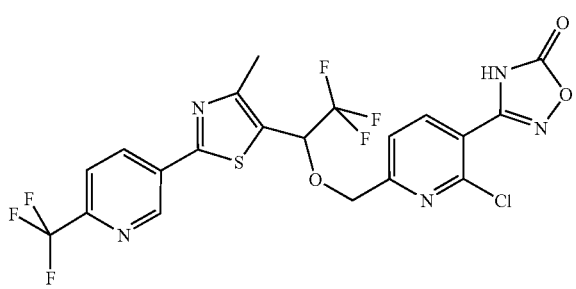

According to the method described in Example 1 3-(2-Chloro-6-{2,2,2-trifluoro-1-[4-methyl-2-(6-trifluoromethyl-pyridin-3-yl)-thiazol-5-yl]-ethoxymethyl}-pyridin-3-yl)-4H-[1,2,4]oxadiazol-5-one was obtained from 2-Chloro-6-{2,2,2-trifluoro-1-[4-methyl-2-(6-trifluoromethyl-pyridin-3-yl)-thiazol-5-yl]-ethoxymethyl}-nicotinonitrile (derived from 2,2,2-Trifluoro-1-[4-methyl-2-(6-trifluoromethyl-pyridin-3-yl)-thiazol-5-yl]-ethanol and 6-Bromomethyl-2-chloro-nicotinonitrile according to the method described in example 30).

C (551.86), MS (ESI): 552.0 (M+H$^+$).

EXAMPLE 38

3-(2-Cyclopropyl-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one

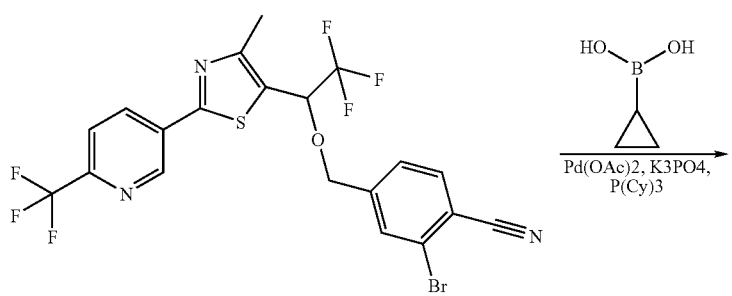

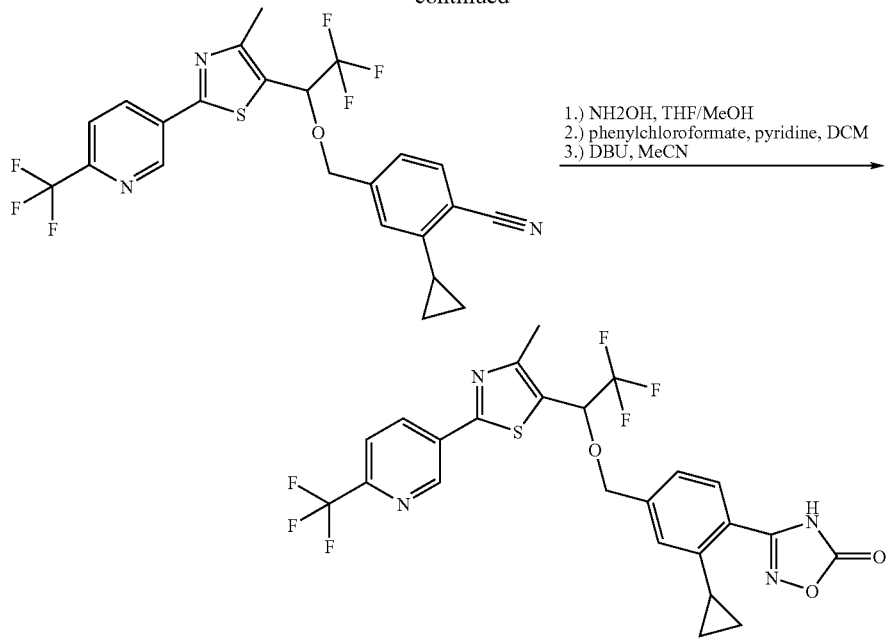

2-Cyclopropyl-4-{2,2,2-trifluoro-1-[4-methyl-2-(6-trifluoromethyl-pyridin-3-yl)-thiazol-5-yl]-ethoxymethyl}-benzonitrile

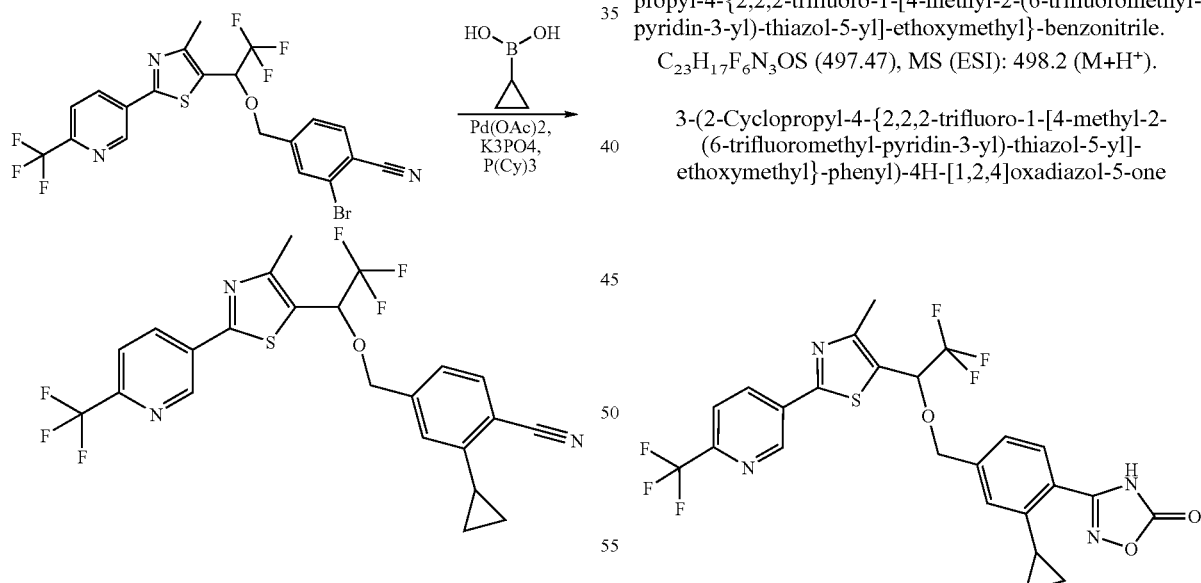

309 mg 2-Bromo-4-{2,2,2-trifluoro-1-[4-methyl-2-(6-trifluoromethyl-pyridin-3-yl)-thiazol-5-yl]-ethoxymethyl}-benzonitrile (derived from 2,2,2-Trifluoro-1-[4-methyl-2-(6-trifluoromethyl-pyridin-3-yl)-thiazol-5-yl]-ethanol and 2-Bromo-4-bromomethyl-benzonitrile according to the method described in example 30), 32 mg tricyclohexylphosphine, 148 mg cyclopropylboronic acid and 470 mg K3PO4 mono hydrate were dissolved in a mixture of 4 ml toluene and 0.4 ml water. The reaction mixture was purged with argon, then 130 mg palladium (II) acetate were added. The reaction mixture was stirred at 100° C. for three hours. The cooled reaction mixture was diluted by addition of 100 ml ethyl acetate and filtered through a celite pad. The filtrate was washed twice with 25 ml water, then dried over MgSO4. The solvent was removed in vacuo. The resulting residue was purified by reversed phase HPLC to obtain 185 mg 2-Cyclopropyl-4-{2,2,2-trifluoro-1-[4-methyl-2-(6-trifluoromethyl-pyridin-3-yl)-thiazol-5-yl]-ethoxymethyl}-benzonitrile.

$C_{23}H_{17}F_6N_3OS$ (497.47), MS (ESI): 498.2 (M+H$^+$).

3-(2-Cyclopropyl-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one

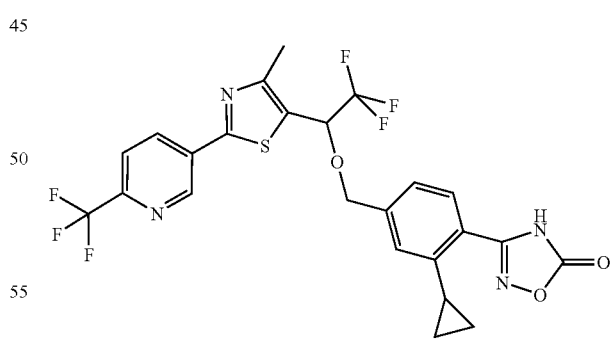

According to the method described in Example 1 3-(2-Cyclopropyl-4-{2,2,2-trifluoro-1-[4-methyl-2-(6-trifluoromethyl-pyridin-3-yl)-thiazol-5-yl]-ethoxymethyl}-phenyl)-4H-[1,2,4]oxadiazol-5-one was obtained from 2-Cyclopropyl-4-{2,2,2-trifluoro-1-[4-methyl-2-(6-trifluoromethyl-pyridin-3-yl)-thiazol-5-yl]-ethoxymethyl}-benzonitrile.

$C_{24}H_{18}F_6N_4O_3S$ (556.49), MS (ESI): 557.1 (M+H$^+$).

EXAMPLE 39

3-(2-Cyclopropyl-4-{2,2,2-trifluoro-1-[4-methyl-2-(trans,1,4-trifluoromethyl-cyclohexyl)-thiazol-5-yl]-ethoxymethyl}-phenyl)-4H-[1,2,4]oxadiazol-5-one

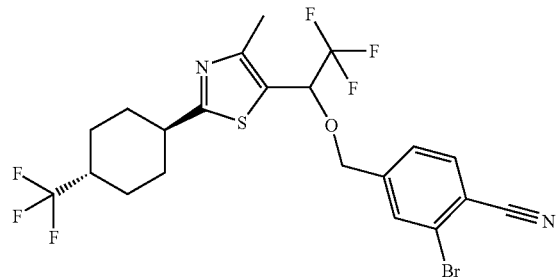
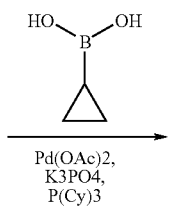

Pd(OAc)2,
K3PO4,
P(Cy)3

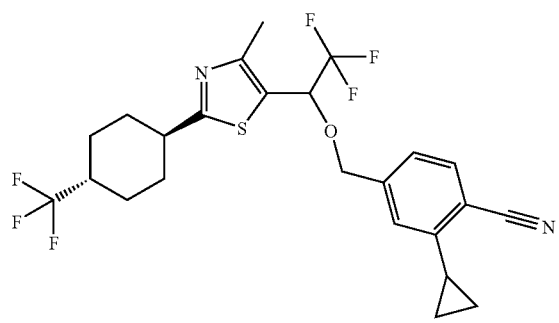

1.) NH2OH, THF/MeOH
2.) phenylchloroformate, pyridine, DCM
3.) DBU, MeCN

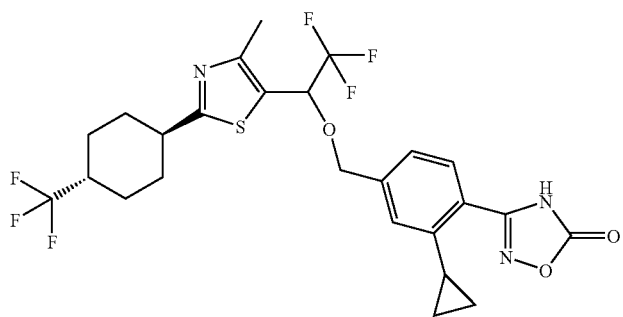

2-Cyclopropyl-4-{2,2,2-trifluoro-1-[4-methyl-2-(trans-1,4-trifluoromethyl-cyclohexyl)-thiazol-5-yl]-ethoxymethyl}-benzonitrile

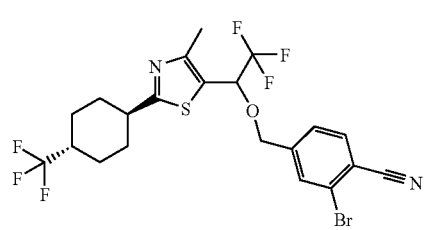

HO–B–OH

Pd(OAc)2,
K3PO4,
P(Cy)3

-continued

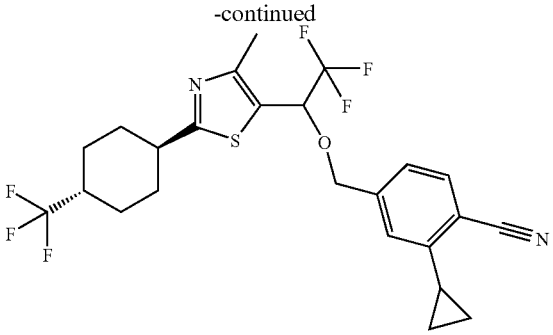

157 mg 2-Bromo-4-{2,2,2-trifluoro-1-[4-methyl-2-(4-trifluoromethyl-cyclohexyl)-thiazol-5-yl]-ethoxymethyl}-benzonitrile (derived from 2,2,2-Trifluoro-1-[4-methyl-2-(trans- 1,4-trifluoromethyl-cyclohexyl)-thiazol-5-yl]-ethanol and 2-Bromo-4-bromomethyl-benzonitrile according to the method described in example 30), 8 mg tricyclohexylphosphine, 32 mg cyclopropylboronic acid and 237 mg K3PO4 mono hydrate were dissolved in a mixture of 2 ml toluene and 0.2 ml water. The reaction mixture was purged with argon, then 65 mg palladium (II) acetate were added. The reaction mixture was stirred at 150° C. for five hours. The cooled reaction mixture was diluted by addition of 100 ml ethyl acetate and filtered through a celite pad. The filtrate was washed twice with 25 ml water, then dried over MgSO4. The solvent was removed in vacuo. The resulting residue was purified on silica gel with the eluent n-heptane:ethyl acetate=2:1 to obtain 44 mg 2-Cyclopropyl-4-{2,2,2-trifluoro-1-[4-methyl-2-(trans-1,4-trifluoromethyl-cyclohexyl)-thiazol-5-yl]-ethoxymethyl}-benzonitrile.

$C_{24}H_{24}F_6N_2OS$ (502.53), MS (ESI): 503.2 (M+H$^+$), Rf (n-heptane:ethyl acetate=2:1)=0.28.

3-(2-Cyclopropyl-4-{2,2,2-trifluoro-1-[4-methyl-2-(trans, 1,4-trifluoromethyl-cyclohexyl)-thiazol-5-yl]-ethoxymethyl}-phenyl)-4H-[1,2,4]oxadiazol-5-one

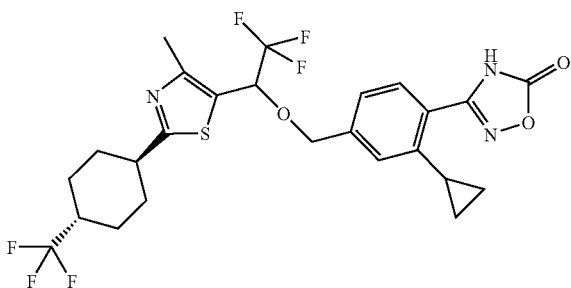

According to the method described in Example 1 3-(2-Cyclopropyl-4-{2,2,2-trifluoro-1-[4-methyl-2-(trans, 1,4-trifluoromethyl-cyclohexyl)-thiazol-5-yl]-ethoxymethyl}-phenyl)-4H-[1,2,4]oxadiazol-5-one was obtained from 2-Cyclopropyl-4-{2,2,2-trifluoro-1-[4-methyl-2-(trans-1,4-trifluoromethyl-cyclohexyl)-thiazol-5-yl]-ethoxymethyl}-benzonitrile.

$C_{25}H_{25}F_6N_3O_3S$ (561.55), MS (ESI): 562.1 (M+H$^+$).

EXAMPLE 40

3-(4-{2,2-Difluoro-1-[4-methyl-2-(6-trifluoromethyl-pyridin-3-yl)-thiazol-5-yl]-butoxymethyl}-phenyl)-4H-[1,2,4]oxadiazol-5-one

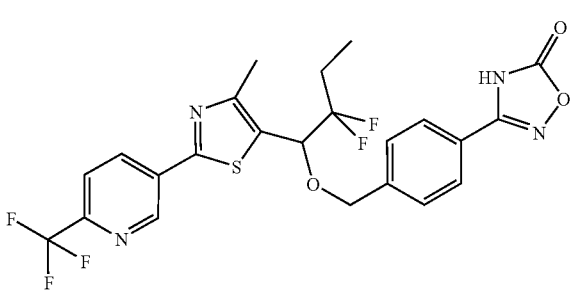

According to the method described in Example 1 3-(4-{2,2-Difluoro-1-[4-methyl-2-(6-trifluoromethyl-pyridin-3-yl)-thiazol-5-yl]-butoxymethyl}-phenyl)-4H-[1,2,4]oxadiazol-5-one was obtained from 4-{2,2-Difluoro-1-[4-methyl-2-(6-trifluoromethyl-pyridin-3-yl)-thiazol-5-yl]-butoxymethyl}-benzonitrile (derived from 2,2-Difluoro-1-[4-methyl-2-(6-trifluoromethyl-pyridin-3-yl)-thiazol-5-yl]-butan-1-ol and commercially available 4-Bromomethyl-benzonitrile according to the method described in example 30).

The racemic mixture was separated into its enantiomers by chromatography on chiral phase (Chiralpak AD-H/54) with the eluent n-heptane:ethanol=5:2+0.1% trifluoroacetic acid, Rt=6.50 min and 8.77 min.

$C_{23}H_{19}F_5N_4O_3S$ (526.49), MS (ESI): 527.0 (M+H$^+$).

EXAMPLE 41

3-(2-Chloro-4-{2,2-difluoro-1-[4-methyl-2-(6-trifluoromethyl-pyridin-3-yl)-thiazol-5-yl]-butoxymethyl}-phenyl)-4H-[1,2,4]oxadiazol-5-one

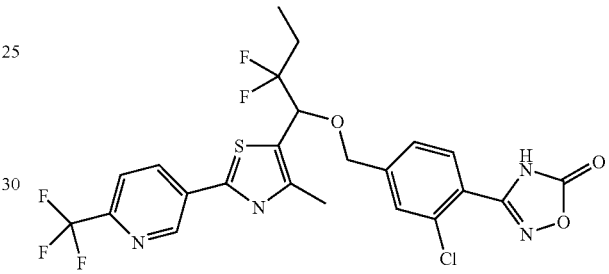

According to the method described in Example 1 3-(2-Chloro-4-{2,2-difluoro-1-[4-methyl-2-(6-trifluoromethyl-pyridin-3-yl)-thiazol-5-yl]-butoxymethyl}-phenyl)-4H-[1,2,4]oxadiazol-5-one was obtained from 2-Chloro-4-{2,2-difluoro-1-[4-methyl-2-(6-trifluoromethyl-pyridin-3-yl)-thiazol-5-yl]-butoxymethyl}-benzonitrile (derived from 2,2-Difluoro-1-[4-methyl-2-(6-trifluoromethyl-pyridin-3-yl)-thiazol-5-yl]-butan-1-ol and 4-Bromomethyl-2-chloro-benzonitrile according to the method described in example 30).

$C_{23}H_{18}ClF_5N_4O_3S$ (560.93), MS (ESI): 561.1 (M+H$^+$).

EXAMPLE 42

3-(4-{2,2-Difluoro-1-[4-methyl-2-(6-trifluoromethyl-pyridin-3-yl)-thiazol-5-yl]-butoxymethyl}-naphthalen-1-yl)-4H-[1,2,4]oxadiazol-5-one

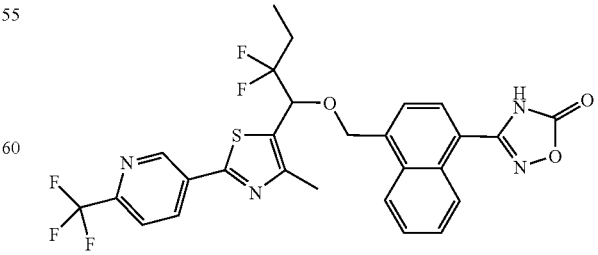

According to the method described in Example 1 3-(4-{2,2-Difluoro-1-[4-methyl-2-(6-trifluoromethyl-pyridin-3-yl)- thiazol-5-yl]-butoxymethyl}-naphthalen-1-yl)-4H-[1,2,4]oxadiazol-5-one was obtained from 4-{2,2-Difluoro-1-[4-methyl-2-(6-trifluoromethyl-pyridin-3-yl)-thiazol-5-yl]-butoxymethyl}-naphthalene-1-carbonitrile (derived from 2,2-Difluoro-1-[4-methyl-2-(6-trifluoromethyl-pyridin-3-yl)-thiazol-5-yl]-butan-1-ol and 4-Bromomethyl-naphthalene-1-carbonitrile according to the method described in example 30).

$C_{27}H_{21}F_5N_4O_3S$ (576.55), MS (ESI): 577.2 (M+H$^+$).

EXAMPLE 43

3-(8-{2,2-Difluoro-1-[4-methyl-2-(6-trifluoromethyl-pyridin-3-yl)-thiazol-5-yl]-butoxymethyl}-quinolin-5-yl)-4H-[1,2,4]oxadiazol-5-one

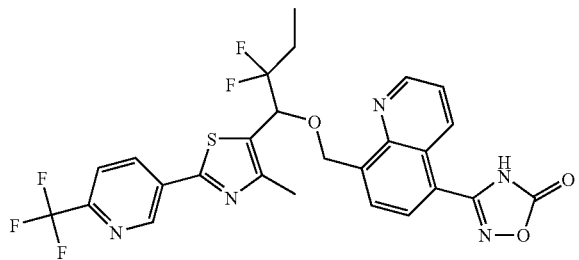

According to the method described in Example 1 3-(8-{2,2-Difluoro-1-[4-methyl-2-(6-trifluoromethyl-pyridin-3-yl)-thiazol-5-yl]-butoxymethyl}-quinolin-5-yl)-4H-[1,2,4]oxadiazol-5-one was obtained from 8-{2,2-Difluoro-1-[4-methyl-2-(6-trifluoromethyl-pyridin-3-yl)-thiazol-5-yl]-butoxymethyl}-quinoline-5-carbonitrile (derived from 2,2-Difluoro-1-[4-methyl-2-(6-trifluoromethyl-pyridin-3-yl)-thiazol-5-yl]-butan-1-ol and 8-Bromomethyl-quinoline-5-carbonitrile according to the method described in example 30).

$C_{26}H_{20}F_5N_5O_3S$ (577.54), MS (ESI): 578.2 (M+H$^+$).

EXAMPLE 44

3-[4-(2-Benzo[b]thiophen-2-yl-4-methyl-thiazol-5-ylmethoxy)-2-chloro-phenyl]-2H-[1,2,4]oxadiazol-5-one

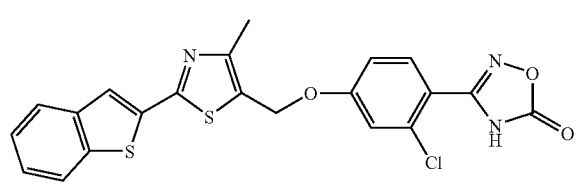

(2-Bromo-4-methyl-thiazol-5-yl)-methanol

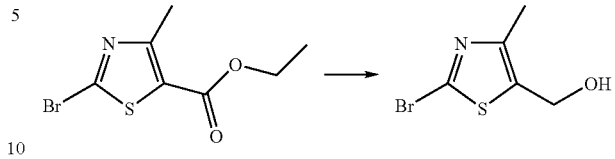

sodium borohydride (1.2 g, 31.2 mmol) is carefully added to a solution of 2-Bromo-4-methyl-thiazole-5-carboxylic acid ethyl ester (3.6 g, 15.6 mmol) in ethanol (100 mL) and water (1 mL) and stirred at room temperature for twelve hours. The solvent is carefully removed under reduced pressure, the residue is taken up in ethylacetate and washed with water. The organic phase is separated and dried over MgSO$_4$. The organic solvent is removed under reduced pressure to give 3.2 g of (2-Bromo-4-methyl-thiazol-5-yl)-methanol, which was used without further purification.

$C_5H_6BrNOS$ (208.08), MS (ESI): 208.0 (M+H$^+$).

Methanesulfonic acid 2-bromo-4-methyl-thiazol-5-ylmethyl ester

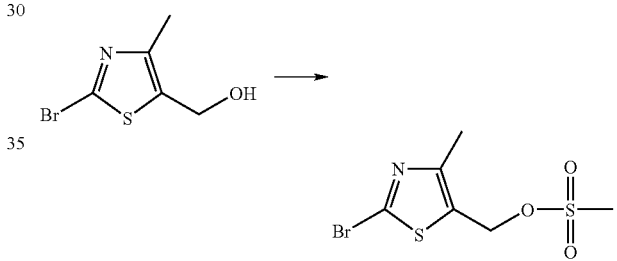

To an ice-cold solution of (2-Bromo-4-methyl-thiazol-5-yl)-methanol (3.2 g, 15.6 mmol) and triethylamine (3.2 mL, 23.4 mmol) in dichloromethane (80 mL) is slowly added a solution of methanesulfonyl chloride (2.1 g, 18.7 mmol) in dichloromethane (20 mL). The mixture is kept at this temperature for 45 minutes and afterwards allowed to warm to room temperature. Water (30 mL) is added after 3 hours and the mixture is extracted with ethylacetate. The organic phase is separated and dried over MgSO$_4$. The organic solvent is removed under reduced pressure to give 3.0 g of Methanesulfonic acid 2-bromo-4-methyl-thiazol-5-ylmethyl ester, which was used without further purification.

4-(2-Bromo-4-methyl-thiazol-5-ylmethoxy)-2-chloro-benzonitrile

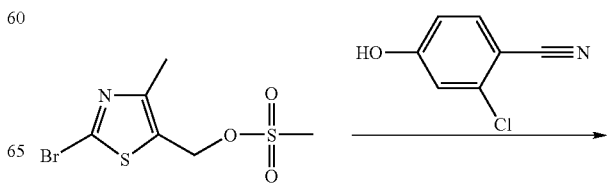

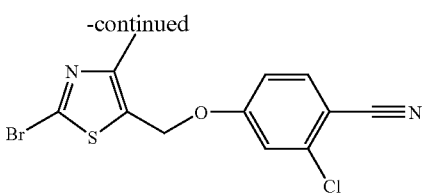

To a solution of 2-Chloro-4-hydroxy-benzonitrile (1.6 g, 10.1 mmol) in dry dimethylformamide (30 mL) is carefully added sodium hydride (486 mg, 12.1 mmol). The resulting mixture is stirred for 20 minutes at room temperature. A solution of Methanesulfonic acid 2-bromo-4-methyl-thiazol-5-ylmethyl ester (3.0 g, 10.1 mmol) in dry dimethylformamide (5 mL) is added and the reaction mixture is stirred at room temperature. The reaction mixture is diluted with 100 mL of ethyl acetate after 5 h and water (20 mL) is carefully added (Caution: development of $H_2$). The phases are separated and the organic phase is dried over $MgSO_4$. The solvent is removed under reduced pressure and the crude product is purified by reversed phase HPLC to yield 2.2 g of 4-(2-Bromo-4-methyl-thiazol-5-ylmethoxy)-2-chloro-benzonitrile. $C_{12}H_8BrClN_2OS$ (343.63), MS (ESI): 343.0 (M+H$^+$).

4-(2-Bromo-4-methyl-thiazol-5-ylmethoxy)-2-chloro-N-hydroxy-benzamidine

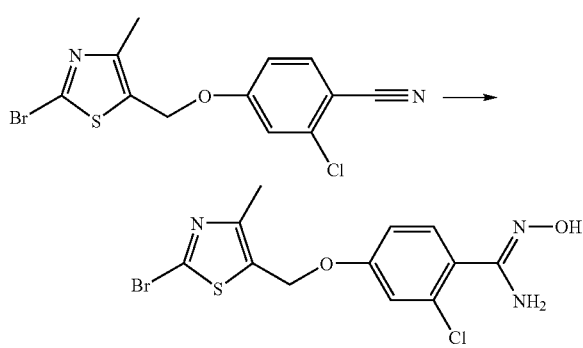

4-(2-Bromo-4-methyl-thiazol-5-ylmethoxy)-2-chlorobenzonitrile (200 mg, 0.6 mmol) was dissolved in a mixture of 4 ml tetrahydrofuran and 4 ml methanol. Hydroxylamine hydrochloride (1.0 g, 14.6 mmol) was added followed by the addition of 2.1 ml triethylamine. The reaction mixture was stirred at 65° C. overnight. The solvents were removed in vacuo and the resulting residue poured into water and extracted five times with ethylacetate. The combined organic extracts were washed with brine, dried over MgSO4 and the solvent was evaporated in vacuo to obtain 199 mg 4-(2-Bromo-4-methyl-thiazol-5-ylmethoxy)-2-chloro-N-hydroxy-benzamidine as an oil.

$C_{12}H_{11}BrClN_3O_2S$ (376.66), MS (ESI): 376.0 (M+H$^+$).

3-[4-(2-Bromo-4-methyl-thiazol-5-ylmethoxy)-2-chloro-phenyl]-2H-[1,2,4]oxadiazol-5-one

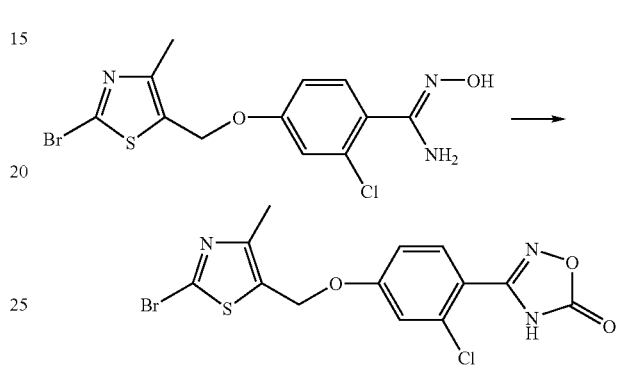

4-(2-Bromo-4-methyl-thiazol-5-ylmethoxy)-2-chloro-N-hydroxy-benzamidine (199 mg, 0.5 mmol) was dissolved in 6 ml dichloromethane. Pyridine (55 mg, 0.7 mmol) and phenylchloroformate (108 mg, 0.7 mmol) were added and the mixture stirred at room temperature for ten minutes. The mixture was diluted by the addition of 25 ml acetonitrile and 0.4 ml 1,8-Diazabicyclo[5.4.0]undec-7-ene were added. The mixture was stirred at room temperature for 10 minutes. The mixture was evaporated in vacuo and the resulting crude material was purified by reversed phase HPLC to obtain 142 mg 3-[4-(2-Bromo-4-methyl-thiazol-5-ylmethoxy)-2-chloro-phenyl]-2H-[1,2,4]oxadiazol-5-one as an amorphous lyophilisate.

$C_{13}H_9BrClN_3O_3$ (402.66), MS (ESI): 402.0 (M+H$^+$).

3-[4-(2-Benzo[b]thiophen-2-yl-4-methyl-thiazol-5-ylmethoxy)-2-chloro-phenyl]-2H-[1,2,4]oxadiazol-5-one

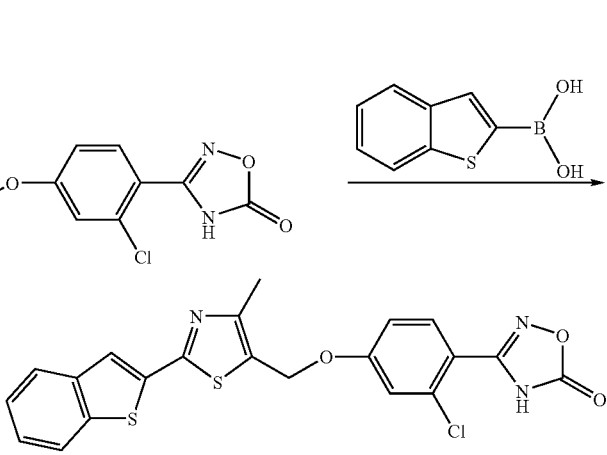

A mixture of 3-[4-(2-Bromo-4-methyl-thiazol-5-yl-methoxy)-2-chloro-phenyl]-2H-[1,2,4]oxadiazol-5-one (300 mg, 0.7 mmol), Benzo[b]thiophene-2-boronic acid (142 mg, 0.8 mmol) and cesium carbonate (730 mg, 2.2 mol) in dimethylformamide (5 mL) and water (1 mL) is degassed using a stream of argon for 15 min. Tetrakis-triphenylphosphine-palladium (0) (34 mg, 0.03 mmol) is added and the mixture is warmed to 40° C. for 4 hours. The solvent is removed under reduced pressure and the residue is taken up in water (10 mL) and ethylacetate (30 mL). The phases are separated and the water phase is additionally extracted two-times with ethylacetate. The combined organic phases are dried over $MgSO_4$ and the solvent is removed under reduced pressure. The crude product is purified using reverse phase HPLC to obtain 147 mg 3-[4-(2-Benzo[b]thiophen-2-yl-4-methyl-thiazol-5-yl-methoxy)-2-chloro-phenyl]-2H-[1,2,4]oxadiazol-5-one as an amorphous lyophilisate.

$C_{21}H_{14}ClN_3O_3S_2$ (455.95), MS (ESI): 456.0 (M+H$^+$).

EXAMPLE 45

3-{2-Chloro-4-[4-methyl-2-(1-methyl-1H-pyrazol-4-yl)-thiazol-5-ylmethoxy]-phenyl}-2H-[1,2,4]oxadiazol-5-one

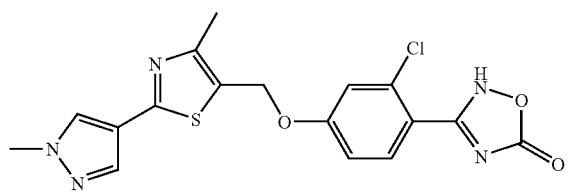

According to the method described in example 44, 3-{2-Chloro-4-[4-methyl-2-(1-methyl-1H-pyrazol-4-yl)-thiazol-5-ylmethoxy]-phenyl}-2H-[1,2,4]oxadiazol-5-one was obtained by the reaction of 3-[4-(2-Bromo-4-methyl-thiazol-5-ylmethoxy)-2-chloro-phenyl]-2H-[1,2,4]oxadiazol-5-one and 1-MethylL-4-(4,4,5,5-Tetramethyl-1,3,2-Dioxaborolan)-1H-pyrazole.

$C_{17}H_{14}ClN_5O_3S$ (403.84), MS (ESI): 404.1 (M+H$^+$).

EXAMPLE 46

3-[2-Chloro-4-(4-methyl-2-quinolin-8-yl-thiazol-5-ylmethoxy)-phenyl]-2H-[1,2,4]oxadiazol-5-one

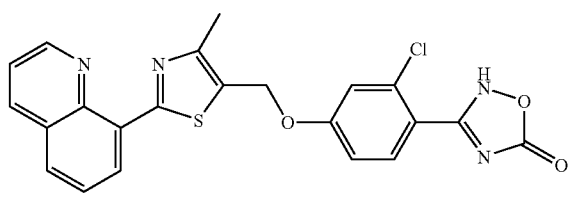

According to the method described in example 44, 3-[2-Chloro-4-(4-methyl-2-quinolin-8-yl-thiazol-5-ylmethoxy)-phenyl]-2H-[1,2,4]oxadiazol-5-one was obtained by the reaction of 3-[4-(2-Bromo-4-methyl-thiazol-5-ylmethoxy)-2-chloro-phenyl]-2H-[1,2,4]oxadiazol-5-one and 8-Quinoline boronic acid.

$C_{22}H_{15}ClN_4O_3S$ (450,91), MS (ESI): 451.1 (M+H$^+$).

The following examples were prepared according to process D:

EXAMPLE 47

3-(2-Methoxy-4-{1-[4-methyl-2-(trans-1,4-trifluoromethyl-cyclohexyl)-oxazol-5-yl]-propoxy}-phenyl)-4H-1,2,4-oxadiazol-5-one

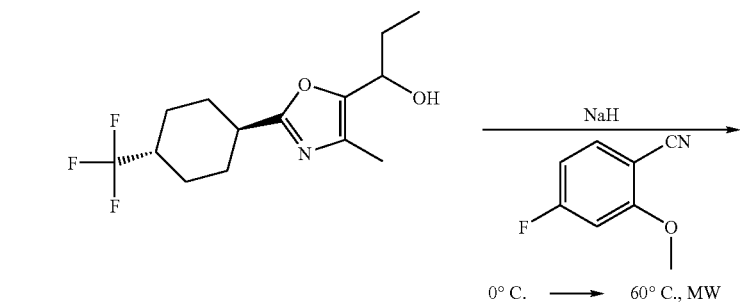

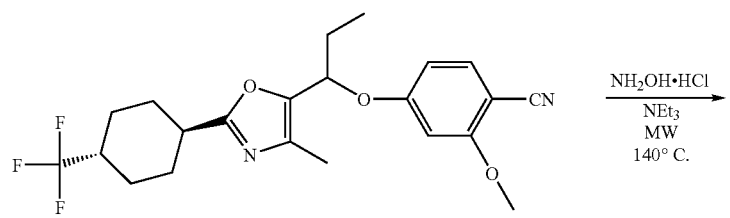

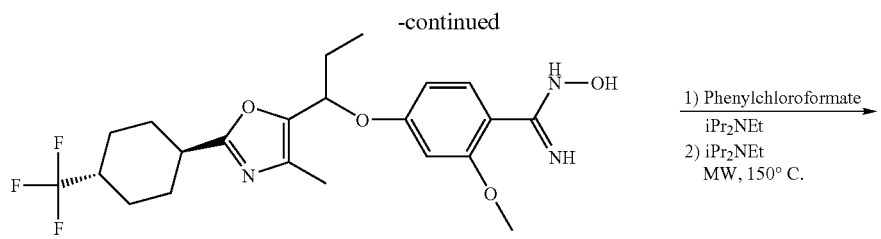

2-Methoxy-4-{1-[4-methyl-2-(trans-1,4-trifluoromethyl-cyclohexyl)-oxazol-5-yl]-propoxy}-benzonitrile N-Hydroxy-2-methoxy-4-{1-[4-methyl-2-(trans-1,4-trifluoromethyl-cyclohexyl)-oxazol-5-yl]-propoxy}-benzamidine

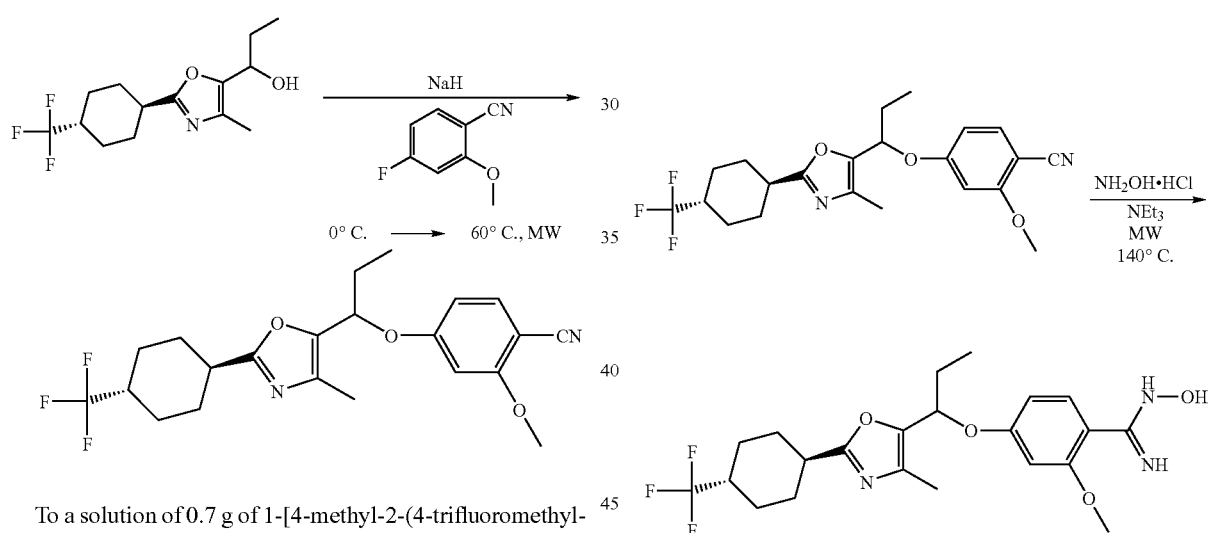

To a solution of 0.7 g of 1-[4-methyl-2-(4-trifluoromethyl-cyclohexyl)-oxazol-5-yl]-propan-1-ol in 3 mL of dimethylformamide at 5° C. was added 113 mg of a 55% suspension of sodium hydride in mineral oil. The reaction mixture was stirred for 30 minutes at 5° C. The resulting mixture was slowly added to a solution of 429 mg of 4-fluoro-2-methoxy-benzonitrile in 1 mL of dimethylformamide at 5° C. The resulting mixture was stirred at 5° C. allowing the temperature to warm up to room temperature. It was then heated in a sealed tube to 60° C. under microwave irradiation for 15 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (gradient from heptane 100 to heptane 50/ethyl acetate 50) to give 1.05 g of 2-methoxy-4-{1-[4-methyl-2-(trans-1,4-trifluoromethyl-cyclohexyl)-oxazol-5-yl]-propoxy}-benzonitrile.

$C_{22}H_{25}F_3N_2O_3$ (422.45), MS (ESI): (M+H$^+$) 423.4 (M+H$^+$).

To a solution of 1.07 g of 2-methoxy-4-{1-[4-methyl-2-(trans-1,4-trifluoromethyl-cyclohexyl)-oxazol-5-yl]-propoxy}-benzonitrile in 15 mL of methanol was added 7 mL of triethylamine followed by 792 mg of hydroxylamine hydrochloride. The resulting mixture was heated in a sealed tube to 140° C. under microwave irradiation for 30 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (gradient from heptane 70/ethyl acetate 30 to heptane 10/ethyl acetate 90) to give 450 mg of N-hydroxy-2-methoxy-4-{1-[4-methyl-2-(trans-1,4-trifluoromethyl-cyclohexyl)-oxazol-5-yl]-propoxy}-benzamidine.

$C_{22}H_{28}F_3N_3O_4$ (455.48), MS (ESI): 456.0 (M+H$^+$).

3-(2-Methoxy-4-{1-[4-methyl-2-(trans-1,4-trifluoromethyl-cyclohexyl)-oxazol-5-yl]-propoxy}-phenyl)-4H-1,2,4-oxadiazol-5-one

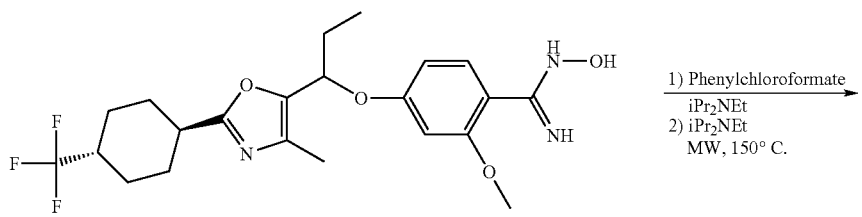

1) Phenylchloroformate
   iPr₂NEt
2) iPr₂NEt
   MW, 150° C.

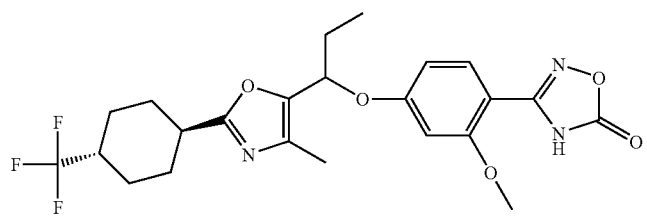

To a solution of 430 mg of N-hydroxy-2-methoxy-4-{1-[4-methyl-2-(trans-1,4-trifluoromethyl-cyclohexyl)-oxazol-5-yl]-propoxy}-benzamidine in 7 mL of tetrahydrofuran at 0° C. was added 2.3 mL of N,N-diisopropylethylamine followed by 0.120 mL of phenyl chloroformate. The resulting mixture was stirred for 5 minutes at 0° C. then poured into water and extracted with dichloromethane. The organic extracts were dried over magnesium sulfate, filtered and concentrated under reduced pressure. The residue was dissolved 7 mL of tetrahydrofuran and 0.5 mL of N,N-diisopropylethylamine. The resulting solution was heated in a sealed tube to 150° C. under microwave irradiation for 15 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (heptane 50/ethyl acetate 50) followed by trituration with dichloromethane/diisopropyl ether to give 210 mg of 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one as a white solid.

$C_{23}H_{26}F_3N_3O_5$ (481.41), MS (ESI): 482.1 (M+H⁺).

The racemate was separated into its enantiomers by supercritical fluid chromatography on chiral phase (Chiralpak AS, column 250×50 mm, 20 µm) with 30% iso-propanol/70% carbon dioxide as eluent (136 bars, flow rate: 300 mL/min, UV 230 nm). The enantiomeric excess of each enantiomer was determined by analytical supercritical fluid chromatography on chiral phase (Chiralpak AS, column 250×4.6 mm, 20 µm) with 15% iso-propanol/85% carbon dioxide as eluent (100 bars, flow rate: 3 mL/min, UV 254 nm): levorotatory enantiomer: >99% ee, Rt=6.62 min; dextrorotatory enantiomer: >99% ee, Rt=11.0 min.

EXAMPLE 48

3-{2-Methoxy-4-[4-methyl-2-(trans-1,4-trifluoromethyl-cyclohexyl)-thiazol-5-ylmethoxy]-phenyl}-4H-1,2,4-oxadiazol-5-one

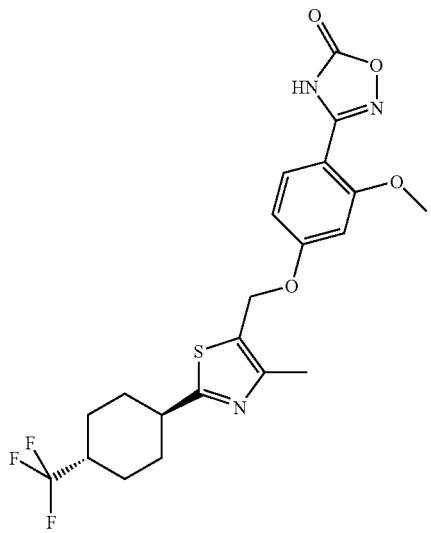

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{2-methoxy-4-[4-methyl-2-(trans-1,4-trifluoromethyl-cyclohexyl)-thiazol-5-ylmethoxy]-phenyl}-4H-1,2,4-oxadiazol-5-one was obtained from [4-methyl-2-(trans-1,4-trifluoromethyl-cyclohexyl)-thiazol-5-yl]-methanol and 4-fluoro-2-methoxybenzonitrile.

$C_{21}H_{22}F_3N_3O_4S$ (469.49), MS (ESI): 470.1 (M+H⁺).

EXAMPLE 49

3-(2-Methoxy-4-{1-[4-methyl-2-(trans-1,4-trifluoromethyl-cyclohexyl)-thiazol-5-yl]-propoxy}-phenyl)-4H-1,2,4-oxadiazol-5-one

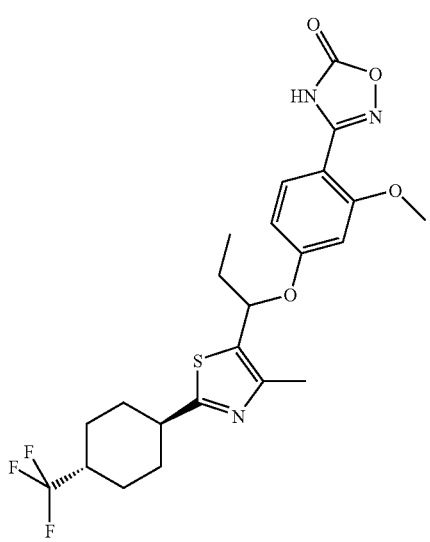

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(2-methoxy-4-{1-[4-methyl-2-(trans-1,4-trifluoromethyl-cyclohexyl)-thiazol-5-yl]-propoxy}-phenyl)-4H-1,2,4-oxadiazol-5-one was obtained from 1-[4-methyl-2-(trans-1,4-trifluoromethyl-cyclohexyl)-thiazol-5-yl]-propan-1-ol and 4-fluoro-2-methoxybenzonitrile.

$C_{23}H_{26}F_3N_3O_4S$ (497.54), MS (ESI): 498.1 (M+H⁺).

The racemate was separated into its enantiomers by supercritical fluid chromatography on chiral phase (Chiralpak AS-H, column 250×21 mm, 5 µm) with 15% methanol/85% carbon dioxide as eluent (flow rate: 90 mL/min, UV 254 nm). The enantiomeric excess of each enantiomer was determined by analytical supercritical fluid chromatography on chiral phase (Chiracel AS, column 250×4.6 mm, 5 µm) with 15% methanol and 0.1% triethylamine in carbon dioxide as eluent (100 bars, flow rate: 3 mL/min, UV 254 nm): levorotatory enantiomer: >99% ee, Rt=6.77 min; dextrorotatory enantiomer: >99% ee, Rt=11.0 min.

EXAMPLE 50

3-{5-Fluoro-2-methoxy-4-[4-methyl-2-(trans-1,4-trifluoromethyl-cyclohexyl)-thiazol-5-ylmethoxy]-phenyl}-4H-1,2,4-oxadiazol-5-one

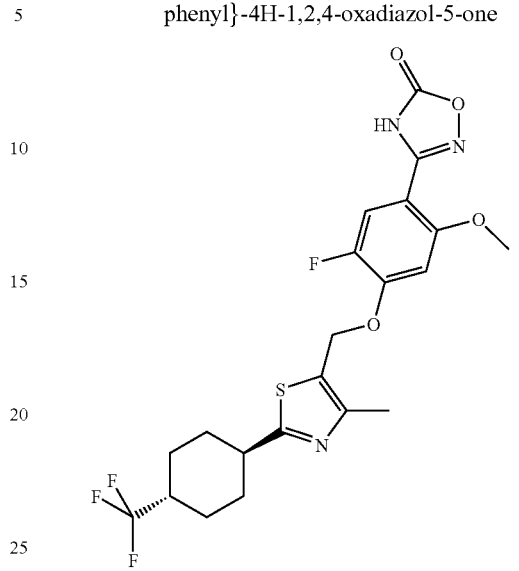

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{5-fluoro-2-methoxy-4-[4-methyl-2-(trans-1,4-trifluoromethyl-cyclohexyl)-thiazol-5-ylmethoxy]-phenyl}-4H-1,2,4-oxadiazol-5-one was obtained from [4-methyl-2-(trans-1,4-trifluoromethyl-cyclohexyl)-thiazol-5-yl]-methanol and commercially available 4,5-difluoro-2-methoxybenzonitrile.

$C_{21}H_{21}F_4N_3O_4S$ (487.48), MS (ESI): 488.1 (M+H⁺).

EXAMPLE 51

3-(5-Fluoro-2-methoxy-4-{1-[4-methyl-2-(trans-1,4-trifluoromethyl-cyclohexyl)-thiazol-5-yl]-propoxy}-phenyl)-4H-1,2,4-oxadiazol-5-one

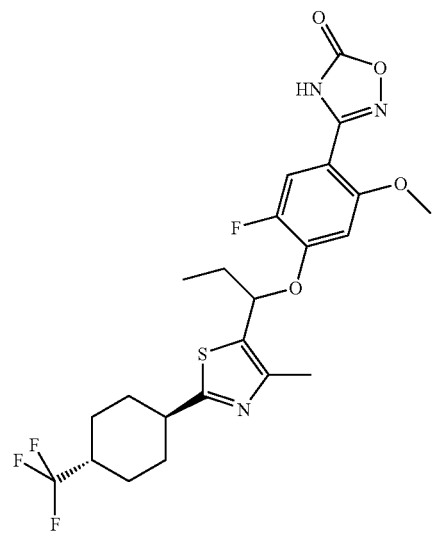

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(5-fluoro-2-methoxy-4-{1-[4-methyl-2-(trans-1,4-trifluoromethyl-cyclohexyl)-thiazol-5-yl]-propoxy}-phenyl)-4H-1,2,4-oxadiazol-5-one was obtained from 1-[4-methyl-2-(trans-1,4-trifluoromethyl-cyclohexyl)-thiazol-5-yl]-propan-1-ol and commercially available 4,5-difluoro-2-methoxybenzonitrile.

$C_{23}H_{25}F_4N_3O_4S$ (515.53), MS (ESI): 516 (M+H$^+$).

The racemate was separated into its enantiomers by supercritical fluid chromatography on chiral phase (Chiralcel OJ-H, column 250×21 mm, 5 µm) with 5% methanol/95% carbon dioxide as eluent (flow rate: 90 mL/min, UV 230 nm). The enantiomeric excess of each enantiomer was determined by analytical supercritical fluid chromatography on chiral phase (Chiralcel OJ, column 250×4.6 mm, 10 µm) with 15% iso-propanol/85% carbon dioxide as eluent (100 bars, flow rate: 3 mL/min, UV 230 nm): first enantiomer: 92.4% ee, Rt=9.03 min; second enantiomer: >99% ee, Rt=12.48 min.

EXAMPLE 52

3-{2-Difluoromethoxy-4-[4-methyl-2-(trans-1,4-trifluoromethyl-cyclohexyl)-thiazol-5-ylmethoxy]-phenyl}-4H-1,2,4-oxadiazol-5-one

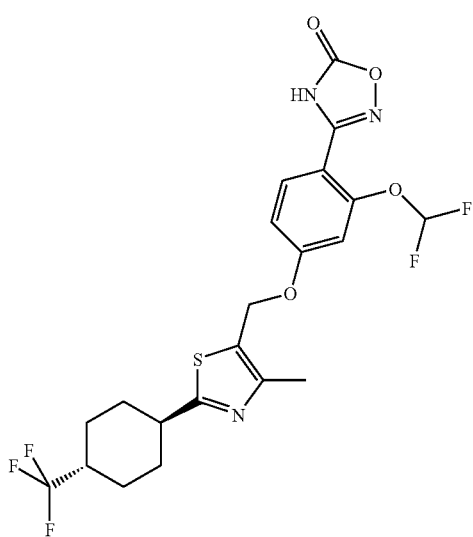

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{2-difluoromethoxy-4-[4-methyl-2-(trans-1,4-trifluoromethyl-cyclohexyl)-thiazol-5-ylmethoxy]-phenyl}-4H-1,2,4-oxadiazol-5-one was obtained from [4-methyl-2-(trans-1,4-trifluoromethyl-cyclohexyl)-thiazol-5-yl]-methanol and 2-difluoromethoxy-4-fluoro-benzonitrile.

$C_{21}H_{20}F_5N_3O_4S$ (505.47), MS (ESI): 506.0 (M+H$^+$).

EXAMPLE 53

3-(2-Difluoromethoxy-4-{1-[4-methyl-2-(trans-1,4-trifluoromethyl-cyclohexyl)-thiazol-5-yl]-propoxy}-phenyl)-4H-1,2,4-oxadiazol-5-one

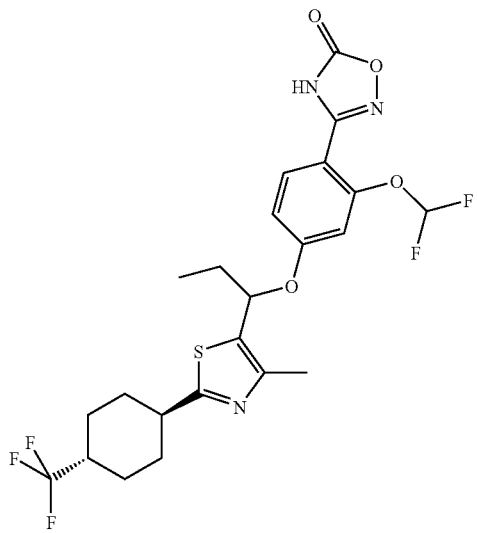

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(2-difluoromethoxy-4-{1-[4-methyl-2-(trans-1,4-trifluoromethyl-cyclohexyl)-thiazol-5-yl]-propoxy}-phenyl)-4H-1,2,4-oxadiazol-5-one was obtained from 1-[4-methyl-2-(trans-1,4-trifluoromethyl-cyclohexyl)-thiazol-5-yl]-propan-1-ol and 2-difluoromethoxy-4-fluoro-benzonitrile.

$C_{23}H_{24}F_5N_3O_4S$ (533.52), MS (ESI): 534.1 (M+H$^+$).

EXAMPLE 54

3-{2-Difluoromethoxy-5-fluoro-4-[4-methyl-2-(trans-1,4-trifluoromethyl-cyclohexyl)-thiazol-5-ylmethoxy]-phenyl}-4H-1,2,4-oxadiazol-5-one

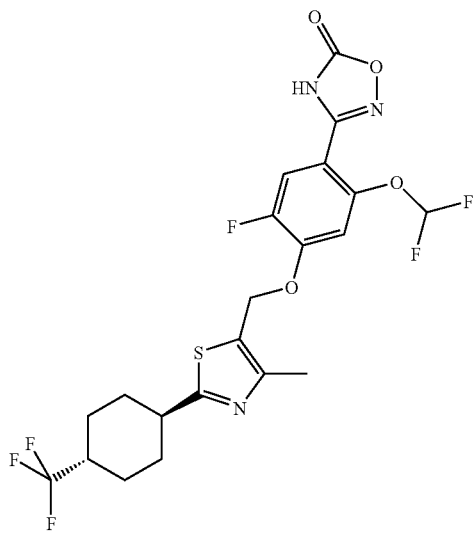

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{2-difluoromethoxy-5-fluoro-4-[4-methyl-2-(trans-1,4-trifluoromethyl-cyclohexyl)-thiazol-5-ylmethoxy]-phenyl}-4H-1,2,4-oxadiazol-5-one was obtained from [4-methyl-2-(trans-1,4-trifluoromethyl-cyclohexyl)-thiazol-5-yl]-methanol and 2-difluoromethoxy-4,5-difluoro-benzonitrile.

$C_{21}H_{19}F_6N_3O_4S$ (523.46), MS (ESI): 524.1 (M+H$^+$).

EXAMPLE 55

3-(2-Difluoromethoxy-5-fluoro-4-{1-[4-methyl-2-(trans-1,4-trifluoromethyl-cyclohexyl)-thiazol-5-yl]-propoxy}-phenyl)-4H-1,2,4-oxadiazol-5-one

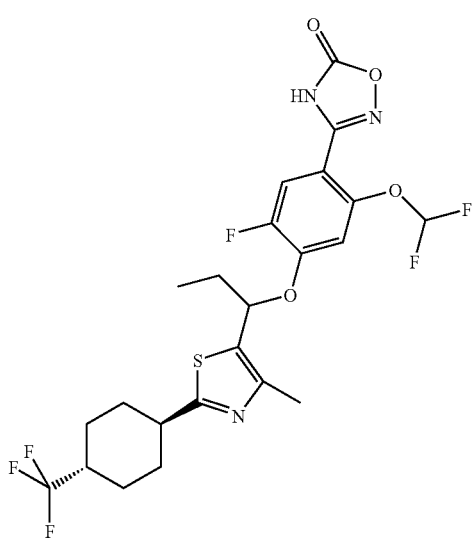

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(2-difluoromethoxy-5-fluoro-4-{1-[4-methyl-2-(trans-1,4-trifluoromethyl-cyclohexyl)-thiazol-5-yl]-propoxy}-phenyl)-4H-1,2,4-oxadiazol-5-one was obtained from 1-[4-methyl-2-(trans-1,4-trifluoromethyl-cyclohexyl)-thiazol-5-yl]-propan-1-ol and 2-difluoromethoxy-4,5-difluoro-benzonitrile.

$C_{23}H_{23}F_6N_3O_4S$ (551.51), MS (ESI): 552.0 (M+H$^+$).

EXAMPLE 56

3-{2-Methoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one

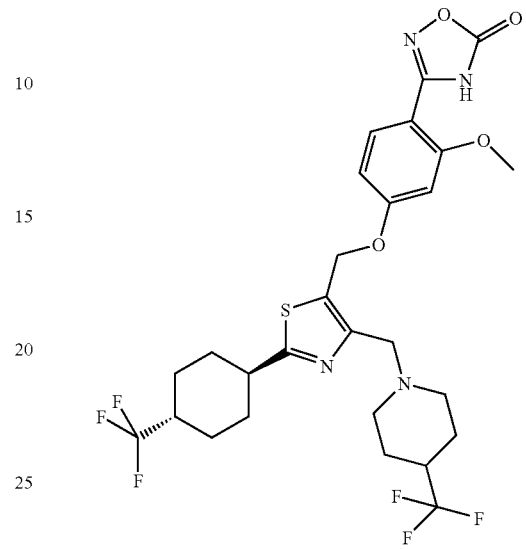

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{2-methoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one was obtained from [2-(trans-1,4-trifluoromethyl-cyclohexyl)-4-(4-trifluoromethyl-piperidin-1-ylmethyl)-thiazol-5-yl]-methanol and 4-fluoro-2-methoxybenzonitrile.

$C_{27}H_{30}F_6N_4O_4S$ (620.19), MS (ESI): 621.2 (M+H$^+$).

EXAMPLE 57

3-(2-Methoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one

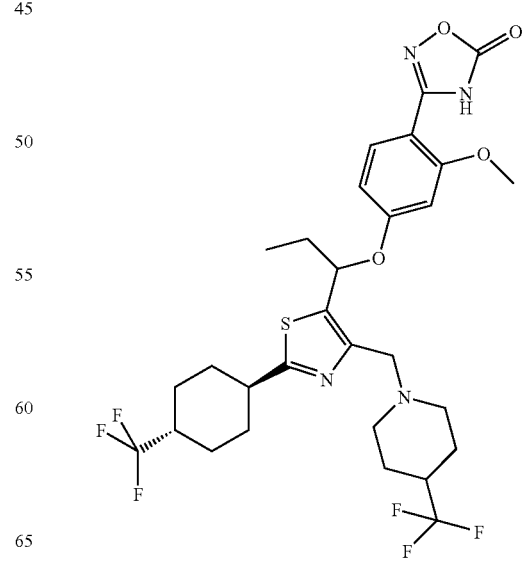

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(2-methoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one was obtained from 1-[2-(trans-1,4-trifluoromethyl-cyclohexyl)-4-(4-trifluoromethyl-piperidin-1-ylmethyl)-thiazol-5-yl]-propan-1-ol and 4-fluoro-2-methoxybenzonitrile.

$C_{29}H_{34}F_6N_4O_4S$ (648.67), MS (ESI): 649.3 (M+H$^+$).

The racemate was separated into its enantiomers by supercritical fluid chromatography on chiral phase (Chiralpak AS-H, column 250×50 mm, 5 μm) with 15% methanol/85% carbon dioxide as eluent (128 bars, flow rate: 100 mL/min, UV 254 nm). The enantiomeric excess of each enantiomer was determined by analytical supercritical fluid chromatography on chiral phase (Chiracel AS-H, column 250×4.6 mm, 5 μm) with 15% methanol/85% carbon dioxide as eluent (100 bars, flow rate: 3 mL/min, UV 254 nm): first enantiomer: >99% ee, Rt=4.24 min; second enantiomer: >99% ee, Rt=8.83 min.

EXAMPLE 58

3-{5-Fluoro-2-methoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one

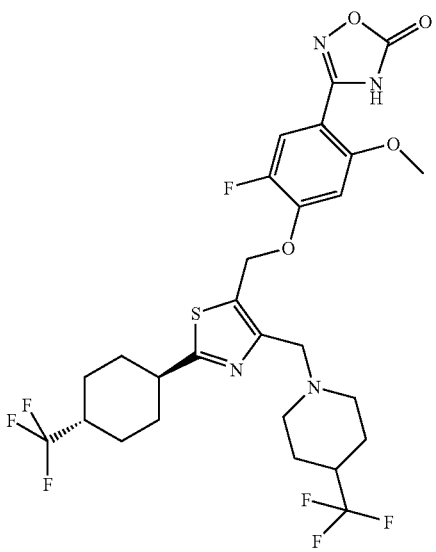

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{5-fluoro-2-methoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one was obtained from [2-(trans-1,4-trifluoromethyl-cyclohexyl)-4-(4-trifluoromethyl-piperidin-1-ylmethyl)-thiazol-5-yl]-methanol and commercially available 4,5-difluoro-2-methoxybenzonitrile.

$C_{27}H_{29}F_7N_4O_4S$ (638.61), MS (ESI): 639.2 (M+H$^+$).

EXAMPLE 59

3-(5-Fluoro-2-methoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one

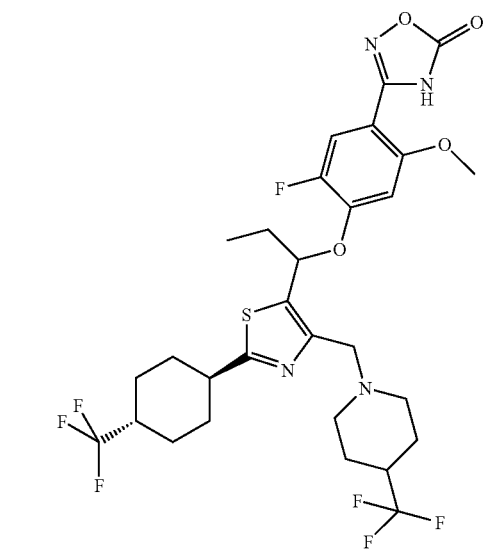

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(5-fluoro-2-methoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one was obtained from 1-[2-(trans-1,4-trifluoromethyl-cyclohexyl)-4-(4-trifluoromethyl-piperidin-1-ylmethyl)-thiazol-5-yl]-propan-1-ol and commercially available 4,5-difluoro-2-methoxybenzonitrile.

$C_{29}H_{33}F_7N_4O_4S$ (666.66), MS (ESI): 667.2 (M+H$^+$).

The racemate was separated into its enantiomers by supercritical fluid chromatography on chiral phase (Chiralcel OD, column 250×20 mm, 5 μm) with 15% of a 75% methanol/25% iso-propanol mixture/85% carbon dioxide as eluent (148 bars, flow rate: 100 mL/min, UV 230 nm). The enantiomeric excess of each enantiomer was determined by analytical supercritical fluid chromatography on chiral phase (Chiralpak OD, column 250×4.6 mm, 5 μm) with 10% of a 75% methanol/25% iso-propanol mixture/90% carbon dioxide as eluent (100 bars, flow rate: 3 mL/min, UV 230 nm): first enantiomer: >99% ee, Rt=4.99 min; second enantiomer: >99% ee, Rt=5.98 min.

EXAMPLE 60

3-{2-Difluoromethoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one

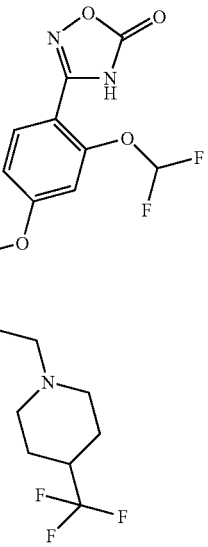

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{2-difluoromethoxy-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one was obtained from [2-(trans-1,4-trifluoromethyl-cyclohexyl)-4-(4-trifluoromethyl-piperidin-1-ylmethyl)-thiazol-5-yl]-methanol and 2-difluoromethoxy-4-fluoro-benzonitrile.

$C_{21}H_{20}F_5N_3O_4S$ (505.47), MS (ESI): 506.0 (M+H$^+$).

EXAMPLE 61

3-(2-Difluoromethoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one

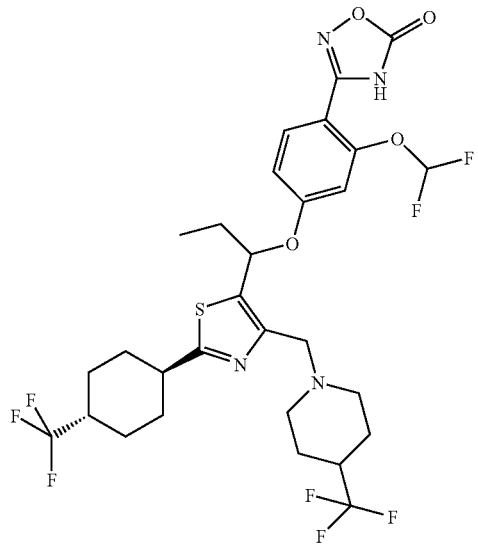

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(2-difluoromethoxy-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one was obtained from 1-[2-(trans-1,4-trifluoromethyl-cyclohexyl)-4-(4-trifluoromethyl-piperidin-1-ylmethyl)-thiazol-5-yl]-propan-1-ol and 2-difluoromethoxy-4-fluoro-benzonitrile.

$C_{29}H_{32}F_8N_4O_4S$ (684.65), MS (ESI): 685.1 (M+H$^+$).

EXAMPLE 62

3-{2-Difluoromethoxy-5-fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one

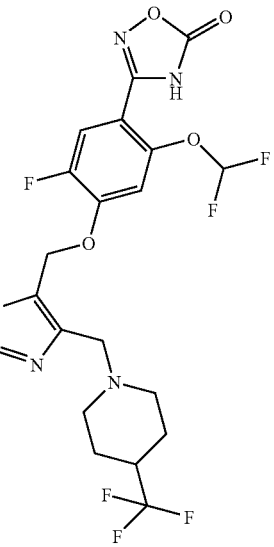

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{2-difluoromethoxy-5-fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one was obtained from [2-(trans-1,4-trifluoromethyl-cyclohexyl)-4-(4-trifluoromethyl-piperidin-1-ylmethyl)-thiazol-5-yl]-methanol and 2-difluoromethoxy-4,5-difluoro-benzonitrile.

$C_{72}H_{27}F_9N_4O_4S$ (674.59), MS (ESI): 675.1 (M+H$^+$).

EXAMPLE 63

3-(2-Difluoromethoxy-5-fluoro-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one

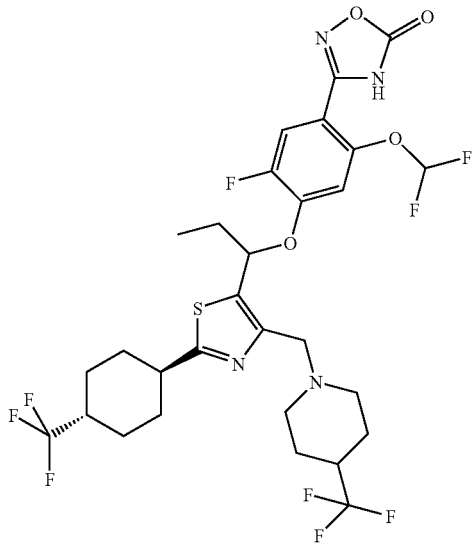

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(2-difluoromethoxy-5-fluoro-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one was obtained from 1-[2-(trans-1,4-trifluoromethyl-cyclohexyl)-4-(4-trifluoromethyl-piperidin-1-ylmethyl)-thiazol-5-yl]-propan-1-ol and 2-difluoromethoxy-4,5-difluoro-benzonitrile.

$C_{29}H_{31}F_9N_4O_4S$ (702.64), MS (ESI): 703.0 (M+H$^+$).

EXAMPLE 64

3-(5-Fluoro-2-(2,2,2-trifluoro-ethoxy)-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one

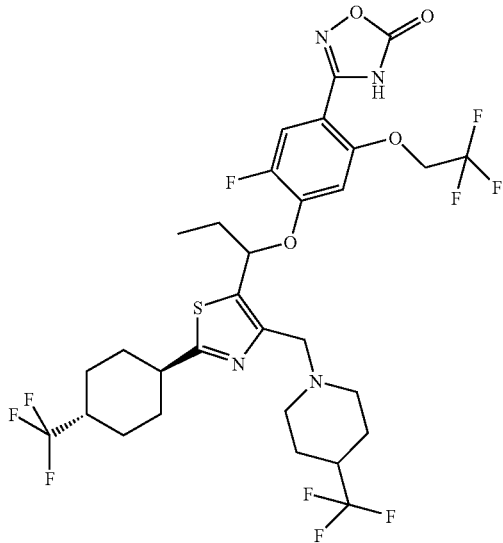

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-(5-fluoro-2-(2,2,2-trifluoro-ethoxy)-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one was obtained from 1-[2-(trans-1,4-trifluoromethyl-cyclohexyl)-4-(4-trifluoromethyl-piperidin-1-ylmethyl)-thiazol-5-yl]-propan-1-ol and 4,5-difluoro-2-(2,2,2-trifluoro-ethoxy)-benzonitrile.[3]

$C_{30}H_{32}F_{10}N_4O_4S$ (734.66), MS (ESI): 735.0 (M+H$^+$).

The following examples were prepared according to process A:

EXAMPLE 65

3-{2-Fluoro-4-[4-methyl-2-(trans-1,4-trifluoromethyl-cyclohexyl)-thiazol-5-ylmethoxy]-phenyl}-4H-1,2,4-oxadiazol-5-one

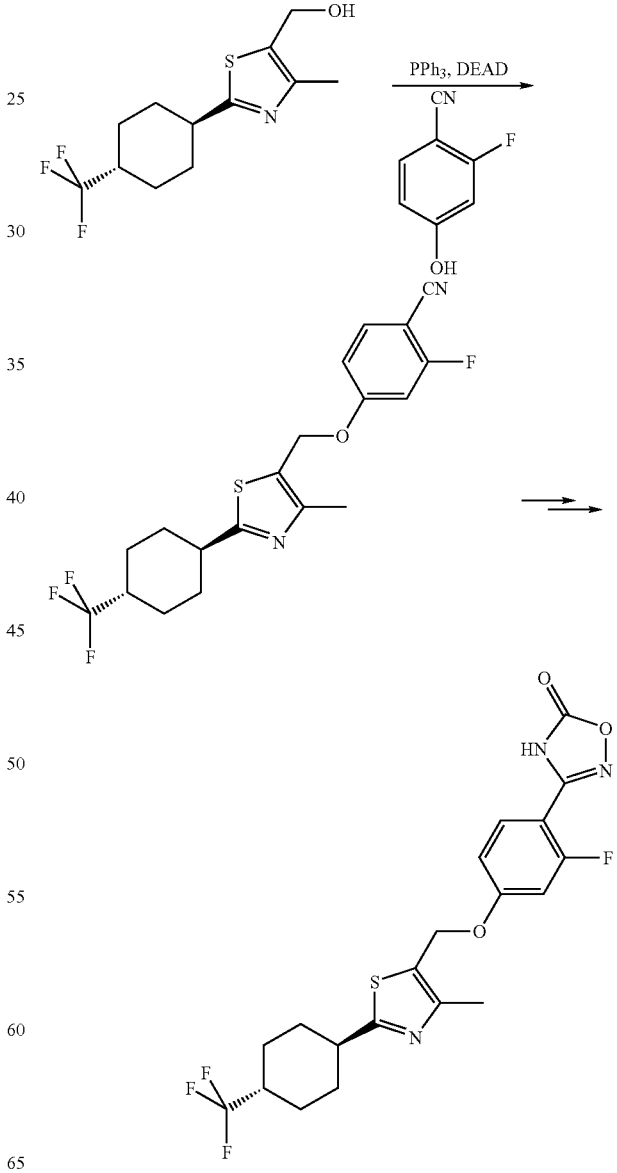

2-Fluoro-4-[4-methyl-2-(trans-1,4-trifluoromethyl-cyclohexyl)-thiazol-5-ylmethoxy]-benzonitrile

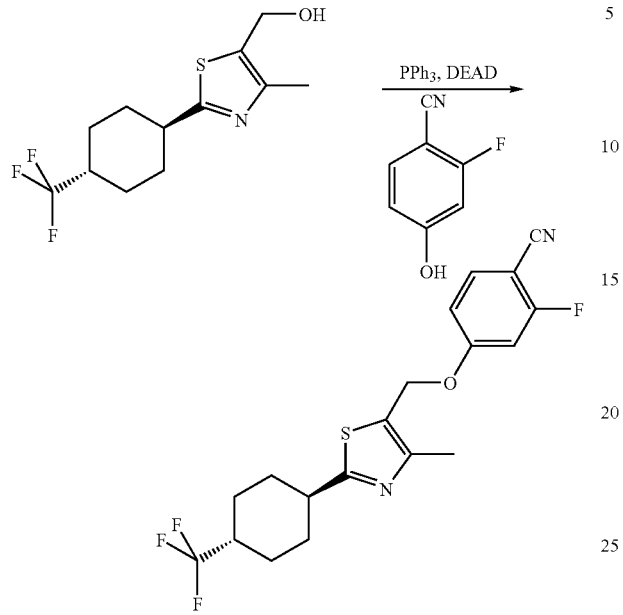

According to the method described for 2-chloro-4-[4-methyl-2-(6-trifluoromethyl-pyridin-3-yl)-thiazol-5-yl-methoxy]-benzonitrile, 2-fluoro-4-[4-methyl-2-(trans-1,4-trifluoromethyl-cyclohexyl)-thiazol-5-ylmethoxy]-benzonitrile was obtained from [4-methyl-2-(trans-1,4-trifluoromethyl-cyclohexyl)-thiazol-5-yl]-methanol and 2-fluoro-4-hydroxy-benzonitrile.

$C_{19}H_{18}F_4N_2OS$ (398.43), MS (ESI): 399.0 (M+H$^+$).

3-{2-Fluoro-4-[4-methyl-2-(trans-1,4-trifluoromethyl-cyclohexyl)-thiazol-5-ylmethoxy]-phenyl}-4H-1,2,4-oxadiazol-5-one

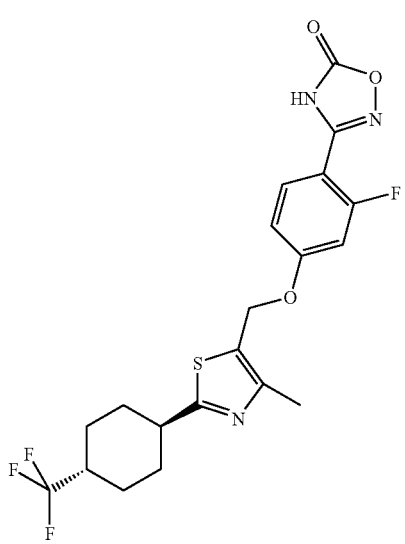

According to the method described for 3-(2-methoxy-4-{1-[4-methyl-2-(trans-1,4-trifluoromethyl-cyclohexyl)-oxazol-5-yl]-propoxy}-phenyl)-4H-1,2,4-oxadiazol-5-one, 3-{2-fluoro-4-[4-methyl-2-(trans-1,4-trifluoromethyl-cyclohexyl)-thiazol-5-ylmethoxy]-phenyl}-4H-1,2,4-oxadiazol-5-one was obtained from 2-fluoro-4-[4-methyl-2-(trans-1,4-trifluoromethyl-cyclohexyl)-thiazol-5-ylmethoxy]-benzonitrile.

$C_{20}H_{19}F_4N_3O_3S$ (457.45), MS (ESI): 458.0 (M+H$^+$).

EXAMPLE 66

3-(2-Fluoro-4-{1-[4-methyl-2-(trans-1,4-trifluoromethyl-cyclohexyl)-thiazol-5-yl]-propoxy}-phenyl)-4H-1,2,4-oxadiazol-5-one

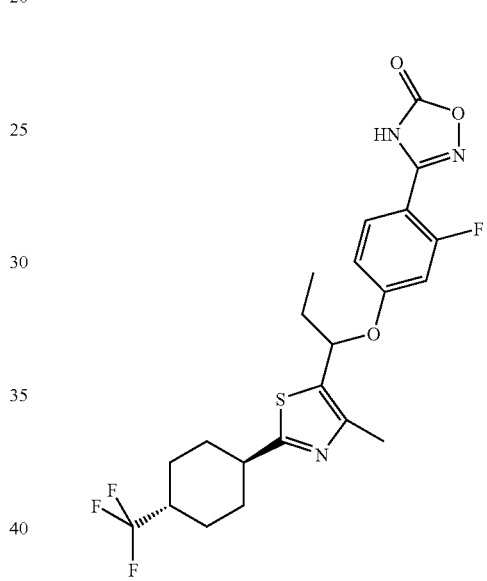

According to the method described for 3-{2-fluoro-4-[4-methyl-2-(trans-1,4-trifluoromethyl-cyclohexyl)-thiazol-5-ylmethoxy]-phenyl}-4H-1,2,4-oxadiazol-5-one, 3-(2-fluoro-4-{1-[4-methyl-2-(trans-1,4-trifluoromethyl-cyclohexyl)-thiazol-5-yl]-propoxy}-phenyl)-4H-1,2,4-oxadiazol-5-one was obtained from 1-[2-(trans-1,4-trifluoromethyl-cyclohexyl)-4-(4-trifluoromethyl-piperidin-1-ylmethyl)-thiazol-5-yl]-propan-1-ol and 2-fluoro-4-hydroxy-benzonitrile.

$C_{22}H_{23}F_4N_3O_3S$ (485.50), MS (ESI): 486.1 (M+H$^+$).

The racemate was separated into its enantiomers by HPLC on chiral phase (Chiralpak QN-AX, column 35×6 cm, 10 µm) with 100% methanol as eluent (flow rate: 103 mL/min, UV 254 nm). The enantiomeric excess of each enantiomer was determined by analytical HPLC on chiral phase (Chiralpak 50801, column 250×4.6 mm, 20 µm) with 2% methanol/2% iso-propanol/96% acetonitrile as eluent (3 bars, flow rate: 3 mL/min, UV 254 nm): dextrorotatory enantiomer: >99% ee, Rt=5.21 min; levorotatory enantiomer: >99% ee, Rt=8.14 min.

EXAMPLE 67
3-{2-Fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one
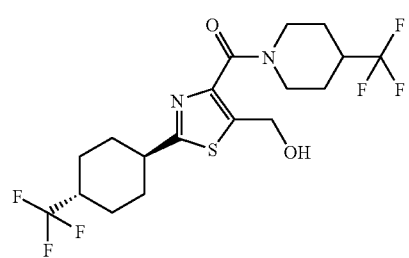 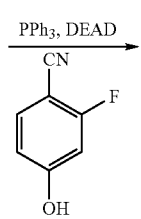 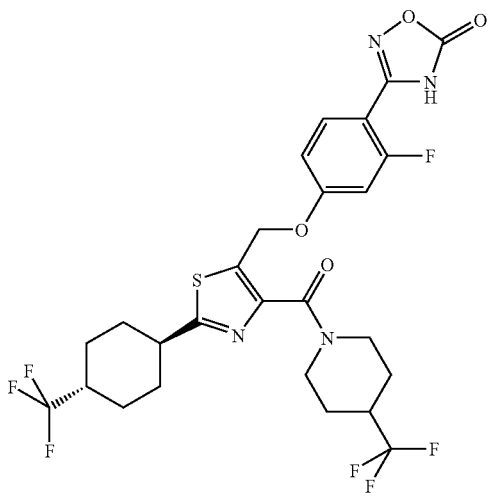
3-{2-Fluoro-4-[2-(trans-1,4-trifluoromethyl-cyclohexyl)-4-(4-trifluoromethyl-piperidine-1-carbonyl)-thiazol-5-ylmethoxy]-phenyl}-4H-1,2,4-oxadiazol-5-one
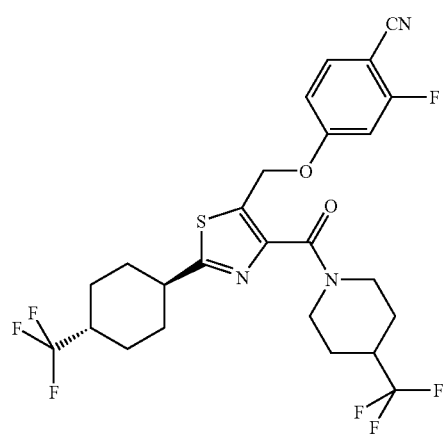  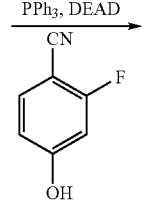
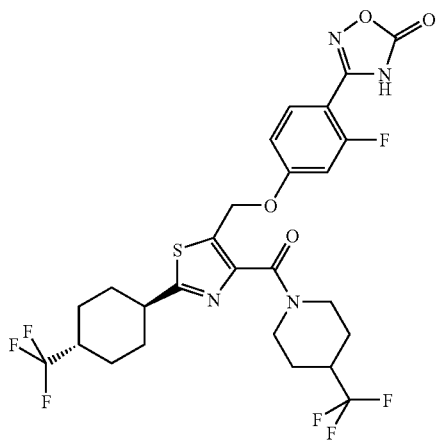  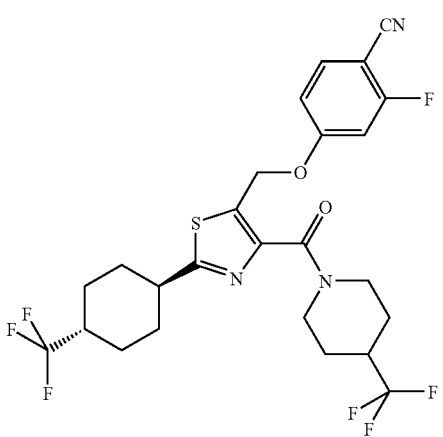

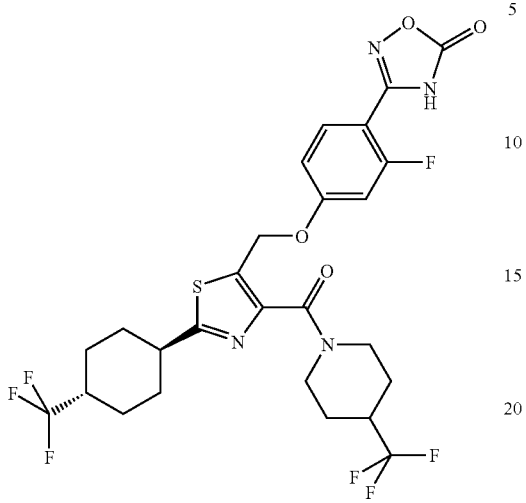

According to the method described for 3-{2-fluoro-4-[4-methyl-2-(trans-1,4-trifluoromethyl-cyclohexyl)-thiazol-5-ylmethoxy]-phenyl}-4H-1,2,4-oxadiazol-5-one, 3-{2-fluoro-4-[2-(trans-1,4-trifluoromethyl-cyclohexyl)-4-(4-trifluoromethyl-piperidine-1-carbonyl)-thiazol-5-ylmethoxy]-phenyl}-4H-1,2,4-oxadiazol-5-one was obtained from [5-hydroxymethyl-2-(trans-1,4-trifluoromethyl-cyclohexyl)-thiazol-4-yl]-(4-trifluoromethyl-piperidin-1-yl)-methanone and 2-fluoro-4-hydroxy-benzonitrile.

$C_{26}H_{25}F_7N_4O_4S$ (622.57), MS (ESI): 623.0 (M+H$^+$).

3-{2-Fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one

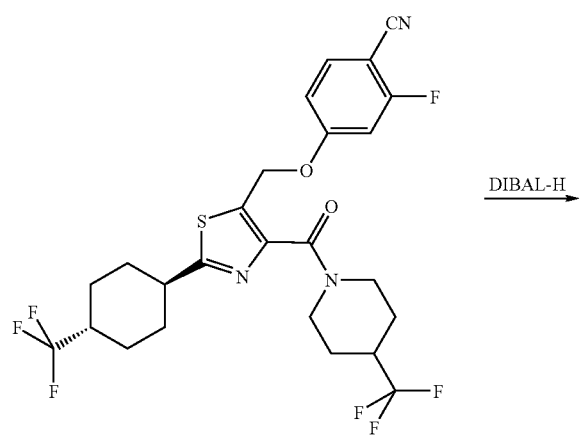

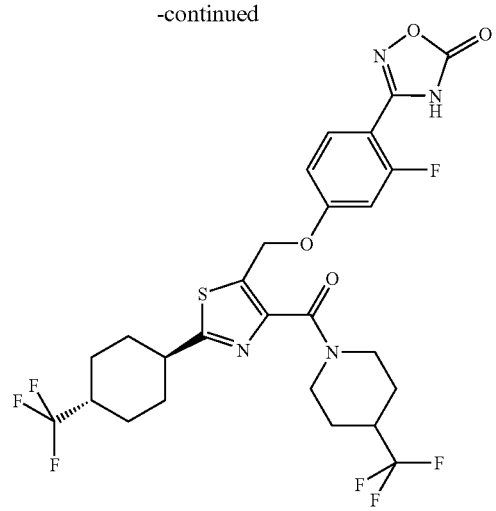

To a solution of 140 mg of 3-{2-fluoro-4-[2-(trans-1,4-trifluoromethyl-cyclohexyl)-4-(4-trifluoromethyl-piperidine-1-carbonyl)-thiazol-5-ylmethoxy]-phenyl}-4H-1,2,4-oxadiazol-5-one in 3 mL of tetrahydrofuran at room temperature was added 1.1 mL of a 1M solution of diisobutyl aluminum hydride in tetrahydrofuran. The resulting mixture was stirred for 1 hour at room temperature. The mixture was poured onto an aqueous solution of NaHSO4 and dichloromethane and extracted with dichloromethane. The combined organic extracts were dried over magnesium sulfate, filtered and concentrated under reduced pressure. The residue was purified by preparative thin layer chromatography on silica gel (dichloromethane 93/acetone 7) to give 37 mg of 3-{2-fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one as a white solid.

$C_{26}H_{27}F_7N_4O_3S$ (608.58), MS (ESI): 609.1 (M+H$^+$).

EXAMPLE 68

3-(2-Fluoro-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one

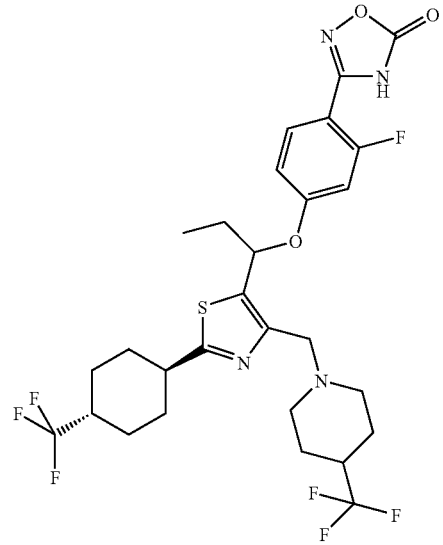

According to the method described for 3-{2-fluoro-4-[2-(trans-1,4-trifluoromethyl-cyclohexyl)-4-(4-trifluoromethyl-piperidin-1-ylmethyl)-thiazol-5-ylmethoxy]-phenyl}-4H-1,2,4-oxadiazol-5-one, 3-(2-fluoro-4-{1-[2-(trans-1,4-trifluoromethyl-cyclohexyl)-4-(4-trifluoromethyl-piperidin-1-ylmethyl)-thiazol-5-yl]-propoxy}-phenyl)-4H-1,2,4-oxadiazol-5-one was obtained from [5-(1-hydroxy-propyl)-2-(trans-1,4-trifluoromethyl-cyclohexyl)-thiazol-4-yl]-(4-trifluoromethyl-piperidin-1-yl)-methanone and 2-fluoro-4-hydroxy-benzonitrile.

$C_{28}H_{31}F_7N_4O_3S$ (636.64), MS (ESI): 637.1 (M+H$^+$).

The following examples were prepared according to process J:

EXAMPLE 69

3-[4-[4-Methyl-2-(trans-1,4-trifluoromethyl-cyclohexyl)-thiazol-5-ylmethoxy]-2-(2,2,2-trifluoro-ethoxy)-phenyl]-4H-1,2,4-oxadiazol-5-one

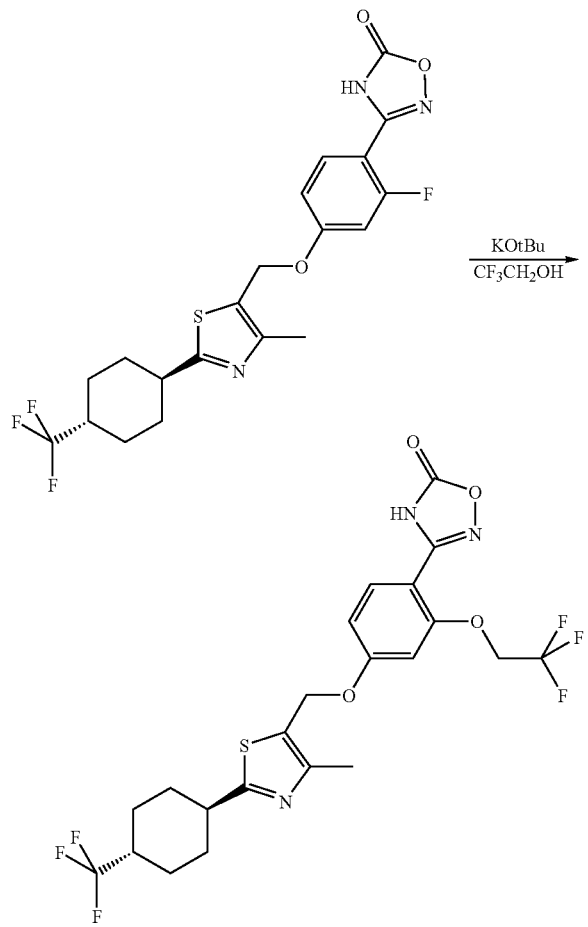

To a solution of 96 μL of trifluoroethanol at 0° C. was slowly added 1.31 mL of a molar solution of potassium tert-butoxide in tert-butanol. The resulting solution was slowly added to a solution of 100 mg of 3-{2-fluoro-4-[4-methyl-2-(trans-1,4-trifluoromethyl-cyclohexyl)-thiazol-5-ylmethoxy]-phenyl}-4H-1,2,4-oxadiazol-5-one in 4 mL of tetrahydrofuran at 0° C. The resulting mixture was stirred overnight allowing the temperature to warm up to room temperature then heated to 120° C. for 45 minutes under microwave irradiation in a sealed tube. A solution containing 48 μL of trifluoroethanol and 0.65 mL of a molar solution of potassium tert-butoxide in tert-butanol was added and the mixture was heated to 120° C. for 20 minutes under microwave irradiation in a sealed tube. The mixture was concentrated under reduced pressure and the residue taken into 25 mL of ethyl acetate and 25 mL of water. The aqueous layer was separated and extracted three times with 10 mL of ethyl acetate. The organic extracts were dried over magnesium sulfate, filtered and concentrated under reduced pressure. The crude product was purified by column chromatography on silica gel (gradient from heptane 100 to heptane 30/ethyl acetate 70) followed by preparative thin layer chromatography on silica gel (heptane 30/ethyl acetate 70) to give 24 mg of 3-[4-[4-methyl-2-(trans-1,4-trifluoromethyl-cyclohexyl)-thiazol-5-ylmethoxy]-2-(2,2,2-trifluoro-ethoxy)-phenyl]-4H-1,2,4-oxadiazol-5-one as a white solid.

$C_{22}H_{21}F_6N_3O_4S$ (537.48), MS (ESI): 538.0 (M+H$^+$).

What is claimed is:
1. A compound of formula I

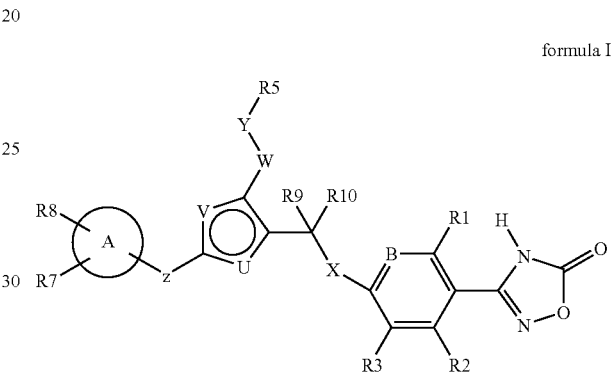

formula I wherein
  B is C(R4) or N;
  R1 is selected from the group consisting of H, halogen, (C1-C8) alkyl, (C0-C4) alkylene-O—(C0-C4) alkylene-H, (C3-C7) cycloalkyl, SCH$_3$ and CN, wherein the alkyl and alkylene are optionally substituted one to five times by F;
  R2, R3 and R4 are independently selected from the group consisting of:
    H, halogen, (C1-C8) alkyl, (C0-C4) alkylene-O—(C0-C4) alkylene-H, SCH$_3$, and CN, wherein the alkyl and alkylene are optionally substituted one to five times by F; or
  R2 and R3 together with the carbon atoms to which they are bonded form a (C6-C10) aryl or a (C5-C10) heteroaryl ring;
  X is selected from the group consisting of O, S, S(O), S(O)$_2$, O—CH$_2$, S—CH$_2$, CH$_2$—O, and CH$_2$—S;
  one of U and V is N and the other is S or O;
  W is a bond, (C1-C8) alkylene, or (C2-C8) alkenylene, wherein the alkylene and alkenylene are optionally mono-, di- or tri-substituted by OH or F;
  Y is a bond, O, S, S(O), S(O)$_2$, or N(R6);
  R5 is selected from the group consisting of H, (C1-C8) alkyl, (C0-C4) alkylene-(C3-C13) cycloalkyl, (C0-C4) alkylene-(C6-C14) aryl, (C2-C8) alkenyl, (C0-C4) alkylene-(C3-C15) heterocycloalkyl, (C0-C4) alkylene-(C3-C15) heterocycloalkenyl, and (C0-C4) alkylene-(C5-C15) heteroaryl, wherein the alkyl and alkylene are optionally mono-, di- or tri-substituted by (C1-C4) alkyl or O—(C0-C4) alkylene-H, and are optionally substituted one to five times by F, and wherein the cycloalkyl, aryl, heterocycloalkyl, heterocycloalkenyl and heteroaryl are optionally mono-, di- or tri-substituted by F, Cl, Br, $CF_3$, (C1-C4) alkyl or O—(C0-C4) alkylene-H;

R6 is selected from the group consisting of H, (C1-C8) alkyl and (C2-C8) alkenyl, wherein the alkyl and alkenyl are optionally mono-, di- or tri-substituted by F or O—(C0-C4)-alkylene-H, or R5 and R6 together with the nitrogen atom to which they are bonded form a (C3-C9)-heterocycloalkyl, a (C3-C9)-heterocycloalkenyl or a (C5-C9)-heteroaryl, each of which can contain additionally 1 to 3 heteroatoms selected from N, O, and S, and each of which is optionally mono-, di- or tri-substituted by F, $CF_3$, (C1-C4) alkyl, O—(C1-C4) alkyl, OH, $CH_2$—OH, $SO_2$-(C1-C4) alkyl, CO—(C1-C4) alkyl, CO—$NH_2$, NH—CO—(C1-C4) alkyl, (C6-C14) aryl or (C5-C15) heteroaryl;

Z is a bond, (C1-C8) alkylene, (C2-C8) alkenylene, (C2-C8) alkylidene, or (C1-C6) alkylene-O—(C1-C6) alkyl;

A is selected from the group consisting of (C3-C13) cycloalkyl, (C4-C15) heterocycloalkyl, (C4-C15) heterocycloalkenyl and (C5-C15) heteroaryl ring;

R7 and R8 are independently selected from the group consisting of H, halogen, (C1-C8) alkyl, (C0-C4) alkylene-O—(C0-C4) alkylene-H, $SCF_3$, $SF_5$, $S(O)_2CF_3$, O—(C6-C12) aryl, (C6-C12) aryl, and NO2, wherein the alkyl and alkylene are optionally mono-, di- or tri-substituted by F, and wherein the aryl is optionally mono-, di- or tri-substituted by halogen, (C1-C4) alkyl or O—(C1-C4) alkyl; and R9 and R10 are independently selected from the group consisting of H, (C1-C6) alkyl, (C2-C6) alkenyl, (C0-C6) alkylene-(C6-C14) aryl, (C0-C6) alkylene-(C5-C15) heteroaryl, (C0-C6) alkylene-(C3-C8) cycloalkyl, and (C0-C6) alkylene-(C3-C8) cycloalkenyl, wherein the alkyl and alkylene are optionally mono-, di- or tri-substituted by F, and wherein the aryl and heteroaryl are optionally mono-, di- or tri-substituted by halogen, (C1-C4) alkyl or O—(C1-C4) alkyl;

or a stereoisomeric form thereof or a mixture in any ratio thereof, or a physiologically acceptable salt or a tautomer thereof.

2. The compound according to claim 1, wherein

R1 is selected from the group consisting of H, halogen, (C1-C8) alkyl, (C0-C4) alkylene-O—(C0-C4) alkylene-H, and (C3-C7) cycloalkyl, wherein the alkyl and alkylene are optionally mono-, di- or tri-substituted by F;

R2 is H;

R3 is H or halogen;

R4 is H; or

R2 and R3 together with the carbon atoms to which they are bonded form a (C6) aryl or a (C5-C6) heteroaryl ring;

X is O or O—$CH_2$;

W is a bond or (C1-C5) alkylene;

Y is a bond, O, or N(R6);

R5 is selected from the group consisting of H, (C1-C8) alkyl and (C0-C4) alkylene-(C6-C14) aryl;

R6 is H or (C1-C8) alkyl; or

R5 and R6 together with the nitrogen atom to which they are bonded form a (C3-C9)-heterocycloalkyl, which is optionally mono-substituted by $CF_3$;

Z is a bond, (C1-C4) alkylene or (C2-C4) alkenylene;

A is selected from the group consisting of (C3-C8) cycloalkyl, (C5-C6) heterocycloalkyl and (C5-C12) heteroaryl ring;

R7 is selected from the group consisting of H, (C1-C8) alkyl, (C0-C4) alkylene-O—(C0-C4) alkylene-H, $S(O)_2CF_3$, and (C6-C12) aryl, wherein the alkyl and alkylene are optionally mono-, di- or tri-substituted by F, and wherein the aryl is optionally mono-, di- or tri-substituted by halogen;

R8 is H;

R9 is selected from the group consisting of H, (C1-C6) alkyl, (C0-C6) alkylene-(C6-C14) aryl, and (C0-C6) alkylene-(C5-C15) heteroaryl, wherein the alkyl and alkylene are optionally mono-, di- or tri-substituted by F, and wherein the aryl is optionally mono-, di- or tri-substituted by halogen; and R10 is H;

or a stereoisomeric form thereof or a mixture in any ratio thereof, or a physiologically acceptable salt or a tautomer thereof.

3. The compound according to claim 1, wherein

B is CH or N;

R1 is selected from the group consisting of H, halogen, (C1-C8) alkyl, (C0-C4) alkylene-O—(C0-C4) alkylene-H, and (C3-C7) cycloalkyl, wherein the alkyl and alkylene are optionally mono-, di- or tri-substituted by F;

R2 and R4 are H;

R3 is H or F; or

R2 and R3 together with the carbon atoms to which they are bonded form a (C6)-aryl or a (C5-C6) heteroaryl;

X is O or $OCH_2$;

V is N;

U is O, S;

W is a bond or (C1-C4) alkylene;

Y is a bond, O or N(R6);

R5 is selected from the group consisting of H, (C1-C8) alkyl, and (C0-C4) alkylene-(C6-C10) aryl, wherein the alkyl and alkylene are optionally mono-, di- or tri-substituted by F, (C1-C4) alkyl or O—(C0-C4) alkylene-H;

R6 is H or (C1-C4) alkyl; or

R5 and R6, together with the nitrogen atom to which they are bonded form a (C3-C6)-heterocycloalkyl, which can contain additionally 1 heteroatom selected from N and O, and the heterocycloalkyl is optionally mono- or disubstituted by F, $CF_3$, $CH_3$, $OCH_3$ or phenyl;

Z is a bond, (C1-C4) alkylene or (C2-C4) alkenylene;

A is selected from the group consisting of (C5-C8) cycloalkyl, (C5-C10) heterocycloalkyl, (C5-C10) heterocycloalkenyl and (C5-C10) heteroaryl ring;

R7 and R8 are independently selected from the group consisting of H, halogen, (C1-C8) alkyl, (C0-C4) alkylen-O—(C0-C4) alkylene-H, (C6-C12) aryl, and $S(O)_2CF_3$, wherein the alkyl and alkylene are optionally mono-, di- or tri-substituted by F and aryl is substituted by halogen;

R9 selected from the group consisting of H, (C1-C4) alkyl, (C0-C4) alkylene-(C6-C10) aryl, and (C0-C4) alkylene-(C5-C6) heteroaryl, wherein the alkyl, alkylene, aryl and heteroaryl are unsubstituted or optionally mono-, di- or tri-substituted by F; and R10 is H;

or a stereoisomeric form thereof or a mixture in any ratio thereof, or a physiologically acceptable salt or a tautomer thereof.

4. The compound according to claim 1, wherein

B is C(R4);

R1 is selected from the group consisting of H, halogen, (C1-C8) alkyl, (C0-C4) alkylene-O—(C0-C4) alkylene-H, and (C3-C7) cycloalkyl, wherein the alkyl and alkylene are optionally mono, di- or trisubstituted by F;

R2 and R4 are H;

R3 is H, or F;

X is O, or S;

V is N;

U is O or S;

W is a bond, or (C1-C4) alkylene;

Y is a bond, O, or N(R6);

R5 is selected from the group consisting of H, (C1-C8) alkyl, (C0-C4) alkylene-(C3-C6) cycloalkyl, (C0-C4) alkylene-(C6-C10) aryl, (C0-C4) alkylene-(C4-C6) heterocycloalkyl, (C0-C4) alkylene-(C4-C6) heterocycloalkenyl, and (C0-C4) alkylene-(C5-C6) heteroaryl, wherein the alkyl and alkylene are optionally mono-, di- or tri-substituted by F, (C1—C4) alkyl or O—(C0-C4) alkylene-H, and wherein the cycloalkyl, aryl, heterocycloalkyl, heterocycloalkenyl and heteroaryl are mono-, di- or tri-substituted by F, $CF_3$, (C1-C4) alkyl and O—(C0-C4) alkylene-H;

R6 is H, or (C1-C4) alkyl; or

R5 and R6 together with the nitrogen atom to which they are bonded form a (C3-C6)-heterocycloalkyl, a (C3-C6)-heterocycloalkenyl or a (C5-C6)-heteroaryl each of which can contain additionally 1 heteroatom selected from N and O, and each of which is optionally mono- or disubstituted by F, $CF_3$, $CH_3$, $OCH_3$, phenyl or (C5-C6) heteroaryl;

Z is a bond, (C1-C4) alkylene, (C2-C4) alkylidene, or (C1-C4) alkylene-O—(C1-C4) alkyl;

A is (C5-C8) cycloalkyl, (C5-C10) heterocycloalkyl, (C5-C10) heterocycloalkenyl or (C5-C10) heteroaryl ring;

R7 and R8 are independently selected from the group consisting of H, halogen, (C1-C8) alkyl, (C0—C4) alkylen-O—(C0-C4) alkylene-H, and (C6-C12) aryl, wherein the alkyl and alkylene are optionally mono-, di- or tri-substituted by F, and wherein the aryl is substituted by halogen; and R9 and R10 are independently selected from the group consisting of H, (C1-C4) alkyl, (C0-C4) alkylene-phenyl and (C0-C4) alkylene-(C5-C6) heteroaryl;

or a stereoisomeric form thereof or a mixture in any ratio thereof, or a physiologically acceptable salt or a tautomer thereof.

5. The compound according to claim 1, wherein R1 selected from the group consisting of H, F, Cl, $CH_3$, $OCH_3$, $OCHF_2$, $OCH_2CF_3$ and cyclopropyl;

or a stereoisomeric form thereof or a mixture in any ratio thereof, or a physiologically acceptable salt or a tautomer thereof.

6. The compound according to claim 1, wherein

R1 is OCH3, $OCHF_2$ or $OCH_2CF_3$;

or a stereoisomeric form thereof or a mixture in any ratio thereof, or a physiologically acceptable salt or a tautomer thereof.

7. The compound according to claim 1, wherein

R1 is selected from the group consisting of H, F, Cl, $CH_3$ and cyclopropyl;

or a stereoisomeric form thereof or a mixture in any ratio thereof, or a physiologically acceptable salt or a tautomer thereof.

8. The compound according to claim 1, wherein

R2 and R3 are H;

or a stereoisomeric form thereof or a mixture in any ratio thereof, or a physiologically acceptable salt or a tautomer thereof.

9. The compounds according to claim 1, wherein X is O or O—CH2—;

or a stereoisomeric form thereof or a mixture in any ratio thereof, or a physiologically acceptable salt or a tautomer thereof.

10. The compound according to claim 1, wherein

V is N and U is O or S;

or a stereoisomeric form thereof or a mixture in any ratio thereof, or a physiologically acceptable salt or a tautomer thereof.

11. The compound according to claim 1, wherein

R5 and R6 together with the nitrogen atom to which they are bonded form a (C3-C7)-heterocycloalkyl, which may can contain 1 to 2 heteroatoms selected from the group consisting of N, O and S, wherein the heterocycloalkyl is optionally mono- or disubstituted by F, $CF_3$, $CH_3$, or $OCH_3$;

or a stereoisomeric form thereof or a mixture in any ratio thereof, or a physiologically acceptable salt or a tautomer thereof.

12. The compound according to claim 1, wherein Z is a bond;

or a stereoisomeric form thereof or a mixture in any ratio thereof, or a physiologically acceptable salt or a tautomer thereof.

13. The compound according to claim 1, wherein R7 is selected from the group consisting of H, F, $CH_3$, $CH_2CH_3$, $CF_3$, $OCH_3$ and phenyl; and R8 is H;

or a stereoisomeric form thereof or a mixture in any ratio thereof, or a physiologically acceptable salt or a tautomer thereof.

14. The compound according to claim 1, wherein R9 is ethyl, $CF_2CH_2CH_3$, $CF_3$, $CH_2$-phenyl, $CH_2$-(4-fluoro-phenyl), or $CH_3$pyridyl; and R10 is H;

or a stereoisomeric form thereof or a mixture in any ratio thereof, or a physiologically acceptable salt or a tautomer thereof.

15. The compound according to claim 1, wherein

A is cyclohexyl;

R7 is 4-$CF_3$;

R8 is H; and

R1 is O—$CH_3$, O—$CH_2CF_3$ or —O—$CHF_2$;

or a stereoisomeric form thereof or a mixture in any ratio thereof, or a physiologically acceptable salt or a tautomer thereof.

16. The compound according to claim 1, wherein

W is —CH2—;

Y is a bond; and

R5 is H;

or a stereoisomeric form thereof or a mixture in any ratio thereof, or a physiologically acceptable salt or a tautomer thereof.

17. The compound according to claim 1, wherein

B is C(R4);

R1 is selected from the group consisting of H, F, and Cl;

R2, R3 and R4 are H;

X is O or O—CH2;

V is N;

U is S;

W is —CH2—;

Y is a bond;

R5 is H;

Z is a bond;

A is pyridinyl or cyclohexyl;

R7 is $CF_3$;

R8 is H;

R9 is $CH_2$—$CH_3$, $CF_3$, $CF_2$—$CH_2$—$CH_3$, $CH_2$; 4-fluoro-phenyl, or $CH_2$-pyridyl; and R10 is H;

or a stereoisomeric form thereof or a mixture in any ratio thereof, or a physiologically acceptable salt or a tautomer thereof.

18. The compound according to claim 1, wherein
B is C(R4);
R1 is O—CH3, O—CH2CF3 or —O—CHF2;
R2 and R4 are H;
R3 is H or F;
X is O;
V is N;
U is O or S;
W is a bond or —CH2—;
Y is a bond or N(R6);
R5 is $CH_3$;
R6 is $CH_3$; or
R5 and R6 together with the nitrogen to which they are bonded form a piperidine ring which is substituted by $CF_3$;
Z is a bond;
A is cyclohexyl;
R7 is 4-CF3;
R8 is H;
R9 is H or ethyl; and
R10 is H;
or a stereoisomeric form thereof or a mixture in any ratio thereof, or a physiologically acceptable salt or a tautomer thereof.

19. A pharmaceutical composition comprising the compound according to claim 1, or a stereoisomeric form thereof or a mixture in any ratio thereof, or a physiologically acceptable salt or a tautomer thereof, and a pharmaceutically acceptable excipient.

20. A pharmaceutical composition comprising the compound according to claim 1, or a stereoisomeric form thereof or a mixture in any ratio thereof, or a physiologically acceptable salt or a tautomer thereof, in combination with one or more additional active substances which are effective in the treatment of a metabolic disorder.

21. A pharmaceutical composition comprising the compound according to claim 1, or a stereoisomeric form thereof or a mixture in any ratio thereof, or a physiologically acceptable salt or a tautomer thereof, in combination with one or more additional active substances which are effective in the treatment of diabetes.

22. A pharmaceutical composition comprising the compound according to claim 1, or a stereoisomeric form thereof or a mixture in any ratio thereof, or a physiologically acceptable salt or a tautomer thereof, in combination with one or more additional active substances which are effective lipid modulators.

23. A pharmaceutical composition comprising the compound according to claim 1, or a stereoisomeric form thereof or a mixture in any ratio thereof, or a physiologically acceptable salt or a tautomer thereof, in combination with one or more additional active substances which are effective in the treatment of fatty acid metabolism and glucose utilization disorders.

24. A pharmaceutical composition comprising the compound according to claim 1, or a stereoisomeric form thereof or a mixture in any ratio thereof, or a physiologically acceptable salt or a tautomer thereof, in combination with one or more additional active substances which are effective in the treatment of a disorder which is the result or manifestation of insulin resistance.

25. A pharmaceutical composition comprising the compound according to claim 1, or a stereoisomeric form thereof or a mixture in any ratio thereof, or a physiologically acceptable salt or a tautomer thereof, in combination with one or more additional active substances which are effective in the treatment of diabetes mellitus or a disorder which is the result or manifestation thereof.

26. A pharmaceutical composition comprising the compound according to claim 1, or a stereoisomeric form thereof or a mixture in any ratio thereof, or a physiologically acceptable salt or a tautomer thereof, in combination with one or more additional active substances which are effective in the treatment of dyslipidemia or a disorder which is the result or manifestation thereof.

27. A method for treating metabolic syndrome, in a patient in need thereof, comprising administering to the patient a pharmaceutically effective amount of the compound according to claim 1, or a stereoisomeric form thereof or a mixture in any ratio thereof, or a physiologically acceptable salt or a tautomer thereof.

28. A method for treating demyelinating or a neurodegenerative disorder of central or peripheral nervous system, in a patient in need thereof, comprising administering to the patient a pharmaceutically effective amount of the compound according to claim 1, or a stereoisomeric form thereof or a mixture in any ratio thereof, or a physiologically acceptable salt or a tautomer thereof.

29. A method for treating a disorder of fatty acid metabolism or glucose utilization disorder, in a patient in need thereof, comprising administering to the patient a pharmaceutically effective amount of the compound according to claim 1, or a stereoisomeric form thereof or a mixture in any ratio thereof, or a physiologically acceptable salt or a tautomer thereof.

30. A method for treating a disorder that results from or is a manifestation thereof, in a patient in need thereof, comprising administering to the patient a pharmaceutically effective amount of the compound according to claim 1, or a stereoisomeric form thereof or a mixture in any ratio thereof, or a physiologically acceptable salt or a tautomer thereof.

* * * * *